(12) United States Patent
Wilton et al.

(10) Patent No.: US 10,781,450 B2
(45) Date of Patent: *Sep. 22, 2020

(54) ANTISENSE MOLECULES AND METHODS FOR TREATING PATHOLOGIES

(71) Applicant: The University of Western Australia, Crawley (AU)

(72) Inventors: Stephen Donald Wilton, Applecross (AU); Sue Fletcher, Bayswater (AU); Abbie Adams, Kalamunda (AU); Penny Meloni, Mount Hawthorn (AU)

(73) Assignee: Sarepta Therapeutics, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/357,918

(22) Filed: Mar. 19, 2019

(65) Prior Publication Data

US 2019/0270994 A1 Sep. 5, 2019

Related U.S. Application Data

(60) Division of application No. 15/661,750, filed on Jul. 27, 2017, now Pat. No. 10,287,586, which is a continuation of application No. 14/944,886, filed on Nov. 18, 2015, now Pat. No. 9,758,783, which is a continuation of application No. 14/108,137, filed on Dec. 16, 2013, now Pat. No. 9,228,187, which is a continuation of application No. 13/509,331, filed as application No. PCT/AU2010/001520 on Nov. 12, 2010, now Pat. No. 8,637,483.

(30) Foreign Application Priority Data

Nov. 12, 2009 (AU) ................. 2009905549

(51) Int. Cl.
*C12N 15/113* (2010.01)
*C12N 15/11* (2006.01)

(52) U.S. Cl.
CPC .......... *C12N 15/113* (2013.01); *C12N 15/111* (2013.01); *C12N 2310/11* (2013.01); *C12N 2310/315* (2013.01); *C12N 2310/3181* (2013.01); *C12N 2310/321* (2013.01); *C12N 2310/3233* (2013.01); *C12N 2310/351* (2013.01); *C12N 2320/33* (2013.01)

(58) Field of Classification Search
None
See application file for complete search history.

(56) References Cited

U.S. PATENT DOCUMENTS

| 4,458,066 A | 7/1984 | Caruthers et al. |
|---|---|---|
| 5,034,506 A | 7/1991 | Summerton et al. |
| 5,138,045 A | 8/1992 | Cook et al. |
| 5,142,047 A | 8/1992 | Summerton et al. |
| 5,149,797 A | 9/1992 | Pederson et al. |
| 5,166,315 A | 11/1992 | Summerton et al. |
| 5,185,444 A | 2/1993 | Summerton et al. |
| 5,190,931 A | 3/1993 | Inouye |
| 5,217,866 A | 6/1993 | Summerton et al. |
| 5,506,337 A | 4/1996 | Summerton et al. |
| 5,521,063 A | 5/1996 | Summerton et al. |
| 5,627,274 A | 5/1997 | Kole et al. |
| 5,665,593 A | 9/1997 | Kole et al. |
| 5,698,685 A | 12/1997 | Summerton et al. |
| 5,801,154 A | 9/1998 | Baracchini et al. |
| 5,869,252 A | 2/1999 | Bouma et al. |
| 5,892,023 A | 4/1999 | Pirotzky et al. |
| 5,916,808 A | 6/1999 | Kole et al. |
| 5,976,879 A | 11/1999 | Kole et al. |
| 6,153,436 A | 11/2000 | Hermonat et al. |
| 6,210,892 B1 | 4/2001 | Bennett et al. |
| 6,312,900 B1 | 11/2001 | Dean et al. |
| 6,391,636 B1 | 5/2002 | Monia |
| 6,451,991 B1 | 9/2002 | Martin et al. |
| 6,653,466 B2 | 11/2003 | Matsuo |
| 6,653,467 B1 | 11/2003 | Matsuo et al. |
| 6,656,732 B1 | 12/2003 | Bennett et al. |
| 6,727,355 B2 | 4/2004 | Matsuo et al. |
| 6,784,291 B2 | 8/2004 | Iversen et al. |
| 6,806,084 B1 | 10/2004 | Debs et al. |
| 7,001,761 B2 | 2/2006 | Xiao |
| 7,070,807 B2 | 7/2006 | Mixson |
| 7,163,695 B2 | 1/2007 | Mixson |
| 7,250,289 B2 | 7/2007 | Zhou |
| 7,314,750 B2 | 1/2008 | Zhou |
| 7,468,418 B2 | 12/2008 | Iversen et al. |
| 7,534,879 B2 | 5/2009 | van Deutekom |
| 7,655,785 B1 | 2/2010 | Bentwich |
| 7,655,788 B2 | 2/2010 | Khvorova et al. |

(Continued)

FOREIGN PATENT DOCUMENTS

AU 780517 11/2001
AU 2003284638 A1 6/2004

(Continued)

OTHER PUBLICATIONS

*University of Western Australia v. Academisch Ziekenhuis Leiden*, Order—Authorizing Motions, Patent Interference No. 106,007, 3 pages, dated Jul. 31, 2014.

(Continued)

*Primary Examiner* — Tracy Vivlemore

(74) *Attorney, Agent, or Firm* — Sterne, Kessler, Goldstein & Fox P.L.L.C.

(57) ABSTRACT

An antisense molecule capable of binding to a selected target site to induce exon skipping in the dystrophin gene, as set forth in SEQ ID NO: 1 to 59.

12 Claims, 20 Drawing Sheets

Specification includes a Sequence Listing.

(56) References Cited

U.S. PATENT DOCUMENTS

| | | |
|---|---|---|
| 7,807,816 B2 | 10/2010 | Wilton et al. |
| 7,902,160 B2 | 3/2011 | Matsuo et al. |
| 7,960,541 B2 | 6/2011 | Wilton et al. |
| 7,973,015 B2 | 7/2011 | van Ommen et al. |
| 8,084,601 B2 | 12/2011 | Popplewell et al. |
| 8,232,384 B2 | 7/2012 | Wilton et al. |
| 8,324,371 B2 | 12/2012 | Popplewell et al. |
| 8,361,979 B2 | 1/2013 | Aartsma-Rus et al. |
| 8,436,163 B2 | 5/2013 | Iversen et al. |
| 8,450,474 B2 | 5/2013 | Wilton et al. |
| 8,455,634 B2 | 6/2013 | Wilton et al. |
| 8,455,635 B2 | 6/2013 | Wilton et al. |
| 8,455,636 B2 | 6/2013 | Wilton et al. |
| 8,461,325 B2 | 6/2013 | Popplewell et al. |
| 8,476,423 B2 | 7/2013 | Wilton et al. |
| 8,486,907 B2 | 7/2013 | Wilton et al. |
| 8,501,703 B2 | 8/2013 | Bennett et al. |
| 8,501,704 B2 | 8/2013 | Mourich et al. |
| 8,524,676 B2 | 9/2013 | Stein et al. |
| 8,524,880 B2 | 9/2013 | Wilton et al. |
| 8,536,147 B2 | 9/2013 | Weller et al. |
| 8,552,172 B2 | 10/2013 | Popplewell et al. |
| 8,592,386 B2 | 11/2013 | Mourich et al. |
| 8,618,270 B2 | 12/2013 | Iversen et al. |
| 8,624,019 B2 | 1/2014 | Matsuo et al. |
| 8,637,483 B2 | 1/2014 | Wilton et al. |
| 8,697,858 B2 | 4/2014 | Iversen |
| 8,741,863 B2 | 6/2014 | Moulton et al. |
| 8,759,307 B2 | 6/2014 | Stein et al. |
| 8,759,507 B2 | 6/2014 | Van Deutekom |
| 8,779,128 B2 | 7/2014 | Hanson et al. |
| 8,785,407 B2 | 7/2014 | Stein et al. |
| 8,785,410 B2 | 7/2014 | Iversen et al. |
| 8,835,402 B2 | 9/2014 | Kole et al. |
| 8,865,883 B2 | 10/2014 | Sazani et al. |
| 8,871,918 B2 | 10/2014 | Sazani et al. |
| 8,877,725 B2 | 11/2014 | Iversen et al. |
| 8,895,722 B2 | 11/2014 | Iversen et al. |
| 8,906,872 B2 | 12/2014 | Iversen et al. |
| 9,018,368 B2 | 4/2015 | Wilton et al. |
| 9,024,007 B2 | 5/2015 | Wilton et al. |
| 9,035,040 B2 | 5/2015 | Wilton et al. |
| 9,175,286 B2 | 11/2015 | Wilton et al. |
| 9,217,148 B2 | 12/2015 | Bestwick et al. |
| 9,228,187 B2 | 1/2016 | Wilton et al. |
| 9,234,198 B1 | 1/2016 | Sazani et al. |
| 9,249,416 B2 | 2/2016 | Wilton et al. |
| 9,416,361 B2 | 8/2016 | Iversen et al. |
| 9,422,555 B2 | 8/2016 | Wilton et al. |
| 9,434,948 B2 | 9/2016 | Sazani et al. |
| 9,441,229 B2 | 9/2016 | Wilton et al. |
| 9,442,555 B2 | 9/2016 | Wilton et al. |
| 9,447,415 B2 | 9/2016 | Wilton et al. |
| 9,447,416 B2 | 9/2016 | Sazani et al. |
| 9,447,417 B2 | 9/2016 | Sazani et al. |
| 9,453,225 B2 | 9/2016 | Sazani et al. |
| 9,506,058 B2 | 11/2016 | Kaye |
| 9,605,262 B2 | 3/2017 | Wilton et al. |
| 9,758,783 B2 | 9/2017 | Wilton et al. |
| 9,994,851 B2 | 6/2018 | Wilton et al. |
| 10,227,590 B2 | 3/2019 | Wilton et al. |
| 10,266,827 B2 | 4/2019 | Wilton et al. |
| 10,287,586 B2 | 5/2019 | Wilson et al. |
| 2001/0056077 A1 | 12/2001 | Matsuo |
| 2002/0049173 A1 | 4/2002 | Bennett et al. |
| 2002/0055481 A1 | 5/2002 | Matsuo et al. |
| 2002/0110819 A1 | 8/2002 | Weller et al. |
| 2002/0156235 A1 | 10/2002 | Manoharan et al. |
| 2003/0166588 A1 | 9/2003 | Iversen et al. |
| 2003/0224353 A1 | 12/2003 | Stein et al. |
| 2003/0235845 A1 | 12/2003 | van Ommen et al. |
| 2004/0248833 A1 | 12/2004 | Emanuele et al. |
| 2004/0254137 A1 | 12/2004 | Ackermann et al. |
| 2004/0266720 A1 | 12/2004 | Iversen et al. |
| 2005/0026164 A1 | 2/2005 | Zhou |
| 2005/0048495 A1 | 3/2005 | Baker et al. |
| 2005/0153935 A1 | 7/2005 | Iversen et al. |
| 2006/0073586 A1 | 4/2006 | Xiao |
| 2006/0099616 A1 | 5/2006 | van Ommen et al. |
| 2006/0147952 A1 | 7/2006 | van Ommen et al. |
| 2006/0148740 A1 | 7/2006 | Platenburg |
| 2006/0287268 A1 | 12/2006 | Iversen et al. |
| 2007/0037168 A1 | 2/2007 | Venter et al. |
| 2007/0082861 A1 | 4/2007 | Matsuo et al. |
| 2007/0265215 A1 | 11/2007 | Iversen et al. |
| 2008/0194463 A1 | 8/2008 | Weller et al. |
| 2008/0200409 A1 | 8/2008 | Wilson et al. |
| 2008/0209581 A1 | 8/2008 | van Ommen et al. |
| 2009/0076246 A1 | 3/2009 | van Deutekom |
| 2009/0082547 A1 | 3/2009 | Iversen et al. |
| 2009/0088562 A1 | 4/2009 | Weller et al. |
| 2009/0099066 A1 | 4/2009 | Moulton et al. |
| 2009/0228998 A1 | 9/2009 | van Ommen et al. |
| 2009/0269755 A1 | 10/2009 | Aartsma-Rus et al. |
| 2009/0312532 A1 | 12/2009 | Van Deutekom et al. |
| 2010/0016215 A1 | 1/2010 | Moulton et al. |
| 2010/0130591 A1 | 5/2010 | Sazani et al. |
| 2010/0168212 A1 | 7/2010 | Popplewell et al. |
| 2011/0015253 A1 | 1/2011 | Wilton et al. |
| 2011/0015258 A1 | 1/2011 | Wilton et al. |
| 2011/0046203 A1 | 2/2011 | Wilton et al. |
| 2011/0046360 A1 | 2/2011 | Matsuo et al. |
| 2011/0110960 A1 | 5/2011 | Platenburg |
| 2011/0263682 A1 | 10/2011 | De Kimpe et al. |
| 2011/0263686 A1 | 10/2011 | Wilton et al. |
| 2011/0281787 A1 | 11/2011 | Lu et al. |
| 2011/0294753 A1 | 12/2011 | De Kimpe et al. |
| 2011/0312086 A1 | 12/2011 | Van Deutekom |
| 2012/0022134 A1 | 1/2012 | De Kimpe et al. |
| 2012/0022144 A1 | 1/2012 | Wilton et al. |
| 2012/0022145 A1 | 1/2012 | Wilton et al. |
| 2012/0029057 A1 | 2/2012 | Wilton et al. |
| 2012/0029058 A1 | 2/2012 | Wilton et al. |
| 2012/0029059 A1 | 2/2012 | Wilton et al. |
| 2012/0029060 A1 | 2/2012 | Wilton et al. |
| 2012/0041050 A1 | 2/2012 | Wilton et al. |
| 2012/0046342 A1 | 2/2012 | Van Deutekom et al. |
| 2012/0053228 A1 | 3/2012 | Iversen et al. |
| 2012/0059042 A1 | 3/2012 | Platenburg et al. |
| 2012/0065169 A1 | 3/2012 | Hanson et al. |
| 2012/0065244 A1 | 3/2012 | Popplewell et al. |
| 2012/0108652 A1 | 5/2012 | Popplewell et al. |
| 2012/0108653 A1 | 5/2012 | Popplewell et al. |
| 2012/0115150 A1 | 5/2012 | Bozzoni et al. |
| 2012/0122801 A1 | 5/2012 | Platenburg |
| 2012/0149756 A1 | 6/2012 | Schumperli et al. |
| 2012/0172415 A1 | 7/2012 | Voit et al. |
| 2012/0202752 A1 | 8/2012 | Lu |
| 2012/0289457 A1 | 11/2012 | Hanson |
| 2013/0072671 A1 | 3/2013 | Van Deutekom |
| 2013/0090465 A1 | 4/2013 | Matsuo et al. |
| 2013/0116310 A1 | 5/2013 | Wilton et al. |
| 2013/0190390 A1 | 7/2013 | Sazani et al. |
| 2013/0197220 A1 | 8/2013 | Ueda |
| 2013/0211062 A1 | 8/2013 | Watanabe et al. |
| 2013/0217755 A1 | 8/2013 | Wilton et al. |
| 2013/0253033 A1 | 9/2013 | Wilton et al. |
| 2013/0253180 A1 | 9/2013 | Wilton et al. |
| 2013/0274313 A1 | 10/2013 | Wilton et al. |
| 2013/0289096 A1 | 10/2013 | Popplewell et al. |
| 2013/0302806 A1 | 11/2013 | Van Deutekom |
| 2013/0331438 A1 | 12/2013 | Wilton et al. |
| 2014/0045916 A1 | 2/2014 | Iversen et al. |
| 2014/0057964 A1 | 2/2014 | Popplewell et al. |
| 2014/0080896 A1 | 3/2014 | Nelson et al. |
| 2014/0080898 A1 | 3/2014 | Wilton et al. |
| 2014/0094500 A1 | 4/2014 | Sazani et al. |
| 2014/0113955 A1 | 4/2014 | De Kimpe et al. |
| 2014/0128592 A1 | 5/2014 | De Kimpe et al. |
| 2014/0155587 A1 | 6/2014 | Wilton et al. |
| 2014/0213635 A1 | 7/2014 | Van Deutekom |
| 2014/0221458 A1 | 8/2014 | De Kimpe et al. |
| 2014/0243515 A1 | 8/2014 | Wilton et al. |
| 2014/0243516 A1 | 8/2014 | Wilton et al. |

(56) References Cited

U.S. PATENT DOCUMENTS

| | | |
|---|---|---|
| 2014/0275212 A1 | 9/2014 | Van Deutekom |
| 2014/0296323 A1 | 10/2014 | Leumann et al. |
| 2014/0315862 A1 | 10/2014 | Kaye |
| 2014/0315977 A1 | 10/2014 | Bestwick et al. |
| 2014/0316123 A1 | 10/2014 | Matsuo et al. |
| 2014/0323544 A1 | 10/2014 | Bestwick et al. |
| 2014/0329762 A1 | 11/2014 | Kaye |
| 2014/0329881 A1 | 11/2014 | Bestwick et al. |
| 2014/0343266 A1 | 11/2014 | Watanabe et al. |
| 2014/0350067 A1 | 11/2014 | Wilton et al. |
| 2014/0350076 A1 | 11/2014 | van Deutekom |
| 2014/0357698 A1 | 12/2014 | Van Deutekom et al. |
| 2014/0357855 A1 | 12/2014 | Van Deutekom et al. |
| 2015/0045413 A1 | 2/2015 | De Visser et al. |
| 2015/0057330 A1 | 2/2015 | Wilton et al. |
| 2015/0152415 A1 | 6/2015 | Sazani et al. |
| 2015/0232839 A1 | 8/2015 | Iversen et al. |
| 2015/0353931 A1 | 12/2015 | Wilton et al. |
| 2015/0361428 A1 | 12/2015 | Bestwick et al. |
| 2015/0376615 A1 | 12/2015 | Wilton et al. |
| 2015/0376616 A1 | 12/2015 | Wilton et al. |
| 2015/0376617 A1 | 12/2015 | Sazani et al. |
| 2015/0376618 A1 | 12/2015 | Sazani et al. |
| 2016/0002631 A1 | 1/2016 | Wilton et al. |
| 2016/0002632 A1 | 1/2016 | Wilton et al. |
| 2016/0002633 A1 | 1/2016 | Sazani et al. |
| 2016/0002634 A1 | 1/2016 | Sazani et al. |
| 2016/0002635 A1 | 1/2016 | Wilton et al. |
| 2016/0002637 A1 | 1/2016 | Sazani et al. |
| 2016/0040162 A1 | 2/2016 | Bestwick et al. |
| 2016/0177301 A1 | 6/2016 | Wilton et al. |
| 2016/0298111 A1 | 10/2016 | Bestwick et al. |
| 2017/0009233 A1 | 1/2017 | Wilton et al. |
| 2017/0009234 A1 | 1/2017 | Wilton et al. |
| 2017/0283799 A1 | 10/2017 | Kaye |
| 2017/0292125 A1 | 10/2017 | Sazani et al. |
| 2017/0369875 A1 | 12/2017 | Bestwick et al. |
| 2017/0369876 A1 | 12/2017 | Bestwick et al. |
| 2018/0002689 A1 | 1/2018 | Bestwick et al. |
| 2018/0002697 A1 | 1/2018 | Wilton et al. |
| 2018/0016574 A1 | 1/2018 | Bestwick et al. |
| 2018/0163205 A1 | 6/2018 | Wilton et al. |
| 2019/0144861 A1 | 5/2019 | Wilton et al. |
| 2019/0262375 A1 | 8/2019 | Frank et al. |

FOREIGN PATENT DOCUMENTS

| | | |
|---|---|---|
| CA | 2507125 A1 | 6/2004 |
| CN | 102203253 B | 4/2016 |
| EP | 1054058 A1 | 11/2000 |
| EP | 1160318 A2 | 12/2001 |
| EP | 1191097 A1 | 3/2002 |
| EP | 1191098 A2 | 3/2002 |
| EP | 1495769 A1 | 1/2005 |
| EP | 1544297 A2 | 6/2005 |
| EP | 1568169 A1 | 8/2005 |
| EP | 1619249 A1 | 1/2006 |
| EP | 1191098 B9 | 6/2006 |
| EP | 1766010 B1 | 3/2007 |
| EP | 1857548 A1 | 11/2007 |
| EP | 1495769 B1 | 2/2008 |
| EP | 1619249 B1 | 4/2008 |
| EP | 1160318 B1 | 5/2008 |
| EP | 1544297 B1 | 9/2009 |
| EP | 2119783 A1 | 11/2009 |
| EP | 2135948 A2 | 12/2009 |
| EP | 2206781 A2 | 7/2010 |
| EP | 2258863 A1 | 12/2010 |
| EP | 2284264 A1 | 2/2011 |
| EP | 2374885 A2 | 10/2011 |
| EP | 2386636 A2 | 11/2011 |
| EP | 2392660 A2 | 12/2011 |
| EP | 2488165 A1 | 8/2012 |
| EP | 2499249 A1 | 9/2012 |
| EP | 2500430 A2 | 9/2012 |
| EP | 2530153 A1 | 12/2012 |
| EP | 2530154 A1 | 12/2012 |
| EP | 2530155 A1 | 12/2012 |
| EP | 2530156 A1 | 12/2012 |
| EP | 2581448 A1 | 4/2013 |
| EP | 2594640 A1 | 5/2013 |
| EP | 2594641 A1 | 5/2013 |
| EP | 2594642 A1 | 5/2013 |
| EP | 2602322 A1 | 6/2013 |
| EP | 2607484 A1 | 6/2013 |
| EP | 2612917 A1 | 7/2013 |
| EP | 2614827 A2 | 7/2013 |
| EP | 2623507 A1 | 8/2013 |
| EP | 2636740 A1 | 9/2013 |
| EP | 2636741 A1 | 9/2013 |
| EP | 2636742 A1 | 9/2013 |
| EP | 2435582 B1 | 10/2013 |
| EP | 1606407 B1 | 12/2013 |
| EP | 2435583 B1 | 7/2014 |
| EP | 2135948 B1 | 9/2014 |
| EP | 2799548 A1 | 11/2014 |
| EP | 2801618 A1 | 11/2014 |
| JP | 2000-325085 A | 11/2000 |
| JP | 2002-010790 A | 1/2002 |
| JP | 2002-529499 A | 9/2002 |
| JP | 2002-325582 | 11/2002 |
| JP | 2002-340857 | 11/2002 |
| JP | 2004-509622 A | 4/2004 |
| JP | 2008507577 A | 3/2008 |
| JP | 2010-268815 | 12/2010 |
| JP | 2011-101655 A | 5/2011 |
| JP | 4777777 B2 | 9/2011 |
| JP | 2011-200235 A | 10/2011 |
| JP | 4846965 | 10/2011 |
| JP | 5138722 | 11/2012 |
| JP | 5378423 B2 | 12/2013 |
| JP | 2014-054250 A | 3/2014 |
| JP | 2014-111638 A | 6/2014 |
| JP | 2014-138589 A | 7/2014 |
| WO | 93/20227 A1 | 10/1993 |
| WO | 94/02595 A1 | 2/1994 |
| WO | 94/26887 A1 | 11/1994 |
| WO | 96/10391 A1 | 4/1996 |
| WO | 96/10392 A1 | 4/1996 |
| WO | 97/30067 A1 | 8/1997 |
| WO | 97/34638 A1 | 9/1997 |
| WO | 00/15780 A1 | 3/2000 |
| WO | 00/44897 A1 | 8/2000 |
| WO | 00/78341 A1 | 12/2000 |
| WO | 01/49775 A2 | 7/2001 |
| WO | 01/72765 A1 | 10/2001 |
| WO | 01/83503 A2 | 11/2001 |
| WO | 01/83740 A2 | 11/2001 |
| WO | 02/018656 A2 | 3/2002 |
| WO | 02/024906 A1 | 3/2002 |
| WO | 02/29406 A1 | 4/2002 |
| WO | 03/053341 A2 | 7/2003 |
| WO | 04/048570 A1 | 6/2004 |
| WO | 04/083432 A1 | 9/2004 |
| WO | 04/083446 A2 | 9/2004 |
| WO | 2005/115419 A2 | 12/2005 |
| WO | 2006/000057 A1 | 1/2006 |
| WO | 2006/021724 A2 | 3/2006 |
| WO | 2006/112705 A2 | 10/2006 |
| WO | 2007/058894 A2 | 5/2007 |
| WO | 2007/133812 A2 | 11/2007 |
| WO | 2007/135105 A1 | 11/2007 |
| WO | 2008/036127 A2 | 3/2008 |
| WO | 2009/054725 A2 | 4/2009 |
| WO | 2009/101399 A1 | 8/2009 |
| WO | 2009/139630 A2 | 11/2009 |
| WO | 2010/048586 A1 | 4/2010 |
| WO | 2010/050801 A1 | 5/2010 |
| WO | 2010/050802 A2 | 5/2010 |
| WO | 2010/115993 A1 | 10/2010 |
| WO | 2010/123369 A1 | 10/2010 |
| WO | 2010/136415 A1 | 12/2010 |
| WO | 2010/136417 A1 | 12/2010 |
| WO | 2010/150231 A1 | 12/2010 |

(56) References Cited

FOREIGN PATENT DOCUMENTS

| | | |
|---|---|---|
| WO | 2011/024077 A2 | 3/2011 |
| WO | 2011/045747 A1 | 4/2011 |
| WO | 2011/057350 A1 | 5/2011 |
| WO | 2011/143008 A1 | 11/2011 |
| WO | 2012/001941 A1 | 1/2012 |
| WO | 2012/029986 A1 | 3/2012 |
| WO | 2012/043730 A1 | 4/2012 |
| WO | 2012/109296 A1 | 8/2012 |
| WO | 2012/150960 A1 | 11/2012 |
| WO | 2013/033407 A2 | 3/2013 |
| WO | 2013/053928 A1 | 4/2013 |
| WO | 2013/100190 A1 | 7/2013 |
| WO | 2013/112053 A1 | 8/2013 |
| WO | 2013/142087 A1 | 9/2013 |
| WO | 2014/007620 A2 | 1/2014 |
| WO | 2014/100714 A1 | 6/2014 |
| WO | 2014/144978 A2 | 9/2014 |
| WO | 2014/153220 A2 | 9/2014 |
| WO | 2014/153240 A2 | 9/2014 |
| WO | 2014/172669 A1 | 10/2014 |
| WO | 2017/059131 A1 | 4/2017 |

OTHER PUBLICATIONS

U.S. Appl. No. 16/312,803, inventors Frank, D., et al., filed Jun. 29, 2017 (Not Published).
Aartsma-Rus; A. et al., "Antisense-Mediated Exon Skipping: A Versatile Tool With Therapeutic and Research Implications," RNA 13:1609-24, Cold Spring Laboratory Press, United States (2011).
McClorey; G. et al., "Antisense oligonucleotide-induced exon skipping restores dystrophin expression in vitro in a canine model of DMD," Gene Therapy 13(19): 1373-81, (2006).
European Decision of the Opposition Division, European Application No. 10004274.6, dated Dec. 19, 2017, 23 pages.
Exon 46 Sequence of Dystrophin, Document D18 as filed in Opposition of European Patent EP1619249, filed Jun. 23, 2009, 1 page.
Extended European Search Report, EP 16172354.9, dated Jan. 23, 2017, 7 pages.
Extended European Search Report, EP 17159328.8, dated Sep. 5, 2017, 10 pages.
International Search Report and Written Opinion, PCT/US2016/054534, dated Jan. 17, 2017, 13 pages.
Kole et al. "Exon skipping therapy for Duchenne muscular dystrophy," Advanced Drug Delivery Reviews, vol. 87:104-107 (2015).
WHO Drug Information, International Nonproprietary Names for Pharmaceutical Substances (INN), Proposed INN: List 115, "Casimersen," vol. 30(2): 3 pages (2016).
WHO Drug Information, International Nonproprietary Names for Pharmaceutical Substances (INN), Proposed INN: List 115, "Golodirsen," vol. 30(2): 3 pages (2016).
"Efficacy Study of AVI-4658 to Induce Dystrophin Expression in Selected Duchenne Muscular Dystrophy Patients" ClinicalTrials. gov dated Jan. 22, 2013.
"Efficacy Study of AVI-4658 to Induce Dystrophin Expression in Selected Duchenne Muscular Dystrophy Patients," Clinical Trial Identifier No. NCT01396239, ClinicalTrials.gov, dated Jul. 15, 2011, p. 1-4.
"Efficacy, Safety, and Tolerability Rollover Study of Eteplirsen in Subjects with Duchenne Muscular Dystrophy," Clinical Trial Identifier No. NCT01540409, ClinicalTrials.gov, published online Feb. 23, 2012, p. 1-4.
"Eteplirsen—Inhibitor of Dystrophin Expression—Treatment of Duchenne Muscular Dystrophy", Drugs of the Future, vol. 38(1):13-17 (2013).
"Open-Label, Multiple-Dose, Efficacy, Safety, and Tolerability Study of Eteplirsen in Subjects With Duchenne Muscular Dystrophy Who Participated in Study 4658-US-201," ClinicalTrials.gov dated Jul. 31, 2012, 3 pages.
"Open-Label, Multiple-Dose, Efficacy, Safety, and Tolerability Study of Eteplirsen in Subjects With Duchenne Muscular Dystrophy Who Participated in Study 4658-US-201," ClinicalTrials.gov dated Oct. 17, 2013, 3 pages.
"Open-Label, Multiple-Dose, Efficacy, Safety, and Tolerability Study of Eteplirsen in Subjects With Duchenne Muscular Dystrophy Who Participated in Study 4658-US-201," ClinicalTrials.gov dated Feb. 27, 2012, 3 pages.
2nd Expert Declaration of Dr. Erik Sontheimer ("2nd S Decl.") (Exhibit No. 1067 filed in interferences 106008, 106007 on Dec. 23, 2014).
3rd Declaration of Erik J. Sontheimer, Ph.D. ("3rd S. Decl."), pp. 123, Exhibit No. 1186 filed in Interferences 106,007 and 106,008 on Feb. 17, 2015.
A Comparative Study on AONs between 20 and 50 Nucleotides Designed to Induce the Skipping of Exon 53 from the Dystrophin Pre-mRNA, pp. 6, Exhibit No. 1128 filed in Interferences 106,007 and 106,008 on Feb. 17, 2015.
A Comparative Study on AONs Between 20 and 50 Nucleotides Designed to Induce the Skipping of Exon 51 from the Dystrophin Pre-mRNA, pp. 6, Exhibit No. 1127 filed in Interferences 106,007 and 106,008 on Feb. 17, 2015.
Aartsma-Rus A, et al. "Theoretic applicability of antisense-mediated exon skipping for Duchenne muscular dystrophy mutations," Hum Mutat 2009;30:293-99.
Aartsma-Rus et al., "Antisense-induced exon skipping for duplications in Duchenne muscular dystrophy," BMC Medical Genetics 8:43 (2007), (University of Western Australia Exhibit 2135, filed Apr. 3, 2015 in Interferences 106007, 106008, and 106013, pp. 1-9.).
Aartsma-Rus, Annemieke et al., "194th ENMC international workshop. 3rd ENMC workshop on exon skipping: Towards clinical application of antisense-mediated exon skipping for Duchenne muscular dystrophy Dec. 8-10, 2012, Naarden, The Netherlands," Neuromuscular Disorders, vol. 23:934-944 (2013).
Aartsma-Rus, Annemieke et al., "Antisense-Induced Multiexon Skipping for Duchenne Muscular Dystrophy Makes More Sense," Am. J. Hum. Genet, vol. 74:83-92 (2004).
Aartsma-Rus, Annemieke et al., "Functional Analysis of 114 Exon-Internal AONs for Targeted DMD Exon Skipping: Indication for Steric Hindrance of SR Protein Binding Sites," Oligonucleotides, vol. 15:284-297 (2005) (Exhibit No. 2016 filed in interferences 106008, 106013, 106007 on Nov. 18, 2014).
Aartsma-Rus, Annemieke et al., "Guidelines for Antisense Oligonucleotide Design and Insight Into Splice-modulating Mechanisms," Molecular Therapy, vol. 17(3):548-553 (2009) (Exhibit No. 2014 filed in interferences 106008, 106013, 106007 on Nov. 18, 2014).
Aartsma-Rus, Annemieke et al., "Guidelines for Antisense Oligonucleotide Design and Insight Into Splice-modulating Mechanisms," Molecular Therapy, vol. 17(3):548-553 (2009). Supplementary Table 1.
Aartsma-Rus, Annemieke et al., "Targeted exon skipping as a potential gene correction therapy for Duchenne muscular dystrophy," Neuromuscular Disorders, vol. 12:S71-S77 (2002).
Aartsma-Rus, Annemieke et al., "Therapeutic antisense-induced exon skipping in cultured muscle cells from six different DMD patients," Human Molecular Genetics, vol. 12(8):907-914 (2003).
Abbs, Stephen et al., "A convenient multiplex PCR system for the detection of dystrophin gene deletions: a comparative analysis with cDNA hybridisation shows mistypings by both methods," J. Med. Genet., vol. 28:304-311 (1991).
Abes, S. et al., "Efficient Splicing Correction by PNA Conjugation to an R6-Penetratin Delivery Peptide", Nucleic Acids Research vol. 35(13):4495-4502 (2007).
Agrawal, Sudhir et al., "GEM 91—An Antisense Oligonucleotide Phosphorothioate as a Therapeutic Agent for AIDS," Antisense Research and Development, vol. 2:261-266 (1992).
Agrawal, Sudhir et al., "Oligodeoxynucleoside phosphoramidates and phosphorothioates as inhibitors of human immunodeficiency virus," Proc. NatL Acad. Sci. USA, vol. 85:7079-7083 (1988).

(56) References Cited

OTHER PUBLICATIONS

Ahmad A, et al., "Mdx mice inducibly expressing dystrophin provide insights into the potential of gene therapy for Duchenne muscular dystrophy," Hum Mol Genet 2000;9:2507-2515.
Akhtar, Saghir et al., "Cellular uptake and intracellular fate of antisense oligonucleotides," Trends in Cell Biology, vol. 2:139-144 (1992).
Akhtar, Saghir, "Delivery Strategies for Antisense Oligonucleotide Therapeutics," CRC Press, Inc., Boca Raton, FL, 160 pages (1995).
Alignments of Dystrophin mRNA and Oligonucleotides, 6 pages, submitted to the Patent Trial and Appeal Board in interference No. 106008, dated Nov. 18, 2014 (Exhibit No. 1054 filed in interferences 106008, 106007 on Nov. 18, 2014).
Alter, Julia et al., "Systemic delivery of morpholino oligonucleotide restores dystrophin expression bodywide and improves dystrophic pathology," Nature Medicine, vol. 12(2):175-177 (2006).
Amendment under 37 CFR 1.312 for U.S. Appl. No. 14/248,279, 5 pages, dated Sep. 19, 2014 (Exhibit No. 0053 filed in interferences 106008, 106013, 106007 on Nov. 18, 2014).
Analysis of Second PCR Product by Gel Electrophoresis, pp. 1, Exhibit No. 1182 filed in Interferences 106,007 and 106,008 on Feb. 16, 2015.
Anderson, W. French, "Human Gene Therapy," Science, vol. 256:808-813 (1992).
Annotated scenario introduced and referred to during Mar. 12, 2015 deposition of Erik J. Sontheimer, Ph.D., University of Western Australia Exhibit 2139, filed Apr. 3, 2015 in Interferences 106007, 106008, and 106013, p. 1.).
Anthony, Karen et al., "Dystrophin quantification: Biological and Translational Research Implications," Neurology, vol. 83:1-8 (2014) (Exhibit No. 2028 filed in interferences 106008, 106013, 106007 on Nov. 18, 2014).
AON PS1958 Mass Spectrometry Data, pp. 7, Exhibit No. 1146 filed in Interferences 106,007 and 106,008 on Feb. 16, 2015.
AON PS1958 UPLC Data, pp. 2, Exhibit No. 1157 filed in Interferences 106,007 and 106,008 on Feb. 16, 2015.
AON PS1959 Mass Spectrometry Data, pp. 5. Exhibit No. 1147 filed in Interferences 106,007 and 106,008 on Feb. 16, 2015.
AON PS1959 UPLC Data, pp. 2, Exhibit No. 1158 filed in Interferences 106,007 and 106,008 on Feb. 16, 2015.
AON PS1960 Mass Spectrometry Data, pp. 8, Exhibit No. 1148 filed in Interferences 106,007 and 106,008 on Feb. 16, 2015.
AON PS1960 UPLC Data, pp. 2, Exhibit No. 1159 filed in Interferences 106,007 and 106,008 on Feb. 16, 2015.
AON PS1961 Mass Spectrometry Data, pp. 5, Exhibit No. 1149 filed in Interferences 106,007 and 106,008 on Feb. 16, 2015.
AON PS1961 UPLC Data, pp. 2, Exhibit No. 1160 filed in Interferences 106,007 and 106,008 on Feb. 16, 2015.
AON PS1962 Mass Spectrometry Data, pp. 7, Exhibit No. 1150 filed in Interferences 106,007 and 106,008 on Feb. 16, 2015.
AON PS1962 UPLC Data, pp. 2, Exhibit No. 1161 filed in Interferences 106,007 and 106,008 on Feb. 16, 2015.
AON PS1963 Mass Spectrometry Data, pp. 10, Exhibit No. 1151 filed in Interferences 106,007 and 106,008 on Feb. 16, 2015.
AON PS1963 UPLC Data, pp. 2, Exhibit No. 1162 filed in Interferences 106,007 and 106,008 on Feb. 16, 2015.
AON PS1964 Mass Spectrometry Data, pp. 13, Exhibit No. 1152 filed in Interferences 106,007 and 106,008 on Feb. 16, 2015.
AON PS1964 UPLC Data, pp. 2, Exhibit No. 1163 filed in Interferences 106,007 and 106,008 on Feb. 16, 2015.
AON PS1965 Mass Spectrometry Data, pp. 9, Exhibit No. 1153 filed in Interferences 106,007 and 106,008 on Feb. 16, 2015.
AON PS1965 UPLC Data, pp. 2, Exhibit No. 1161 filed in Interferences 106,007 and 106,008 on Feb. 16, 2015.
Wilton, Stephen D. et al., "Specific removal of the nonsense mutation from the mdx dystrophin niRNA using antisense oligonucleotides," Neuromuscular Disorders, vol. 9:330-338 (1999).
WO 2002/24906 A1 of AZL, (University of Western Australia Exhibit 2134, filed Apr. 3, 2015 in Interferences 106007, 106008, and 106013, pp. 1-43.).
WO 2004/083432 (the published AZL PCT Application, "Van Ommen"), pp. 71, Exhibit No. 1003 filed in interference 106,013 on Feb. 17, 2015.
WO 2013/112053 A1, (University of Western Australia Exhibit 2130, filed Apr. 3, 2015 in Interferences 106007, 106008, and 106013, pp. 1-177).
Wolff, Jon A. et al., "Direct Gene Transfer into Mouse Muscle in Vivo," Science, vol. 247:1465-1468 (1990).
Wong, Marisa L. et al., "Real-time PCR for mRNA quantitation," BioTechnigues, vol. 39:75-85 (2005) (Exhibit No. 1066 filed in interferences 106008, 106007 on Nov. 18, 2014).
Wood, "Toward an Oligonucleotide Therapy for Duchenne Muscular Dystrophy: A Complex Development Challenge," Science Translational Medicine, vol. 2, No. 25, pp. 1-6 (Mar. 2010), Exhibit No. 1116 filed in interferences 106,007 and 106,008 on Feb. 17, 2015, Doc 335.
Written Opinion for Application No PCT/AU2010/001520, 6 pages, dated Jan. 21, 2011.
Wu, B. et al., "Dose-dependent restoration of dystrophin expression in cardiac muscle of dystrophic mice by systemically delivered morpholino," Gene Therapy, vol. 17:132-140 (2010).
Wu, B. et al., "Effective rescue of dystrophin improves cardiac function in dystrophin-deficient mice by a modified morpholino oligomer," PNAS, vol. 105(39):14814-14819 (2008).
Wu, Bo et al., "Targeted Skipping of Human Dystrophin Exons in Transgenic Mouse Model Systemically for Antisense Drug Development," PLoS One, vol. 6(5):e19906, 11 pages (2011).
Wu, George Y. et al., "Receptor-mediated Gene Delivery and Expression in Vivo," The Journal of Biological Chemistry, vol. 263(29):14621-14624 (1988).
Wu, George Y. et al, "Receptor-mediated in Vitro Gene Transformation by a Soluble DNA Carrier System," The Journal of Biological Chemistry, vol. 262(10):4429-4432 (1987).
Wyatt et al. "Site-specific cross-linking of mammalian U5 snRNP to the 5' splice site before the first step of pre-mRNA splicing," Genes & Development, vol. 6, pp. 2542-2553 (1992), Exhibit No. 1198 filed in Interferences 106,007 and 106,008 on Feb. 17, 2015.
Yin et al, "A fusion peptide directs enhanced systemic dystrophin exon skipping and functional restoration in dystrophin-deficient mdx mice," Human Mol. Gen., vol. 18, No. 22, pp. 4405-4414 (2009), Exhibit No. 1200 filed in interferences 106,007 and 106,008 on Feb. 17, 2015.
Yin et al, "Cell Penetrating peptide-conjugated antisense oligonucleotides restore systemic muscle and cardiac dystrophin expression and function," Human Mol. Gen., vol. 11, No. 24, pp. 3909-3918 (2008), Exhibit No. 1199 filed in Interferences 106,007 and 106,008 on Feb. 17, 2015.
Yin et al., "Functional Rescue of Dystrophin-deficient mdx Mice by a ChimericPeptide-PMO," Mol. Therapy, vol. 18, No. 10, pp. 1822-1829 (Oct. 2010), Exhibit No. 1117 filed in interferences 106,007 and 106,008 on Feb. 17, 2015.
Yokota et al., "Efficacy of Systematic Morpholino Exon-Skipping in Duchenne Dystrophy Dogs," American Neurological Assoc., vol. 65, No. 6, pp. 667-676 (Jun. 2009), Exhibit No. 1214 filed in Interferences 106,007 and 106,008 on Feb. 17, 2015.
*Zoltek Corp. v. U.S.*, 95 Fed. Cl. 681 (2011), 23 pages, (Academisch Ziekenhuis Leiden Exhibit 1236, filed May 5, 2015 in Interference 106007 and 106008).
U.S. Appl. No. 13/550,210, 27 pages; excerpts of prosecution history including: Response and Amendment dated May 12, 2014; Response to Non-final Office Action dated Jan. 21, 2014; Second Preliminary Amendment dated Jan. 3, 2013 (Exhibit No. 2055 filed in interferences 106008, 106013, 106007 on Nov. 18, 2014).
US Claim amendments for U.S. Appl. No. 13/550,210, 3 pages, dated May 12, 2014 (Exhibit No. 2078 filed in interferences 106008, 106013, 106007 on Nov. 18, 2014).
US Claims for U.S. Appl. No. 12/976,381, 1 page, dated Dec. 22, 2010 (Exhibit No. 2065 filed in interferences 106008, 106013, 106007 on Nov. 18, 2014).
US Declaration of Richard K. Bestwick, for U.S. Appl. No. 11/570,691, 5 pages, dated Jun. 15, 2010 (Exhibit No. 1044 filed in interferences 106008, 106007 on Nov. 18, 2014).

(56) References Cited

OTHER PUBLICATIONS

US E-mail from Patent Trial and Appeal Board to Danny Huntington, 2 pages, dated Oct. 9, 2014 (Exhibit No. 2002 filed in interferences 106008 on Oct. 17, 2014).
US Non-Final Office Action for U.S. Appl. No. 11/570,691, 16 pages, dated Mar. 15, 2010 (Exhibit No. 1042 filed in interferences 106008, 106007 on Nov. 18, 2014).
US Office Action for U.S. Appl. No. 13/271,080, 25 pages, dated Jul. 30, 2012 (Exhibit No. 1048 filed in interferences 106008, 106007 on Nov. 18, 2014).
US Office Action for U.S. Appl. No. 13/550,210, 12 pages, dated Sep. 27, 2013 (Exhibit No. 2080 filed in interferences 106008, 106013, 106007 on Nov. 18, 2014).
US Office Action for U.S. Appl. No. 13/902,376, 7 pages, dated Jan. 7, 2014 (Exhibit No. 1045 filed in interferences 106008, 106007 on Nov. 18, 2014).
U.S. Appl. No. 12/198,007 as-filed, 64 pages, dated Aug. 25, 2008 (Exhibit No. 2092 filed in interferences 106008, 106013, and 106007 on Nov. 18, 2014).
US Preliminary Amendment and application as-filed for U.S. Appl. No. 12/916,381, 64 pages, dated Dec. 22, 2010 (Exhibit No. 2089 filed in Interferences 106007, 106008, and 106013 on Nov. 18, 2014).
US Preliminary Amendment for U.S. Appl. No. 11/233,495, 10 pages, dated Sep. 21, 2005 (Exhibit No. 2069 filed in interferences 106008, 106013, 106007 on Nov. 18, 2014).
US Preliminary Remarks for U.S. Appl. No, 14/198,992, 1 page, dated Mar. 6, 2014 (Exhibit No. 2097 filed in interferences 106008, 106013, 106007 on Nov. 18, 2014).
US Proposed Terminal Disclaimer for U.S. Appl. No. 12/860,078, 2 pages, dated Oct. 17, 2014 (Exhibit No. 0001 filed in interference 106008 on Oct. 17, 2014).
US Remarks for U.S. Appl. No. 14/248,279, 2 pages, dated Aug. 27, 2014 (Exhibit No. 2110 filed in interferences 106008, 106013, 106007 on Nov. 18, 2014).
US Response and amendments for U.S. Appl. No. 13/550,210, 12 pages, dated Jan. 21, 2014 (Exhibit No. 2063 filed in interferences 106008, 106013, 106007 on Nov. 18, 2014).
US Revised Figure 4H, U.S. Appl. No. 13/271,080, 1 page (Exhibit No. 1050 filed in interferences 106008, 106007 on Nov. 18, 2014).
US Terminal Disclaimer for U.S. Appl. No. 14/198,992, 1 page, dated Jul. 15, 2014 (Exhibit No. 2096 filed in interferences 106008, 106013, 106007 on Nov. 18, 2014).
US Terminal Disclaimer for U.S. Appl. No. 14/248,279, 1 page, dated Aug. 7, 2014 (Exhibit No. 2109 filed in interferences 106008, 106013, 106007 on Nov. 18, 2014).
US Track One Request, Application as-filed, and Application Data Sheet for U.S. Appl. No. 14/248,279, 68 pages, dated Apr. 8, 2014 (Exhibit No. 2108 filed in interferences 106008, 106013, 106007 on Nov. 18, 2014).
US Transmittal, application as-filed, and Preliminary Amendment for U.S. Appl. No. 11/570,691, 102 pages, dated Dec. 15, 2006 (Exhibit No. 2103 filed in interferences 106008, 106013, 106007 on Nov. 18, 2014).
US Transmittal, application as-filed, and Preliminary Amendment for U.S. Appl. No. 13/270,992, 101 pages, dated Oct. 11, 2011 (Exhibit No. 2098 filed in interferences 106008, 106013, 106007 on Nov. 18, 2014).
US Transmittal, application as-filed, and Preliminary Amendment for U.S. Appl. No. 13/271,080, 115 pages, dated Oct. 11, 2011 (Exhibit No. 2111 filed in interferences 106008, 106013, 106007 on Nov. 18, 2014).
US Updated Filing Receipt for U.S. Appl. No. 13/550,210, 3 pages, dated Dec. 11, 2012 (Exhibit No. 2044 filed in interferences 106008, 106013, 106007 on Nov. 18, 2014).
USPTO "2014 Procedure for Subject Matter Eligibility Analysis of Claims Reciting or Involving . . . Natural Products" ("the March Guidance"), 19 pages, (Exhibit No. 2118 filed in interferences 106,007 and 106,008 on Feb. 17, 2015).

USPTO Written Description Training Materials, Revised Mar. 25, 2008, Example 12, 6 pages, (Exhibit No. 1068 filed in interferences 106008, 106007 on Dec. 23, 2014).
UWA Clean Copy of Claims and Sequence, as filed in Interference No. 106,007 on Aug. 1, 2014 (Paper 12), 8 pages, (Exhibit No. 2126 filed in interferences 106,007 and 106,008 on Feb. 17, 2015.
UWA Clean Copy of Claims and Sequence, as filed in Interference No. 106,007 on Aug. 7, 2014 (Paper 12), 8 pages, (Exhibit No. 2127 filed in interferences 106,007 and 106,008 on Feb. 17, 2015.
UWA Motion 1 (For Judgment Under 35 § 112(a)) from Int. No. 106,007 (PN210), 40 pages, Exhibit No. 1005 filed Interference 106,013 on Feb. 17, 2015.
UWA Motion 1 (For Judgment Under 35 § 112(a)) from Int. No. 106,008 (Doc 213), pp. 38, Exhibit No. 1004 filed in Interference 106,013 on Feb. 17, 2015.
UWA submission of teleconference transcript, 28 pages, dated Dec. 12, 2014 (Exhibit No. 2114 filed in interferences 106008 and 106007 on Dec. 12, 2014).
Valorization Memorandum published by the Dutch Federation of University Medical Centers in Mar. 2009, (University of Western Australia Exhibit 2140, filed Apr. 3, 2015 in Interferences 106007, 106008, and 106013, pp. 1-33).
Van Deutekom el al., "Antisense-induced exon skipping restores dystrophin expression in DMD patient derived muscle cells," Human Molecular Genetics vol. 10, No. 15: 1547-1554 (2001) (Exhibit No. 1084 filed in interferences 106008, 106007 on Dec. 23, 2014).
Van Deutekom et al., "Local Dystrophin Restoration with Antisense Oligonucleotide PRO051," N. Engl. J. Med., vol. 357, No. 26, pp. 2677-2686 (Dec. 2007), Exhibit No. 1213 filed in Interferences 106,007 and 106,008 on Feb. 17, 2015.
Van Deutekom, Judith C. T. et al., "Advances in Duchenne Muscular Dystrophy Gene Therapy," Nature Reviews Genetics, vol. 4(10):774-783 (2003).
Van Ommen 2002 PCT (WO 02/24906 A1), 43 pages,(Exhibit No. 1071 filed in interferences 106008, 106007 on Dec. 23, 2014).
van Putten M, et al., The Effects of Low Levels of Dystrophin on Mouse Muscle Function and Pathology. PLoS ONE 2012;7:e31937, 13 pages.
Van Vliet, Laura et al., "Assessment of the Feasibility of Exon 45-55 Multiexon Skipping for Duchenne Muscular Dystrophy" BMC Medical Genetics, vol. 9(1):105 (2008).
Verma, Sandeep et al. "Modified Oligonucleotides: Synthesis and Strategy for Users," Annu. Rev. Biochem., vol. 67:99-134 (1998) (Exhibit No. 1040 filed in interferences 106008, 106007 on Nov. 18, 2014).
*Vikase Corp.* v. *Am. Nat'l. Can Co.*, No. 93-7651, 1996 WL 377054 (N.D. Ill. Jul. 1, 1996), 3 pages (Exhibit No. 2152 filed in interference 106013 on Oct. 29, 2015).
Voit, Thomas et al., "Safety and efficacy of diisapersen for the treatment of Duchenne muscular dystrophy (Demand II): an exploratory, randomised, placebo-controlled phase 2 study," Lancet Neurol., vol. 13:987-996 (2014) (Exhibit No. 2037 filed in interferences 106008, 106013, 106007 on Nov. 18, 2014).
Volloch, Vladimir et al., "Inhibition of Pre-mRNA Splicing by Antisense RNA in Vitro: Effect of RNA Containing Sequences Complementary to Exons," Biochemical and Biophysical Research Communications, vol. 179 (3):1593-1599 (1991).
Wahlestedt et al., "Potent and nontoxic antisense oligonucleotides containing locked nucleic acids," PNAS, vol. 97, No. 10, pp. 5633-5638 (May 2000), Exhibit No. 1201 filed in Interferences 106,007 and 106,008 on Feb. 17, 2015.
Wang et al., "In Vitro evaluation of novel antisense oligonucleotides is predictive of in vivo exon skipping activity for Duchenne muscular dystrophy," J. Gene Medicine, vol. 12, pp. 354-364 (Mar. 2010), Exhibit No. 1115 filed in interferences 106,007 and 106,008 on Feb. 17, 2015.
Wang, Chen-Yen et al., "pH-sensitive irnmunoliposomes mediate target-cell-specific delivery and controlled expression of a foreign gene in mouse," Proc. Natl. Acad. Sci. USA, vol. 84:7851-7855 (1987).
Watakabe, Akiya et al., "The role of exon sequences in splice site selection," Genes & Development, vol. 7:407-418 (1993).

(56) References Cited

OTHER PUBLICATIONS

Watanabe et al., "Plasma Protein Binding of an Antisense Oligonucleotide Targeting Human ICAM-1 (ISIS 2302)," Oliganudeotides, vol. 16, pp. 169-180 (2006), Exhibit No. 1197 filed in Interferences 106,007 and 106,008 on Feb. 17, 2015.
Wijnaendts, L.C.D. et al., "Prognostic importance of DNA flow cytometric variables in rhabdomyosarcomas," J. Clin. Pathol., vol. 46:948-952 (1993) (Exhibit No. 1041 filed in interferences 106008, 106007 on Nov. 18, 2014).
Wilton et al. (2007) "Antisense Oligonucleotide-induced Exon Skipping Across the Human Dystrophin Gene Transcript," Molecular Therapy 15(7):1288-1296, 10 pages, (Exhibit No. 2121 filed in interferences 106,007 and 106,008 on Feb. 17, 2015.
Wilton, Stephen D. et al., "Antisense oligonucleotides in the treatment of Duchenne muscular dystrophy: where are we now?" Neuromuscular Disorders, vol. 15:399-402 (2005).
*University of Western Australia v. Academisch Ziekenhuis Leiden*, UWA Notice of Recent Authority, filed in Patent Interference No. 106,008, Sep. 2, 2015, pp. 1-18 (Doc 478).
*University of Western Australia v. Academisch Ziekenhuis Leiden*, UWA Notice of Related Proceedings, Patent Interference No. 106,007, 3 pages, dated Aug. 1, 2014 (Doc 11).
*University of Western Australia v. Academisch Ziekenhuis Leiden*, UWA Notice of Related Proceedings, Patent Interference No. 106,008, 5 pages, dated Aug. 7, 2014 (Doc 11).
*University of Western Australia v. Acadernisch Ziekenhuis Leiden*, UWA Notice of Related Proceedings, Patent Interference No. 106,013, 3 pages, dated Oct. 14, 2014 (Doc 6).
U.S. Pat. No. 7,960,541 (Wilton et al.), pp. 84, Exhibit No. 1002 filed in interferences 106,007 and 106,008 on Nov. 18,2014.
U.S. Pat. No. 8,450,474 (Wilton et al.), pp. 95, Exhibit No. 1087 filed in interferences 106,007 and 106,008 on Feb. 13, 2015.
U.S. Pat. No. 8,455,634 (Wilton et al.) pp. 96, Exhibit No. 1088 filed in interferences 106,007 and 106,008 on Feb. 13, 2015.
U.S. Pat. No. 8,455,635 (Wilton et al.), pp. 96, Exhibit No. 1089 filed in interferences 106,007 and 106,008 on Feb. 13, 2015.
U.S. Pat. No. 8,455,636 (Wilton et al.), pp. 92, Exhibit No. 1003 filed in interferences 106,007 and 106,008 on Nov. 18, 2014.
U.S. Pat. No. 8,476,423 (Wilton et al.), pp. 95, Exhibit No. 1111 filed in interferences 106,007 and 106,008 on Feb. 13, 2015.
U.S. Pat. No. 8,501,703 (Bennett et al), pp. 16, Exhibit No. 1090 filed in interferences 106,007 and 106,008 on Feb. 13, 2015.
U.S. Pat. No. 8,501,704 (Mourich et al.), pp. 39, Exhibit No. 1091 filed in interferences 106,007 and 106,008 on Feb. 13, 2015.
U.S. Pat. No. 8,524,676 (Stein et al.), pp. 28, Exhibit No. 1092 filed in interferences 106,007 and 106,008 on Feb. 13, 2015.
U.S. Pat. No. 8,524,880 (Wilton et al.), pp. 89, Exhibit No. 1093 filed in interferences 106,007 and 106,008 on Feb. 13, 2015.
U.S. Pat. No. 8,536,147 (Weller et al.), pp. 95, Exhibit No. 1094 filed in interferences 106,007 and 106,008 on Feb. 17, 2015.
U.S. Pat. No. 8,592,386 (Mourich et al.), pp. 46, Exhibit No. 1095 filed in interferences 106,007 and 106,008 on Feb. 13, 2015.
U.S. Pat. No. 8,618,270 (Iversen et al.), pp. 28, Exhibit No. 1096 filed in interferences 106,007 and 106,008 on Feb. 13, 2015.
U.S. Pat. No. 8,637,483 (Wilton et al.), pp. 157, Exhibit No. 1097 filed in interferences 106,007 and 106.008 on Feb. 13, 2015.
U.S. Pat. No. 8,697,858 (Iversen), pp. 95, Exhibit No. 1098 filed in interferences 106,007 and 106,008 on Feb. 13, 2015.
U.S. Pat. No. 8,703,735 (Iversen et al.) pp. 73, Exhibit No. 1099 filed in interferences 106,007 and 106,008 on Feb. 13, 2015.
U.S. Pat. No. 8,741,863 (Moulton et al.), pp. 68, Exhibit No. 1100 filed in interferences 106,007 and 106,008 on Feb. 13, 2015.
U.S. Pat. No. 8,759,307 (Stein et al.), pp. 35, Exhibit No. 1101 filed ininterferences 106,007 and 106,008 on Feb. 13, 2015.
U.S. Pat. No. 8,779,128 (Hanson et al.), pp. 104, Exhibit No. 1102 filed in interferences 106,007 and 106,008 on Feb. 13, 2015.
U.S. Pat. No. 8,785,407 (Stein et al.), pp. 35, Exhibit No. 1103 filed in interferences 106,007 and 106,008 on Feb. 13, 2015.
U.S. Pat. No. 8,785,410 (Iversen et al.)., Pages 20, Exhibit No. 1104 filed in interferences 106,007 and 106,008 on Feb. 13, 2015.
U.S. Pat. No. 8,835,402 (Kole et al.), pp. 27, Exhibit No. 1105 filed in interferences 106,007 and 106,008 on Feb. 13, 2015.
U.S. Pat. No. 8,865,883 (Sazani et al.), pp. 199, Exhibit No. 1106 filed in interferences 106,007 and 106,008 on Feb. 13, 2015.
U.S. Pat. No. 8,871,918 (Sazani et al.), pp. 195, Exhibit No. 1107 filed in interferences 106,007 and 106,008 on Feb. 13, 2015.
U.S. Pat. No. 8,877,725 (Iversen et al.), pp. 34, Exhibit No. 1108 filed in interferences 106,007 and 106,008 on Feb. 13, 2015.
U.S. Pat. No. 8,895,722 (Iversen et al.), pp. 29, Exhibit No. 1109 filed in interferences 106,007 and 106,008 on Feb. 13, 2015.
U.S. Pat. No. 8,906,872 (Iversen et al.), pp. 69, Exhibit No. 1110 filed in interferences 106,007 and 106,008 on Feb. 13, 2015.
US Abandonment for U.S. Appl. No. 13/902,376, 1 page, dated Jun. 12, 2014 (Exhibit No. 1047 filed in interferences 106008, 106007 on Nov. 18, 2014).
US Amendment After Non-Final Action for U.S. Appl. No. 11/233,495, 31 pages, dated Jun. 24, 2010 (Exhibit No. 2073 filed in interferences 106008, 106013, 106007 on Nov. 18, 2014).
US Amendment for U.S. Appl. No. 11/233,495, 15 pages, dated Apr. 1, 2009 (Exhibit No. 2071 filed in interferences 106008, 106013, 106007 on Nov. 18, 2014).
US Amendment for U.S. Appl. No. 11/233,495, 19 pages, dated Sep. 16, 2009 (Exhibit No. 2072 filed in interferences 106008, 106013, 106007 on Nov. 18, 2014).
US Amendment for U.S. Appl. No. 11/233,495, 9 pages, dated Oct. 31, 2007 (Exhibit No. 2070 filed in interferences 106008, 106013, 106007 on Nov. 18, 2014).
US Amendment for U.S. Appl. No. 11/570,691, 9 pages, dated Jun. 15, 2010 (Exhibit No. 1043 filed in interferences 106008, 106007 on Nov. 18, 2014).
US Amendment for U.S. Appl. No. 13/271,080, 30 pages, dated Jan. 30, 2013 (Exhibit No. 1049 filed in interferences 106008, 106007 on Nov. 18, 2014).
US Amendment for U.S. Appl. No. 13/902,376, 36 pages, dated Mar. 21, 2014 (Exhibit No. 1046 filed in interferences 106008, 106007 on Nov. 18, 2014).
US Amendment in Response to Advisory Action for U.S. Appl. No. 11/233,495, 23 pages, dated Mar. 14, 2011 (Exhibit No. 2074 filed in interferences 106008, 106013, 106007 on Nov. 18, 2014).
US Amendments to the Claims for U.S. Appl. No. 11/233,495, 4 pages, dated May 8, 2014 (Exhibit No. 2077 filed in interferences 106008, 106013, 106007 on Nov. 18, 2014).
US Amendments to the Claims for U.S. Appl. No. 14/198,992, 3 pages, dated Jul. 16, 2014 (Exhibit No. 2079 filed in interferences 106008, 106013, 106007 on Nov. 18, 2014).
US Applicant-Initiated Interview Summary and Notice of Allowance for U.S. Appl. No. 13/550,210, 9 pages dated May 19, 2014 (Exhibit No. 2076 filed in interferences 106008, 106013, 106007 on Nov. 29, 2014).
US application as-filed and Preliminary Amendment for U.S. Appl. No. 13/550,210, 59 pages dated Jul. 16, 2012 (Exhibit No. 2087 filed in interferences 106008, 106013, 106007 on Nov. 18, 2014).
US Application as-filed for U.S. Appl. No. 14/198,992, 52 pages, dated Mar. 6, 2014 (Exhibit No. 2086 filed in interferences 106008, 106013, 106007 on Nov. 18, 2014).
US Application as-filed, Application Data Sheet, and Preliminary Amendment for U.S. Appl. No. 12/837,359, 101 pages, dated Jul. 15, 2010 (Exhibit No. 2100 filed in interferences 106008, 106013, 106007 on Nov. 18, 2014).
US Application for Letters Patent for U.S. Appl. No. 11/233,495 as-filed and preliminary amendment, 77 pages, dated Sep. 21, 2005 (Exhibit No. 2095 filed in interferences 106008, 106013, 106007 on Nov. 18, 2014).
U.S. Appl. No. 11/233,495, 74 pages; excerpts of prosecution history including: US Supplemental Amendment and Response dated May 8, 2014; Second Supplemental Response dated Jul. 25, 2013; Supplemental Amendment dated Jun. 26, 2013; Amendment after Non-final Action dated Nov. 1, 2010; Amendment under 35 USC 1.114 dated Sep. 16, 2009 (Exhibit No. 2054 filed in interferences 106008, 106013, 106007 on Nov. 18, 2014).
U.S. Appl. No. 14/198,992, 17 pages; excerpts of prosecution history including: Supplemental Amendment dated Jul. 16, 2014;

(56) References Cited

OTHER PUBLICATIONS

Response to Non-Final Office Action dated Jul. 14, 2014 (Exhibit No. 2056 filed in interferences 106008, 106013, 106007 on Nov. 18, 2014).
U.S. Appl. No. 14/248,279, 29 pages; excerpts of prosecution history including: Amendment under 37 CFR 1.312 dated Sep. 19, 2014; Amendment in Response to Final Office Action dated Aug. 7, 2014; Declaration under 37 CFR 1.132 dated May 26, 2014; Declaration under 37 CFR 1.132 dated May 27, 2014; Response dated Jun. 3, 2014 (Exhibit No. 2057 filed in interferences 106008, 106013, 106007 on Nov. 18, 2014).
*University of Western Australia* v. *Academisch Ziekenhuis Leiden*, University of Western Australia Miscellaneous Motion 4 (to exclude evidence), filed in Patent Interference No. 106,008, Apr. 10, 2015, pp. 1-21 (Doc 463).
*University of Western Australia* v. *Academisch Ziekenhuis Leiden*, University of Western Australia Opposition 1 (Regarding Patentability Under 35 U.S.C. § 102/103), 38 pages, Patent Interference No. 106,007, (Doc 393), dated Feb. 17, 2015.
*University of Western Australia* v. *Academisch Ziekenhuis Leiden*, University of Western Australia Opposition 1 (Regarding Patentability Under 35 U.S.C. § 102/103), 39 pages, Patent Interference No. 106,008, (Doc 402), dated Feb. 17, 2015.
*University of Western Australia* v. *Academisch Ziekenhuis Leiden*, University of Western Australia Opposition 2 (To Retain UWA's Benefit of AU 2004903474), 31 pages, Patent Interference No. 106,008, (Doc 403), dated Feb. 17, 2015.
*University of Western Australia* v. *Academisch Ziekenhuis Leiden*, University of Western Australia Opposition 2 (To Retain UWA's Benefit of AU 2004903474), 37 pages, Patent Interference No. 106,007, (Doc 394), dated Feb. 17, 2015.
*University of Western Australia* v. *Academisch Ziekenhuis Leiden*, University of Western Australia Opposition (Regarding Patentability Under 35 U.S.C. § 101), 22 pages, Patent Interference No. 106,007, (Doc 395), dated Feb. 17, 2015.
*University of Western Australia* v. *Academisch Ziekenhuis Leiden*, University of Western Australia Opposition 3 (Regarding Patentability Under 35 U.S.C. § 101), 22 pages, Patent Interference No. 106,008, (Doc 404), dated Feb. 17, 2015.
*University of Western Australia* v. *Academisch Ziekenhuis Leiden*, University of Western Australia Opposition 4 (To deny entry of AZL's Proposed New Claims 104 and 105), 36 pages, Patent Interference No. 106,007, (Doc 397), dated Feb. 17, 2015.
*University of Western Australia* v. *Academisch Ziekenhuis Leiden*, University of Western Australia Opposition 4 (To deny entry of AZL's Proposed New Claims 30 and 31), 36 pages, Patent Interference No. 106,008, (Doc 405), dated Feb. 17, 2015.
*University of Western Australia* v. *Academisch Ziekenhuis Leiden*, University of Western Australia Reply 1 (to AZL Opposition 1), filed Apr. 3, 2015 in Interference 106007, pp. 1-28 (Doc 428).
*University of Western Australia* v. *Academisch Ziekenhuis Leiden*, University of Western Australia Reply 1 (to AZL Opposition 1), filed Apr. 3, 2015 in Interference 106008, pp. 1-28, (Doc 436).
*University of Western Australia* v. *Acadernisch Ziekenhuis Leiden*, University of Western Australia Reply 1 (to Maintain the Interference) filed Apr. 3. 2015 in Interference 106013, pp. 1-17 (Doc 152).
*University of Western Australia* v. *Academisch Ziekenhuis Leiden*, University of Western Australia Reply 2 (to AZL Opposition 2) filed Apr. 3, 2015 in Interference 106007, pp. 1-22 (Doc 429).
*University of Western Australia* v. *Academisch Ziekenhuis Leiden*, University of Western Australia Reply 2 (to AZL Opposition 2) filed Apr. 3, 2015 in Interference 106008, pp. 1-22 (Doc 437).
*University of Western Australia* v. *Academisch Ziekenhuis Leiden*, University of Western Australia Reply 3 (for Judgment under 35 U.S.C. §135(b)) filed Apr. 3, 2015 in Interference 106008, pp. 1-19 (Doc 438).
*University of Western Australia* v. *Academisch Ziekenhuis Leiden*, University of Western Australia Reply 3 (to Institute an Interference) filed Apr. 3, 2015 in Interference 106007, pp. 1-17 (Doc 430).
*University of Western Australia* v. *Academiscla Ziekenhuis Leiden*, University of Western Australia Reply 4 (To Exclude Evidence), filed in Patent Interference No. 106,007, May 12, 2015, pp. 1-13 (Doc 467).
*University of Western Australia* v. *Academisch Ziekenhuis Leiden*, University of Western Australia Reply 4 (To Exclude Evidence), filed in Patent Interference No. 106,008, May 12, 2015, pp. 1-13 (Doc 475).
*University of Western Australia* v. *Acadernisch Ziekenhuis Leiden*, University of Western Australia Request for Oral Argument, filed in Patent Interference No. 106,007, Apr. 10, 2015, pp. 1-4 (Doc 457).
*University of Western Australia* v. *Academisch Ziekenhuis Leiden*, University of Western Australia Request for Oral Argurnent, filed in Patent Interference No. 106,008, Apr. 10, 2015, pp. 1-4 (Doc 465).
*University of Western Australia* v. *Academisch Ziekenhuis Leiden*, University of Western Australia Request for Oral Argument, filed in Patent Interference No. 106,013, Apr. 10, 2015, pp. 1-3 (Doc 190).
*University of Western Australia* v. *Acadernisch Ziekenhuis Leiden*, University of Western Australia Request for Rehearing, filed in Patent Interference No. 106,013, Oct. 29, 2015, pp. 1-20 (Doc 198).
*University of Western Australia* v. *Acadernisch Ziekenhuis Leiden*, University of Western Australia Revised Designator of Lead and Backup Counsel, 4 pages, Patent Interference No. 106,007, (Doc 415), dated Mar. 10, 2015.
*University of Western Australia* v. *Acadernisch Ziekenhuis Leiden*, University of Western Australia Revised Designation of Lead and Backup Counsel, 4 pages, Patent Interference No. 106,013, (Doc 150), dated Mar. 10, 2015.
*University of Western Australia* v. *Academisch Ziekenhuis Leiden*, University of Western Australia Revised Designation of Lead and Backup Counsel, 5 pages, Patent Interference No. 106,008, (Doc 423), dated Mar. 10, 2015.
*University of Western Australia* v. *Academisch Ziekenhuis Leiden*, University of Western Australia, Exhibit List as of Feb. 17, 2015, 8 pages, Patent Interference No. 106,007, (Doc No. 398) dated Feb. 17, 2015.
*University of Western Australia* v. *Academisch Ziekenhuis Leiden*, University of Western Australia, Exhibit List as of Feb. 17, 2015, 8 pages, Patent Interference No. 106,008, (Doc No. 406) dated Feb. 17, 2015.
*University of Western Australia* v. *Academisch Ziekenhuis Leiden*, UWA Clean Copy of Involved Claims and Sequence, Patent Interference No. 106,007, 8 pages, dated Aug. 1, 2014 (Doc 12).
*University of Western Australia* v. *Acadernisch Ziekenhuis Leiden*, UWA Clean Copy of Involved Claims and Sequence, Patent Interference No. 106,013, 7 pages, dated Oct. 14, 2014 (Doc 7).
*University of Western Australia* v. *Acadernisch Ziekenhuis Leiden*, UWA Clean Copy of Involved Claims and Sequences, Patent Interference No. 106,008, 8 pages, dated Aug. 7, 2014 (Doc 12).
*University of Western Australia* v. *Acadernisch Ziekenhuis Leiden*, UWA Exhibit List as of Nov. 18, 2014, 7 pages, Patent Interference No. 106,008, dated Nov. 18, 2014 (Doc 216).
*University of Western Australia* v. *Academisch Ziekenhuis Leiden*, UWA Exhibit list, 7 pages, Patent Interference No. 106,007, dated Nov. 18, 2014 (Doc 213).
*University of Western Australia* v. *Academisch Ziekenhuis Leiden*, UWA Exhibit list, 7 pages, Patent Interference No. 106,013, dated Nov. 18, 2014 (Doc 134).
*University of Western Australia* v.*Academisch Ziekenhuis Leiden*, UWA Exhibit List, 7 pages, Patent Interference Nos. 106,008, dated Dec. 12, 2014 (Doc 221).
*University of Western Australia* v. *Academisch Ziekenhuis Leiden*, UWA Exhibit List, 8 pages, Patent Interference No. 106,007, dated Dec. 12, 2014 (Doc 217).
*University of Western Australia* v. *Academisch Ziekenhuis Leiden*, UWA List of Proposed Motions, Patent Interference No. 106,007, 7 pages, dated Sep. 10, 2014 (Doc 17).
*University of Western Australia* v. *Academisch Ziekenhuis Leiden*, UWA List of Proposed Motions, Patent Interference No. 106,008, 6 pages, dated Sep. 10, 2014 (Doc 16).

(56) References Cited

OTHER PUBLICATIONS

*University of Western Australia* v. *Academisch Ziekenhuis Leiden*, UWA Miscellaneous Motion 1 (for authorization to file terminal disclaimer), 5 pages, Patent Interference No. 106,008, dated Oct. 17, 2014 (Doc 22).
*University of Western Australia* v. *Academisch Ziekenhuis Leiden*, UWA Motion 1 (For Judgement Under 35 U.S.C., section 112(a)), 40 pages, Patent Interference No. 106,007, dated Nov. 18, 2014 (Doc 210).
*University of Western Australia* v. *Academisch Ziekenhuis Leiden*, UWA Motion 1 (For Judgement Under 35 § 112(a)) Patent Interference No. 106,008 (Doc 213), 38 Pages, on Nov. 18, 2014.
*University of Western Australia* v. *Academisch Ziekenhuis Leiden*, UWA Motion 1 (To Maintain Interference between UWA U.S. Pat. No. 8,486,907 and AZL U.S. Appl. No. 14/198,998), 45 pages, Patent Interference No. 106,013, dated Nov. 18, 2014 (Doc 133).
*University of Western Australia* v. *Academisch Ziekenhuis Leiden*, UWA Motion 2 (For Judgment Under 35 U.S.C. section 112(b)), 32 pages, Patent Interference No. 106,008, dated Nov. 18, 2014 (Doc 214).
*University of Western Australia* v. *Academisch Ziekenhuis Leiden*, UWA Motion 2 (For Judgment Under 35 U.S.C. section 112(b)), 34 pages, Patent Interference No. 106,007, dated Nov. 18, 2014 (Doc 211).
*University of Western Australia* v. *Academisch Ziekenhuis Leiden*, UWA Motion 3 (For judgment that Claims 11-12, 14-15, and 17-29 of U.S. Appl. No. 13/550,210 are barred under 35 U.S.C. section 135(b)), 25 Pages, Patent Interference No. 106,608, dated Nov. 18, 2014 (Doc 215).
*University of Western Australia* v. *Academisch Ziekenhuis Leiden*, UWA Motion 3 Requesting an additional interference between UWA U.S. Pat. No. 8,455,636 and AZL U.S. Appl. No. 14/248,279, 36 pages, Patent Interference No. 106,007, dated Nov. 18, 2014 (Doc 212).
*University of Western Australia* v. *Academisch Ziekenhuis Leiden*, UWA Notice of Filing Priority Statement, 2 pages, Patent Interference No. 106,007, dated Nov. 18, 2014 (Doc 215).
*University of Western Australia* v. *Academisch Ziekenhuis Leiden*, UWA Notice of Filing Priority Statement, 2 pages, Patent Interference No. 106,008, dated Nov. 18, 2014 (Doc 218).
*University of Western Australia* v. *Academisch Ziekenhuis Leiden*, UWA Notice of Recent Authority, filed in Patent Interference No. 106,007, Jul. 2, 2015, pp. 1-16 (Doc 469).
*University of Western Australia* v. *Academisch Ziekenhuis Leiden*, UWA Notice of Recent Authority, filed in Patent Interference No. 106,007, Sep. 2, 2015, pp. 1-18 (Doc 470).
*University of Western Australia* v. *Academisch Ziekenhuis Leiden*, UWA Notice of Recent Authority, filed in Patent Interference No. 106,008, Jul. 2, 2015, pp. 1-16 (Doc 477).
*University of Western Australia* v. *Academisch Ziekenhuis Leiden*, AZL List of Proposed Motions, Patent Interference No. 106,008, 8 pages, dated Sep. 10, 2014 (Doc 15).
*University of Western Australia* v. *Academisch Ziekenhuis Leiden*, AZL Motion 1 (For Judgment that UWA's Claims are Unpatentable Under 35 U.S.C. sections 102 and 103), 69 pages, Patent Interference No. 106,007, dated Nov. 18, 2014 (Doc 181).
*University of Western Australia* v. *Academisch Ziekenhuis Leiden*, AZL Motion 1 (For Judgment that UWA's Claims are Unpatentable Under 35 U.S.C. sections 102 and 103), 69 pages, Patent Interference No. 106,008, dated Nov. 18, 2014 (Doc 184).
*University of Western Australia* v. *Academisch Ziekenhuis Leiden*, AZL Motion 2 (To Deny UWA the Benefit of AU 2004903474), 23 pages, Patent Interference No. 106,007, dated Nov. 18, 2014 (Doc 26).
*University of Western Australia* v. *Academisch Ziekenhuis Leiden*, AZL Motion 2 (To Deny UWA the Benefit of AU 2004903474), 24 pages, Patent Interference No. 106,008, dated Nov. 18, 2014 (Doc 29).

*University of Western Australia* v. *Academisch Ziekenhuis Leiden*, AZL Motion 3 (For Judgment of Unpatentability based on Myriad) 20 pages, Patent Interference No. 106,008, dated Nov. 18, 2014 (Doc 30).
*University of Western Australia* v. *Academisch Ziekenhuis Leiden*, AZL Motion 3 (For Judgment of Unpatentability based on Myriad), 19 pages, Patent Interference No. 106,007, dated Nov. 18, 2014 (Doc 27).
*University of Western Australia* v. *Academisch Ziekenhuis Leiden*, AZL Notice of Related Proceedings, Patent Interference No. 106,007, 3 pages, dated Jul. 31, 2014 (Doc 6).
*University of Western Australia* v. *Academisch Ziekenhuis Leiden*, AZL Notice of Related Proceedings, Patent Interference No. 106,008, 3 pages, dated Aug. 5, 2014 (Doc 7).
*University of Western Australia* v. *Academisch Ziekenhuis Leiden*, AZL Notice of Related Proceedings, Patent No. 106,013, 3 pages, dated oct. 15, 2014 (Doc 11).
*University of Western Australia* v. *Academisch Ziekenhuis Leiden*, Clean Copy of Claims and Sequences, 5 pages, dated Aug. 5, 2014, Interference No. 106,008, (Exhibit No. 2047 filed in interferences 106,008, 106,013, 106,007 on Nov. 18, 2014).
*University of Western Australia* v. *Academisch Ziekenhuis Leiden*, Clean Copy of Claims and Sequences, 5 pages, dated Jul. 31, 2014, Interference No. 106,007, (Exhibit No. 2045 filed in interferences 106,008, 106,013, 106,007 on Nov. 18, 2014).
*University of Western Australia* v. *Academisch Ziekenhuis Leiden*, Clean Copy of Claims and Sequences, 5 pages, dated Oct. 15, 2014., Interference No. 106,013, (Exhibit No. 2050 filed in interferences 106,008, 106,013, 106,007 on Nov. 18, 2014).
*University of Western Australia* v. *Academisch Ziekenhuis Leiden*, Decision—Motions—37 CFR § 41.125(a), filed in Patent Interference No. 106007, Apr. 29, 2016, pp. 1-53, (Doc 472).
*University of Western Australia* v. *Academisch Ziekenhuis Leiden*, Decision—Motions—37 CFR§ 41.125(a), filed in Patent Interference No. 106,013, Jun. 22, 2015, pp. 1-12 (Doc 192).
*University of Western Australia* v. *Academisch Ziekenhuis Leiden*, Decision—Priority 37 CFR § 41.125 (a), 18 pages, Patent Interference No. 106,013, (Doc 196), dated Sep. 29, 2015.
*University of Western Australia* v. *Academisch Ziekenhuis Leiden*, Decision—Rehearing—37 CFR § 41.125(c), filed in Patent Interference No. 106,013, Dec. 29, 2015, pp. 1-12 (Doc 202).
*University of Western Australia* v. *Academisch Ziekenhuis Leiden*, Declaration of Erik Sontheimer dated Nov. 17, 2014, Exhibit 1012 filed in Patent Interference Nos. 106,007 and 106,008, 112 pages, filed Nov. 18, 2014.
*University of Western Australia* v. *Academisch Ziekenhuis Leiden*, Declaration of interference, Patent Interference No. 106,007, 7 pages, dated Jul. 18, 2014 (Doc 1).
*University of Western Australia* v. *Academisch Ziekenhuis Leiden*, Declaration of Interference, Patent Interference No. 106,008, 7 pages, dated Jul. 24, 2014 (Doc 1).
*University of Western Australia* v. *Academisch Ziekenhuis Leiden*, Declaration of Interference, Patent Interference No. 106,013, 8 pages, dated Sep. 29, 2014 (Doc 1).
*University of Western Australia* v. *Academisch Ziekenhuis Leiden*, Declaration of Matthew J.A. Wood, Patent Interference Nos. 106,007, 106,008 and 106,013, 184 pages, dated Nov. 18, 2014 (Exhibit No. 2081 filed in Interferences 106008, 106013, 106007 on Nov. 18, 2014).
*University of Western Australia* v. *Academisch Ziekenhuis Leiden*, Joint Stipulation regarding Time Periods 2, 3 and 4, 3 pages, Patent Interference No. 106,013, (Doc 135), dated Nov. 25, 2015.
*University of Western Australia* v. *Academisch Ziekenhuis Leiden*, Joint Stipulation regarding Time Periods 3-4, 4 pages, Patent Interference No. 106,007, (Doc 243), dated Jan. 29, 2015.
*University of Western Australia* v. *Academisch Ziekenhuis Leiden*, Joint Stipulation regarding Time Periods 3-4, 4 pages, Patent Interference No. 106,008, (Doc 247), dated Jan. 29, 2015.
*University of Western Australia* v. *Academisch Ziekenhuis Leiden*, Joint Stipulation regarding Time Periods 3-4, 4 pages, Patent Interference No. 106,013, (Doc 137), dated Jan. 29, 2015.

(56) References Cited

OTHER PUBLICATIONS

*University of Western Australia v. Academisch Ziekenhuis Leiden*, Joint Stipulation Regarding Time Periods 4-6, 4 pages, Patent Interference No. 106,007, dated Mar. 19, 2015 (Doc 416).
*University of Western Australia v. Academisch Ziekenhuis Leiden*, Joint Stipulation Regarding Time Periods 4-6, 4 pages, Patent Interference No. 106013, (Doc 151), dated Mar. 19, 2015.
*University of Western Australia v. Academisch Ziekenhuis Leiden*, Joint Stipulation Regarding Time Periods 4-6, 4 pages, Patent Interference No. 106,008, (Doc 424), dated Mar. 19, 2015.
*University of Western Australia v. Acadernisch Ziekenhuis Leiden*, Judgment—37 CFR § 41.127, 2 pages, Patent Interference No. 106,013, (Doc 197), dated Sep. 29, 2015.
*University of Western Australia v. Acadernisch Ziekenhuis Leiden*, Miscellaneous Order under 37 CFR 41.104(a), 4 pages, Patent Interference Nos. 106,007 and 106,008, dated Dec. 15, 2014.
*University of Western Australia v. Academisch Ziekenhuis Leiden*, Order—Authorizing Motions, Patent Interference No. 106,007, 3 pages, dated Sep. 26, 2014 (Doc 20).
*University of Western Australia v. Academisch Ziekenhuis Leiden*, Order—Authorizing Motions, Patent Interference No. 106,007, 6 pages, dated Sep. 23, 2014 (Doc 19).
*University of Western Australia v. Academisch Ziekenhuis Leiden*, Order—Authorizing Motions, Patent Interference No. 106,008, 6 pages, dated Sep. 23, 2014 (Doc 18).
*University of Western Australia v. Academisch Ziekenhuis Leiden*, Order—Miscellaneous 37 C.F.R. 41.104(a), 2 pages, Patent Interference Nos. 106,007, 106,008, 106,013, dated Nov. 14, 2014.
*University of Western Australia v. Academisch Ziekenhuis Leiden*, Order to Show Cause—37 CFR§ 41.104(a), filed in Patent Interference No. 106,013, Jun. 22, 2015, pp. 1-3 (Doc 193).
*University of Western Australia v. Academisch Ziekenhuis Leiden*, Redeclaration, Patent Interference No. 106,008, 2 pages, dated Sep. 23, 2014 (Doc 19).
*University of Western Australia v. Academisch Ziekenhuis Leiden*, Second Declaration of Matthew J. A. Wood, M.D., D. Phil., Patent Interference Nos. 106,007 and 106,008, 78 pages, dated Feb. 17, 2015 (Exhibit No. 2116 filed in interferences 106,007 and 106,008, on Feb. 17, 2015.
*University of Western Australia v. Academisch Ziekenhuis Leiden*, Statement Concerning Initial Settlement Discussions, 3 pages, Patent Interference No. 106,013, (Doc 136), dated Dec. 30, 2014.
*University of Western Australia v. Academisch Ziekenhuis Leiden*, Statement Concerning Subsequent Settlement Discussions, 3 pages, Patent Interference No. 106,007, (Doc 242), dated Dec. 30, 2014.
*University of Western Australia v. Academisch Ziekenhuis Leiden*, Statement Concerning Subsequent Settlement Discussions, 3 pages, Patent Interference No. 106,008, (Doc 246), dated Dec. 30, 2014.
*University of Western Australia v. Academisch Ziekenhuis Leiden*, Statement Concerning Subsequent Settlement Discussions, filed in Patent Interference No. 106,013, Aug. 24, 2015, pp. 1-3 (Doc 195).
*University of Western Australia v. Academisch Ziekenhuis Leiden*, University of Western Austalia Response to Order show Cause, filed in Patent Interference No. 106,013, Jul. 20, 2015, pp. 1-28 (Doc 194).
*University of Western Australia v. Academisch Ziekenhuis Leiden*, University of Western Australia Exhibit List as of Apr. 10, 2015, filed in Patent Interference No. 106,007, Apr. 10, 2015, pp. 1-10 (Doc 456).
*University of Western Australia v. Academisch Ziekenhuis Leiden*, University of Western Australia Exhibit List as of Apr. 10, 2015, filed in Patent Interference No. 106,008, Apr. 10, 2015, pp. 1-10 (Doc 464).
*University of Western Australia v. Academisch Ziekenhuis Leiden*, University of Western Australia Exhibit List as of Apr. 3, 2015, filed in Interference 106007, Apr. 3, 2015, pp. 1-10 (Doc 431).
*University of Western Australia v. Academisch Ziekenhuis Leiden*, University of Western Australia Exhibit List as of Apr. 3, 2015, filed in Interference 106008, Apr. 3, 2015, pp. 1-10 (Doc 439).

*University of Western Australia v. Academisch Ziekenhuis Leiden*, University of Western Australia Exhibit List as of Apr. 3, 2015, filed in Interference 106013, Apr. 3, 2015, pp. 1-10 (Doc 153).
*University of Western Australia v. Academisch Ziekenhuis Leiden*, University of Western Australia Exhibit List As of Oct. 29, 2015, filed in Patent Interference No. 106,013, Oct. 29, 2015, pp. 1-10 (Doc 199).
*University of Western Australia v. Academisch Ziekenhuis Leiden*, University of Western Australia Miscellaneous Motion 4 (to exclude evidence), filed in Patent Interference No. 106,007, Apr. 10, 2015, pp. 1-21 (Doc 455).
*Siemens Healthcare Diagnostics, Inc. v. Enzo Life Sciences, Inc.*, 2013 WL 4411227, *11 [Parallel cite: U.S.D.C., D. Mass., Civil No. 10-40124-FDS], Decided Aug. 14, 2013 (12 pages); [Cited as: 2013 WL 4411227], Exhibit No. 1210 filed in Interferences 106,007 and 106,008 on Feb. 17, 2015.
Sierakowska, Halina et al., "Repair of thalassemic human beta-globin mRNA in mammalian cells by antisense oligonucleotides," Proc. Natl. Acad. Sci. USA, vol. 93:12840-12844 (1996).
Sontheimer et al., "Metal ion catalysis during group II intron self-splicing: parallels with the spliceosome," Genes & Development, vol. 13, pp. 1729-1741 (1999), Exhibit No. 1195 filed in Interferences 106,007 and 106,008 on Feb. 17, 2015.
Sontheimer et al., "Three Novel Functional Variants of Human U5 Small Nuclear RNA," vol. 12, No. 2, pp. 734-746 (Feb. 1992), Exhibit No. 1194 filed in Interferences 106,007 and 106,008 on Feb. 17, 2015.
Sontheimer, Erik J. et al., "Metal ion catalysis during splicing of premessenger RNA," Nature, vol. 388:801-805 (1997) (Exhibit No. 1036 filed in interferences 106008, 106007 on Nov. 18, 2014).
Sontheimer, Erik J. et al., "The U5 and U6 Small Nuclear RNAs as Active Site Components of the Spliceosome," Science, vol. 262:1989-1997 (1993) (Exhibit No. 1058 filed in interferences 106008, 106007 on Nov. 18, 2014).
Standard Operating Procedure FPLC Desalting, pp. 6, Exhibit No. 1144 filed in Interferences 106,007 and 106,008 on Feb. 16, 2015.
Stanton, Robert et al., "Chemical Modification Study of Antisense Gapmers", Nucleic Acid Therapeutics, vol. 22(5): 344-359 (2012).
Statement On A Nonproprietary Name Adopted by the USAN Council, Eteplirsen, Chemical Structure, 2010, pp. 1-5.
Stein, CA, "Delivery of antisense oligonucleotides to cells: a consideration of some of the barriers," Monographic supplement series: Oligos & Peptides—Chimica Oggi—Chemistry Today, vol. 32(2):4-7 (2014) (Exhibit No. 2022 filed in interferences 106008, 106013, 106007 on Nov. 18, 2014).
Stein, Cy A. et al., "Therapeutic Oligonucleotides: The Road Not Taken," Clin. Cancer Res., vol. 17(20):6369-6372 (2011) (Exhibit No. 2026 filed in interferences 106008, 106013, 106007 on Nov. 18, 2014).
Stein, David et al., "A Specificity Comparison of Four Antisense Types: Morpholino, 2'-O-Methyl RNA, DNA, and Fhosphorothioate DNA," Antisense & Nucleic Acid Drug Development, vol. 7:151-157 (1997).
Strober JB, "Therapeutics in Duchenne muscular dystrophy," NeuroRX 2006; 3:225-34.
Summary of Professional Experience (Dr. Erik J. Sontheimer), pp. 4, Exhibit No. 1223 filed in Interferences 106,007 and 106,008 on Feb. 17, 2015.
Summerton, James et al., "Morpholine and Phosphorothioate Antisense Oligomers Compared in Cell-Free and In-Cell Systems," Antisense & Nucleic Acid Drug Development, vol. 7:63-70 (1997).
Summerton, James et al., "Morpholino Antisense Oligomers: Design, Preparation, and Properties," Antisense & Nucleic Acid Drug Development, vol. 7:187-195 (1997).
Summerton, James, "Morpholino antisense oligomers: the case for an Rnase H-independent structural type," Biochimica et Biophysica Acta, vol. 1489:141-158 (1999) (Exhibit No. 1038 filed in interferences 106008, 106013, 106007 on Nov. 18, 2014).
Supplementary European Search Report for Application No. 10829367. 1, 8 pages, dated May 22, 2013.
Suter et al., "Double-target antisense U7 snRNAs promote efficient skipping of an aberrant exon in three human Beta-thalassemic

(56) References Cited

OTHER PUBLICATIONS mutations," 8:13 Human Molecular Genetics 2415-2423 (1999) (Exhibit No. 1083 filed in interferences 106008, 106007 on Dec. 23, 2014).
T Hoen, Peter A.C. et al., "Generation and Characterization of Transgenic Mice with the Full-length Human DMD Gene," The Journal of Biological Chemistry, vol. 283(9):5899-5907 (2008) Exhibit No. 2030 filed in interferences 106008, 106013, 106007 on Nov. 18, 2014).
Table 1: Primer and Product Details for Exon 51 and 53 Reports on AONs of 20 to 50 Nucleotides dated Jan. 7, 2015, pp. 1, Exhibit No. 1177 filed in Interferences 106,007 and 106,008 on Feb. 16, 2015.
Takeshima et al., "Oligonucleotides against a splicing enhancer sequence led to dystrophin production in muscle cells from a Duchenne muscular dystrophy patient," Brain & Dev., vol. 23, pp. 788-790 (2001), Exhibit No. 1196 filed in interferences 106,007 and 106,008 on Feb. 17, 2015.
Takeshima, Yasuhiro et al., "Modulation of In Vitro Splicing of the Upstream Intron by Modifying an Intra-Exon Sequence Which Is Deleted from the Dystrophin Gene in Dystrophin Kobe," J. Clin. Invest, vol. 95:515-520 (1995).
Tanaka, Kenji et al., "Polypurine Sequences within a Downstream Exon Function as a Splicing Enhancer," Molecular and Cellular Biology, vol. 14(2):1347-1354 (1994).
*Telios Pharms., Inc. v. Merck KgaA*, No. 96-1307, 1998 WL 35272018 (S.D. Cal. Nov. 18, 1998), 11 pages (Exhibit No. 2153 filed in interference 106013 on Oct. 29, 2015).
Thanh, Le Thiet et al., "Characterization of Revertant Muscle Fibers in Duchenne Muscular Dystrophy, Using Exon-Specific Monoclonal Antibodies against Dystrophin," Am. J. Hum. Genet., vol. 56:725-731 (1995).
*The Regents of the University of California v. Dako North America, Inc.*, U.S.D.C., N.D. California, No. C05-03955 MHP, Apr. 22, 2009 (2009 WL 1083446 (N.D.Cal.), Exhibit No. 1206 filed in Interferences 106,007 and 106,008 on Feb. 17, 2015.
Tian, Xiaobing et al., "Imaging Oncogene Expression," Ann. N.Y. Acad. Sci., vol. 1002:165-188 (2003) (Exhibit No. 2029 filed in interferences 106008, 106013, 106007 on Nov. 18, 2014).
Transcript of 2nd Deposition of Erik J. Sontheimer, Ph.D., dated Mar. 12, 2015, (Academisch Ziekenhuis Leiden Exhibit 1231, filed Apr. 3, 2015 in Interference 106007 and 106008, pp. 1-185).
Transcript of 2nd Deposition of Matthew J.A. Wood, M.D., D. Phil, dated Mar. 5, 2015, (Academisch Ziekenhuis Leiden Exhibit 1230, filed Apr. 3, 2015 in Interference 106007 and 106008, pp. 1-117).
Transcript of Dec. 12, 2014 Teleconference with Administrative Patent Judge Schafer (rough draft) (previously filed in Int. No. 106,008 as Ex. 2114), pp. 28 Exhibit No. 1001 filed in Interference 106,013 on Feb. 17, 2015.
Transcript of the Jan. 21, 2015 deposition of Erik Sontheimer, Ph.D., Patent Interference Nos. 106,007 and 106,008, 98 pages, dated Jan. 21, 2015 (Exhibit No. 2122 filed in interferences 106,007 and 106,008 on Feb. 17, 2015.
Transcript of the Mar. 11, 2015 deposition of Judith van Deutekom, Ph.D., (University of Western Australia Exhibit 2141, filed Apr. 3, 2015 in Interferences 106007, 106008, and 106013, pp. 1-168).
Transcript of the Mar. 12, 2015 deposition of Erik J. Sontheimer, Ph.D., (University of Western Australia Exhibit 2142, filed Apr. 3, 2015 in Interferences 106007, 106008, and 106013, pp. 1-183).
Transcript of the Mar. 5, 2015 deposition of Matthew J. A. Wood, M.D., D. Phil., (University of Western Australia Exhibit 2146, filed Apr. 3, 2015 in Interferences 106007, 106008, and 106013, pp. 1-115).
Transfection of AON, pp. 1, Exhibit No. 1170 filed in Interferences 106,007 and 106,008 on Feb. 16, 2015.
U.S. Food and Drug Administration Presentation at Peripheral and Central Nervous System Drugs Advisory Committee, Apr. 25, 2016, 178 pages.
U.S. Food and Drug Administration Statement, dated Dec. 30, 2014 (2 pages), Exhibit No. 1204 filed in Interferences 106,007 and 106,008 on Feb. 17, 2015.

U.S. Appl. No. 12/198,007, as-filed Aug. 25, 2008 ("the '007 Application") (Exhibit No. 1073 filed in Interferences 106008, 106007 on Dec. 23, 2014).
U.S. Appl. No. 12/976,381, as-filed Dec. 22, 2010 ("the '381 Application") (Exhibit No. 1074 filed in interferences 106008, 106007 on Dec. 23, 2014).
U.S. Patent Application Publication No. 2001/0056077 ("Matsuo") 10 pages, (Exhibit No. 1080 filed in Interferences 106008, 106007 on Dec. 23, 2014).
U.S. Patent Application Publication No. 2002/0049173 ("Bennett et al.") 50 pages, (Exhibit No. 1081 filed in Interferences 106008, 106007 on Dec. 23, 2014).
U.S. Pat. No. 5,190,931 ("the '931 Patent") 22 pages, (Exhibit No. 1069 filed in interferences 106008, 106007 on Dec. 23, 2014).
U.S. Pat. No. 7,001,761 (the "Xiao" Patent) 64 pages, (Exhibit No. 1070 filed in interferences 106008, 106007 on Dec. 23, 2014).
University of Western Australia Objections to Opposition Evidence, served on Feb. 24, 2015 filed in Interference No. 106,007, Exhibit 2150, filed Apr. 10, 2015 in Interference Nos. 106007 and 106008, pp. 1-15.
University of Western Australia Objections to Opposition Evidence, served on Feb. 24, 2015, filed in Interference No. 106,008, Exhibit 2151, filed Apr. 10, 2015, in Interference Nos. 106007and 106008, pp. 1-15.
*University of Western Australia v. Academisch Ziekenhuis Leiden*, Decision—Motions—37 C.F.R. § 41.125(a), filed in Patent Interference No. 106008, Sep. 20, 2016, pp. 1-20 (Doc 480).
*University of Western Australia v. Academisch Ziekenhuis Leiden*, Decision—Motions—37 CFR § 41.125(a) (Substitute), filed in Patent Interference No. 106007, May 12, 2016, pp. 1-53 (Doc 476).
*University of Western Australia v. Academisch Ziekenhuis Leiden*, Judgment—Motions—37 C.F.R. § 41.127 filed in Patent Interference No. 106008, Sep. 20, 2016, pp. 1-3 (Doc 481).
*University of Western Australia v. Academisch Ziekenhuis Leiden*, Judgment—Motions—37 CFR § 41.127, filed in Patent Interference No. 106007, Apr. 29, 2016, pp. 1-3, (Doc 474).
*University of Western Australia v. Academisch Ziekenhuis Leiden*, Redeclaration—37 CFR 41.203(c). filed in Patent Interference No. 106007, Apr. 29, 2016, pp. 1-2, (Doc 473).
*University of Western Australia v. Academisch Ziekenhuis Leiden*, Withdrawal and Reissue Decision on Motions, filed in Patent Interference No. 106007, May 12, 2016, pp. 1-2 (Doc 475).
*University of Western Australia v. Academisch Ziekenhuis Leiden*, Academisch Ziekenhuis Leiden List of Exhibits (as of Apr. 3, 2015), filed in Patent Interference No. 106,007, Apr. 3, 2015, pp. 1-18, (Doc 423).
*University of Western Australia v. Academisch Ziekenhuis Leiden*, Academisch Ziekenhuis Leiden List of Exhibits (as of Apr. 3, 2015), filed in Patent Interference No. 106,008, Apr. 3, 2015, pp. 1-18 (Doc 435).
*University of Western Australia v. Academisch Ziekenhuis Leiden*, Academisch Ziekenhuis Leiden List of Exhibits, 18 pages, Patent Interference No. 106,007, (Doc 391), dated Feb. 17, 2015.
*University of Western Australia v. Academisch Ziekenhuis Leiden*, Academisch Ziekenhuis Leiden List of Exhibits, 18 pages, Patent Interference No. 106,008, (Doc 398), dated Feb. 17, 2015.
*University of Western Australia v. Academisch Ziekenhuis Leiden*, Academisch Ziekenhuis Leiden List of Exhibits, 3 pages, Patent Interference No. 106,013, (Doc 147), dated Feb. 17, 2015.
*University of Western Australia v. Academisch Ziekenhuis Leiden*, Academisch Ziekenhuis Leiden Notice of Service of Supplemental Evidence, 3 pages, Patent Interference No. 106,007, (Doc 414), dated Mar. 9, 2015.
*University of Western Australia v. Academisch Ziekenhuis Leiden*, Academisch Ziekenhuis Leiden Notice of Service of Supplemental Evidence, 3 pages, Patent Interference No. 106,008 (Doc 422), dated Mar. 9, 2015.
*University of Western Australia v. Academisch Ziekenhuis Leiden*, Academisch Ziekenhuis Leiden Opposition 1 (35 U.S.C. § 112(a)), 83 pages, Patent Interference No. 106,008, (Doc 400), dated Feb. 17, 2015.

(56) References Cited

OTHER PUBLICATIONS

*University of Western Australia v. Academisch Ziekenhuis Leiden*, Academisch Ziekenhuis Leiden Opposition 1 (35 U.S.C. § 112(a)), 93 pages, Patent Interference No. 106,007, (Doc 392), dated Feb. 17, 2015.
*University of Western Australia v. Academisch Ziekenhuis Leiden*, Academisch Ziekenhuis Leiden Opposition 1 (Standing Order ¶203.1 and 37 C.F.R. § 41.202(a) and (e)), 20 pages, Patent Interference No. 106,013, (Doc 148), dated Feb. 17, 2015.
*University of Western Australia v. Academisch Ziekenhuis Leiden*, Academisch Ziekenhuis Leiden Opposition 2 (Indefiniteness), 31 pages, Patent Interference No. 106,007, (Doc 396), dated Feb. 17, 2015.
*University of Western Australia v. Academisch Ziekenhuis Leiden*, Academisch Ziekenhuis Leiden Opposition 2 (Indefiniteness), 32 pages, Patent Interference No. 106,008, (Doc 401), dated Feb. 17, 2015.
*University of Western Australia v. Academisch Ziekenhuis Leiden*, Academisch Ziekenhuis Leiden Opposition 3 (35 U.S.C. §135(b)), 44 pages, Patent Interference No. 106,008, (Doc 397), dated Feb. 17, 2015.
*University of Western Australia v. Academisch Ziekenhuis Leiden*, Academisch Ziekenhuis Leiden Opposition 3 (Standing Order § 203.1 and 37 C.F.R. § 41.202(a) and (e)), 20 pages, Patent Interference No. 106,007, (Doc 389), dated Feb. 17, 2015.
*University of Western Australia v. Academisch Ziekenhuis Leiden*, Academisch Ziekenhuis Leiden Reply 1 (For Judgment that UWA'a Claims are Unpatentable Under 35 U.S.C. §§ 102 and 103), dated Apr. 3, 2015, filed in Patent Interference No. 106008, pp. 1-17 (Doc 431).
*University of Western Australia v. Academisch Ziekenhuis Leiden*, Academisch Ziekenhuis Leiden Reply 1 (For Judgment that UWA's Claims are Unpatentable Under 35 U.S.C. §§ 102 and 103), dated Apr. 3, 2015, filed in Patent Interference No. 106007, pp. 1-17 (Doc 424).
*University of Western Australia v. Academisch Ziekenhuis Leiden*, Academisch Ziekenhuis Leiden Reply 2 (To Deny the Benefit of AU 2004903474), dated Apr. 3, 2015, filed in Patent Interference No. 106007, pp. 1-11(Doc 425).
*University of Western Australia v. Academisch Ziekenhuis Leiden*, Academisch Ziekenhuis Leiden Reply 2 (To Deny the Benefit of AU 2004903474), dated Apr. 3, 2015, filed in Patent Interference No. 106008, pp. 1-23 (Doc 432).
*University of Western Australia v. Academisch Ziekenhuis Leiden*, Academisch Ziekenhuis Leiden Reply 3 (For Judgement of Unpatentability based on Myriad) dated Apr. 3, 2015, filed in Patent Interference No. 106007, pp. 1-12 (Doc 426).
*University of Western Australia v.Academisch Ziekenhuis Leiden*, Academisch Ziekenhuis Leiden Reply 3 (For Judgement of Unpatentability based on Myriad) dated Apr. 3, 2015, filed in Patent Interference No. 106008, pp. 1-13 (Doc 433).
*University of Western Australia v. Academisch Ziekenhuis Leiden*, Academisch Ziekenhuis Leiden Reply 4 (In Support of Responsive Motion 4 to Add Two New Claims) dated Apr. 3, 2015, filed in Patent Interference No. 106007, pp. 1-17 (Doc 427).
*University of Western Australia v. Academisch Ziekenhuis Leiden*, Academisch Ziekenhuis Leiden Reply 4 (In Support of Responsive Motion 4 to Add Two New Claims) dated Apr. 3, 2015, filed in Patent Interference No. 106008, pp. 1-17 (Doc 434).
*University of Western Australia v. Academisch Ziekenhuis Leiden*, Academisch Ziekenhuis Leiden Request For Oral Argument, filed in Patent Interference No. 106,007, Apr. 10, 2015, pp. 1-3 (Doc 454).
*University of Western Australia v. Academisch Ziekenhuis Leiden*, Academisch Ziekenhuis Leiden Request For Oral Argument, filed in Patent Interference No. 106,008, Apr. 10, 2015, pp. 1-3 (Doc 462).
*University of Western Australia v. Academisch Ziekenhuis Leiden*, Academisch Ziekenhuis Leiden Responsive Motion 4 (To Add Two New Claims), 57 pages, Patent Interference No. 106,008, (Doc 245), dated Dec. 23, 2014.
*University of Western Australia v. Academisch Ziekenhuis Leiden*, Academisch Ziekenhuis Leiden Responsive Motion 4 (To Add Two New Claims), 65 pages, Patent Interference No. 106,007, (Doc 241), dated Dec. 23, 2014.
*University of Western Australia v. Academisch Ziekenhuis Leiden*, Academisch Ziekenhuis Leiden Statement Regarding Oral Argument, filed in Patent Interference No. 106,013, Apr. 10, 2015, pp. 1-3 (Doc 189).
*University of Western Australia v. Academisch Ziekenhuis Leiden*, Academisch Ziekenhuis Leiden's List of Exhibits as of May 5, 2015, filed in Patent Interference No. 106,007, May 5, 2015, pp. 1-18 (Doc 466).
*University of Western Australia v. Academisch Ziekenhuis Leiden*, Academisch Ziekenhuis Leiden's List of Exhibits as of May 5, 2015, filed in Patent Interference No. 106,008, May 5, 2015, pp. 1-18 (Doc 474).
*University of Western Australia v. Academisch Ziekenhuis Leiden*, Academisch Ziekenhuis Leiden's Opposition 4 (To Not Exclude Evidence), filed in Patent Interference No. 106,007, May 5, 2015, pp. 1-22 (Doc 465).
*University of Western Australia v. Academisch Ziekenhuis Leiden*, Academisch Ziekenhuis Leiden's Opposition 4 (To Not Exclude Evidence), filed in Patent Interference No. 106,008, May 5, 2015, pp. 1-21 (Doc 473).
*University of Western Australia v. Academisch Ziekenhuis Leiden*, Academisch Ziekenhuis Leiden's Second supplemental Notice of Real Party in Interest, filed in Patent Interference No. 106,007, May 28, 2015, pp. 1-3, (Doc 468).
*University of Western Australia v. Academisch Ziekenhuis Leiden*, Academisch Ziekenhuis Leiden's Second Supplemental Notice of Real Party in Interest, filed in Patent Interference No. 106,008, May 28, 2015; pp. 1-3, (Doc 476).
*University of Western Australia v. Academisch Ziekenhuis Leiden*, Academisch Ziekenhuis Leiden's Second Supplemental Notice of Real Party in Interest, filed in Patent Interference No. 106013, May 28, 2015, pp. 1-3, (Doc 191).
*University of Western Australia v. Academisch Ziekenhuis Leiden*, Academish Ziekenhuis Leiden Supplemental Notice of Real Party in Interest, pp. 3, Doc 149, Patent Interference No. 106,013 dated Feb. 23, 2015.
*University of Western Australia v. Academisch Ziekenhuis Leiden*, Academish Ziekenhuis Leiden Supplemental Notice of Real Party in Interest, pp. 3, Doc 413, Patent Interference No. 106,007 dated Feb. 23, 2015.
*University of Western Australia v. Academisch Ziekenhuis Leiden*, Academisch Ziekenhuis Leiden Supplemental Notice of Real Party in Interest, pp. 3, Doc 421, Patent Interference No. 106,0008 dated Feb. 23, 2015.
*University of Western Australia v. Academisch Ziekenhuis Leiden*, Amendment and Response, U.S. Appl. No. 11/233,495, filed Jan. 22, 2014, 8 pages, (Exhibit No. 2117 filed in interferences 106,007 and 106, 008, on Feb. 17, 2015.
*University of Western Australia v. Academisch Ziekenhuis Leiden*, AZL Annotated Copy of Claims, Patent Interference No. 106,007, 15 pages, dated Aug. 15, 2014 (Doc 15).
*University of Western Australia v. Academisch Ziekenhuis Leiden*, AZL Annotated Copy of Claims, Patent Interference No. 106,008, 14 pages, dated Aug. 21, 2014 (Doc 14).
*University of Western Australia v. Academisch Ziekenhuis Leiden*, AZL Annotated Copy of Claims, Patent Interference No. 106,013, 14 pages, dated Oct. 27, 2014 (Doc 16).
*University of Western Australia v. Academisch Ziekenhuis Leiden*, AZL Clean Copy of Claims and Sequence, filed in Patent Interference No. 106,013, 5 pages, dated Oct. 15, 2014 (Doc 12).
*University of Western Australia v. Academisch Ziekenhuis Leiden*, AZL Corrected Notice of Related Proceedings, Patent Interference No. 106,007, 3 pages, dated Aug. 1, 2014 (Doc 13).
*University of Western Australia v. Academisch Ziekenhuis Leiden*, AZL Exhibit List, 10 pages, Patent Interference No. 106,007 dated Dec. 23, 2014 (Doc 240).
*University of Western Australia v. Academisch Ziekenhuis Leiden*, AZL Exhibit List, 10 pages, Patent Interference No. 106,008, dated Dec. 23, 2014 (Doc 244).

(56) References Cited

OTHER PUBLICATIONS

*University of Western Australia* v. *Academisch Ziekenhuis Leiden*, AZL List of Exhibits, 9 pages, Patent Interference No. 106,007, dated Nov. 18, 2014 (Doc 209).
*University of Western Australia* v. *Academisch Ziekenhuis Leiden*, AZL List of Exhibits, as of Nov. 18, 2014, 9 pages, Patent Interference No. 106,008, dated Nov. 18, 2014 (Doc 212).
*University of Western Australia* v. *Academisch Ziekenhuis Leiden*, AZL List of Proposed Motions, Patent Interference No. 106,007, 6 pages, dated Sep. 10, 2014 (Doc 16).
Reply to EPO Communication dated Jun. 26, 2014 in European Application Serial No. 13160338, (University of Western Australia Exhibit 2145, filed Apr. 3, 2015 in Interferences 106007, 106008, and 106013, pp. 1-4).
Reply to EPO Communication dated Oct. 21, 2014 in European Application Serial No. 12198517, (University of Western Australia Exhibit 2148, filed Apr. 3, 2015 in Interferences 106007, 106008, and 106013, pp. 1-7).
Reply to EPO Communication dated Oct. 23, 2014 in European Application Serial No. 12198485, (University of Western Australia Exhibit 2147, filed Apr. 3, 2015 in Interferences 106007, 106008, and 106013, pp. 1-8).
Response to Office Action and Amendments to the Claims for U.S. Appl. No. 13/550,210, 10 pages, dated May 12, 2014 (Exhibit No. 2064 filed in interferences 106008, 106013, 106007 on Nov. 18, 2014).
Rhodes et al., "BioMarin Bulks Up," BioCentury, pp. 6-8 (Dec. 2014), Exhibit No. 1193 filed in Interferences 1106,007 and 106,008 on Feb. 17, 2015.
RNA Isolation Using RNA-BEE, pp. 1, Exhibit No. 1175 filed in Interferences 106,007 and 106,008 on Feb. 16, 2015.
Roberts, Roland G. et al., "Exon Structure of the Human Dystrophin Gene," Genomics, vol. 16:536-538 (1993).
Roest et al., "Application of In Vitro Myo-Differentiation of Non-Muscle Cells to Enhance Gene Expression and Facilitate Analysis of Muscle Proteins," Neuromuscul. Disord., vol. 6, No. 3, pp. 195-202 (May 1996), Exhibit No. 1124 filed in interferences 106,007 and 106,008 on Feb. 17, 2015.
Rosso, Mario G. et al., "An Arabidopsis thaliana T-DNA mutagenized population (GABI-Kat) for flanking sequence tag-based reverse genetics," Plant Molecular Biology, vol. 53:247-259 (2003).
Sito, T. et al., "First-in-Human Study of NS-065/NCNP-01; the Morpholino Based Antisense Oligonucleotide for Exon 53 Skipping in Duchenne Muscular Dystrophy," ASGCT meeting, May 13, 2015, Abstract [136] 1 page.
Saito, T. et al., "First-in-Human Study of NS-065/NCNP-01; the Morpholino Based Antisense Oligonucleotide for Exon 53 Skipping in Duchenne Muscular Dystrophy," ASGCT meeting, May 13, 2015, pp. 1-11.
Sarepta Briefing Information for the Apr. 25, 2016 Meeting of the Peripheral and Central Nervous System Drugs Advisory Committee, Eteplirsen Briefing Document, NDA 206488, 186 pages.
Sarepta Presentation at Peripheral and Central Nervous System Drugs Advisory Committee, Apr. 25, 2016, 133 pages.
Sarepta Press Release, Sarepta Issues Statement on Advisory Committee Outcome for Use of Eteplirsen in the Treatment of Duchenne Muscular Dystrophy, Apr. 25, 2016, 2 pages.
Sarepta Therapeutics, Sarepta Therapeutics Announces a Continued Benefit on Walking Test Through 62 Weeks in Phase IIb Open-Label Extension Study of Eteplirsen in Duchenne Muscular Dystrophy, Press Release, Dec. 7, 2012, pp. 1-4.
Sarepta Therapeutics, Sarepta Therapeutics Announces Eteplirsen Demonstrates Continued Stability on Walking Test Through 96 Weeks in Phase IIb Study in Duchenne Muscular Dystrophy, Press Release, Sep. 26, 2013, pp. 1-4.
Sarepta Therapeutics, Sarepta Therapeutics Announces Eteplirsen Meets Primary Endpoint of Increased Novel Dystrophin and Achieves Significant Clinical Benefit on 6-Minute Walk Test After 48 Weeks of Treatment in Phase IIb Study in Duchenne Muscular Dystrophy, Press Release, Oct. 3, 2012, pp. 1-5.
Sarepta Therapeutics Press Release, dated Jan. 12, 2015, Exhibit No. 1119 filed in interferences 106,007 and 106,008 on Feb. 17, 2015.
Sarepta Therapeutics, Advisory Committee Briefing Materials: Available for Public Release, "Peripheral and Central Nervous System Drugs Advisory Committee," Eteplirsen Briefing Document Addendum, NDA 206488, pp. 1-9, dated Jan. 22, 2016.
Sarepta Therapeutics, Advisory Committee Briefing Materials: Available for Public Release, "Peripheral and Central Nervous System Drugs Advisory Committee," Eteplirsen Briefing Document, NDA 206488, pp. 1-166, dated Jan. 22, 2016.
Sarepta Therapeutics, Inc. News Release, "Sarepta Therapeutics Announces FDA Accelerated Approval of EXONDYS 61™ (eteplirsen) injection, an Exon Skipping Therapy to Treat Duchenne Muscular Dystrophy (DMD) Patients Amenable to Skipping Exon 51," Sep. 19, 2016, 2 pages.
Sarepta Therapeutics, Sarepta Therapeutics Announces Eteplirsen Demonstrates a Continued Benefit on Walking Test Through 84 Weeks in Phase IIb Study in Duchenne Muscular Dystroph, Press Release, Jun. 19, 2013, pp. 1-4.
Sarepta Therapeutics, Sarepta Therapeutics Announces Eteplirsen Demonstrates Continued Stability on Walking Test through 120 Weeks in Phase IIb Study in Duchenne Muscular Dystrophy, Press Release, Jan. 15, 2014, pp. 1-4.
Sarepta Therapeutics, Sarepta Therapeutics Announces Eteplirsen Demonstrates Stability on Pulmonary Function Tests through 120 Weeks in Phase IIb Study in Duchenne Muscular Dystrophy, Press Release, Feb. 5, 2014, pp. 1-4.
Sarepta Therapeutics, Sarepta Therapeutics Announces Eteplirsen Demonstrates Sustained Benefit on Walking Test Through 74 Weeks in Phase IIb Study in Duchenne Muscular Dystrophy, Press Release, Apr. 5, 2013, pp. 1-4.
Sarepta Therapeutics, Sarepta Therapeutics Announces FDA Considers NDA Filing for Eteplirsen Premature in Light of Recent Competitive Drug Failure and Recent DMD Natural History Data, Press Release, Nov. 12, 2013, pp. 1-3.
Sarepta Therapeutics, Sarepta Therapeutics Announces First Patient Dosed in Confirmatory Study of Eteplirsen in Ambulant Patients with Duchenne Muscular Dystrophy, Press Release, Nov. 18, 2014, pp. 1-4.
Sarepta Therapeutics, Sarepta Therapeutics Announces First Patient Dosed in European Phase I/II Study of SRP—? 4053 in Duchenne Muscular Dystrophy Patients, Press Release, Jan. 14, 2015, pp. 1-3.
Sarepta Therapeutics, Sarepta Therapeutics Announces First Patient Dosed in Study of Eteplirsen in Non-Ambulant Patients with Duchenne Muscular Dystrophy, Press Release, Nov. 12, 2014, pp. 1-4.
Sarepta Therapeutics, Sarepta Therapeutics Announces Plans to Submit Rolling NDA for Eteplirsen following Today's pre-NDA Meeting with the FDA, Press Release, May 19, 2015, pp. 1-3.
Sarepta Therapeutics, Sarepta Therapeutics Announces Significant Clinical Benefit With Eteplirsen After 36 Weeks in Phase IIb Study for the Treatment of Duchenne Muscular Dystrophy, Press Release, Jul. 24, 2012, pp. 1-4.
Sarepta Therapeutics, Sarepta Therapeutics Completes NDA Submission to FDA for Eteplirsen for the Treatment of Duchenne Muscular Dystrophy Amenable to Exon 51 Skipping, Press Release, Jun. 29, 2015, pp. 1-3.
Sarepta Therapeutics, Sarepta Therapeutics Reports Long-Term Outcomes Through 144 Weeks from Phase IIb Study of Eteplirsen in Duchenne Muscular Dystrophy, Press Release, Jul. 10, 2014, pp. 1-6.
Sarepta Therapeutics, Sarepta Therapeutics Reports Long-Term Outcomes through 168 Weeks from Phase IIb Study of Eteplirsen in Duchenne Muscular Dystrophy, Press Release, Jan. 12, 2015, pp. 1-9.
Sarepta Therapeutics, Systemic Treatment with AVI-4658 Demonstrates RNA Exon Skipping and Dystrophin Protein Expression in Duchenne Muscular Dystrophy Patients, Press Release, Dec. 22, 2009, pp. 1-3.
Sarepta, "AVI BioPharma Initiates Dosing in Phase 2 Study of Eteplirsen in Duchenne Muscular Dystrophy Patients," press release,

(56) References Cited

OTHER PUBLICATIONS 4 pages, dated Aug. 15, 2011 (Exhibit No. 2082 filed in interferences 106008, 106013, 106007 on Nov. 18, 2014).
Sarepta, "Sarepta Therapeutics Announces Eteplirsen Demonstrates Continued Stability on Walking Test through 120 weeks in Phase IIb Study in Duchenne Muscular Dystrophy," press release, 3 pages, dated Jan. 15, 2014 (Exhibit No. 2034 filed in interferences 106008, 106013, 106007 on Nov. 18, 2014).
Sarepta, "Sarepta Therapeutics Reports Long-Term Outcomes through 144 Weeks from Phase IIb Study of Eteplirsen in Duchenne Muscular Dystrophy," press release, http://investorrelations.sarepta.com/phoenix.zhtml?c=64231&o=irol-newsArticle&id=1946426, 4 pages, dated Jul. 10, 2014.
Scully, Michele et al., "Review of Phase II and Phase III Clinical Trials for Duchenne Muscular Dystrophy", Expert Opinion on Orphan Drugs, vol. 1(1):33-46 (2013).
Second Preliminary Amendment filed in U.S. Appl. No. 13/550,210, 5 pages, dated Jan. 3, 2013 (Exhibit No. 2062 filed in interferences 106008, 106013, 106007 on Nov. 18, 2014).
Second Written Opinion for Application No. PCT/AU2010/001520, 7 pages, dated Oct. 13, 2011.
Semi Quantitative Lab-on-Chip Analysis of Second PCR Product pp. 1, Exhibit No. 1183 filed in Interferences 106,007 and 106,008 on Feb. 16, 2015.
Sequence Listing—U.S. Appl. No. 13/550,210, as filed Jul. 16, 2012 (9 pages), Exhibit No. 1205 filed in Interferences 106,007 and 106,008 on Feb. 17, 2015.
Sequence of Exon 46 of Dystrophin Gene, 1 page.
Sequence of Exon 51 of Dystrophin Gene, 1 page.
Shabanpoor et al., "Bi-specific splice-switching PMO oligonucleotides conjugated via a single peptide active in a mouse model of Duchenne muscular dystrophy," Nucleic Acids Res., pp. 1-11 (Dec. 2014), Exhibit No. 1114 filed in interferences 106,007 and 106,008 on Feb. 17, 2015.
Shapiro, Marvin B. et al, "RNA splice junctions of different classes of eukaryotes: sequence statistics and functional implications in gene expression," Nucleic Acids Research, vol. 15(17)1155-7174 (1987).
Sherratt, Tim G. et al., "Exon Skipping and Translation in Patients with Frameshift Deletions in the Dystrophin Gene," Am. J. Hum. Genet, vol. 53:1007-1015 (1993).
Shiga, Nobuyuki et al., "Disruption of the Splicing Enhancer Sequence within Exon 27 of the Dystrophin Gene by a Nonsense Mutation Induced Partial Skipping of the Exon and Is Responsible for Becker Muscular Dystrophy," J. Clin. Invest, vol. 100(9):2204-2210 (1997).
Shimizu, Miho et al., "Oligo(2'-O-methyl)ribonucleotides Effective probes for duplex DNA," FEBS Letters, vol. 302 (2):155-158 (1992) (Exhibit No. 1035 filed in interferences 106008, 106007 on Nov. 18, 2014).
McClorey, Graham et al., "Splicing intervention for Duchenne muscular dystrophy," Current Opinion in Pharmacology, vol. 5:529-534 (2005).
McDonald CM, et al., "Profiles of Neuromuscular Diseases, Duchenne muscular dystrophy," Am J Phys Med Rehabil 1995;74:S70-S92.
McDonald CM, et al., "The 6-minute walk test as a new outcome measure in Duchenne muscular dystrophy," Muscle Nerve 2010;41:500-10.
McDonald CM, et al., "The 6-minute walk test in Duchenne/Becker muscular dystrophy: longitudinal observations," Muscle Nerve 2010;42:966-74.
Mendell JR et al., "Evidence-based path to newborn screening for Duchenne muscular Dystrophy," Ann Neurol 2012;71:304-13.
Mendell JR, et al., "Dystrophin immunity revealed by gene therapy in Duchenne muscular dystrophy," N Engl J Med 2010;363:1429-37.
Mendell JR, et al., "Randomized, double-blind six-month trial of prednisone in Duchenne's muscular dystrophy," N Engl Med 1989;320:1592-97.

Mendell, Jerry R. et al., "Eteplirsen for the Treatment of Duchenne Muscular Dystrophy," Ann. Neurol., vol. 74:637-647 (2013) (Exhibit No. 2058 filed in interferences 106008, 106013, 106007 on Nov. 18, 2014)
Mendell, Jerry R. et al., "Eteplirsen in Duchenne Muscular Dystrophy (DMD): 144 Week Update on Six-Minute Walk Test (6MWT) and Safety," slideshow, presented at the 19th International Congress of the World Muscle Society, 17 pages (2014) (Exhibit No. 2059 filed in interferences 106008, 106013, 106007 on Nov. 18, 2014)
Mendell, Jerry R. et al., "Gene therapy for muscular dystrophy: Lessons learned and path forward," Neuroscience Letters, vol. 527:90-99 (2012).
Mertini L, et al., "Early corticosteroid treatment in 4 Duchenne muscular dystrophy patients: 14-year follow-up," Muscle Nerve 2012;45:796-802
Mfold illustrations for Exon 51 and Exon 53 with varying amounts of intron sequence, (University of Western Australia Exhibit 2132, filed Apr. 3, 2015 in Interferences 106007, 106008, and 106013, pp. 1-2).
Mitrpant, Chalermchai el al., "Rational Design of Antisense Oligomers to Induce Dystrophin Exon Skipping," Molecular Therapy, vol. 17(8):1418-1426 (2009).
Monaco, Anthony P. et al., "An Explanation for the Phenotypic Differences between Patients Bearing Partial of the DMD Locus," Genomics, vol. 2:90-95 (1988).
Morcos, Paul A., "Gene switching: analyzing a broad range of mutations using steno block antisense oligonucleotides," Methods in Enzymology, vol. 313:174-189 (1999).
Moulton, H.M., "Compound and Method for Treating Myotonic Dystrophy," U.S. Appl. No. 12/493,140, 82 pages, filed Jun. 26, 2009.
Moulton, Hong M. et al., "Morpholines and their peptide conjugates: Therapeutic promise and challenge for Duchenne muscular dystrophy," Biochimica et Biophysica Acta, vol. 1798:2296-2303 (2010).
Muntoni F. et al., "Dystrophin and mutations: one gene, several proteins, multiple phenotypes," Lancet Neurol. 2003;2:731-40.
Muntoni, Francesco et al., "128th ENMC International Workshop on 'Preclinical optimization and Phase I/II Clinical trials Using Antisense Oligonucleotides in Duchenne Muscular Dystrophy' Oct. 22-24, 2004, Naarden, The Netherlands," Neuromuscular Disorders, vol. 15:450-457 (2005) (Exhibit No. 2025 filed in interferences 106008, 106013, 106007 on Nov. 18, 2014).
Muntoni, Francesco et al., "149th ENMC International Workshop and 1st TREAT-NMD Workshop on: 'Planning Phase I/II Clinical trials using Systemically Delivered Antisense Oligonucleotides in Duchenne Muscular Dystrophy," Neuromuscular Disorders, vol. 18:268-275 (2008).
Nelson, David L. et al., "Nucleotides and Nucleic Acids," Lehninger Principles of Biochemistry, 3rd Edition, Chapter 10, pp. 325-328 and glossary p. G-11, Worth Publishers, New York (2000).
Nguyen TM, et. Al., "Use of Epitope libraries to identity exon-specific monoclonal antibodies for characterization of altered dystrophins in muscular dystrophy," Am J Hum Genet 1993;52:1057-66.
Oberbauer, "Renal uptake of an 18-mer phosphorothioate oligonucleotide," Kidney Int'l, vol. 48, pp. 1226-1232 (1995), Exhibit No. 1191 filed in Interferences 106,007 and 106,008 on Feb. 17, 2015.
Oligonucleotide Cleavage and Deprotection Laboratory Notebook Entry, pp. 1, Exhibit No. 1138 filed in Interferences 106,007 and 106,008 on Feb. 16, 2015.
Oligonucleotide diagrams, 5 pages (Exhibit No. 1053 filed in interterences 106008, 106007 on Nov. 18, 2014).
Partial European Search Report for Application No. 10004274.6, 6 pages, dated Oct. 2, 2012.
Partial European Search Report for Application No. 12162995.0, 6 pages, dated Oct. 2, 2012.
Patentee's Response to European Patent Application No. 05076770.6, dated Jul. 28, 2006, 4 pages.
Patrick O. Brown and Tidear D. Shalon v. Stephen P.A. Fodor, Dennis W. Solas and William J. Dower: Interference Merits Panel,

(56) References Cited

OTHER PUBLICATIONS

Interference No. 104,358, 24 pages, dated Aug. 9, 1999 (Exhibit No. 2113 filed in interferences 106008, 106013, 106007 on Nov. 18, 2014).
PCT Application as-filed for application No. PCT/NL03/00214, 71 pages, dated Sep. 21, 2005 (Exhibit No. 2042 filed in interferences 106008, 106013, 106007 on Nov. 18, 2014).
PD-10 Desalting Columns, pp. 12, Exhibit No. 1141 filed in Interferences 106,007 and 106,008 on Feb. 16, 2015.
Popplewell, et al., Design of Phosphorodiamidate Morpholino Oligomers (PMOs) for the Induction of Exon Skipping of the Human DMD Gene, DSGT Poster, 2008, 1 page.
Popplewell, Linda el al., "Design of phosphorodiamidate morpholino oligomers (PMOs) for the induction of exon skipping of the human DMD gene," Human Gene Therapy 19(10): ESGCT 2008 Poster Presentations, p. 1174, Poster No. P203.
Popplewell, Linda J. et al., "Comparative analysis of antisense oligonucleotide sequences targeting exon 53 of the human DMD gene: Implications for future clinical trials," Neuromuscular Disorders, vol. 20(2):102-110 (2010) 9 pages (Exhibit No. 2031 filed in interferences 106008, 106013, 106007 on Nov. 18, 2014).
Popplewell, Linda J. et al., "Design of Antisense Oligonucleotides for Exon Skipping of the Human Dystrophin Gene," Human Gene Therapy 19(4): BSGT 2008 Poster Presentation, p. 407, Poster No. P-35.
Popplewell, Linda J. et al., "Design of Phosphorodiamidate Morpholino Oligomers (PMOs) for the Induction of Exon Skipping of the Human DMD Gene," Molecular Therapy, vol. 17(3):554-561 (2009).
Popplewell, Linda J. et al., "Targeted Skipping of Exon 53 of the Human DMD Gene Recommendation of the Highly Efficient Antisense Oligonucleotide for Clinical Trial," Human Gene Therapy 20(4): BSGT 2009 Poster Presentations, p. 399, Poster No. P10.
Poster Abstract Listing for The Tenth Annual Meeting of the RNA Society, held at the Banff Centre for Conferences, in Banff, Alberta, Canada, from May 24-29, 2005, (University of Western Australia Exhibit 2137, filed Apr. 3, 2015 in Interferences 106007, 106008, and 106013, pp. 1-11).
Pramono, "Induction of Exon Skipping of the Dystrophin Transcript in Lymphoblastoid Cells by Transfecting an Antisense Oligodeoxynudeofide Complementary to an Exon Recognition Sequence," Biochem. and Brophy. Res. Comm., vol. 226, pp. 445-449 (1996), Exhibit No. 1192 filed in Interferences 106,007 and 106,008 on Feb. 17, 2015.
Preliminary Amendment for U.S. Appl. No. 12/976,381, 4 pages, dated Dec. 22, 2010 (Exhibit No. 2066 filed in interferences 106008, 106013, 106007 on Nov. 18, 2014).
Preliminary Amendment for U.S. Appl. No. 12/198,007, 3 pages, dated Nov. 7, 2008 (Exhibit No. 2067 filed in interferences 106008, 106013, 106007 on Nov. 18, 2014).
Prescribing Information for EXONDYS 51 (eteplirsen) Injection, dated Sep. 2016, 10 pages.
Program Schedule for The Tenth Annual Meeting of the RNA Society, held at the Banff Centre for Conferences, in Banff, Alberta, Canada, from May 24-29, 2005, (University of Western Australia Exhibit 2136, filed Apr. 3, 2015 in interferences 106007, 106008, and 106013, pp. 1-4).
Proliferation and Differentiation of Myoblast Cultures, pp. 2, Exhibit No. 1169 filed in Interferences 106,007 and 106,008 on Feb. 16, 2015.
Prosensa Press Release, dated Oct. 10, 2014 (2 pages), Exhibit No. 1203 filed in Interferences 106,007 and 106,008 on Feb. 17, 2015.
Prosensa, "GSK and Prosensa Announce Primary Endpoint Not Met in Phase III Study of Drisapersen in Patients With Duchenne Muscular Dystrophy," press release, 4 pages, dated Sep. 20, 2013 (Exhibit No. 2039 filed in Interferences 106008, 106013, 106007 on Nov. 18, 2014).
Raz et al. v. Davis et al., Board of Patent Appeals and Inteferences, Patent and Trademark Office, Int. No. 105,712, Tech. Ctr. 1600, Sep. 29, 2011 (24 pages) (2011 WL 4568986 (Bd.Pat.App. & Interf.), Exhibit No. 1209 filed in Interferences 106,007 and 106,008 on Feb. 17, 2015
Reese, Colin B. et al., "Reaction Between 1-Arenesulphonyl-3-Nitro-1,2,4-Triazoles and Nucleoside Base Residues. Elucidation of the Nature of Side-Reactions During Oligonucleotide Synthesis," Tetrahedron Letters, vol. 21:2265-2266 (1980).
Reese, Colin B. et al., "The Protection of Thymine and Guanine Residues in Oligodeoxyribonucleotide Synthesis," Chem. Soc. Perkin Trans. 1, pp. 1263-1271 (1984).
Reexamination Certificate—U.S. Appl. No. 90/011,320, dated Mar. 27, 2012, 2 pages, (Exhibit No. 1072 filed in Interferences 106008, 106007 on Dec. 23, 2014).
Job Posting by Sarepta for "Scientist II, Muscle Biology" (2 pages), (Academisch Ziekenhuis Leiden Exhibit 1233, filed Apr. 3, 2015 in Interference 106007 and 106008).
Jones, Simon S. et al., "The Protection of Uracil and Guanine Residues in Oligonucleotide Synthesis," Tetrahedron Letters, vol. 22(47):4755-4758 (1981).
Karlen, Yann et al., "Statistical significance of quantitative PCR," BMC Bioinformatics, 8:131, 16 pages (2007) (Exhibit No. 1033 filed in interferences 106008, 106007 on Nov. 18, 2014).
Karras, James G. et al., "Deletion of Individual Exons and Induction of Soluble Murine Interleukin-5 Receptor-alpha Chain Expression through Antisense Oligonucleotide-Mediated Redirection of Pre-mRNA splicing," Molecular Pharmacology, vol. 58:380-387 (2000).
Kaye, Ed, "Results of the Eteplirsen Phase 2b and Phase 2b Extension Study in Duchenne Muscular Dystrophy," 8th Annual Meeting of the Oligonucleotide Therapeutics Society, Session 9: Advances in Oligonucleotide Clinical Development II, p. 48 (2012).
Kinali, Maria et al., "Local restoration of dystrophin expression with the morpholino oligomer AVI-4658 in Duchenne muscular dystrophy: a single-blind, placebo-controlled, dose-escalation, proof-of-concept study," Lancet Neurol., vol. 8:918-928 (2009).
King et al., "A Dictionary of Genetics," Oxford University Press, 4th Ed. (1990), Exhibit No. 1189 filed in interferences 106,007 and 106,008 on Feb. 17, 2015.
Koenig, M. el al., "The Complete Sequence of Dystrophin Predicts a Rod-Shaped Cytoskeleton Protein," Cell, vol. 53:219-228 (1988) (Exhibit No. 1010 filed in interferences 106008, 106007 on Nov. 18, 2014).
Koenig, M. et al., "The Molecular Basis for Duchenne versus Becker Muscular Dystrophy: Correlation of Severity with Type of Deletion," Am. J. Hum. Genet., vol. 45:498-506 (1989) (Exhibit No. 1011 filed in interferences 106008, 106007 on Nov. 18, 2014).
Kohler M, et al., "Quality of life, physical disability and respiratory impairment in Duchenne muscular dystrophy," Am J Respir Crit Care Med 2005;172:1032-6.
Koshkin, Alexei A. et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition," Tetrahedron, vol. 54:3607-3630 (1998) (Exhibit No. 2007 filed in interferences 106008, 106013, 106007 on Nov. 18, 2014).
Kurreck J., "Antisense Technologies: Improvement Through Novel Chemical Modifications", European Journal of Biochemistry, vol. 270(8):1628-1644 (2003).
Lab-on-a-Chip Data, pp. 28, Exhibit No. 1185 filed in Interferences 106,007 and 106,008 on Feb. 16, 2015.
Laboratory Notebook Entry (Exon 51 Experiments): RT-PCR Analysis of 8036 Cells, pp. 2, Exhibit No. 1179 filed in Interferences 106,007 and 106,008 on Feb. 16, 2015.
Laboratory Notebook Entry (Exon 51 Experiments): RT-PCR Analysis of KM155.C25 Cells, pp. 2, Exhibit No. 1178 filed in Interferences 106,001 and 106,008 on Feb. 16, 2015.
Laboratory Notebook Entry (Exon 51 Experiments): Transfection of 8036 Cells, pp. 1, Exhibit No. 1172 filed in Interferences 106,007 and 106,008 on Feb. 16, 2015.
Laboratory Notebook Entry (Exon 51 Experiments): Transfection of KM155.C25 Cells, pp. 1, Exhibit No. 1171 filed in Interferences 106,007 and 106,008 on Feb. 16, 2015.

(56) References Cited

OTHER PUBLICATIONS

Laboratory Notebook Entry (Exon 53 Experiments): RT-PCR Analysis of KM155.C25 Cells, pp. 2, Exhibit No. 1180 filed in Interferences 106,007 and 106,008 on Feb. 16, 2015.
Laboratory Notebook Entry (Exon 53 Experiments): RT-PCR Analysis of R1809 Cells, pp. 2, Exhibit No. 1181 filed in Interferences 106,007 and 106,008 on Feb. 16, 2015.
Laboratory Notebook Entry (Exon 53 Experiments): Transfection of KM155.C25 Cells, pp. 1, Exhibit No. 1173 filed in Interferences 106,007 and 106,008 on Feb. 16, 2015.
Laboratory Notebook Entry (Exon 53 Experiments): Transfection of R1809 Cells, pp. 1, Exhibit No. 1174 filed in Interferences 106,007 and 106,008 on Feb. 16, 2015.
Laboratory Notebook Entry: General RNA recovery, 1 Page, Exhibit No. 1176 filed in Interferences 106,007 and 106,008 on Feb. 16, 2015.
Laboratory Notebook Entry: Lab-on-a-Chip Analysis, pp. 3, Exhibit No. 1184 filed in Interferences 106,007 and 106,008 on Feb. 16, 2015.
Larsen et al., "Antisense properties of peptide nucleic acid," Biochim. Et Biophys. Acta, vol. 1489, pp. 159-166 (1999) Exhibit No. 1190 filed in Interferences 106,007 and 106,008 on Feb. 17, 2015.
Letter from the FDA to Sarepta Therapeutics, Inc., Re: Accelerated Approval for the use of Exondys 51 (eteplirsen), FDA Reference ID: 3987286, dated Sep. 19, 2016, 11 pages.
Letter to the U.S. Food and Drug Administration, (Dr. Billy Dunn, M.D. Director Division of Neurology Products, Office of Drug Evaluation 1, Center for Drug Evaluation and Research), for the Peripheral and Central Nervous System Advisory Committee Meeting (AdComm) supporting approval of eteplirsen, dated Feb. 24, 2016, 4 pages.
Letter to the U.S. Food and Drug Administration, (Dr. Janet Woodcock, M.D. Director, CDER), from The Congress of The United States regarding Duchenne muscular dystrophy, dated Feb. 17, 2016, 7 pages.
List of Publications for Matthew J. A. Wood, M.D., D. Phil., 11 pages, (Exhibit No. 2124 filed in interferences 106,007 and 106,008 on Feb. 17, 2015.
Liu, Hong-Xiang et al., "Identification of functional exonic splicing enhancer motifs recognized by individual SR proteins," Genes & Development, vol. 12:1998-2012 (1998).
Lu et al, "Massive Idiosyncratic Exon Skipping Corrects the Nonsense Mutation in Dystrophic Mouse Muscle and Produces Functional Revertant Fibers by Clonal Expansion," The Journal of Cell Biology, vol. 148(5): 985-995, Mar. 6, 2000 ("Lu et al.") (Exhibit No. 1082 filed in interferences 106008, 106007 on Dec. 23, 2014).
Lu, Qi Long et al., "Functional amounts of dystrophin produced by skipping the mutated exon in the mdx dystrophic mouse," Nature Medicine, vol. 9(8):1009-1014 (2003).
Lu, Qi-long et al., "What Can We Learn From Clinical Trials of Exon Skipping for DMD?" Molecular Therapy—Nucleic Acids, vol. 3:e152, doi:10.1038/mtna.2014.6, 4 pages (2014).
Lyophilisation of Oligonucleotides, pp. 2, Exhibit No. 1133 filed in Interferences 106,007 and 106,008 on Feb. 17, 2015.
Mann, Christopher J. et al., "Antisense-induced exon skipping and synthesis of dystrophin in the mdx mouse," PNAS, vol. 98(1):42-47 (2001).
Mann, Christopher J. et al., "Improved antisense oligonucleotide induced exon skipping in the mdx mouse model of muscular dystrophy," The Journal of Gene Medicine, vol. 4:644-654 (2002).
Mannino, Raphael J. et al., "Liposome Mediated Gene Transfer," BioTechniques, vol. 6(7):682-690 (1988).
Manual of Patent Examining Procedure 2308.02 (6th ed., rev. 3, Jul. 1997), (University of Western Australia Exhibit 2143, filed Apr. 3, 2015 in Interferences 106007, 106008, and 106013, pp. 1-2).
Manzur A, et al., "Glucocorticoid corticosteroids for Duchenne muscular dystrophy," Cochrane Database Syst Rev. 2004;(2):CD003725.

Marshall, N.B. et. al., "Arginine-rich cell-penetrating peptides facilitate delivery of antisense oligomers into murine leukocytes and alter pre-mRNA splicing," Journal of Immunological Methods, vol. 325:114-126 (2007).
Mathews et al., "Expanded Sequence Dependence of Thermodynamic Parameters Improves Prediction of RNA Secondary Structure," J. Mol. Biol. 288:911-940 (1999), (University of Western Australia Exhibit 2131, filed Apr. 3, 2015 in Interferences 106007, 106008, and 106013, pp. 1-31).
Mathews et al., "Expanded Sequence Dependence of Thermodynamic Parameters Improves Prediction of Secondary Structure," J. Mol. Biol., vol. 288, pp. 911-940 (1999), Exhibit No. 1212 filed in Interferences 106,007 and 106,008 on Feb. 17, 2015.
Matsuo, Masafumi et al., "Exon Skipping during Splicing of Dystrophin mRNA Precursor due to an Intraexon Deletion in the Dystrophin Gene of Duchenne Muscular Dystrophy Kobe," J. Clin. Invest., vol. 87:2127-2131 (1991).
Matsuo, Masafumi et al.. "Treatment of Duchenne Muscular Dystrophy with Oligonucleotides against an Exonic Splicing Enhancer Sequence," Basic Appl. Myol., vol. 13(6):281-285 (2003).
Matsuo, Masafumi, "Duchenne and Becker Muscular Dystrophy: From Gene Diagnosis to Molecular Therapy," IUBMB Life, vol. 53:147-152 (2002).
Matsuo, Masafumi, "Duchenne/Becker muscular dystrophy: from molecular diagnosis to gene therapy," Brain & Development, vol. 18:167-172 (1996).
Matteucci, Mark, "Structural modifications toward improved antisense oligonucleotides," Perspectives in Drug Discovery and Design, vol. 4:1-16 (1996).
Mazzone E, et at "Functional changes in Duchenne muscular dystrophy: a 12-month longitudinal cohort study," Neurology 2011;77(3):250-6.
McCarville, M. Beth et al., "Rhabdomyosarcoma in Pediatric Patients: The Good, the Bad, and the Unusual," AJR, vol. 176:1563-1569 (2001) (Exhibit No. 1034 filed in interferences 106008, 106007 on Nov. 18, 2014).
McClorey, G. et al., "Antisense oligonucleotide-induced exon skipping restores dystrophin expression in vitro in a canine model of DMD," Gene Therapy, vol. 13:1373-1381 (2006).
McClorey, G. et al., "Induced dystrophin exon skipping in human muscle explants," Neuromuscular Disorders, vol. 16:583-590 (2006).
GenBank AF213437.1 dated Jan. 17, 2002.
Generic Method for Average Mass Determination Using LC-UV-MS in the Negative Mode, pp. 15, Exhibit No. 1145 filed in Interferences 106,007 and 106,008 on Feb. 16, 2015.
Generic UPLC Purity Method for Oligonucleotides (19- to 25-mers), pp. 18, Exhibit No. 1156 filed in Interferences 106,007 and 106,008 on Feb. 16, 2015.
Gennaro, Alfonso R., (ed.), Remington's Pharmaceutical Sciences, 18th Edition, Mack Publishing, Co., Easton PA, 2020 pages (1990).
Giles, Richard V. et al., "Antisense Morpholino Oligonucleotide Analog Induces Missplicing of C-myc mRNA," Antisense & Nucleic Acid Drug Development, vol. 9:213-220 (1999).
GlaxoSmithKline Press Release, Issued in London, UK, dated Jun. 27, 2013 (5 pages), Exhibit No. 1202 filed in Interferences 106,007 and 106,008 on Feb. 17, 2015.
GlaxoSmithKline, "GSK and Prosensa announce start of Phase III study of investigational Duchenne Muscular Dystrophy medication," press release, 6 pages, dated Jan. 19, 2011 (Exhibit No. 2060 filed in interferences 106008, 106013, 106007 on Nov. 18, 2014).
GlaxoSmithKline, Prosensa regains rights to drisapersen from GSK and retains rights to all other programmes for the treatment of Duchenne muscular dystrophy (DMD), press release, 4 pages, dated Jan. 13, 2014 (Exhibit 2040 in Interferences 106007, 106008, and 106013 on Nov. 18, 2014).
Goemans, Nathalie M. et al., "Systemic Administration of PRO051 in Duchenne's Muscular Dystrophy," The New England Journal of Medicine, vol. 364:1513-1522 (2011) (Exhibit No. 2036 filed in interferences 106008, 106013, 106007 on Nov. 18, 2014).
Gordon, Peter M. et al., "Metal ion catalysis during the exon-ligation step of nuclear pre-mRNA splicing: Extending the parallels

(56) References Cited

OTHER PUBLICATIONS between the spliceosome and group II introns," RNA, vol. 6:199-205 (2000) (Exhibit No. 1055 filed in Interferences 106008, 106007 on Nov. 18, 2014).

Gordon, Peter M., et al., "Kinetic Characterization of the Second Step of Group II Intron Splicing: Role of Metal Ions and the Cleavage Sie 2'-OH in Catalysis," Biochemistry, vol. 39, pp. 12939-12952 (2000), Exhibit No. 1188 filed in Interferences 106,007 and 106,008 on Feb. 17, 2015.

Goyenvalle, Aurelie et al., "Prevention of Dystrophic Pathology in Severely Affected Dystrophin/Utrophin-deficient Mice by Morpholino-oligomer-mediated Exon-skipping," Molecular Therapy, vol. 18(1):198-205 (2010).

Hammond, Suzan M. et al., "Correlating In Vitro Splice Switching Activity With Systemic In Vivo Delivery Using Novel ZEN-modified Oligonucleotides," Molecular Therapy—Nucleic Acids, vol. 3:1, 11 pages (2014) (Exhibit No. 2011 filed in interferences 106008, 106013, 106007 on Nov. 18, 2014).

Hammond, Suzan M., et al., "Genetic therapies for RNA mis-splicing diseases." Cell, vol. 27, No. 5, pp. 196-205 (May 2011), Exhibit No. 1113 filed in interferences 106,007 and 106,008 on Feb. 17, 2015.

Hammond, Suzan M., et al., "PRO-051, an antisense oligonucleotide for the potential treatment of Duchenne muscular dystrophy," Curr. Opinion Mol. Therap., vol. 12, No. 4, pp. 478-486 (2010), Exhibit No. 1121 filed in interferences 106,007 and 106,008 on Feb. 13, 2015.

Harding, PL et al., "The Influence of Antisense Oligonucleotide Length on Dystrophin Exon Skipping," Molecular Therapy, vol. 15(1):157-166 (2007) (Exhibit No. 1030 filed in interferences 106008, 106007 on Nov. 18, 2014).

Harel-Bellan, Annick et al., "Specific Inhibition of c-myc Protein Biosynthesis Using an Antisense Synthetic Deoxy-Oligonucleotide in Human T Lymphocytes," The Journal of Immunology, vol. 140(7):2431-2435 (1988).

Havenga, M.J.E., et al., "Exploiting the Natural Diversity in Adenovirus Tropism for Therapy and Prevention of Disease," J. Virol., vol. 76, No. 9, pp. 4612-4620 (May 2002), Exhibit No. 1123 filed in interferences 106,007 and 106,008 on Feb. 13, 2015.

Heasman, Janet, "Morpholino Oligos: Making Sense of Antisense?" Developmental Biology, vol. 243:209-214 (2002).

Heemskerk, Hans A. et al., "In vivo comparison of 2'-O-methyl phosphorothioate and morpholino antisense Oligonucleotides for Duchenne muscular dystrophy exon skipping," The Journal of Gene Medicine, vol. 11:257-266 (2009) (Exhibit No. 2020 filed in interferences 106008, 106013, 106007 on Nov. 18, 2014).

Heid, Christian A. et al., "Real Time Quantitative PCR," Genome Research, vol. 6:986-994 (1996) (Exhibit No. 1061 filed in interferences 106008, 106007 on Nov. 18, 2014).

Herschlag, Daniel et al., "Contributions of 2' Hydroxyl Groups of the RNA Substrate to Binding and Catalysis by the Tetrahymena Ribozyme: An Energetic Picture of an Active Site Composed of RNA," Biochemistry, vol. 32:8299-8311 (1993) (Exhibit No. 1031 filed in interferences 106008, 106007 on Nov. 18, 2014).

Hoffman EP, et al., "Characterization of dystrophin in muscle-biopsy specimens from patients with Duchenne's or Becker's muscular dystrophy" N Engl J Med 1988;318:1363-68.

Hoffman EP, et al., "Restoring dystrophin expression in Duchenne muscular dystrophy muscle: Progress in exon skipping and stop codon read through," Am J Path 2011;179:12-22.

Hudziak, Robert M. et al., "Antiproliferative Effects of Steric Blocking Phosphorodiamidate Morpholino Antisense Agents Directed against c-myc," Antisense & Nucleic Acid Drug Development, vol. 10:163-176 (2000) (Exhibit No. 1032 filed in interferences 106008, 106007 on Nov. 18, 2014).

Hudziak, Robert M. et al., "Resistance of Morpholino Phosphorodiamidate Oligomers to Enzymatic Degradation," Antisense & Nucleic Acid Drug Development, vol. 6:267-272 (1996).

Hussey, Nicole D. et al., "Analysis of five Duchenne muscular dystrophy exons and gender determination using conventional duplex polymerase chain reaction on single cells," Molecular Human Reproduction, vol. 5(11):1089-1094 (1999).

Interim Guidance on Patent Subject Matter Eligibility ("the December Guidance," 16 pages, (Exhibit No. 2119 filed in interferences 106,007 and 106,008 on Feb. 17, 2015.

International Patent Application No. PCT/AU2000/00693 ("Wraight"), published as WO 00/78341 dated Dec. 28, 2000, 201 pages, (Exhibit No. 2125 filed in interferences 106,007 and 106,008 on Feb. 17, 2015.

International Preliminary Report on Patentability and Written Opinion for Application No. PCT/U52009/061960, 8 pages, dated Apr. 26, 2011.

Interational Preliminary Report on Patentability for Application No. PCT/AU2005/000943, 8 pages, dated Dec. 28, 2006.

International Preliminary Report on Patentability, PCT/US2013/077216, dated Jun. 23, 2015, pp. 1-7.

International Preliminary Report on Patentability, PCT/US2014/029610, dated Jul. 1, 2015, pp. 1-122.

International Preliminary Report on Patentability, PCT/US2014/029689, dated Sep. 15, 2015, pp. 1-10.

Interational Preliminary Report on Patentability, PCT/US2014/029766, dated Sep. 15, 2015, pp. 1-10.

Interational Search Report and Written Opinion of the International Searching Authority issued in International Patent Application No. PCT/US2013/077216, 5 pages, dated Mar. 27, 2014.

Interational Search Report and Written Opinion of the International Searching Authority issued in International Patent Application No. PCT/US2014/029610, 6 pages, dated Sep. 18, 2014.

International Search Report and Written Opinion of the International Searching Authority issued in International Patent Application No. PCT/US2014/029689, 8 pages, dated Oct. 21, 2014.

International Search Report and Written Opinion of the International Searching Authority issued in International Patent Application No. PCT/US2014/029766, 8 pages, dated Oct. 21, 2014.

International Search Report for Application No. PCT/AU20051000943, 5 pages, dated Oct. 20, 2005.

International Search Report for Application No. PCT/US01/14410, 5 pages, dated Mar. 6, 2002.

International Search Report for Application No. PCT/US2009/061960, 9 pages, dated Apr. 6, 2010.

Invitation to pay fees and Partial International Search Report issued by the International Search Authority in International Patent Application No. PCT/US2014/029689, 8 pages, dated Jul. 29, 2014.

ISIS Pharmaceuticals website, 2 pages, http://www.isispharm.com/Pipeline/Therapeutic-Areas/Other.htm (2014) (Exhibit No. 2021 filed in interferences 106008, 106013, 106007 on Nov. 18, 2014).

Iversen, Patrick L. et al., "Efficacy of Antisense Morpholino Oligomer Targeted to c-myc in Prostate Cancer Xenograft Murine Model and a Phase I Safety Study in Humans," Clinical Cancer Research, vol. 9:2510-2519 (2003).

Jarver, Peter et al., "A Chemical View of Oligonucleotides for Exon Skipping and Related Drug Applications," Nucleic Acid Therapeutics, vol. 24(1):37-47 (2014) (Exhibit No. 2061 filed in interferences 106008, 106013, 106007 on Nov. 18, 2014).

Jason, Tracey L.H. et al., "Toxicology of antisense therapeutics," Toxicology and Applied Pharmacology, vol. 201:66-83 (2004) (Exhibit No. 2027 filed in interferences 106008, 106013, 106007 on Nov. 18, 2014).

Jearawiriyapaisarn, Natee et al., "Long-term improvement in mdx cardiomyopathy after therapy with peptide-conjugated morpholino oligomers," Cardiovascular Research, vol. 85:444-453 (2010).

Jearawiriyapaisarn, Natee et al., "Sustained Dystrophin Expression Induced by Peptide-conjugated Morpholino Oligomers in the Muscles of mdx Mice," Mol. Ther., vol. 16(9):1624-1629 (2008).

Jett Foundation Presentation by McSherry, C. "Patient and Caregiver-Reported Outcomes of Patients in Clinical Trials of Eteplirsen for Treatment of Duchenne" at Peripheral and Central Nervous System Drugs Advisory Committee, Apr. 25, 2016, 17 pages.

Errata sheet for the Jan. 22, 2015 deposition of Matthew J. A. Wood, M.D., D. Phil., 2 pages, (Exhibit No. 2128 filed in interferences 106,007 and 106,008 on Feb. 17, 2015.

(56) References Cited

OTHER PUBLICATIONS

Errata sheet for the Mar. 12, 2015 deposition of Erik J. Sontheimer, Ph.D., (University of Western Australia Exhibit 2149, filed Apr. 3, 2015 in Interferences 106007, 106008, and 106013, p. 1).
Errata to the Sarepta Briefing Information for the Apr. 25, 2016 Meeting of the Peripheral and Central Nervous System Drugs Advisory Committee, Eteplirsen Errata Document, NDA 206488, 5 pages.
Errington, Stephen J. et al., "Target selection for antisense oligonucleotide induced exon skipping in the dystrophin gene," The Journal of Gene Medicine, vol. 5:518-527 (2003).
European Office Action for Application No. 09752572.9, 5 pages, dated Feb. 29, 2012.
European Response, Application No. 10004274.6, 7 pages, dated Nov. 5, 2013 (Exhibit No. 1060 filed in Interferences 106008, 106007 on Nov. 18, 2014).
European Response, Application No. 12198517.0, 7 pages, dated Oct. 21, 2014 (Exhibit No. 2084 filed in Interferences 106008, 106013, 106007 on Nov. 18, 2014).
European Response, Application No. 13160338.3, 4 pages, dated Jun. 26, 2014 (Exhibit No. 2085 filed in Interferences 106008, 106013, 106007 on Nov. 18, 2014).
European Search Report for Application No. 10004274.6, 12 pages, dated Jan. 2, 2013.
European Search Report for Application No. 12162995.0, 11 pages, dated Jan. 15, 2013.
European Search Report, EP15168694.6, dated Jul. 23, 2015, pp. 1-8.
Excerpts from Prosecution History of U.S. Appl. No. 13/741,150: Notice of Allowance dated Mar. 16, 2015; List of References cited by Applicant and Considered by Examiner; Notice of Allowance and Fees due dated Sep. 18, 2014; Amendment in Response to Non-Final Office Action dated Jul. 11, 2014, (Academisch Ziekenhuis Leiden Exhibit 1229, filed Apr. 3, 2015 in Interference 106007 and 106008, pp. 1-133).
Excerpts from Prosecution History of U.S. Appl. No. 13/826,880: Notice of Allowance dated Jan. 26 2015 and Amendment in Response to Non-Final Office Action dated Oct. 15, 2014, (Academisch Ziekenhuis Leiden Exhibit 1228, filed Apr. 3, 2015 in Interference 106007 and 106008, pp. 1-16).
Excerpts from Yeo (Ed.), "Systems Biology of RNA Binding Proteins," Adv. Exp. Med. Biol., Chapter 9, 56 pages (2014) (Academisch Ziekenhuis Leiden Exhibit 1232, filed Apr. 3, 2015 in Interference 106007 and 106008, pp. 1-56).
Excerpts of SEC Form 8-K, dated Nov. 23, 2014, for BioMarin Pharmaceutical Inc., (University of Western Australia Exhibit 2129, filed Apr. 3, 2015 in Interferences 106007, 106008, and 106013, pp. 1-9).
Exon 51 Internal Sequence Schematic, pp. 1, Exhibit No. 1224 filed in Interferences 106,007 and 106,008 on Feb. 17, 2015.
Exon 53 Internal Sequence Schematic, pp. 1, Exhibit No. 1225 filed in Interferences 106,007 and 106,008 on Feb. 17, 2015.
Extended European Search Report, EP 15190341.6, dated Apr. 28, 2016, 9 pages.
Fairclough et al., "Therapy for Duchenne muscular dystrophy: renewed optimism from genetic approaches," Nature Reviews, vol. 14, pp. 373-378 (Jun. 2013), Exhibit No. 1112 filed in interferences 106,007 and 106,008 on Feb. 17, 2015.
Fall, Abbie M. et al., "Induction of revertant fibres in the mdx mouse using antisense oligonucleotides," Genetic Vaccines and Therapy, vol. 4:3, doi:10.1186/1479-0556-4-3, 12 pages (2006).
FDA Briefing Document, "Peripheral and Central Nervous System," Drugs Advisory Committee Meeting, NDA 206488 Eteplirsen, Food and Drug Administration, pp. 1-73, Jan. 22, 2016.
FDA Briefing Information for the Apr. 25, 2016 Meeting of the Peripheral and Central Nervous System Drugs Advisory Committee, Eteplirsen, NDA 206488, 115 pages.
FDA News Release, "FDA grants accelerated approval to first drug for Duchenne muscular dystrophy," Sep. 19, 2016, 3 pages.

Federal Register, vol. 58, No. 183, pp. 49432-49434, Sep. 23, 1993 (6 pages); [Cited as: 58 FR 49432-01, 1993 WL 371451 (F.R.)], Exhibit No. 1221 filed in Interferences 106,007 and 106,008 on Feb. 17, 2015.
Federal Register, vol. 69, No. 155, pp. 49960-50020 dated Aug. 12, 2004 (62 pages), Exhibit No. 1220 filed in Interferences 106,007 and 106,008 on Feb. 17, 2015.
Feener, C. et al., "Alternative splicing of human dystrophin mRNA generates isoforms at the carboxy terminus," Nature, vol. 338:509-511 (1989).
File Excerpt from AZL U.S. Appl. No. 11/233,495: Amendment After Non-Final Office Action. as-filed Nov. 1, 2010 (Exhibit No. 1085 filed in interferences 106008, 106007 on Dec. 23, 2014).
File Excerpt from AZL U.S. Appl. No. 11/233,495: Claims examined in Non-Final Office Action, dated Dec. 1, 2008 (Exhibit No. 1079 filed in interferences 106008, 106007 on Dec. 23, 2014).
File Excerpt from AZL U.S. Appl. No. 11/233,495: Final Office Action dated Aug. 31, 2010 (Exhibit No. 1086 filed in interferences 106008, 106007 on Dec. 23, 2014).
File Excerpt from U.S. Appl. No. 11/233,495: Non-Final Office Action dated Dec. 1, 2008 and Final Office Action dated Jun. 25, 2009 (Exhibit No. 1078 filed in interferences 106008, 106007 on Dec. 23, 2014).
File Excerpt from U.S. Appl. No. 12/198,007: AZL's Preliminary Amendment and Response, as-filed Nov. 7, 2008 (Exhibit No. 1075 filed in interferences 106008, 106007 on Dec. 23, 2014).
File Excerpt from U.S. Appl. No. 12/976,381: AZL's First Preliminary Amendment, as-filed Dec. 22, 2010 (Exhibit No. 1076 filed in interferences 106008, 106007 on Dec. 23, 2014).
File Excerpts from Prosecution History of U.S. Appl. No. 13/270,992 (UWA's U.S. Pat. No. 8,486,907), pp. 122, Exhibit No. 1006 filed in Interference 106,013 on Feb. 17, 2015.
File Excerpts from U.S. Appl. No. 11/233,495: Response to Non-Final Office Action, as filed Jul. 26, 2011 (14 pages), Exhibit No. 1222 filed in Interferences 106,007 and 106,008 on Feb. 17, 2015.
File Excerpts from U.S. Appl. No. 13/270,992 (UWA's U.S. Pat. No. 8,486,907): NFOA, dated Jul. 30, 2012; Applicant-Initiated Interview Summary, dated Nov. 8, 2012; Amendment, as filed Jan. 30, 2013; NOA, dated Apr. 4, 2013, Exhibit No. 1118 (122 pages) filed in interferences 106,007 and 106,008 on Feb. 17, 2015.
Flanagan, W. Michael, et al., "A cytosine analog that confers enhanced potency to antisense oligonucleotides," Proc. Nat'l Acad. Sci. USA, vol. 96, pp. 3513-3518 (Mar. 1999), Exhibit No. 1211 filed in Interferences 106,007 and 106,008 on Feb. 17, 2015.
Flanigan, Kevin M. et al., "Pharrnacokinetics and safety of single doses of drisapersen in non-ambulant subjects with Duchenne muscular dystrophy: Results of a double-blind randomized clinical trial," Neuromuscular Disorders, 24:16-24 (2014) (Exhibit No. 2038 filed in interferences 106008, 106013, 106007 on Nov. 18, 2014).
Flanigan, Kevin M., et al. (2003) "Rapid Direct Sequence Analysis of the Dystrophin Gene," Am. J. Hum. Genet. 72:931-939, dated Feb. 17, 2015 (Exhibit No. 2120 filed in interferences 106,007 and 106,008 on Feb. 17, 2015.
Fletcher S., et al, Morpholino oligomer-mediated exon skipping averts the onset of dystrophic pathology in the mdx mouse. Mol Ther 2007;15:1587-1592.
Fletcher, Sue et al., "Dystrophin Isoform Induction In Vivo by Antisense-mediated Alternative Splicing," Molecular Therapy, vol. 18(6):1218-1223 (2010).
Fletcher, Sue et al., "Targeted Exon Skipping to Address 'Leaky' Mutations in the Dystrophin Gene," Molecular Therapy-Nucleic Acids, vol. 1, e48, doi:10.1038/mtna.2012.40, 11 pages (2012).
Fletcher, Susan et al., "Dystrophin expression in the mdx mouse after localised and systemic administration of a morpholino antisense oligonucleotide," J. Gene Med., vol. 8:207-216 (2006).
Fletcher, Susan et al.., "Gene therapy and molecular approaches to the treatment of hereditary muscular disorders," Curr. Opin. Neurol. vol. 13:553-560 (2000).
Foster, Helen et al., "Genetic Therapeutic Approaches for Duchenne Muscular Dystrophy," Human Gene Therapy, vol. 23:676-687 (2012).
Fourth Declaration of Erik Sontheimer, Ph.D. (Pursuant to Bd.R. 41.155(b)(2) and SO 155.1.3 and 155.1.4), dated Mar. 9, 2015,

(56) References Cited

OTHER PUBLICATIONS (University of Western Australia Exhibit 2138, filed Apr. 3, 2015 in Interferences 106007, 106008, and 106013, pp. 1-4).
Fragall, Clayton T. et al., "Mismatched single stranded antisense oligonucleotides can induce efficient dystrophin splice switching," BMC Medical Genetics, vol. 12:141, 8 pages (2011) (Exhibit No. 2019 filed in interferences 106008, 106013, 106007 on Nov. 18, 2014).
Fraley, Robert et al., "New generation liposomes: the engineering of an efficient vehicle for intracellular delivery of nucleic acids," Trends Biochem., vol. 6:77-80 (1981).
Frazier, Kendall S. et al., "Species-specific Inflammatory Responses as a Primary Component for the Development of Glomerular Lesions in Mice and Monkeys Following Chronic Administration of a Second-generation Antisense Oligonucleotide," Toxicologica Pathology, 13 pages (2013).
Freidmann, Theodore, "Progress Toward Human Gene Therapy," Science, vol. 244(4910):1275-1281 (1989).
Gebski, Bianca L. et al., "Morpholino antisense oligonucleotide induced dystrophin exon 23 skipping in mdx mouse muscle," Human Molecular Genetics, vol. 12(15):1801-1811 (2003).
Canonico, A.E et al., "Expression of a CMV Promoter Drive Human alpha-1 Antitrypsin Gene in Cultured Lung Endothelial Cells and in the Lungs of Rabbits," Clinical Research, vol. 39(2):219A (1991).
Cirak, Sebahattin et al., "Exon skipping and dystrophin restoration in patients with Duchenne muscular dystrophy after systemic phosphorodiamidate morpholino oligomer treatment: an open-label, phase 2, dose-escalation study," Lancet, vol. 378(9791):595-605 (2011).
Claim Chart U.S. Appl. No. 11/233,495, pp. 57, Exhibit No. 1216 filed in Interferences 106,007 and 106,008 on Feb. 17, 2015.
Claim Chart U.S. Appl. No. 13/550,210, pp. 45, Exhibit No. 1217 filed in Interferences 106,007 and 106,008 on Feb. 17, 2015.
Claim Chart, U.S. Pat. No. 7,807,816, 14 pages (Exhibit No. 1063 filed in interferences 106008, 106007 on Nov. 18, 2014).
Claim Chart, U.S. Pat. No. 7,960,541, 17 pages (Exhibit No. 1064 filed in interferences 106008, 106007 on Nov. 18, 2014).
Claim Chart, U.S. Pat. No. 8,455,636, 32 pages (Exhibit No. 1062 filed in interferences 106008, 106007 on Nov. 18, 2014).
Claim Comparison Chart—Claims 11 and 29 in U.S. Appl. No. 13/550,210, pp. 1, Exhibit No. 1226 filed in Interferences 106,007 and 106,008 on Feb. 17, 2015.
Claim Comparison Chart U.S. Appl. No. 13/550,210 vs U.S. Appl. No. 11/233,495, pp. 12, Exhibit No. 1218 filed in Interferences 106,007 and 106,008 on Feb. 17, 2015.
Claim Comparison Chart U.S. Appl. No. 13/550,210 vs U.S. Appl. No. 12/198,007, pp. 1, Exhibit No. 1219 filed in Interferences 106,007 and 106,008 on Feb. 17, 2015.
Claims from U.S. Appl. No. 11/233,495, 6 pages, dated Sep. 21, 2005 (Exhibit No. 2068 filed in Interferences 106008, 106013, 106007 on Nov. 18, 2014).
Classification Excerpts from USPC System, 21 pages, (Academisch Ziekenhuis Leiden Exhibit 1234, filed May 5, 2015 in Interference 106007 and 106008).
Collins, C.A. et al., "Duchenne's muscular dystrophy: animal models used to investigate pathogenesis and develop therapeutic strategies," Int. J. Exp. Pathol., vol. 84(4):165-172 (2003).
Confirmation of Dystrophin Exon 48 to 50 Deletion in Cell Line 8036 Laboratory Notebook Entry, pp. 3, Exhibit No. 1167 filed in Interferences 106,007 and 106,008 on Feb. 16, 2015.
Confirrnation of Dystrophin Exon 52 Deletion in Cell Line R1809 Laboratory; Notebook Entry, pp. 3, Exhibit No. 1168 filed in Interferences 106,007 and 106,008 on Feb. 16, 2015.
Confirmatory Study of Eteplirsen in DMD Patients, An Open-Label. Multi-Center, 48-Week Study With a Concurrent Untreated Control Aim to Evaluate the Efficacy and Safety of Eteplirsen in Duchenne Muscular Dystrophy, ClinicalTrials.gov, Clinical Trial Identifier NCT02255552, Oct. 1, 2014, 3 pages.
Confirmatory Study of Eteplirsen in DMD Patients, An Open-Label. Multi-Center, 48-Week Study With a Concurrent Untreated Control Arm to Evaluate the Efficacy and Safety of Eteplirsen in Duchenne Muscular Dystrophy, ClinicalTrials.gov, Clinical Trial Identifier NCT02255552, May 26, 2015, 3 pages.
Coolidge v. Efendic,2008 WL 2080735, Int. No. 105,457 (BPAI May 16, 2008), 42 pages, (Academisch Ziekenhuis Leiden Exhibit 1235, filed May 5, 2015 in Interference 106007 and 106008).
Corey, David R. et al., Morpholino antisense oligonucleotides: tools tor investigating vertebrate development,' Genome Biology, vol. 2(5):1015.1-1015.3 (2001) (Exhibit No. 1026 filed in interferences 106008, 106007 on Nov. 18, 2014).
Corrected Priority Statement filed by UWA in Int. No. 106,008 (as PN 219), pp. 5, Exhibit No. 1002 filed in Interference 106,013 on Feb. 17, 2015.
Cortes, Jesus J., et al., "Mutations in the conserved loop of human U5 snRNA generate use of novel cryptic 5' splice sites in vivo," EMBO J., vol. 12, No. 13, pp. 5181-5189 (1993), Exhibit No. 1187 filed in Interferences 106,007 and 106,008 on Feb. 17, 2015.
Crooke. Stanley T., Antisense Drug Technology. Principles, Strategies, and Applications, Marcel Dekker, Inc., New York, Chapters 15 and 16, pp. 375-389, 391-469 (2001) (Exhibit No. 2075 filed in interferences 106008, 106013, 106007 on Nov. 18, 2014).
Curriculum Vitae of Judith van Deutekom, pp. 6, Exhibit No. 1126 filed in interferences 106,007 and 106,008 on Feb. 17, 2015.
Curriculum Vitae, Erik Joseph Sontheimer, 18 pages, dated Sep. 29, 2014 (Exhibit No. 1013 filed in interferences 106008, 106007 on Nov. 18, 2014).
CV, Professor Matthew J.A. Wood, 3 pages (Exhibit No. 2003 filed in interferences 106008, 106007 on Nov. 8, 2014).
Davis, Richard J. et al., "Fusion of PAX7 to FKHR by the Variant t(1;13)(p36;q14) Translocation in Alveolar Rhabdomyosarcorna," Cancer Research, vol. 54:2869-2872 (1994) (Exhibit No. 1027 filed in interferences 106008, 106007 on Nov. 18, 2014).
De Angelis, Fernanda Gabriella et al., "Chimeric snRNA molecules carrying antisense sequences against the splice junctions of exon 51 of the dystrophic pre-mRNA induce exon skipping and restoration of a dystrophin synthesis in 48-50 DMD cells," PNAS, vol. 99(14):9456-9461 (2002).
Decision on Appeal, Ex Parte Martin Gleave and Hideaki Miyake, Appeal No. 2005-2447, U.S. Appl. No. 09/619,908 (dated Jan. 31, 2006) (2009 WL 6927761 (Bd.Pat App.& Interf.), pp. 12, Exhibit No. 1207 filed in Interferences 106,007 and 106,008 on Feb. 17, 2015.
Decision on Request for ReHearing, Ex Parte Roderick John Scott, Appeal No. 2008-004077, U.S. Appl. No. 10/058,825 (dated Jan. 6, 2010) (2010 WL 191079 (Bd.Pat.App. & Interf.), pp. 21, Exhibit No. 1208 filed in Interferences 106,007 and 106,008 on Feb. 17, 2015.
Declaration of Judith C.T. van Deutekom Under 37 C.F.R. §1.132, filed on Jan. 27, 2012, in U.S. Patent Reexamination Control No. 90/011,320, regarding U.S. Pat. No. 7,534,879, (University of Western Australia Exhibit 2133, filed Apr. 3, 2015 in Interferences 106007, 106008, and 106013, pp. 1-10).
Declaration of Judith van Deutekom, pp. 45, Exhibit No. 1125 filed in interferences 106,007 and 106,008 on Feb. 17, 2015.
Dellorusso, Christiana et al., "Functional correction of adult mdx mouse muscle using gutted adenoviral vectors expressing full-length dystrophin," PNAS, vol. 99(20):12979-12984.
Deposition Transcript of Erik J. Sontheimer, Ph.D. of Jan. 21, 2015 (99 pages), Exhibit No. 1215 filed in Interferences 106,007 and 106,008 on Feb. 17, 2015.
Deposition Transcript of Matthew J. A. Wood, M.D., D. Phil., Jan. 22, 2015, including Errata Sheet, pp. 198, Exhibit No. 1007 filed in Interference 106,013 on Feb. 17, 2015.
Deposition Transcript of Matthew J. A. Wood, M.D., D. Phil., pp. 196, Exhibit No. 1122 filed in interferences 106,007 and 106,008 on Feb. 17, 2015.
Desalting of Oligonucleotides, pp. 2, Exhibit No. 1132 filed in Interferences 106,007 and 106,008 on Feb. 17, 2015.
Dirksen, Wessel P. et al., "Mapping the SF2/ASF Binding Sites in the Bovine Growth Hormone Exonic Splicing Enhancer," The Journal of Biological Chemistry, vol. 275(37):29170-29177 (2000).

(56) References Cited

OTHER PUBLICATIONS

Dominski, Zbigniew et al., "Identification and Characterization by Antisense Oligonucleotides of Exon and Intron Sequences Required for Splicing," Molecular and Cellular Biology, vol. 14(11):7445-7454.
Dominski, Zbigniew et al., "Restoration of correct splicing in thalassemic pre-mRNA by antisense oligonucleotides," Proc. Natl. Acad. Sci. USA, vol. 90:8673-8677 (1993).
Doran, Philip et al., "Proteomic profiling of antisense-induced exon skipping reveals reversal of pathobiochemical abnormalities in dystrophic mdx diaphragm," Proteomics, vol. 9:671-685, DOI 10.1002/pmic.200800441 (2009).
Douglas, Andrew G.L. et al., "Splicing therapy for neuromuscular disease," Molecular and Cellular Neuroscience, vol. 56:169-185 (2013) (Exhibit No. 2005 filed in interferences 106008, 106013, 106007 on Nov. 18, 2014).
Doyle, Donald F., et al. (2001) "Inhibition of Gene Expression Inside Cells by PeptideNucleic Acids: Effect of mRNA Target Sequence, Mismatched Bases, and PNA Length," Biochemistry 40:53-64, (Exhibit No. 2123 filed in Interferences 106,007 and 106,008 on Feb. 17, 2015.
Dr. Wood Errata Sheet—Jan. 22, 2015, pp. 2, Exhibit No. 1227 filed in Interferences 106,007 and 106,008 on Feb. 17, 2015.
Dunckley, Matthew G. et al., "Modification of splicing in the dystrophin gene in cultured Mdx muscle cells by antisense oligoribonucleotides," Human Molecular Genetics, vol. 5(1):1083-1090 (1995).
Dunckley, Matthew G. et al., "Modulation of Splicing in the DMD Gene by Antisense Oligorihonucleotides," Nucleosides & Nucleotides, vol. 16(7-9):1665-1668 (1997).
Eckstein, F., "Nucleoside Phosphorothioates," Ann. Rev. Biochem., vol. 54:367-402 (1985) (Exhibit No. 1028 filed in interferences 106008, 106007 on Nov. 18, 2014).
Elayadi, Anissa N. el al., "Application of PNA and LNA oligomers to chemotherapy," Current Opinion in Investigational Drugs, vol. 2(4):558-561 (2001).
Email from Danny Huntington to Interference Trial Section, dated Sep. 21, 2014, pp. 2, Exhibit No. 3001 filed in Interference 106,007, 106,008, and 106,013 on Sep. 26, 2014.
Email From Sharon Crane to Interference Trial Section, dated Nov. 13, 2014, pp. 2, Exhibit No. 3002 filed on Interference 106,007, 106,008, and 106,013 on dated Nov. 14, 2014.
Emery, A.E. H., "Population frequencies of inherited neuromuscular diseases—a world survey," Neuromuscul Disord 1991;1:19-29.
AON PS531966 Mass Spectrometry Data, pp. 8, Exhibit No. 1154 filed in interferences 106,807 and 106,008 on Feb. 16, 2015.
AON PS1966 UPLC Data, pp. 2, Exhibit No. 1165 filed in Interferences 106,007 and 106,008 on Feb. 16, 2015.
AON PS1967 Mass Spectrometry Data, pp. 7, Exhibit No. 1155 filed in Interferences 106,007 and 106,008 on Feb. 16, 2015.
AON PS1967 UPLC Data, pp. 2, Exhibit No. 1166 filed in Interferences 106,007 and 106,008 on Feb. 16, 2015.
AON PS229 (h53AON1) HPLC Chromatograph pp. 2, Exhibit No. 1140 filed in Interferences 106,007 and 106,008 on Feb. 16, 2015.
AON PS229 (h53AON1) Method Report, pp. 3, Exhibit No. 1139 filed in Interferences 106,007 and 106,008 on Feb. 16, 2015.
AON PS229 (h53AON1) Mass Spectrometry Data, pp. 3, Exhibit No. 1142 filed in Interferences 106,007 and 106,008 on Feb. 16, 2015.
AON PS229 (h53AON1) Synthesis Laboratory Notebook Entry, pp. 1, Exhibit No. 1137 filed in Interferences 106,007 and 106,008 on Feb. 16, 2015.
AON PS229L (h53AON229L) Certificate of Analysis, pp. 1, Exhibit No. 1129 filed in Interferences 106,007 and 106,008 on Feb. 17, 2015.
AON PS43 (h51AON1) Certificate of Analysis, pp. 1, Exhibit No. 1134 filed in Interferences 106,007 and 106,008 on Feb. 16, 2015.
AON PS43 (h51AON1) HPLC Chromatogram, pp. 1, Exhibit No. 1131 filed in Interferences 106,007 and 106,008 on Feb. 17, 2015.
AON PS43 (h51AON1) HPLC Method Report, pp. 4, Exhibit No. 1130 filed in Interferences 106,007 and 106,008 on Feb. 17, 2015.
AON PS43 (h51AON1) Mass Spectrometry Data, pp. 3, Exhibit No. 1135 filed in Interferences 106,007 and 106,008 on Feb. 16, 2015.
AON PS43 (h51AON1) UPLC-UV Data, pp. 2, Exhibit No. 1136 filed in Interferences 106,007 and 106,008 on Feb. 16, 2015.
AONs PS1958, PS1959, PS1960, PS1961, PS1962, PS1963, PS1964, PS1965, PS1966, and PS1967 HPLC Method Report, pp. 3, Exhibit No. 1143 filed in Interferences 106,007 and 106,008 on Feb. 16, 2015.
Applicant- Initiated Interview Summary dated Apr. 8, 2013 in U.S. Appl. No. 13/094,548, (University of Western Australia Exhibit 2144, filed Apr. 3, 2015 in Interferences 106007, 106008, and 106013, pp. 1-11).
Arechavala-Gomeza V, et al., "Immunohistological intensity measurements as a tool to assess sarcolemma-associatect protein expression," Neuropathol Appl Neurobiol 2010;36: 265-74.
Arechavala-Gomeza, V. et al., "Comparative Analysis of Antisense Oligonucleotide Sequences for Targeted Skipping of Exon 51 During Dystrophin Pre-mRNA Splicing in Human Muscle," Human Gene Therapy, vol. 18:798-810 (2007).
Arora, Vikram et al., "c-Myc Antisense Limits Rat Liver Regeneration and Indicates Role for c-Myc in Regulating Cytochrome P-450 3A Activity," The Journal of Pharmacology and Experimental Therapeutics, vol. 292(3):921-928 (2000).
*Asetek Danmark A/S v. CMI USA, Inc.*, 2014 WL 5990699, N.D. Cal. 2014, 8 pages, (Academisch Ziekenhuis Leiden Exhibit 1237, filed May 5, 2015 in Interference 106007 and 106008).
Asvadi, Parisa et al., "Expression and functional analysis of recombinant scFv and diabody fragments with specificity for human RhD," Journal of Molecular Recognition, vol. 15:321-330 (2002).
Australian Application No. 2004903474, 36 pages, dated Jul. 22, 2005 (Exhibit No. 1004 filed in interferences 106008, 106007 on Nov. 18, 2014).
AVI BioPharma, AVI BioPharma Announces Eteplirsen Meets Primary Endpoint, Demonstrating a Significant Increase in Dystrophin at 24 Weeks Compared to Placebo in Phase IIb Trial for the Treatment of Duchenne Muscular Dystrophy, Press Release, Apr. 2, 2012, pp. 1-3.
AVI BioPharma, AVI BioPharma Announces Late-Breaker Oral Presentation of Phase IIb DMD Study at 2012 AAN Annual Meeting in Apr., Press Release, Mar. 12, 2012, pp. 1-2.
AVI BioPharma, AVI BioPhamia Announces Successful Clinical Trial of AVI-4658 for Treatment of Duchenne Muscular Dystrophy by Exon Skipping, Press Release, Jan. 20, 2009, pp. 1-2.
AVI BioPharma, AVI BioPhamia Announces Treatment of First Patient in Systemic Clinical Trial of AVI-4658 for Treatment of Duchenne Muscular Dystrophy, Press Release, Feb. 19, 2009, pp. 1-2.
AVI BioPharrna, AVI BioPhamia Opens Investigational New Drug (IND) Application for AVI-4658 in Duchenne Muscular Dystrophy, Press Release, Jul. 7, 2010, pp. 1-2.
AVI BioPharma, AVI BioPharma Phase 1 Proof of Concept and Safety Data for AVI-4658 in Duchenne Muscular Dystrophy Featured in Lancet Neurology, Press Release, Aug. 25, 2009, pp. 1-3.
AVI BioPharma, AVI BioPharma Provides Update on Initiation of Eteplirsen Phase 2 Clinical Trial, Press Release, Jun. 9, 2011, pp. 1-2.
AVI BioPharma, AVI BioPharma's Investigational Drug Candidate AVI-4658 Demonstrates Broadly Favorable Profile of Safety and Tolerability, New Dystrophin Expression, Stable Clinical Performance and Inflammatory Modulation in the Treatrnent of Duchenne Muscular Dystrophy, Press Release, Oct. 15, 2010, pp. 1-4.
AVI BioPharma, AVI-4658 Demonstrates First Ever Reported Generation of Greater Than 50% Dystrophin-Positive Muscle Fibers in a Patient Following Systemic Administration in Duchenne Muscular Dystrophy; All Patients in Two Highest Dose Cohorts Generated New Dystrophin-Positive Fibers, Press Release, Jun. 2, 2010, pp. 1-3.
AVI BioPharma, Inc., "Exon 51 Sequence of Dystrophin," Document D19 as filed in Opposition of European Patent EP1619249, filed Jun. 23, 2009, 7 pages.

(56) References Cited

OTHER PUBLICATIONS

AVI BioPharma, The Lancet Published Clinical Trial Data That Demonstrate Statistically Significant and Dose-Dependent Expression of Dystrophin in Duchenne Muscular Dystrophy Patients With AVI BioPharma's Eteplirsen, Press Release, Jul. 25, 2011, pp. 1-2.
AZL's PCT/NL03/00214 (the as-filed AZL PCT Application) Exhibit No. 1006, filed in Interference No. 106,007, 64 pages, Dec. 23, 2014.
AZL's U.S. Appl. No. 14/295,311 and claims, as-filed Jun. 3, 2014 ("The '311 Application") (Exhibit No. 1077 filed in interferences 106008, 106007 on Dec. 23, 2014).
Azofeifa J, et al., "X-chromosome methylation in manifesting and healthy carriers of dystrophinopathies: concordance of activation ratios among first degree female relatives and skewed inactivation as cause of the affected phenotypes," Hum Genet 1995;96:167-176.
Beaucage, S.L. et al, "Deoxynucleoside Phosphoramidites—A New Class of Key Intermediates for Deoxypolynucleotide Synthesis," Tetrahedron Letters, vol. 22(20):1859-1862 (1981).
Bellare, Priya et al., "A role for ubiquitin in the spliceosome assembly pathway," Nature Structural & Molecular Biology, vol. 15(5):444-451 (2008) (Exhibit No. 1057 filed in interferences 106008, 106007 on Nov. 18, 2014).
Bellare, Priya et al., "Ubiquitin binding by a variant Jab1/MPN domain in the essential pre-mRNA splicing factor Prp8p," RNA, vol. 12:292-302 (2006) (Exhibit No. 1056 filed in interferences 106008, 106007 on Nov. 18, 2014).
Bennett, C. Frank et al., "RNA Targeting Therapeutics: Molecular Mechanisms of Antisense Oligonucleotides as a Therapeutic Platform," Annu. Rev. Pharmacol. Toxicol., vol. 50:259-293 (2010) (Exhibit No. 1025 filed in Interferences 106008, 106007 on Nov. 18, 2014).
Berge, Stephen M. el al., "Pharmaceutical Salts," Journal of Pharmaceutical Sciences, vol. 66(1):1-18 (1977).
Bestas et al., "Design and Application of Bispecific Splice Switching Oligonucleotides," Nuc. Acid Therap., vol. 24, No. 1, pp. 13-24 (2014), Exhibit No. 1120 filed in interferences 106,007 and 106,008 on Feb. 17, 2015.
Braasch, Dwaine A. el al., "Locked nucleic acid (LNA): fine-tuning the recognition of DNA and RNA," Chemistry & Biology, vol. 8:1-7 (2001) (Exhibit No. 2009 filed in interferences 106008, 106013, 106007 on Nov. 18, 2014).
Braasch, Dwaine A. et al., "Novel Antisense and Peptide Nucleic Acid Strategies for Controlling Gene Expression," Biochemistry, vol. 41(14):4503-4510 (2002) (Exhibit No. 2006 filed in interferences 106008, 106013, 106007 on Nov. 18, 2014).
Bremmer-Bout, Mattie et al., "Targeted Exon Skipping in Transgenic hDMD Mice: A Model for Direct Preclinical Screening of Human-Specific Antisense Oligonucleotides," Molecular Therapy, vol. 10(2):232-240 (2004) (Exhibit No. 2024 filed in interferences 106008, 106013, 106007 on Nov. 18, 2014).
Brooke MH, et al., "Clinical investigation in Duchenne dystrophy: 2. Determination of the "power" of therapeutic trials based on the natural history," Muscle Nerve. 1983;6:91-103.
Brown, Susan C. el al., "Dystrophic phenotype induced in vitro by antibody blockade of muscle alpha-dystroglycan-aminin interaction," Journal of Cell Science, vol. 112:209-216 (1999).
Bushby K, et al. "Diagnosis and management of Duchenne muscular dystrophy, part 1: diagnosis, and pharmacological and psychosocial management," Lancet Neural 2010;9:77-93.
Bushby KM, et al., "The clinical, genetic and dystrophin characteristics of Becker muscular dystrophy," II. Correlation of phenotype with genetic and protein abnormalities. J Neurol 1993;240: 105-112.
Bushby KM, et al., "The clinical, genetic and dystrophin characteristics of Becker muscular dystrophy," I. Natural history. J Neurol 1993;240:98-104.

bp          Acceptor                    ESE              Donor uca|ugcacugagugaccucuuucucgagGCGCUAGCUGGAGCA////CCGUGCACACUGAGCGgucuca|

Fig. 1

Exon 57

H57A(-10+20)

Exon 59

H59A(+96+120)

Exon 60

H60A(-08+19) & H60A(+37+66)   H60A(+86+116) & H60A(+37+66)

Exon 63

H63A(+20+49)

Exon 64

H64A(+34+62)

Exon 66

H66A(+13-17) & H66A(-02+28)

Exon 67

H67A(+17+47)

Exon 68

H68A(+48+72) & H68A(-03+23)

Exon 69 & 70

H69A(+32-60) & H70A(-06+18)

| SEQ ID | Exon | Sequence |
|---|---|---|
| 1 | H5A(+35+65) | AAA CCA CGC GUC AGU UUA UGA UUU CCA UCU A |
| 2 | H12A(+52+75) | UCU UCU GUU UUU GUU AGC CAG UCA |
| 3 | H17A(-07+23) | GUG GUG GUG ACA GCC UGU GAA AUC UGU GAG |
| 4 | H17A(+61+86) | UGU UCC CUU GUG GUC ACC GUA GUU AC |
| 5 | H21A(+86+114) | CAC AAA GUC UGC AUC CAG GAA CAU GGG UC |
| 6 | H21A(+90+119) | AAG GCC ACA AAG UCU GCA UCC AGG AAC AUG |
| 7 | H22A(+125+146) | CUG CAA UUC CCC GAG UCU CUG C |
| 8 | H24A(+51+73) | CAA GGG CAG GCC AUU CCU CCU UC |
| 9 | H43A(+92+117) | GAG AGC UUC CUG UAG CUU CAC CCU UU |
| 10 | H44A(+65+90) | UGU UCA GCU UCU GUU AGC CAC UGA |
| 11 | H45A(-09+25) | GCU GCC CAA UGC CAU CCU GGA GUU CCU GUA AGA U |
| 12 | H46A(+81+109) | UCC AGG UUC AAG UGG AUA CUA GC AAU GU |
| 13 | H47A(+01+29) | UGG CGC AGG GGC AAC UCU UCC ACC AGU AA |
| 14 | H49A(+45+70) | ACA AAU GCU GCC UUA GAC AAA UC |
| 15 | H50A(+48+74) | GGC UGC UUU GCC CUC AGC UCU UGA AGU |
| 16 | H54A(+67+97) | UGG UCU CAU CUG CAG AAU AAU CCC GGA GAA G |
| 17 | H55A(-10+20) | CAG CCU CUC GCU CAC UCA CCC UGC AAA GGA |
| 18 | H56A(+92+121) | CCA AAC GUC UUU GUA ACA GGA CUG CAU |
| 19 | H56A(+112+141) | CCA CUU GAA GUU CAU GUU AUC CAA ACG UCU |
| 20 | H57A(-10+20) | AAC UGG CUU CCA AAU GGG ACC UGA AAA AGA |
| 21 | H58A(+34+64) | UUC GUC CAG UCU CAA GAG UAC UCA UGA UUA C |
| 22 | H58D(+17-07) | CAA UUA CCU CUG GGC UCC UGG UAG |
| 23 | H59A(+96+120) | CUA UUU UUC UCU GCC AGU CAG CGG A |
| 24 | H60A(+33+62) | CGA GCA AGG UCA UUG ACG UGG CUC ACG UUC |
| 25 | H61A(+10+40) | GGG CUU CAU GCA GCU GCC UGA CUC GGU CCU C |
| 26 | H62A(23+52) | UAG GGC ACU UUG UUU GGC GAG AUG GCU CUC |
| 27 | H63A(+20+49) | GAG CUC UGU CAU UUU GGG AUG GUC CCA GCA |
| 28 | H64A(+34+62) | CUG CAG UCU UCG GAG UUU CAU GGC AGU CC |
| 29 | H66A(-8+19) | GAU CCU CCC UGU UCG UCC CUA UU AUG |
| 30 | H67A(+17+47) | GCG CUG GUC ACA AAA UCC UGU UGA ACU UGC |
| 31 | H3A(+30+60) | UAG GAG GCG CCU CCC AUC CUG UAG GUC ACU G |
| 32 | H3A(+61+85) | G CCC UGU CAG GCC UUC GAG GAG GUC |
| 33 | H4A(+11+40) | UGU UCA GGG CAU GAA CUC UUG UGG AUC CUU |
| 34 | H4D(+14-11) | GUA CUA CUU ACA UUA UUG UUC UGC A |
| 35 | H8A(-06+24) | UAU CUG GAU AGG UGG UAU CAA CAU CUG UAA |

*Fig. 46A*

| SEQ ID | Exon | Sequence |
|---|---|---|
| 36 | H8A(+134+158) | AUG UAA CUG AAA AUG UUC UUC UUU A |
| 37 | H10A(-05+16) | CAG GCG CUU CCA AAU GCU GCA |
| 38 | H10A(+98+119) | UCC UCA GCA GAA AGA AGC CAC G |
| 39 | H26A(-07+19) | CCU CCU UUC UGG CAU AGA CCU UCC AC |
| 40 | H26A(+24+50) | CUU ACA GUU UUC UCC AAA CCU CCC UUC |
| 41 | H26A(+68+92) | UGU GUC AUC CAU UCG UGC AUC UCU G |
| 42 | H36A(-16+09) | CUG GUA UUC CUU AAU UGU ACA GAG A |
| 43 | H36A(+22+51) | UGU GAU GUG GUC CAC AUU CUG GUC AAA AGU |
| 44 | H48A(+01+28) | CUU GUU UCU CAG GUA AAG CUC UGG AAA C |
| 45 | H48A(+40+67) | CAA GCU GCC CAA GGU CUU UUA UUU GAG C |
| 46 | H60A(+87+116) | UCC AGA GUG CUG AGG UUA UAC GGU GAG AGC |
| 47 | H60A(+37+66) | CUG GCG AGC AAG GUC UUG ACG UGG CUC AC |
| 48 | H66A(-02+28) | CAG GAC ACG GAU CCU CCC UGU UCG UCC CCU |
| 49 | H66D(+13-17) | UAA UAU ACA CGA CUU ACA UCU GUA CUU GUC |
| 50 | H68A(+48+72) | CAC CAU GGA CUG GGG UUC CAG UCU C |
| 51 | H68D(+23-03) | UAC CUG AAU CCA AUG AUU GGA CAC UC |
| 52 | H11A(+50+79) | CUG UUC CAA UCA GCU ACU UCC AAU UGU A |
| 53 | H12A(+30+57) | CAG UCA UUC AAC UCU UUC AGU UUC UGA U |
| 54 | H44A(+59+85) | CUG UUC AGC UUC UGU UAG CCA CUG AUU |
| 55 | H45A(-03+25) | GCU GCC CAA UGA CAU CCU GGA GUU CCU G |
| 56 | H46A(+93+122) | GUU GCU GCU CUU UUC CAG GUU CAA GUG GGA |
| 57 | H51A(+71+100) | GGU ACC UCC AAC AUC AAG GAA GAU GGC AUU |
| 58 | H52A(+09+38) | UCC AAC UGG GGA CGC CUC UGU UCC AAA UCC UGC |
| 59 | H53A(+33+65) | UUC AAC UGU UGC CUC CGG UUC UGA AGG UGU UCU |
| 60 | H73A(+02+26) | CAU UGC UGU UUU CCA UUU CUG GUA G |
| 61 | H45A(-06+25) | GCU GCC CAA UGC CAU CU\CU GGA GUU CCU GUA A |
| 62 | H45A(-12+19) | CAA UGC CAU CCU GGA GUU CCU GUA AGA UAC C |

*Fig. 46B*

SEQUENCE LISTING

<160> NUMBER OF SEQ ID NOS: 464

<210> SEQ ID NO 1
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H5A(+35+65)

<400> SEQUENCE: 1
aaaccaagag ucaguuuaug auuuccaucu a                          31

<210> SEQ ID NO 2
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H12A(+52+75)

<400> SEQUENCE: 2
ucuucuguuu uuguuagcca guca                                  24

<210> SEQ ID NO 3
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H17A(−07+23)

<400> SEQUENCE: 3
guggugguga cagccuguga aaucugugag                            30

<210> SEQ ID NO 4
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H17A(+61+86)

<400> SEQUENCE: 4
uguucccuug uggucaccgu aguuac                                26

-continued

```
<210> SEQ ID NO 5
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: H21A(+86+114)

<400> SEQUENCE: 5
cacaaagucu gcauccagga acauggguc                                    29

<210> SEQ ID NO 6
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H21A(+90+119)

<400> SEQUENCE: 6
aaggccacaa agucugcauc caggaacaug                                   30

<210> SEQ ID NO 7
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: Exon: H22A(+125+146)

<400> SEQUENCE: 7
cugcaauucc ccgagucucu gc                                           22

<210> SEQ ID NO 8
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: Exon: H24A(+51+73)

<400> SEQUENCE: 8
caagggcagg ccauuccucc uuc                                          23

<210> SEQ ID NO 9
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H43A(+92 +117)

<400> SEQUENCE: 9
gagagcuucc uguagcuuca cccuuu                                       26

<210> SEQ ID NO 10
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H44A(+65+90)
```

```
<400> SEQUENCE: 10
uguucagcuu cuguuagcca cuga                                              24

<210> SEQ ID NO 11
<211> LENGTH: 34
<212> TYPE: RNA
<213> ORGANISM: Homo sapiens
<220> FEATURE:
<221> NAME/KEY: misc_feature
<222> LOCATION: (1)..(34)
<223> OTHER INFORMATION: Exon: H45A (-09+25)

<400> SEQUENCE: 11
gcugcccaau gccauccugg aguuccugua agau                                   34

<210> SEQ ID NO 12
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: H46A(+81+109)

<400> SEQUENCE: 12
uccagguuca agugggauac uagcaaugu                                         29

<210> SEQ ID NO 13
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: H47A(+01+29)

<400> SEQUENCE: 13
uggcgcaggg gcaacucuuc caccaguaa                                         29

<210> SEQ ID NO 14
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H49A(+45+ 70)

<400> SEQUENCE: 14
acaaaugcug cccuuuagac aaaauc                                            26

<210> SEQ ID NO 15
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H50A(+48+74)

<400> SEQUENCE: 15
ggcugcuuug cccucagcuc uugaagu                                           27

<210> SEQ ID NO 16
<211> LENGTH: 31
<212> TYPE: RNA
<213> ORGANISM: Homo sapiens
```

```
<220> FEATURE:
<221> NAME/KEY: misc_feature
<222> LOCATION: (1)..(31)
<223> OTHER INFORMATION: Exon: H54A(+67+97)

<400> SEQUENCE: 16
uggucucauc ugcagaauaa ucccggagaa g                              31

<210> SEQ ID NO 17
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H55A(-10 +20)

<400> SEQUENCE: 17
cagccucucg cucacucacc cugcaaagga                                30

<210> SEQ ID NO 18
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H56A(+92+121)

<400> SEQUENCE: 18
ccaaacgucu uuguaacagg acugcau                                   27

<210> SEQ ID NO 19
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H56A(+112+141)

<400> SEQUENCE: 19
ccacuugaag uucauguuau ccaaacgucu                                30

<210> SEQ ID NO 20
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H57A(-10+20)

<400> SEQUENCE: 20
aacuggcuuc caaaugggac cugaaaaga                                 30

<210> SEQ ID NO 21
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H58A(+34+64)

<400> SEQUENCE: 21
uucguacagu cucaagagua cucaugauua c                              31
```

```
<210> SEQ ID NO 22
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H58D(+17-07)

<400> SEQUENCE: 22
caauuaccuc ugggcuccug guag                                          24

<210> SEQ ID NO 23
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H59A(+96 +120)

<400> SEQUENCE: 23
cuauuuuucu cugccaguca gcgga                                         25

<210> SEQ ID NO 24
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H60A(+33+62)

<400> SEQUENCE: 24
cgagcaaggu cauugacgug gcucacguuc                                    30

<210> SEQ ID NO 25
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H61A(+10+40)

<400> SEQUENCE: 25
gggcuucaug cagcugccug acucgguccu c                                  31

<210> SEQ ID NO 26
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H62A(23+52)

<400> SEQUENCE: 26
uagggcacuu uguuggcga gauggcucuc                                     30

<210> SEQ ID NO 27
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H63A(+20+49)
```

<400> SEQUENCE: 27
gagcucuguc auuuugggau ggucccagca                                              30

<210> SEQ ID NO 28
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: H64A(+34+62)

<400> SEQUENCE: 28
cugcagucuu cggaguuuca uggcagucc                                               29

<210> SEQ ID NO 29
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H66A(-8+19)

<400> SEQUENCE: 29
gauccucccu guucgucccc uauuaug                                                 27

<210> SEQ ID NO 30
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H67A(+17+47)

<400> SEQUENCE: 30
gcgcugguca caaaauccug uugaacuugc                                              30

<210> SEQ ID NO 31
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H3A(+30+60)

<400> SEQUENCE: 31
uaggaggcgc cucccauccu guaggucacu g                                            31

<210> SEQ ID NO 32
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H3A(+61 +85)

<400> SEQUENCE: 32
gcccugucag gccuucgagg agguc                                                   25

<210> SEQ ID NO 33
<211> LENGTH: 30
<212> TYPE: RNA

```
<213> ORGANISM: Homo sapiens
<220> FEATURE:
<221> NAME/KEY: misc_feature
<222> LOCATION: (1)..(30)
<223> OTHER INFORMATION: Exon: H4A(+11+40)

<400> SEQUENCE: 33
uguucagggc augaacucuu guggauccuu                                30

<210> SEQ ID NO 34
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H4D(+14-11 )

<400> SEQUENCE: 34
guacuacuua cauuauuguu cugca                                     25

<210> SEQ ID NO 35
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H8A(-06+24)

<400> SEQUENCE: 35
uaucuggaua ggugguauca acaucuguaa                                30

<210> SEQ ID NO 36
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H8A

<400> SEQUENCE: 36
auguaacuga aaauguucuu cuuua                                     25

<210> SEQ ID NO 37
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: Exon: H10A

<400> SEQUENCE: 37
caggagcuuc gaaauggugg a                                         21

<210> SEQ ID NO 38
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: Exon: H10A(+98+119)

<400> SEQUENCE: 38
```
uccucagcag aaagaagcca cg                                              22

<210> SEQ ID NO 39
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H26A(-07+19)

<400> SEQUENCE: 39
ccuccuuucu ggcauagacc uuccac                                          26

<210> SEQ ID NO 40
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H26A

<400> SEQUENCE: 40
cuuacaguuu ucuccaaacc ucccuuc                                         27

<210> SEQ ID NO 41
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H26A

<400> SEQUENCE: 41
ugugucaugc auucgugcau gucug                                           25

<210> SEQ ID NO 42
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H36A( -16+09)

<400> SEQUENCE: 42
cugguauucc uuaauuguac agaga                                           25

<210> SEQ ID NO 43
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H36A(+22+51)

<400> SEQUENCE: 43
ugugaugugg uccacauucu ggucaaaagu                                      30

<210> SEQ ID NO 44
<211> LENGTH: 28
<212> TYPE: RNA
<213> ORGANISM: Homo sapiens
<220> FEATURE:

```
<221> NAME/KEY: misc_feature
<222> LOCATION: (1)..(28)
<223> OTHER INFORMATION: Exon: H48A(+01 +28)

<400> SEQUENCE: 44
cuuguuucuc agguaaagcu cuggaaac                                              28

<210> SEQ ID NO 45
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H48A(+40+67)

<400> SEQUENCE: 45
caagcugccg aaggucuuuu auuugagc                                              28

<210> SEQ ID NO 46
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H60A(+87+116)

<400> SEQUENCE: 46
uccagagugc ugagguuaua cggugagagc                                            30

<210> SEQ ID NO 47
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H60A(+37+66)

<400> SEQUENCE: 47
cuggcgagca agguccuuga cguggcucac                                            30

<210> SEQ ID NO 48
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H66A(-02+28)

<400> SEQUENCE: 48
caggacacgg auccucccug uuggucccu                                             30

<210> SEQ ID NO 49
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H66D(+13-17)

<400> SEQUENCE: 49
uaauauacac gacuuacauc uguacuuguc                                            30
```

```
<210> SEQ ID NO 50
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H68A(+48+ 72)

<400> SEQUENCE: 50
cagcauggac ugggguucca gucuc                                    25

<210> SEQ ID NO 51
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H68D(+23-03)

<400> SEQUENCE: 51
uaccugaauc caaugauugg acacuc                                   26

<210> SEQ ID NO 52
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H11A(+50+79)

<400> SEQUENCE: 52 cguuccaau cagcuuacuu cccaauugua                                30

<210> SEQ ID NO 53
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H12A(+30+57)

<400> SEQUENCE: 53
cagucauuca agucuuucag uuugugau                                 28

<210> SEQ ID NO 54
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H44A(+59+85)

<400> SEQUENCE: 54 cguucagcu ucuguuagcc acugauu                                   27

<210> SEQ ID NO 55
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H45A(-03+25)
```

```
<400> SEQUENCE: 55
gcugcccaau gccauccugg aguuccug                                          28

<210> SEQ ID NO 56
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H46A(+93+122)

<400> SEQUENCE: 56
guugcugcuc uuuuccaggu ucaagugggu                                        30

<210> SEQ ID NO 57
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H51A(+71 +100)

<400> SEQUENCE: 57
gguaccucca acaucaagga agauggcauu                                        30

<210> SEQ ID NO 58
<211> LENGTH: 33
<212> TYPE: RNA
<213> ORGANISM: Homo sapiens
<220> FEATURE:
<221> NAME/KEY: misc_feature
<222> LOCATION: (1)..(33)
<223> OTHER INFORMATION: Exon: H52A(+09+38)

<400> SEQUENCE: 58
uccaacuggg gacgccucug uuccaaaucc ugc                                    33

<210> SEQ ID NO 59
<211> LENGTH: 33
<212> TYPE: RNA
<213> ORGANISM: Homo sapiens
<220> FEATURE:
<221> NAME/KEY: misc_feature
<222> LOCATION: (1)..(33)
<223> OTHER INFORMATION: Exon: H53A(+33+65)

<400> SEQUENCE: 59
uucaacuguu gccuccgguu cugaaggugu ucu                                    33

<210> SEQ ID NO 60
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H73A(+02+26)

<400> SEQUENCE: 60
cauugcuguu uuccauuucu gguag                                             25

<210> SEQ ID NO 61
<211> LENGTH: 31
<212> TYPE: RNA
<213> ORGANISM: Homo sapiens
```

```
<220> FEATURE:
<221> NAME/KEY: misc_feature
<222> LOCATION: (1)..(31)
<223> OTHER INFORMATION: Exon: H45A(-06+25)

<400> SEQUENCE: 61
gcugcccaau gccauccugg aguuccugua a                                              31

<210> SEQ ID NO 62
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H45A(-12+19)

<400> SEQUENCE: 62
caaugccauc cuggaguucc uguaagauac c                                              31

<210> SEQ ID NO 63
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: Exon: H45A(-3+19)

<400> SEQUENCE: 63
caaugccauc cuggaguucc ug                                                        22

<210> SEQ ID NO 64
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H45A(-9+19)

<400> SEQUENCE: 64
caaugccauc cuggaguucc uguaagau                                                  28

<210> SEQ ID NO 65
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H45A(-9+16)

<400> SEQUENCE: 65
ugccauccug gaguuccugu aagau                                                     25

<210> SEQ ID NO 66
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H45A(-7+21)

<400> SEQUENCE: 66
ugccauccug gaguuccugu aagauacc                                                  28
```

```
<210> SEQ ID NO 67
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H53A(+27+56)

<400> SEQUENCE: 67
ccuccgguuc ugaaggguguu cuuguacuuc                                    30

<210> SEQ ID NO 68
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H44A(-6+20)

<400> SEQUENCE: 68
caacagaucu gucaaaucgc cugcag                                         26

<210> SEQ ID NO 69
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H51A(+71+100)

<400> SEQUENCE: 69
gguaccucca acaucaagga agauggcauu                                     30

<210> SEQ ID NO 70
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H8A(+57+83)

<400> SEQUENCE: 70
gcucacuugu ugaggcaaaa cuuggaa                                        27

<210> SEQ ID NO 71
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H8A(+42+66)

<400> SEQUENCE: 71
aaacuuggaa gagugaugug augua                                          25

<210> SEQ ID NO 72
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: Exon: H7A(+49+71)
```

```
<400> SEQUENCE: 72
ugaaugcaug uuccagucgu ugu                                    23

<210> SEQ ID NO 73
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H7A(+41+67)

<400> SEQUENCE: 73
ugcauguucc agucguugug uggcuga                                27

<210> SEQ ID NO 74
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: H43A(+92+120)

<400> SEQUENCE: 74
ggagagagcu uccuguagcu ucacccuuu                              29

<210> SEQ ID NO 75
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H2A(-14+10)

<400> SEQUENCE: 75
ucucuuucau cuaaaaugca aaau                                   24

<210> SEQ ID NO 76
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H2A(-1+23)

<400> SEQUENCE: 76
cuuuugaaca ucuucucuuu cauc                                   24

<210> SEQ ID NO 77
<211> LENGTH: 32
<212> TYPE: RNA
<213> ORGANISM: Homo sapiens
<220> FEATURE:
<221> NAME/KEY: misc_feature
<222> LOCATION: (1)..(32)
<223> OTHER INFORMATION: Exon: H2A(+7+38)

<400> SEQUENCE: 77
uuuugugaau guuuucuuuu gaacaucuuc uc                          32

<210> SEQ ID NO 78
<211> LENGTH: 24
<212> TYPE: RNA
```

```
<213> ORGANISM: Homo sapiens
<220> FEATURE:
<221> NAME/KEY: misc_feature
<222> LOCATION: (1)..(24)
<223> OTHER INFORMATION: Exon: H2A(+16+39)

<400> SEQUENCE: 78
auuuugugaa uguuuucuuu ugaa                                      24

<210> SEQ ID NO 79
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H2A(+30+60)

<400> SEQUENCE: 79
uagaaaauug ugcauuuacc cauuuuguga a                              31

<210> SEQ ID NO 80
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H2D(+19-11)

<400> SEQUENCE: 80
accauucuua ccuuagaaaa uugugcauuu                                30

<210> SEQ ID NO 81
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H2D(+03-21)

<400> SEQUENCE: 81
aaaguaacaa accauucuua ccuu                                      24

<210> SEQ ID NO 82
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H3A(+14+38)

<400> SEQUENCE: 82
aggucacuga agagguucuc aauau                                     25

<210> SEQ ID NO 83
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: Exon: H3A(+20+40)

<400> SEQUENCE: 83
guaggucacu gaagagguuc u                                         21
```

```
<210> SEQ ID NO 84
<211> LENGTH: 35
<212> TYPE: RNA
<213> ORGANISM: Homo sapiens
<220> FEATURE:
<221> NAME/KEY: misc_feature
<222> LOCATION: (1)..(35)
<223> OTHER INFORMATION: Exon: H3A(+25+60)

<400> SEQUENCE: 84
aggaggcguc ucccauccug uaggucacug aagag                              35

<210> SEQ ID NO 85
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: Exon: H3A(+45+65)

<400> SEQUENCE: 85
aggucuagga ggcgccuccc a                                             21

<210> SEQ ID NO 86
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H3A(+48+73)

<400> SEQUENCE: 86
cuucgaggag gucuaggagg cgccuc                                        26

<210> SEQ ID NO 87
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H30D(+17-08)

<400> SEQUENCE: 87
ucacauacag uuuuugcccu gucag                                         25

<210> SEQ ID NO 88
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: Exon: H3D(+19-02)

<400> SEQUENCE: 88
uacaguuuuu gcccugucag g                                             21

<210> SEQ ID NO 89
<211> LENGTH: 24
<212> TYPE: RNA
<213> ORGANISM: Homo sapiens
<220> FEATURE:
<221> NAME/KEY: misc_feature
<222> LOCATION: (1)..(24)
```

<223> OTHER INFORMATION: Exon: H3D(+14-10)

<400> SEQUENCE: 89
aagucacaua caguuuugc ccug       24

<210> SEQ ID NO 90
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: Exon: H3D(+12-07)

<400> SEQUENCE: 90
ucacauacag uuuugccc       19

<210> SEQ ID NO 91
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H4A(-08+17)

<400> SEQUENCE: 91
gauccuuuuu cuuuggcug agaac       25

<210> SEQ ID NO 92
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H4A(+36+60)

<400> SEQUENCE: 92
ccgcagugcc uuguugacau uguuc       25

<210> SEQ ID NO 93
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H4D(+14-11)

<400> SEQUENCE: 93
guacuacuua cauuauuguu cugca       25

<210> SEQ ID NO 94
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H5D(+26-05)

<400> SEQUENCE: 94
cuuaccugcc aguggaggau uauauuccaa a       31

<210> SEQ ID NO 95
<211> LENGTH: 26

-continued

```
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H6A

<400> SEQUENCE: 95
uucauuacau uuuugaccua caugug                                              26

<210> SEQ ID NO 96
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H6A(+32+57)

<400> SEQUENCE: 96
cuuuucacug uugguuuguu gcaauc                                              26

<210> SEQ ID NO 97
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: KH9 6A(+66+94)

<400> SEQUENCE: 97
aauuacgagu ugauugucgg acccagcuc                                           29

<210> SEQ ID NO 98
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H6A(+69+96)

<400> SEQUENCE: 98
auaauuacga guugauuguc ggacccag                                            28

<210> SEQ ID NO 99
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H6A(+98+123)

<400> SEQUENCE: 99
ggugaaguug auuacauuaa ccugug                                              26

<210> SEQ ID NO 100
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H6D(+18-06)

<400> SEQUENCE: 100
```
ucuuaccuau gacuauggau gaga                                24

<210> SEQ ID NO 101
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: Exon: H6D(+07-15)

<400> SEQUENCE: 101
caguaaucuu cuuaccuaug ac                                  22

<210> SEQ ID NO 102
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: Exon: H6D(+07-16)

<400> SEQUENCE: 102
ucaguaaucu cuuaccuau gac                                  23

<210> SEQ ID NO 103
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H6D(+04-20)

<400> SEQUENCE: 103
ugucucagua aucuucuuac cuau                                24

<210> SEQ ID NO 104
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: Exon: H7A(-07+15)

<400> SEQUENCE: 104
ucaaauaggu cuggccuaaa ac                                  22

<210> SEQ ID NO 105
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: Exon: H7A(-03+18)

<400> SEQUENCE: 105
ccagucaaau aggucuggcc ua                                  22

<210> SEQ ID NO 106
<211> LENGTH: 23
<212> TYPE: RNA
<213> ORGANISM: Homo sapiens
<220> FEATURE:
<221> NAME/KEY: misc_feature

```
<222> LOCATION: (1)..(23)
<223> OTHER INFORMATION: Exon: H7A(+41+63)

<400> SEQUENCE: 106
uguuccaguc guugugggc uga                                              23

<210> SEQ ID NO 107
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H7A(+47+74)

<400> SEQUENCE: 107
uguugaaugc auguuccagu cguugugu                                        28

<210> SEQ ID NO 108
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H8A(-10+20)

<400> SEQUENCE: 108
uggauaggug guaucaacau cuguaagcac                                      30

<210> SEQ ID NO 109
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: Exon: H8A(-07+15)

<400> SEQUENCE: 109
aggugguauc aacaucugua ag                                              22

<210> SEQ ID NO 110
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: Exon: H8A(-04+18)

<400> SEQUENCE: 110
gauagguggu aucaacaucu gu                                              22

<210> SEQ ID NO 111
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H8A(+96+120)

<400> SEQUENCE: 111
gccuuggcaa cauuuccacu uccug                                           25

<210> SEQ ID NO 112
```

```
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H8D(+13-12)

<400> SEQUENCE: 112
uacacacuuu accuguugag aauag                                               25

<210> SEQ ID NO 113
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H9A(+154+184)

<400> SEQUENCE: 113
agcagccugu guguaggcau agcucuugaa u                                        31

<210> SEQ ID NO 114
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H9D(+26-04)

<400> SEQUENCE: 114
agaccuguga aggaaauggg cuccguguag                                          30

<210> SEQ ID NO 115
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H10A(-09+16)

<400> SEQUENCE: 115
caggagcuuc caaaugcugc acaau                                               25

<210> SEQ ID NO 116
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H10A(+08+27)

<400> SEQUENCE: 116
ugacuugucu ucaggagcuu                                                     20

<210> SEQ ID NO 117
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: Exon: H10A (+21 +42)

<400> SEQUENCE: 117
```
caaugaacug ccaaaugacu ug                                                    22

<210> SEQ ID NO 118
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H10A(+27+51)

<400> SEQUENCE: 118
acucuccauc aaugaacugc caaau                                                 25

<210> SEQ ID NO 119
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H10A(+55+79)

<400> SEQUENCE: 119
cuguuugaua acguccagg uuuac                                                  25

<210> SEQ ID NO 120
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H10A(+80+103)

<400> SEQUENCE: 120
gccacgauaa uacuucuucu aaag                                                  24

<210> SEQ ID NO 121
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H10D(+16-09)

<400> SEQUENCE: 121
uuaguuuacc ucaugaguau gaaac                                                 25

<210> SEQ ID NO 122
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H10A(+130+149)

<400> SEQUENCE: 122
uuagaaaucu cuccuugugc                                                       20

<210> SEQ ID NO 123
<211> LENGTH: 20
<212> TYPE: RNA
<213> ORGANISM: Homo sapiens
<220> FEATURE:

```
<221> NAME/KEY: misc_feature
<222> LOCATION: (1)..(20)
<223> OTHER INFORMATION: Exon: H11A(-07+13)

<400> SEQUENCE: 123
ccaucaugua ccccugacaa                                              20

<210> SEQ ID NO 124
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H11A+(+134+157)

<400> SEQUENCE: 124
cccugaggca uucccaucuu gaau                                         24

<210> SEQ ID NO 125
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H11A(+20+45)

<400> SEQUENCE: 125
auuaccaacc cggcccugau gggcug                                       26

<210> SEQ ID NO 126
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H11A(+46+75)

<400> SEQUENCE: 126
uccaaucagc uuacuuccca auguagaau                                    30

<210> SEQ ID NO 127
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H11A(+50+75)

<400> SEQUENCE: 127
uccaaucagc uuacuuccca auugua                                       26

<210> SEQ ID NO 128
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H11A(+80+105)

<400> SEQUENCE: 128
aguuucuuca ucuucugaua auuuc                                        26
```

```
<210> SEQ ID NO 129
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H11A(+106+135)

<400> SEQUENCE: 129
auuuaggaga uucaucugcu cuuguacuuc                                          30

<210> SEQ ID NO 130
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H11A(+110+135)

<400> SEQUENCE: 130
auuuaggaga uucaucugcu cuugua                                              26

<210> SEQ ID NO 131
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H11A(+110+139)

<400> SEQUENCE: 131
uugaauuuag gagauucauc ugcucuugua                                          30

<210> SEQ ID NO 132
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: Exon: H12D(+06-16)

<400> SEQUENCE: 132
cauaagauac accuaccuua ug                                                  22

<210> SEQ ID NO 133
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H12A(+60+87)

<400> SEQUENCE: 133
uuccuuguuc uuucuucugu uuuuguua                                            28

<210> SEQ ID NO 134
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H12A(+90+117)
```

-continued

<400> SEQUENCE: 134
agaucagguc caagaggcuc uuccucca                                        28

<210> SEQ ID NO 135
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H12A(+120+147)

<400> SEQUENCE: 135
uguuguugua cuuggcguuu uaggucuu                                        28

<210> SEQ ID NO 136
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H13A(-12+12)

<400> SEQUENCE: 136
uucuugaagc accugaaaga uaaa                                            24

<210> SEQ ID NO 137
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: H14A(+45 +73)

<400> SEQUENCE: 137
gaaggauguc uuguaaaaga acccagcgg                                       29

<210> SEQ ID NO 138
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H16A(-07+19)

<400> SEQUENCE: 138
cuagauccgc uuuuaaaacc uguuaa                                          26

<210> SEQ ID NO 139
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: Exon: H16A(+09+31)

<400> SEQUENCE: 139
gcuuuuucuu uucuagaucc gcu                                             23

<210> SEQ ID NO 140
<211> LENGTH: 25
<212> TYPE: RNA
<213> ORGANISM: Homo sapiens

```
<220> FEATURE:
<221> NAME/KEY: misc_feature
<222> LOCATION: (1)..(25)
<223> OTHER INFORMATION: Exon: H16D(+18-07)

<400> SEQUENCE: 140
cacuaaccug ugcuguacuc uuuuc                                              25

<210> SEQ ID NO 141
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H17A(+48+78)

<400> SEQUENCE: 141
uguggucacc guaguuacug uuccauuca a                                        31

<210> SEQ ID NO 142
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H17A(+55+85)

<400> SEQUENCE: 142
guucccuugu ggucaccgua guuacuguuu c                                       31

<210> SEQ ID NO 143
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H18A(-09+11)

<400> SEQUENCE: 143
caacauccuu ccuaagacug                                                    20

<210> SEQ ID NO 144
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H18A(+24+43)

<400> SEQUENCE: 144
gcgaguaauc cagcugugaa                                                    20

<210> SEQ ID NO 145
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H18A(+41 +70)

<400> SEQUENCE: 145
uucaggacuc ugcaacagag cuucugagcg                                         30
```

```
<210> SEQ ID NO 146
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H18A(+83+108)

<400> SEQUENCE: 146
uugucuguga aguugccuuc cuuccg                                              26

<210> SEQ ID NO 147
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H18D(+04-16)

<400> SEQUENCE: 147
uuaaugcaua accuacauug                                                    20

<210> SEQ ID NO 148
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H19A(+19+48)

<400> SEQUENCE: 148
ggcaucuugc aguuuucuga acuucucagc                                         30

<210> SEQ ID NO 149
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H19A(+27+54)

<400> SEQUENCE: 149
ucugcuggca ucuugcaguu uucugaac                                           28

<210> SEQ ID NO 150
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H19D(+3-17)

<400> SEQUENCE: 150
ucaacucgug uaauuaccgu                                                    20

<210> SEQ ID NO 151
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H20A(+23+47)
```

```
<400> SEQUENCE: 151
guucaguugu ucugaggcuu guuug                                          25

<210> SEQ ID NO 152
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H20A(+140+164)

<400> SEQUENCE: 152
aguaguuguc aucugcucca auugu                                          25

<210> SEQ ID NO 153
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H23(+69+98)-SNP

<400> SEQUENCE: 153
cggcuaauuu cagagggcgc uuucuuugac                                     30

<210> SEQ ID NO 154
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H25A(+10+33)

<400> SEQUENCE: 154
ugggcugaau ugucugaaua ucac                                           24

<210> SEQ ID NO 155
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H25D(+06-14)

<400> SEQUENCE: 155
gagauugucu auaccuguug                                                20

<210> SEQ ID NO 156
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: H25A(+10+38)

<400> SEQUENCE: 156
agacugggcu gaauugucug aauaucacu                                      29

<210> SEQ ID NO 157
<211> LENGTH: 26
<212> TYPE: RNA
```

```
<213> ORGANISM: Homo sapiens
<220> FEATURE:
<221> NAME/KEY: misc_feature
<222> LOCATION: (1)..(26)
<223> OTHER INFORMATION: Exon: H25A(+95+119)-DupA

<400> SEQUENCE: 157
uugaguucug uucucaaguc ucgaag                                26

<210> SEQ ID NO 158
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H25D(+13-14)

<400> SEQUENCE: 158
gagauugucu auaccuguug gcacaug                               27

<210> SEQ ID NO 159
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H26A(-16+09)

<400> SEQUENCE: 159
ggcauagacc uuccacaaaa caaac                                 25

<210> SEQ ID NO 160
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H26A(-7+23)

<400> SEQUENCE: 160
aaggccuccu uucuggcaua gaccuuccac                            30

<210> SEQ ID NO 161
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H26A(-03+27)

<400> SEQUENCE: 161
cuucaaggcc uccuuucugg cauagaccuu                            30

<210> SEQ ID NO 162
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H26A(+5+35)

<400> SEQUENCE: 162
aaccucccuu caaggccucc uuucuggcau                            30
```

<210> SEQ ID NO 163
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H26D(+06-19)

<400> SEQUENCE: 163 uucuuuuuu uuuuuuacc uucau                                    25

<210> SEQ ID NO 164
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H26D(+21-04)

<400> SEQUENCE: 164
uuaccuucau cucuucaacu gcuuu                                  25

<210> SEQ ID NO 165
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H26D(+10-10)

<400> SEQUENCE: 165 uuuuuuuac cuucaucucu                                         20

<210> SEQ ID NO 166
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H31D(+12-18)

<400> SEQUENCE: 166
uucugaaauu ucauauaccu gugcaacauc                             30

<210> SEQ ID NO 167
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H31D(+08-22)

<400> SEQUENCE: 167
uaguuucuga aauaacauau accgugcaa                              30

<210> SEQ ID NO 168
<211> LENGTH: 30
<212> TYPE: RNA
<213> ORGANISM: Homo sapiens
<220> FEATURE:
<221> NAME/KEY: misc_feature
<222> LOCATION: (1)..(30)

```
<223> OTHER INFORMATION: Exon: H31D(+06-24)

<400> SEQUENCE: 168
cuuaguuucu gaaauaacau auaccugugc                                    30

<210> SEQ ID NO 169
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H31D(+02-22)

<400> SEQUENCE: 169
uaguuucuga aauaacauau accu                                          24

<210> SEQ ID NO 170
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H31D(+01-25)

<400> SEQUENCE: 170
ccuuaguuuc ugaaauaaca uauacc                                        26

<210> SEQ ID NO 171
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H32A(+49+78)

<400> SEQUENCE: 171
acuuucuugu agacgcugcu caaaauuggc                                    30

<210> SEQ ID NO 172
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H34A(+36+59)

<400> SEQUENCE: 172
uuucgcaucu uacgggacaa uuuc                                          24

<210> SEQ ID NO 173
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H34A(+41+70)

<400> SEQUENCE: 173
cauucauuuc cuuucgcauc uuacgggaca                                    30

<210> SEQ ID NO 174
<211> LENGTH: 30
```

```
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H34A(+43+72)

<400> SEQUENCE: 174
gacauucauu uccuuucgca ucuuacggga                                 30

<210> SEQ ID NO 175
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H34A(+51+83)

<400> SEQUENCE: 175
ucugucaaga cauucauuuc cuuucgcauc                                 30

<210> SEQ ID NO 176
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H34A(+91+120)

<400> SEQUENCE: 176
ugaucucuuu gucaauucca uaucuguagc                                 30

<210> SEQ ID NO 177
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H34A(+92+121)

<400> SEQUENCE: 177
cugaucucuu ugucaauucc auaucugugg                                 30

<210> SEQ ID NO 178
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H34A(+95+120)

<400> SEQUENCE: 178
ugaucucuuu gucaauucca uaucug                                     26

<210> SEQ ID NO 179
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H34A(+95+124)

<400> SEQUENCE: 179
```
cugcugaucu cuuugucaau uccauaucug                                           30

<210> SEQ ID NO 180
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H35A(+14+43)

<400> SEQUENCE: 180
ucuucaggug caccuucugu uucucaaucu                                           30

<210> SEQ ID NO 181
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H35A(+24+53)

<400> SEQUENCE: 181
ucugugauac ucuucaggug caccuucugu                                           30

<210> SEQ ID NO 182
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H36A(-01+19)

<400> SEQUENCE: 182
ccauguguuu cugguauucc                                                      20

<210> SEQ ID NO 183
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H36A(+10+39)

<400> SEQUENCE: 183
cacauucugg ucaaaaguuu ccauguguuu                                           30

<210> SEQ ID NO 184
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H36A(+27+51)

<400> SEQUENCE: 184
ugugaugugg uccacauucu gguca                                                25

<210> SEQ ID NO 185
<211> LENGTH: 30
<212> TYPE: RNA
<213> ORGANISM: Homo sapiens
<220> FEATURE:
<221> NAME/KEY: misc_feature

```
<222> LOCATION: (1)..(30)
<223> OTHER INFORMATION: Exon: H36A(+27+56)

<400> SEQUENCE: 185
cacuuuguga ugugguccac auucugguca                                   30

<210> SEQ ID NO 186
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H36A(+32+61)

<400> SEQUENCE: 186
ugauccacuu ugugaugugg uccacauucu                                   30

<210> SEQ ID NO 187
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H36A(+59+78)

<400> SEQUENCE: 187
aaguguguca gccugaauga                                              20

<210> SEQ ID NO 188
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H36A(+65+94)

<400> SEQUENCE: 188
ucucugauuc auccaaaagu gugucagccu                                   30

<210> SEQ ID NO 189
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H36A(+80+109)

<400> SEQUENCE: 189 gcuggguuu cuuuuucucu gauucaucca                                    30

<210> SEQ ID NO 190
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H36D(+15-10)

<400> SEQUENCE: 190
uauuugcuac cuuaagcacg ucuuc                                        25

<210> SEQ ID NO 191
```

```
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: Exon: H38A(-21-01)

<400> SEQUENCE: 191
cuaaaaaaaa agauagugcu a                                           21

<210> SEQ ID NO 192
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H38A(-12+14)

<400> SEQUENCE: 192
aaaggaaugg aggccuaaaa aaaaag                                      26

<210> SEQ ID NO 193
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H38D(+14-11)

<400> SEQUENCE: 193
aaccaauuua ccauaucuuu auuga                                       25

<210> SEQ ID NO 194
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: H39A(-07+23)

<400> SEQUENCE: 194
acaguaccau cauugucuuc auucugauc                                   29

<210> SEQ ID NO 195
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: H39A(-07+23)

<400> SEQUENCE: 195
acaguacccu cauugucuuc auucugauc                                   29

<210> SEQ ID NO 196
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H39A(+58+87)

<400> SEQUENCE: 196
```
cucucgcuuu cucucaucug ugauucuuug                                30

<210> SEQ ID NO 197
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H39A(+60+89)

<400> SEQUENCE: 197
uccucucgcu uucucucauc ugugauucuu                                30

<210> SEQ ID NO 198
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H39A(+102+126)

<400> SEQUENCE: 198
uauguuuugu cuguaacagc ugcug                                     25

<210> SEQ ID NO 199
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H41A(-15+5)

<400> SEQUENCE: 199
auuuccuauu gagcaaaacc                                           20

<210> SEQ ID NO 200
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H41A(+66+90)

<400> SEQUENCE: 200
cauugcggcc ccauccucag acaag                                     25

<210> SEQ ID NO 201
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: H41A(+92+120)

<400> SEQUENCE: 201
gcugagcugg aucugaguug gcuccacug                                 29

<210> SEQ ID NO 202
<211> LENGTH: 29
<212> TYPE: RNA
<213> ORGANISM: Homo sapiens
<220> FEATURE:

```
<221> NAME/KEY: misc_feature
<222> LOCATION: (1)..(29)
<223> OTHER INFORMATION: Exon: H41A(+143+171)

<400> SEQUENCE: 202
guugagucuu cgaaacugag caaauuugc                                      29

<210> SEQ ID NO 203
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H41D(+5-15)

<400> SEQUENCE: 203
ccaguaacaa cucacaauuu                                                20

<210> SEQ ID NO 204
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: Exon: H42D(+18-02)

<400> SEQUENCE: 204
accuucagag acuccucuug c                                              21

<210> SEQ ID NO 205
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H43A(+83+110)

<400> SEQUENCE: 205
uccuguagcu ucacccuuuc cacaggcg                                       28

<210> SEQ ID NO 206
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: H43A(+101 +130)

<400> SEQUENCE: 206
aaucagcugg gagagagcuu ccuguagcu                                      29

<210> SEQ ID NO 207
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H43D(+08-12)

<400> SEQUENCE: 207
uguguuaccu acccuugucg                                                20
```

```
<210> SEQ ID NO 208
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H43A(-09+18)

<400> SEQUENCE: 208
uagacuaucu uuuauauucu guaauau                                                27

<210> SEQ ID NO 209
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: H43A(+89+117)

<400> SEQUENCE: 209
gagagcuucc uguagcuuca cccuuucca                                              29

<210> SEQ ID NO 210
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H43A(+81+111)

<400> SEQUENCE: 210
uuccuguagc uucacccuuu ccacaggcgu u                                           31

<210> SEQ ID NO 211
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: Exon: H43A(+92+114)

<400> SEQUENCE: 211
agcuuccugu agcuucaccc uuu                                                    23

<210> SEQ ID NO 212
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: Exon: H43A(+95+117)

<400> SEQUENCE: 212
gagagcuucc uguagcuuca ccc                                                    23

<210> SEQ ID NO 213
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H44A(-13+13)
```

```
<400> SEQUENCE: 213
ucugucaaau cgccugcagg uaaaag                                          26

<210> SEQ ID NO 214
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H44A(-06+24)

<400> SEQUENCE: 214
uucucaacag aucugucaaa ucgccugcag                                      30

<210> SEQ ID NO 215
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H44A(+44+68)

<400> SEQUENCE: 215
gccacugauu aaauaucuuu auauc                                           25

<210> SEQ ID NO 216
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H44A(+46+75)

<400> SEQUENCE: 216
ucuguuagcc acugauuaaa uaucuuuaua                                      30

<210> SEQ ID NO 217
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H44A(+61+84)

<400> SEQUENCE: 217
uguucagcuu cuguuagcca cuga                                            24

<210> SEQ ID NO 218
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H44A(+61+91)

<400> SEQUENCE: 218
gagaaacugu ucagcuucug uuagccacug a                                    31

<210> SEQ ID NO 219
<211> LENGTH: 31
<212> TYPE: RNA
<213> ORGANISM: Homo sapiens
```

```
<220> FEATURE:
<221> NAME/KEY: misc_feature
<222> LOCATION: (1)..(31)
<223> OTHER INFORMATION: Exon: H44A(+68+98)

<400> SEQUENCE: 219
ucuuucugag aaacuguuca gcuucuguua g                              31

<210> SEQ ID NO 220
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H44A(-09+17)

<400> SEQUENCE: 220
cagaucuguc aaaucgccug caggua                                   26

<210> SEQ ID NO 221
<211> LENGTH: 33
<212> TYPE: RNA
<213> ORGANISM: Homo sapiens
<220> FEATURE:
<221> NAME/KEY: misc_feature
<222> LOCATION: (1)..(33)
<223> OTHER INFORMATION: Exon: H44A(+56+88)

<400> SEQUENCE: 221
aaacuguuca gcuucuguua gccacugauu aaa                           33

<210> SEQ ID NO 222
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H44A(+59+89)

<400> SEQUENCE: 222
gaaacuguuc agcuucuguu agccacugau u                             31

<210> SEQ ID NO 223
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H44A(+61+88)

<400> SEQUENCE: 223
aaacuguuca gcuucuguua gccacuga                                 28

<210> SEQ ID NO 224
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H44A(+65+92)

<400> SEQUENCE: 224
ugagaaacug uucagcuucu guuagcca                                 28
```

```
<210> SEQ ID NO 225
<211> LENGTH: 32
<212> TYPE: RNA
<213> ORGANISM: Homo sapiens
<220> FEATURE:
<221> NAME/KEY: misc_feature
<222> LOCATION: (1)..(32)
<223> OTHER INFORMATION: Exon: H44A(+64+95)

<400> SEQUENCE: 225
uucugagaaa cuguucagcu ucuguuagcc ac                                 32

<210> SEQ ID NO 226
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H44A(+70+95)

<400> SEQUENCE: 226
uucugagaaa cuguucagcu ucuguu                                        26

<210> SEQ ID NO 227
<211> LENGTH: 32
<212> TYPE: RNA
<213> ORGANISM: Homo sapiens
<220> FEATURE:
<221> NAME/KEY: misc_feature
<222> LOCATION: (1)..(32)
<223> OTHER INFORMATION: Exon: H45A(-14+25)

<400> SEQUENCE: 227
gcugcccaau gccauccugg aguuccugua ag                                 32

<210> SEQ ID NO 228
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H45A(-10 +20)

<400> SEQUENCE: 228
ccaaugccau ccuggaguuc cuguaagaua                                    30

<210> SEQ ID NO 229
<211> LENGTH: 39
<212> TYPE: RNA
<213> ORGANISM: Homo sapiens
<220> FEATURE:
<221> NAME/KEY: misc_feature
<222> LOCATION: (1)..(39)
<223> OTHER INFORMATION: Exon: H45A(-09+30)

<400> SEQUENCE: 229
uugccgcugc ccaaugccau ccuggaguuc cuguaagau                          39

<210> SEQ ID NO 230
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H45A(-08 +19)
```

<400> SEQUENCE: 230
caaugccauc cuggaguucc uguaaga                                    27

<210> SEQ ID NO 231
<211> LENGTH: 32
<212> TYPE: RNA
<213> ORGANISM: Homo sapiens
<220> FEATURE:
<221> NAME/KEY: misc_feature
<222> LOCATION: (1)..(32)
<223> OTHER INFORMATION: Exon: HM45A(-07+25)

<400> SEQUENCE: 231
gcugcccaau gccauccugg aguuccugua ag                              32

<210> SEQ ID NO 232
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H45A(+09 +34)

<400> SEQUENCE: 232
caguuugccg cugcccaaug ccaucc                                     26

<210> SEQ ID NO 233
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H45A(+41 +64)

<400> SEQUENCE: 233
cuuccccagu ugcauucaau guuc                                       24

<210> SEQ ID NO 234
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: Exon: H45A(+76 +98)

<400> SEQUENCE: 234
cuggcaucug uuuugagga uug                                         23

<210> SEQ ID NO 235
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H45D(+02-18)

<400> SEQUENCE: 235
uuagaucugu cgcccuaccu                                            20

<210> SEQ ID NO 236
<211> LENGTH: 39
<212> TYPE: RNA

```
<213> ORGANISM: Homo sapiens
<220> FEATURE:
<221> NAME/KEY: misc_feature
<222> LOCATION: (1)..(39)
<223> OTHER INFORMATION: Exon: H45A(-14+25)

<400> SEQUENCE: 236
gcugcccaau gccauccugg aguuccugua agauaccaa                                  39

<210> SEQ ID NO 237
<211> LENGTH: 34
<212> TYPE: RNA
<213> ORGANISM: Homo sapiens
<220> FEATURE:
<221> NAME/KEY: misc_feature
<222> LOCATION: (1)..(34)
<223> OTHER INFORMATION: Exon: H45A(-12+22)

<400> SEQUENCE: 237
gcccaaugcc auccuggagu uccuguaaga uacc                                       34

<210> SEQ ID NO 238
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H45A(-12+13)

<400> SEQUENCE: 238
cauccuggag uuccuguaag auacc                                                 25

<210> SEQ ID NO 239
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H45A(-09+22)

<400> SEQUENCE: 239
gcccaaugcc auccuggagu uccuguaaga u                                          31

<210> SEQ ID NO 240
<211> LENGTH: 39
<212> TYPE: RNA
<213> ORGANISM: Homo sapiens
<220> FEATURE:
<221> NAME/KEY: misc_feature
<222> LOCATION: (1)..(39)
<223> OTHER INFORMATION: Exon: H45A(-09+30)

<400> SEQUENCE: 240
uugccgcugc ccaaugccau ccuggaguuc cuguaagau                                  39

<210> SEQ ID NO 241
<211> LENGTH: 32
<212> TYPE: RNA
<213> ORGANISM: Homo sapiens
<220> FEATURE:
<221> NAME/KEY: misc_feature
<222> LOCATION: (1)..(32)
<223> OTHER INFORMATION: Exon: HM45A(-07+25)

<400> SEQUENCE: 241
gcugcccaau gccauccugg aguuccugua ag                                         32
```

<210> SEQ ID NO 242
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H45A(-06+22)

<400> SEQUENCE: 242
gcccaaugcc auccuggagu uccuguaa                                  28

<210> SEQ ID NO 243
<211> LENGTH: 34
<212> TYPE: RNA
<213> ORGANISM: Homo sapiens
<220> FEATURE:
<221> NAME/KEY: misc_feature
<222> LOCATION: (1)..(34)
<223> OTHER INFORMATION: Exon: H45A(-06+28)

<400> SEQUENCE: 243
gccgcugccc aaugccaucc uggaguuccu guaa                           34

<210> SEQ ID NO 244
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H45A(-03+22)

<400> SEQUENCE: 244
gcccaaugcc auccuggagu uccug                                     25

<210> SEQ ID NO 245
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H45A(-03+28)

<400> SEQUENCE: 245
gccgcugccc aaugccaucc uggaguuccu g                              31

<210> SEQ ID NO 246
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: H45D(+10-19)

<400> SEQUENCE: 246
auuagaucug ucgcccuacc ucuuuuuuc                                 29

<210> SEQ ID NO 247
<211> LENGTH: 27
<212> TYPE: RNA
<213> ORGANISM: Homo sapiens
<220> FEATURE:
<221> NAME/KEY: misc_feature
<222> LOCATION: (1)..(27)

<223> OTHER INFORMATION: Exon: H45D(+16-11)

<400> SEQUENCE: 247
ugucgcccua ccucuuuuuu cugucug      27

<210> SEQ ID NO 248
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H46A(-05+19)

<400> SEQUENCE: 248
auucuuuugu ucuucuagcc ugga      24

<210> SEQ ID NO 249
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H46A(+16+42)

<400> SEQUENCE: 249
ucucuuugaa auucugacaa gauauuc      27

<210> SEQ ID NO 250
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H46A(+27+44)

<400> SEQUENCE: 250
uuaaaucucu uugaaauucu      20

<210> SEQ ID NO 251
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H46A(+35+60)

<400> SEQUENCE: 251
aaaacaaauu cauuuaaauc ucuuug      26

<210> SEQ ID NO 252
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: Exon: H46A(+56+77)

<400> SEQUENCE: 252
cugcuuccuc caaccauaaa ac      22

<210> SEQ ID NO 253
<211> LENGTH: 25

```
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H46A(+63+87)

<400> SEQUENCE: 253
gcaauguuau cugcuuccuc caacc                                              25

<210> SEQ ID NO 254
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: Exon: H46A(+83+103)

<400> SEQUENCE: 254
uucaagnggg auacuagcaa u                                                  21

<210> SEQ ID NO 255
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H46A(+90+109)

<400> SEQUENCE: 255
uccagguuca agugggauac                                                    20

<210> SEQ ID NO 256
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H46A(+91+118)

<400> SEQUENCE: 256
cugcucuuuu ccagguucaa gugggaua                                           28

<210> SEQ ID NO 257
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H46A(+95+122)

<400> SEQUENCE: 257
guugcugcuc uuuuccaggu ucaagugg                                           28

<210> SEQ ID NO 258
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H46A(+101+128)

<400> SEQUENCE: 258
```

```
cuuuuaguug cugcucuuuu ccagguuc                                        28
```

```
<210> SEQ ID NO 259
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H46A(+113+136)

<400> SEQUENCE: 259
aagcuuuucu uuaguugcu gcuc                                             24
```

```
<210> SEQ ID NO 260
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H46A(+115+134)

<400> SEQUENCE: 260
gcuuuucuuu uaguugcugc                                                 20
```

```
<210> SEQ ID NO 261
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H46A(+116+145)

<400> SEQUENCE: 261
gacuugcuca agcuuuucuu uuaguugcug                                      30
```

```
<210> SEQ ID NO 262
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H46D(+02-18)

<400> SEQUENCE: 262
uucagaaaau aaaauuaccu                                                 20
```

```
<210> SEQ ID NO 263
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H46A(+95+124)

<400> SEQUENCE: 263
uaguugcugc ucuuuuccag guucaagugg                                      30
```

```
<210> SEQ ID NO 264
<211> LENGTH: 31
<212> TYPE: RNA
<213> ORGANISM: Homo sapiens
<220> FEATURE:
<221> NAME/KEY: misc_feature
```

```
<222> LOCATION: (1)..(31)
<223> OTHER INFORMATION: Exon: H46A(+107 +137)

<400> SEQUENCE: 264
caagcuuuuc uuuuaguugc ugcucuuuuc c                              31

<210> SEQ ID NO 265
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H47A(-07+19)

<400> SEQUENCE: 265
gcaacucuuc caccaguaac ugaaac                                    26

<210> SEQ ID NO 266
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H47A(+44+70)

<400> SEQUENCE: 266 gcacggguccuccaguuuca uuuaauu                                    27

<210> SEQ ID NO 267
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H47A(+68+92)

<400> SEQUENCE: 267
gggcuuaugg gagcacuuac aagca                                     25

<210> SEQ ID NO 268
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H47A(+73+103)

<400> SEQUENCE: 268
cuugcucuuc ugggcuuaug ggagcacuua c                              31

<210> SEQ ID NO 269
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H47A(+76+103)

<400> SEQUENCE: 269
cuugcucuuc ugggcuuaug ggagcacu                                  28

<210> SEQ ID NO 270
```

```
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H47D(+17-10)

<400> SEQUENCE: 270
aaugucuaac cuuuauccac uggagau                                              27

<210> SEQ ID NO 271
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H48A(-09+21)

<400> SEQUENCE: 271
cucagguaaa gcucuggaaa ccugaaagga                                           30

<210> SEQ ID NO 272
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H48A(-08+19)

<400> SEQUENCE: 272
cagguaaagc ucuggaaacc ugaaagg                                              27

<210> SEQ ID NO 273
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H48A(-07+23)

<400> SEQUENCE: 273
uucucaggua aagcucugga aaccugaaag                                           30

<210> SEQ ID NO 274
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H48A(-05+25)

<400> SEQUENCE: 274
guuucucagg uaaagcucug gaaaccugaa                                           30

<210> SEQ ID NO 275
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H48A(+07+33)

<400> SEQUENCE: 275
```

-continued uucuccuugu uucucaggua aagcucu     27

<210> SEQ ID NO 276
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H48A(+75+100)

<400> SEQUENCE: 276
uuaacugcuc uucaaggucu ucaagc     26

<210> SEQ ID NO 277
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H48A(+96+122)

<400> SEQUENCE: 277
gauaaccaca gcagcagaug auuuaac     27

<210> SEQ ID NO 278
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H48D(+17-10)

<400> SEQUENCE: 278
aguucccuac cugaacguca aaugguc     27

<210> SEQ ID NO 279
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H48D(+16-09)

<400> SEQUENCE: 279
guucccuacc ugaacgucaa auggu     25

<210> SEQ ID NO 280
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H49A(-07+19)

<400> SEQUENCE: 280
gaacugcuau uucaguuucc ugggga     26

<210> SEQ ID NO 281
<211> LENGTH: 26
<212> TYPE: RNA
<213> ORGANISM: Homo sapiens
<220> FEATURE:

-continued

```
<221> NAME/KEY: misc_feature
<222> LOCATION: (1)..(26)
<223> OTHER INFORMATION: Exon: H49A(+22+47)

<400> SEQUENCE: 281
aucucuucca cauccgguug uuuagc                                          26

<210> SEQ ID NO 282
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H49D(+18-08)

<400> SEQUENCE: 282
uucauuaccu ucacuggcug aguggc                                          26

<210> SEQ ID NO 283
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H50A(-07+20)

<400> SEQUENCE: 283
cucagaucuu cuaacuuccu cuuuaac                                         27

<210> SEQ ID NO 284
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: H50A(-02+27)

<400> SEQUENCE: 284
cucagagcuc agaucuucua acuuccucu                                       29

<210> SEQ ID NO 285
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H50A(+10+36)

<400> SEQUENCE: 285
cgccuuccac ucagagcuca gaucuuc                                         27

<210> SEQ ID NO 286
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H50A(+35+61)

<400> SEQUENCE: 286
ucagcucuug aaguaaacgg uuuaccg                                         27
```

```
<210> SEQ ID NO 287
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H50A(+42+68)

<400> SEQUENCE: 287
uuugcccuca gcucuugaag uaaacgg                                27

<210> SEQ ID NO 288
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H50A(+63+88)

<400> SEQUENCE: 288
caggagcuag gucaggcugc uuugcc                                 26

<210> SEQ ID NO 289
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H50A(+81+105)

<400> SEQUENCE: 289
uccaauagug gucaguccag gagcu                                  25

<210> SEQ ID NO 290
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H50D(-01-27)

<400> SEQUENCE: 290
aaagagaaug ggauccagua uacuuac                                27

<210> SEQ ID NO 291
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H50D(-15-41)

<400> SEQUENCE: 291
aaauagcuag agccaaagag aauggga                                27

<210> SEQ ID NO 292
<211> LENGTH: 33
<212> TYPE: RNA
<213> ORGANISM: Homo sapiens
<220> FEATURE:
<221> NAME/KEY: misc_feature
<222> LOCATION: (1)..(33)
<223> OTHER INFORMATION: Exon: H50A(+42+74)
```

<400> SEQUENCE: 292
ggcugcuuug cccucagcuc uugaaguaaa cgg                33

<210> SEQ ID NO 293
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H50A(+46+75)

<400> SEQUENCE: 293
aggcugcuuu gcccucagcu cuugaaguaa                30

<210> SEQ ID NO 294
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H50A(+48+78)

<400> SEQUENCE: 294
gucaggcugc uuugcccuca gcucuugaag u                31

<210> SEQ ID NO 295
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H50A(+51+80)

<400> SEQUENCE: 295
aggucaggcu gcuuugcccu cagcucuuga                30

<210> SEQ ID NO 296
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: Hint49(-72-46)

<400> SEQUENCE: 296
aagauaauuc augaacaucu uaaucca                27

<210> SEQ ID NO 297
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H51A(-29-10)

<400> SEQUENCE: 297
uuuggguuuu ugcaaaaagg                20

<210> SEQ ID NO 298
<211> LENGTH: 22
<212> TYPE: RNA
<213> ORGANISM: Homo sapiens

```
<220> FEATURE:
<221> NAME/KEY: misc_feature
<222> LOCATION: (1)..(22)
<223> OTHER INFORMATION: Exon: H51A(-22-01)

<400> SEQUENCE: 298
cuaaaauauu uuggguuuuu gc                                              22

<210> SEQ ID NO 299
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H51A(-14+10)

<400> SEQUENCE: 299
ugaguaggag cuaaaauauu uugg                                            24

<210> SEQ ID NO 300
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H51(+26+52)

<400> SEQUENCE: 300
guuuccuuag uaaccacagg uuguguc                                         27

<210> SEQ ID NO 301
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H51A(+40+67)

<400> SEQUENCE: 301
aguuuggaga uggcaguuuc cuuaguaa                                        28

<210> SEQ ID NO 302
<211> LENGTH: 12
<212> TYPE: RNA
<213> ORGANISM: Homo sapiens
<220> FEATURE:
<221> NAME/KEY: misc_feature
<222> LOCATION: (1)..(12)
<223> OTHER INFORMATION: Exon: H51A(+66+77)

<400> SEQUENCE: 302
uggcauuucu ag                                                         12

<210> SEQ ID NO 303
<211> LENGTH: 15
<212> TYPE: RNA
<213> ORGANISM: Homo sapiens
<220> FEATURE:
<221> NAME/KEY: misc_feature
<222> LOCATION: (1)..(15)
<223> OTHER INFORMATION: Exon: H51A(+66+80)

<400> SEQUENCE: 303
agauggcauu ucuag                                                      15
```

```
<210> SEQ ID NO 304
<211> LENGTH: 18
<212> TYPE: RNA
<213> ORGANISM: Homo sapiens
<220> FEATURE:
<221> NAME/KEY: misc_feature
<222> LOCATION: (1)..(18)
<223> OTHER INFORMATION: Exon: H51A(+66+83)

<400> SEQUENCE: 304
ggaagauggc auuucuag                                                   18

<210> SEQ ID NO 305
<211> LENGTH: 18
<212> TYPE: RNA
<213> ORGANISM: Homo sapiens
<220> FEATURE:
<221> NAME/KEY: misc_feature
<222> LOCATION: (1)..(18)
<223> OTHER INFORMATION: Exon: H51A(+78+95)

<400> SEQUENCE: 305
cuccaacauc aaggaaga                                                   18

<210> SEQ ID NO 306
<211> LENGTH: 15
<212> TYPE: RNA
<213> ORGANISM: Homo sapiens
<220> FEATURE:
<221> NAME/KEY: misc_feature
<222> LOCATION: (1)..(15)
<223> OTHER INFORMATION: Exon: H51A(+81+95)

<400> SEQUENCE: 306
cuccaacauc aagga                                                      15

<210> SEQ ID NO 307
<211> LENGTH: 12
<212> TYPE: RNA
<213> ORGANISM: Homo sapiens
<220> FEATURE:
<221> NAME/KEY: misc_feature
<222> LOCATION: (1)..(12)
<223> OTHER INFORMATION: Exon: H51A(+84+95)

<400> SEQUENCE: 307
cuccaacauc aa                                                         12

<210> SEQ ID NO 308
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H51A(+90+116)

<400> SEQUENCE: 308
gaaaucugcc agagcaggua ccuccaa                                         27

<210> SEQ ID NO 309
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H51A(+53+79)
```

```
<400> SEQUENCE: 309
gauggcauuu cuaguuugga gauggca                                      27

<210> SEQ ID NO 310
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: H51A(+57+85)

<400> SEQUENCE: 310
aaggaagaug gcauuucuag uuuggagau                                    29

<210> SEQ ID NO 311
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: H51A(+76+104)

<400> SEQUENCE: 311
agcagguacc uccaacauca aggaagaug                                    29

<210> SEQ ID NO 312
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H52A(-12+13)

<400> SEQUENCE: 312
ccugcauugu ugccuguaag aacaa                                        25

<210> SEQ ID NO 313
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H52A(-10+10)

<400> SEQUENCE: 313
gcauuguugc cuguaagaac                                              20

<210> SEQ ID NO 314
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H52A(+07+33)

<400> SEQUENCE: 314
gggacgccuc uguuccaaau ccugcau                                      27

<210> SEQ ID NO 315
<211> LENGTH: 30
<212> TYPE: RNA
```

```
<213> ORGANISM: Homo sapiens
<220> FEATURE:
<221> NAME/KEY: misc_feature
<222> LOCATION: (1)..(30)
<223> OTHER INFORMATION: Exon: H52A(+17+46)

<400> SEQUENCE: 315
guucuuccaa cugggggacgc cucuguucca                    30

<210> SEQ ID NO 316
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: Exon: H52A(+17+37)

<400> SEQUENCE: 316
acuggggacg ccucuguucc a                              21

<210> SEQ ID NO 317
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H52A(+67+94)

<400> SEQUENCE: 317
ccucuugauu gcuggucuug uuuuucaa                       28

<210> SEQ ID NO 318
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: Hint51(-40-14)

<400> SEQUENCE: 318
uaccccuuag uaucaggguu cuucagc                        27

<210> SEQ ID NO 319
<211> LENGTH: 33
<212> TYPE: RNA
<213> ORGANISM: Homo sapiens
<220> FEATURE:
<221> NAME/KEY: misc_feature
<222> LOCATION: (1)..(33)
<223> OTHER INFORMATION: Exon: H52A(+09+41)

<400> SEQUENCE: 319
uccaacuggg gacgccucug uuccaaaucc ugc                 33

<210> SEQ ID NO 320
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H52A(+15+44)

<400> SEQUENCE: 320
ucuuccaacu ggggacgccu cguuccaaa                      30
```

```
<210> SEQ ID NO 321
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H53A(-49-26)

<400> SEQUENCE: 321
auaguaguaa augcuagucu ggag                                          24

<210> SEQ ID NO 322
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H53A(-38-13)

<400> SEQUENCE: 322 gaaaauaaa uauauaguag uaaaug                                         26

<210> SEQ ID NO 323
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H53A(-32-06)

<400> SEQUENCE: 323
auaaaaggaa aaauaaauau auaguag                                       27

<210> SEQ ID NO 324
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H53A(-15+15)

<400> SEQUENCE: 324
ucugaauucu uucaacuaga auaaaaggaa                                    30

<210> SEQ ID NO 325
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H53A(+39+65)

<400> SEQUENCE: 325
caacuguugc cuccgguucu gaaggug                                       27

<210> SEQ ID NO 326
<211> LENGTH: 29
<212> TYPE: RNA
<213> ORGANISM: Homo sapiens
<220> FEATURE:
<221> NAME/KEY: misc_feature
<222> LOCATION: (1)..(29)
```

```
<223> OTHER INFORMATION: Exon: H53A(+39+67)

<400> SEQUENCE: 326
uucaacuguu gccuccgguu cugaaggug                                    29

<210> SEQ ID NO 327
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H39A(+39+69)SNP

<400> SEQUENCE: 327
cguucaacug uugccuccgg uucugaaggu g                                 31

<210> SEQ ID NO 328
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H53A(+40+70)

<400> SEQUENCE: 328
ucauucaacu guugccuccg guucugaagg u                                 31

<210> SEQ ID NO 329
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: H53A(+41+69)

<400> SEQUENCE: 329
cauucaacug uugccuccgg uucugaagg                                    29

<210> SEQ ID NO 330
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H53A(+43+69)

<400> SEQUENCE: 330
cauucaacug uugccuccgg uucugaa                                      27

<210> SEQ ID NO 331
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H53A(+69+98)

<400> SEQUENCE: 331
cagccauugu guugaauccu uuaacauuuc                                   30

<210> SEQ ID NO 332
<211> LENGTH: 25
```

```
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: Hint52(-47-23)

<400> SEQUENCE: 332
uauauaguag uaaaugcuag ucugg                                          25

<210> SEQ ID NO 333
<211> LENGTH: 33
<212> TYPE: RNA
<213> ORGANISM: Homo sapiens
<220> FEATURE:
<221> NAME/KEY: misc_feature
<222> LOCATION: (1)..(33)
<223> OTHER INFORMATION: Exon: H53A(+27+59)

<400> SEQUENCE: 333
uugccuccgg uucugaaggu guucuuguac uuc                                 33

<210> SEQ ID NO 334
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H53A(+30+59)

<400> SEQUENCE: 334
uugccuccgg uucugaaggu guucuuguac                                     30

<210> SEQ ID NO 335
<211> LENGTH: 35
<212> TYPE: RNA
<213> ORGANISM: Homo sapiens
<220> FEATURE:
<221> NAME/KEY: misc_feature
<222> LOCATION: (1)..(35)
<223> OTHER INFORMATION: Exon: H53A(+30+64)

<400> SEQUENCE: 335
aacuguugcc uccgguucug aagguguucu uguac                               35

<210> SEQ ID NO 336
<211> LENGTH: 40
<212> TYPE: RNA
<213> ORGANISM: Homo sapiens
<220> FEATURE:
<221> NAME/KEY: misc_feature
<222> LOCATION: (1)..(40)
<223> OTHER INFORMATION: Exon: H53A(+30+69)

<400> SEQUENCE: 336
cauucaacug uugccuccgg uucugaaggu guucuuguac                          40

<210> SEQ ID NO 337
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H53A(+33+63)

<400> SEQUENCE: 337
```
acuguugccu ccgguucuga agguguucuu g                              31

<210> SEQ ID NO 338
<211> LENGTH: 35
<212> TYPE: RNA
<213> ORGANISM: Homo sapiens
<220> FEATURE:
<221> NAME/KEY: misc_feature
<222> LOCATION: (1)..(35)
<223> OTHER INFORMATION: Exon: H53A(+33+67)

<400> SEQUENCE: 338
uucaacuguu gccuccgguu cugaaggugu ucuug                          35

<210> SEQ ID NO 339
<211> LENGTH: 33
<212> TYPE: RNA
<213> ORGANISM: Homo sapiens
<220> FEATURE:
<221> NAME/KEY: misc_feature
<222> LOCATION: (1)..(33)
<223> OTHER INFORMATION: Exon: H53A(+35+67)

<400> SEQUENCE: 339
uucaacuguu gccuccgguu cugaaggugu ucu                            33

<210> SEQ ID NO 340
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H53A(+37+67)

<400> SEQUENCE: 340
uucaacuguu gccuccgguu cugaaggugu u                              31

<210> SEQ ID NO 341
<211> LENGTH: 35
<212> TYPE: RNA
<213> ORGANISM: Homo sapiens
<220> FEATURE:
<221> NAME/KEY: misc_feature
<222> LOCATION: (1)..(35)
<223> OTHER INFORMATION: Exon: H53A(+36+70)

<400> SEQUENCE: 341
ucauucaacu guugccuccg guucugaagg uguuc                          35

<210> SEQ ID NO 342
<211> LENGTH: 33
<212> TYPE: RNA
<213> ORGANISM: Homo sapiens
<220> FEATURE:
<221> NAME/KEY: misc_feature
<222> LOCATION: (1)..(33)
<223> OTHER INFORMATION: Exon: H53A(+39+71)

<400> SEQUENCE: 342
uucauucaac uguugccucc gguucugaag gug                            33

<210> SEQ ID NO 343
<211> LENGTH: 30
<212> TYPE: RNA
<213> ORGANISM: Homo sapiens
<220> FEATURE:
<221> NAME/KEY: misc_feature

```
<222> LOCATION: (1)..(30)
<223> OTHER INFORMATION: Exon: H53A(+42+71)

<400> SEQUENCE: 343
uucauucaac uguugccucc gguucugaag                                30

<210> SEQ ID NO 344
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: Exon: H54A(+13+34)

<400> SEQUENCE: 344
uugucugcca cuggcggagg uc                                        22

<210> SEQ ID NO 345
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H54A(+60+90)

<400> SEQUENCE: 345
aucugcagaa uaaucccgga gaaguuucag                                30

<210> SEQ ID NO 346
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: Exon: H54A (+67+89)

<400> SEQUENCE: 346
ucugcagaau aaucccggag aag                                       23

<210> SEQ ID NO 347
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H54A(+77+106)

<400> SEQUENCE: 347
ggacuuuucu gguaucaucu gcagaauaau                                30

<210> SEQ ID NO 348
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H55A(-10+14)

<400> SEQUENCE: 348
cucgcucacu cacccugcaa agga                                      24

<210> SEQ ID NO 349
```

```
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: Exon: H55A(+39 +61)

<400> SEQUENCE: 349
cagggggaac uguugcagua auc                                              23

<210> SEQ ID NO 350
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H55A(+41+71)

<400> SEQUENCE: 350
ucuuuuacuc ccuuggaguc uucuaggagc c                                     31

<210> SEQ ID NO 351
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: Exon: H55A(+73+93)

<400> SEQUENCE: 351
ucuguaagcc aggcaagaaa c                                                21

<210> SEQ ID NO 352
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H55A(+107+137)

<400> SEQUENCE: 352
ccuuacgggu agcauccuga uggacauugg c                                     31

<210> SEQ ID NO 353
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H55A(+112 +136)

<400> SEQUENCE: 353
cuuacgggua gcauccugua ggaca                                            25

<210> SEQ ID NO 354
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H55A(+132 +161)

<400> SEQUENCE: 354
```
ccuuggaguc uucuaggagc cuuuccuuac                30

<210> SEQ ID NO 355
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H55A(+141 +160)

<400> SEQUENCE: 355
cuuggagucu ucuaggagcc                20

<210> SEQ ID NO 356
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H55A(+143 +171)

<400> SEQUENCE: 356
cucuuuuacu cccuuggagu cuucuaggag                30

<210> SEQ ID NO 357
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H55D(+11 -09)

<400> SEQUENCE: 357
ccugacuuac uugccauugu                20

<210> SEQ ID NO 358
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: H56A(-06+23)

<400> SEQUENCE: 358
gcuucaauuu caccuuggag guccuacag                29

<210> SEQ ID NO 359
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: Exon: H56A(-06+15)

<400> SEQUENCE: 359
uucaccuugg agguccuaca g                21

<210> SEQ ID NO 360
<211> LENGTH: 22
<212> TYPE: RNA
<213> ORGANISM: Homo sapiens
<220> FEATURE:

```
<221> NAME/KEY: misc_feature
<222> LOCATION: (1)..(22)
<223> OTHER INFORMATION: Exon: H56A(+23 +44)

<400> SEQUENCE: 360
guugugauaa acaucugugu ga                                              22

<210> SEQ ID NO 361
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H56A(+56+81)

<400> SEQUENCE: 361
ccagggaucu caggauuuuu uggcug                                          26

<210> SEQ ID NO 362
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H56A(+67+91)

<400> SEQUENCE: 362
cggaaccuuc cagggaucuc aggau                                           25

<210> SEQ ID NO 363
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H56A(+102+126)

<400> SEQUENCE: 363
guuauccaaa cgucuuugua acagg                                           25

<210> SEQ ID NO 364
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H56A(+102+131)

<400> SEQUENCE: 364
uucauguuau ccaaacgucu uguaacagg                                       30

<210> SEQ ID NO 365
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H56A(+117+146)

<400> SEQUENCE: 365
ucacuccacu ugaaguucau guuauccaaa                                      30
```

```
<210> SEQ ID NO 366
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: Exon: H56A(+121+143)

<400> SEQUENCE: 366
cuccacuuga aguucauguu auc                                              23

<210> SEQ ID NO 367
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: Exon: H56D(+11-10)

<400> SEQUENCE: 367 cuuuccuac caaauguuga g                                                 21

<210> SEQ ID NO 368
<211> LENGTH: 33
<212> TYPE: RNA
<213> ORGANISM: Homo sapiens
<220> FEATURE:
<221> NAME/KEY: misc_feature
<222> LOCATION: (1)..(33)
<223> OTHER INFORMATION: Exon: H57A(-15+18)

<400> SEQUENCE: 368
cuggcuucca aaugggaccu gaaaaagaac agc                                   33

<210> SEQ ID NO 369
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H57A (-12 +18)

<400> SEQUENCE: 369
cuggcuucca aaugggaccu gaaaaagaac                                       30

<210> SEQ ID NO 370
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H57A(-06 +24)

<400> SEQUENCE: 370
ucagaacugg cuuccaaaug ggaccugaaa                                       30

<210> SEQ ID NO 371
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H57A(+21+44)
```

<400> SEQUENCE: 371
ggugcagacg cuuccacugg ucag                                          24

<210> SEQ ID NO 372
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H57A(+47 +77)

<400> SEQUENCE: 372
gcuguagcca caccagaagu uccugcagag a                                  31

<210> SEQ ID NO 373
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H57A(+79+103)

<400> SEQUENCE: 373
cugccggcuu aauucaucau cuuuc                                         25

<210> SEQ ID NO 374
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H57A(+105+131)

<400> SEQUENCE: 374
cugcuggaaa gucgccucca auaggug                                       27

<210> SEQ ID NO 375
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: Exon: H59A (-06 +16)

<400> SEQUENCE: 375
uccucaggag gcagcucuaa au                                            22

<210> SEQ ID NO 376
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H59A(+31 +61)

<400> SEQUENCE: 376
uccucgccug cuuucguaga agccgaguga                                    30

<210> SEQ ID NO 377
<211> LENGTH: 26
<212> TYPE: RNA
<213> ORGANISM: Homo sapiens

```
<220> FEATURE:
<221> NAME/KEY: misc_feature
<222> LOCATION: (1)..(26)
<223> OTHER INFORMATION: Exon: H59A(+66+91)

<400> SEQUENCE: 377
agguucaauu uucccacuc aguauu                                          26

<210> SEQ ID NO 378
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H59A(+96+125)

<400> SEQUENCE: 378
cucaucuauu uuucucugcc agucagcgga                                     30

<210> SEQ ID NO 379
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H59A(+101 +132)

<400> SEQUENCE: 379
cagggucuca ucuauuuuuc ucugccaguc a                                   31

<210> SEQ ID NO 380
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H59A(+141 +165)

<400> SEQUENCE: 380
cauccguggc cucuugaagu uccug                                          25

<210> SEQ ID NO 381
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H59A(+151 +175)

<400> SEQUENCE: 381
agguccagcu cauccguggc cucuu                                          25

<210> SEQ ID NO 382
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H59A(+161 +185)

<400> SEQUENCE: 382
gcgcagcuug agguccagcu caucc                                          25
```

<210> SEQ ID NO 383
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H59A(+161+190)

<400> SEQUENCE: 383
gcuuggcgca gcuugagguc cagcucaucc                                    30

<210> SEQ ID NO 384
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H59A(+171+197)

<400> SEQUENCE: 384
caccucagcu uggcgcagcu ugagguc                                       27

<210> SEQ ID NO 385
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H59A(+181+205)

<400> SEQUENCE: 385
cccuugauca ccucagcuug gcgca                                         25

<210> SEQ ID NO 386
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: Exon: H59A(+200+220)

<400> SEQUENCE: 386
acgggcugcc aggaucccuu g                                             21

<210> SEQ ID NO 387
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H59A(+221+245)

<400> SEQUENCE: 387
gagagaguca augaggagau cgccc                                         25

<210> SEQ ID NO 388
<211> LENGTH: 34
<212> TYPE: RNA
<213> ORGANISM: Homo sapiens
<220> FEATURE:
<221> NAME/KEY: misc_feature
<222> LOCATION: (1)..(34)
<223> OTHER INFORMATION: Exon: H59A(+92+125)

```
<400> SEQUENCE: 388
cucaucuauu uuucucugcc agucagcgga gugc                                   34

<210> SEQ ID NO 389
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H60A(-10+20)

<400> SEQUENCE: 389
gcaauuucuc cucgaagugc cugugugcaa                                        30

<210> SEQ ID NO 390
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H60A(-8+19)

<400> SEQUENCE: 390
caauuucucc ucgaagugcc ugugugc                                           27

<210> SEQ ID NO 391
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H60A(+29+58)

<400> SEQUENCE: 391
caaggucauu gacguggcuc acguucucuu                                        30

<210> SEQ ID NO 392
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H60A(+37+66)

<400> SEQUENCE: 392
cuggcgagca aggucauuga cguggcucac                                        30

<210> SEQ ID NO 393
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H60A(+39+66)

<400> SEQUENCE: 393
cuggcgagca aggccuuga cguggcuc                                           28

<210> SEQ ID NO 394
<211> LENGTH: 31
<212> TYPE: RNA
```

```
<213> ORGANISM: Homo sapiens
<220> FEATURE:
<221> NAME/KEY: misc_feature
<222> LOCATION: (1)..(31)
<223> OTHER INFORMATION: Exon: H60A(+43+73)

<400> SEQUENCE: 394
ugguaagcug gcgagcaagg uccuugacgu g                           31

<210> SEQ ID NO 395
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H60A(+51+75)

<400> SEQUENCE: 395
agugguaagc uggcgugcaa gguca                                  25

<210> SEQ ID NO 396
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H60A(+72+102)

<400> SEQUENCE: 396
uuauacggug agagcugaau gcccaaagug                             30

<210> SEQ ID NO 397
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H60A(+75+105)

<400> SEQUENCE: 397
gagguuauac ggugagagcu gaaugcccaa a                           31

<210> SEQ ID NO 398
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H60A(+80+109)

<400> SEQUENCE: 398
ugcugagguu auacggugag agcugaa                                27

<210> SEQ ID NO 399
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H60D(+25-5)

<400> SEQUENCE: 399
cuuuccugca gaagcuucca ucuggguuc                              30
```

```
<210> SEQ ID NO 400
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H61A(-7+19)

<400> SEQUENCE: 400
cucgguccuc gacggccacc ugggag                                              26

<210> SEQ ID NO 401
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H61A(+05+34)

<400> SEQUENCE: 401
caugcagcug ccugacucgg uccucgccgg                                          30

<210> SEQ ID NO 402
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H61A(+16+40)

<400> SEQUENCE: 402
gggcuucaug cagcugccug acucg                                               25

<210> SEQ ID NO 403
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H61A(+16+45)

<400> SEQUENCE: 403
ccugugggcu ucaugcagcu gccugacucg                                          30

<210> SEQ ID NO 404
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H61A(+42+67)

<400> SEQUENCE: 404
gcugagaugc uggaccaaag ucccug                                              26

<210> SEQ ID NO 405
<211> LENGTH: 26
<212> TYPE: RNA
<213> ORGANISM: Homo sapiens
<220> FEATURE:
<221> NAME/KEY: misc_feature
<222> LOCATION: (1)..(26)
```

<223> OTHER INFORMATION: Exon: H61D(+10-16)

<400> SEQUENCE: 405
gcugaaaaug acuuacugga aagaaa                                        26

<210> SEQ ID NO 406
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H62A(-15+15)

<400> SEQUENCE: 406
gacccuggac agacgcugaa aagaagggag                                    30

<210> SEQ ID NO 407
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H62A(-10+20)

<400> SEQUENCE: 407
ccagggaccc uggacagacg cugaaaagaa                                    30

<210> SEQ ID NO 408
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H62A(-05+15)

<400> SEQUENCE: 408
gacccuggac agacgcugaa                                               20

<210> SEQ ID NO 409
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H62A(-3+25)

<400> SEQUENCE: 409
cucucccagg gacccuggac agacgcug                                      28

<210> SEQ ID NO 410
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H62A(+01+30)

<400> SEQUENCE: 410
uggcucucuc ccagggaccc uggacagacg                                    30

<210> SEQ ID NO 411
<211> LENGTH: 27

<210> SEQ ID NO 411
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H62A(+8+34)

<400> SEQUENCE: 411
gagauggcuc ucucccaggg acccugg                27

<210> SEQ ID NO 412
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H62A(+13+43)

<400> SEQUENCE: 412
uuguuuggug agauggcucu cucccaggga c            31

<210> SEQ ID NO 413
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H62D(+17-03)

<400> SEQUENCE: 413
uacuugauau aguagggcac                         20

<210> SEQ ID NO 414
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H62D(+25-5)

<400> SEQUENCE: 414
cuuacuugau auaguagggc acuuuguuug              30

<210> SEQ ID NO 415
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H63A(-14+11)

<400> SEQUENCE: 415
gagucucgug gcuaaaacac aaaac                   25

<210> SEQ ID NO 416
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H63A(+11+35)

<400> SEQUENCE: 416
ugggaugguc ccagcaaguu guuug                                    25

<210> SEQ ID NO 417
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H63A(+33+57)

<400> SEQUENCE: 417
gacugguaga gcucugucau uuugg                                    25

<210> SEQ ID NO 418
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: Exon: H63A(+40+62)

<400> SEQUENCE: 418
cuaaagacug guagagcucu guc                                      23

<210> SEQ ID NO 419
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H63D(+8-17)

<400> SEQUENCE: 419
cauggccaug uccuuaccua aagac                                    25

<210> SEQ ID NO 420
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H64A(-3+27)

<400> SEQUENCE: 420
cugagaaucu gacauuauuc aggucagcug                               30

<210> SEQ ID NO 421
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H64A(+43+72)

<400> SEQUENCE: 421
aaagggccuu cugcagucuu cggaguuuca                               30

<210> SEQ ID NO 422
<211> LENGTH: 27
<212> TYPE: RNA
<213> ORGANISM: Homo sapiens
<220> FEATURE:
<221> NAME/KEY: misc_feature

```
<222> LOCATION: (1)..(27)
<223> OTHER INFORMATION: Exon: H64A(+47+74)

<400> SEQUENCE: 422
gcaaagggcc uucugcaguc uucggag                                              27

<210> SEQ ID NO 423
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H64D(+15-10)

<400> SEQUENCE: 423
caauacuuac agcaaagggc cuucu                                                25

<210> SEQ ID NO 424
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H65A(+123+148)

<400> SEQUENCE: 424
uugaccaaau uguugugcuc uugcuc                                               26

<210> SEQ ID NO 425
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: H67A(+120+147)

<400> SEQUENCE: 425
agcuccggac acuuggcuca auguuacu                                             28

<210> SEQ ID NO 426
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H67A(+125+149)

<400> SEQUENCE: 426
gcagcuccgg acacuuggcu caaug                                                25

<210> SEQ ID NO 427
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H67D(+22-08)

<400> SEQUENCE: 427
uaacuuacaa auuggaagca gcuccggaca                                           30

<210> SEQ ID NO 428
```

```
<210> SEQ ID NO 428
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H68A(-4+21)

<400> SEQUENCE: 428
gaucucuggc uuauuauuag ccugc                                          25

<210> SEQ ID NO 429
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H68A(+22+48)

<400> SEQUENCE: 429
cauccagucu aggaagaggg ccgcuuc                                        27

<210> SEQ ID NO 430
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H68A(+74+103)

<400> SEQUENCE: 430
cagcagccac ucugugcagg acgggcagcc                                     30

<210> SEQ ID NO 431
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H69A(-12+19)

<400> SEQUENCE: 431
gugcuuuaga cuccuguacc ugauaaagag c                                   31

<210> SEQ ID NO 432
<211> LENGTH: 31
<212> TYPE: RNA
<213> ORGANISM: Homo sapiens
<220> FEATURE:
<221> NAME/KEY: misc_feature
<222> LOCATION: (1)..(31)
<223> OTHER INFORMATION: Exon: H69A(+09 +39)

<400> SEQUENCE: 432
uggcagaugu cauaauuaaa gugcuuuaga c                                   31

<210> SEQ ID NO 433
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: H69A(+29 +57)

<400> SEQUENCE: 433
```
ccagaaaaaa agcagcuuug gcagauguc                                      29

<210> SEQ ID NO 434
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H69A(+51+74)

<400> SEQUENCE: 434
ggccuuuugc aacucgacca gaaa                                           24

<210> SEQ ID NO 435
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H69A(+51+80)

<400> SEQUENCE: 435
uuuuauggcc uuuugcaacu cgaccagaaa                                     30

<210> SEQ ID NO 436
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H69D(+08-16)

<400> SEQUENCE: 436
cuggcgucaa acuuaccgga gugc                                           24

<210> SEQ ID NO 437
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H70A(-09+15)

<400> SEQUENCE: 437
uucuccugau guagucuaaa aggg                                           24

<210> SEQ ID NO 438
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H70A(-07 +23)

<400> SEQUENCE: 438
cgaacaucuu cuccugaugu agucuaaaag                                     30

<210> SEQ ID NO 439
<211> LENGTH: 25
<212> TYPE: RNA
<213> ORGANISM: Homo sapiens
<220> FEATURE:

```
<221> NAME/KEY: misc_feature
<222> LOCATION: (1)..(25)
<223> OTHER INFORMATION: Exon: H70A(+16 +40)

<400> SEQUENCE: 439
guaccuuggc aaagucucga acauc                                        25

<210> SEQ ID NO 440
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H70A(+25 +48)

<400> SEQUENCE: 440 guuuuuagu accuuggcaa aguc                                          24

<210> SEQ ID NO 441
<211> LENGTH: 29
<212> TYPE: RNA
<213> ORGANISM: Homo sapiens
<220> FEATURE:
<221> NAME/KEY: misc_feature
<222> LOCATION: (1)..(29)
<223> OTHER INFORMATION: Exon: H70A(+32+60)

<400> SEQUENCE: 441
gguucgaaau uuguuuuuua guaccuugg                                    29

<210> SEQ ID NO 442
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H70A(+64 +93)

<400> SEQUENCE: 442
gcccauucgg ggaugcuucg caaaauaccu                                   30

<210> SEQ ID NO 443
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H71A(-08+16)

<400> SEQUENCE: 443
gaucagagua acgggacugc aaaa                                         24

<210> SEQ ID NO 444
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H71A(+07+30)

<400> SEQUENCE: 444
acuggccaga aguugaucag agua                                         24
```

```
<210> SEQ ID NO 445
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H71A(+16+39)

<400> SEQUENCE: 445
gcagaaucua cuggccagaa guug                                              24

<210> SEQ ID NO 446
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H71D(+19-05)

<400> SEQUENCE: 446
cucacgcaga aucuacuggc caga                                              24

<210> SEQ ID NO 447
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H72A(-8+22)

<400> SEQUENCE: 447
aagcugaggg gacgaggcag gccuauaagg                                        30

<210> SEQ ID NO 448
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H72A(+02+28)

<400> SEQUENCE: 448
gugugaaagc ugagggacg aggcagg                                            27

<210> SEQ ID NO 449
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: Exon: H72D(+14-10)

<400> SEQUENCE: 449
agucucauac cugcuagcau aaug                                              24

<210> SEQ ID NO 450
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H73A(+24+49)
```

```
<400> SEQUENCE: 450
augcuaucau uuagauaaga uccau                                              25

<210> SEQ ID NO 451
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H73A(-16+10)

<400> SEQUENCE: 451
uucugcuagc cugauaaaaa acguaa                                             26

<210> SEQ ID NO 452
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H73D(+23-02)

<400> SEQUENCE: 452
acaugcucuc auuaggagag augcu                                              25

<210> SEQ ID NO 453
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: HM73A(+19+44)

<400> SEQUENCE: 453
uaucauuuag auaagaucca uugcug                                             26

<210> SEQ ID NO 454
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: HM74A(+20+46)

<400> SEQUENCE: 454
guucaaacuu uggcaguaau gcuggau                                            27

<210> SEQ ID NO 455
<211> LENGTH: 28
<212> TYPE: RNA
<213> ORGANISM: Homo sapiens
<220> FEATURE:
<221> NAME/KEY: misc_feature
<222> LOCATION: (1)..(28)
<223> OTHER INFORMATION: Exon: HM74A(+50+77)

<400> SEQUENCE: 455
gacuacgagg cuggcucagg ggggaguc                                           28

<210> SEQ ID NO 456
<211> LENGTH: 27
<212> TYPE: RNA
<213> ORGANISM: Homo sapiens
```

-continued

```
<220> FEATURE:
<221> NAME/KEY: misc_feature
<222> LOCATION: (1)..(27)
<223> OTHER INFORMATION: Exon: HM74A(+96+122)

<400> SEQUENCE: 456
gcuccccucu uuccucacuc ucuaagg                                              27

<210> SEQ ID NO 457
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H76A(-02+25)

<400> SEQUENCE: 457
cauucacuuu ggccucugcc ugggcu                                               27

<210> SEQ ID NO 458
<211> LENGTH: 27
<212> TYPE: RNA
<213> ORGANISM: Homo sapiens
<220> FEATURE:
<221> NAME/KEY: misc_feature
<222> LOCATION: (1)..(27)
<223> OTHER INFORMATION: Exon: H76A(+80+106)

<400> SEQUENCE: 458
gacugccaac cacucggagc agcauag                                              27

<210> SEQ ID NO 459
<211> LENGTH: 30
<212> TYPE: RNA
<213> ORGANISM: Homo sapiens
<220> FEATURE:
<221> NAME/KEY: misc_feature
<222> LOCATION: (1)..(30)
<223> OTHER INFORMATION: Exon: H17A(-12 +18)

<400> SEQUENCE: 459
ggugacagcc ugugaaaucu gugagaagua                                           30

<210> SEQ ID NO 460
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: Exon: H17A(-07+16)

<400> SEQUENCE: 460
ugacagccug ugaaucugu gag                                                   23

<210> SEQ ID NO 461
<211> LENGTH: 26
<212> TYPE: RNA
<213> ORGANISM: Homo sapiens
<220> FEATURE:
<221> NAME/KEY: misc_feature
<222> LOCATION: (1)..(26)
<223> OTHER INFORMATION: Exon: H17A(+10 +35)

<400> SEQUENCE: 461
agugauggcu gagugguggu gacagc                                               26
```

```
<210> SEQ ID NO 462
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H17A(+31+50)

<400> SEQUENCE: 462
acaguugucu guguuaguga                                              20

<210> SEQ ID NO 463
<211> LENGTH: 20
<212> TYPE: RNA
<213> ORGANISM: Homo sapiens
<220> FEATURE:
<221> NAME/KEY: misc_feature
<222> LOCATION: (1)..(20)
<223> OTHER INFORMATION: Exon: H17A(+144+163)

<400> SEQUENCE: 463
cagaauccac aguaaucugc                                              20

<210> SEQ ID NO 464
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: Exon: H3A(+30+54)

<400> SEQUENCE: 464
gcgccuccca uccuguaggu cacug                                        25
```

ANTISENSE MOLECULES AND METHODS FOR TREATING PATHOLOGIES

RELATED APPLICATIONS

This application is a division of U.S. application Ser. No. 15/661,750, filed on Jul. 27, 2017, which is a continuation of U.S. application Ser. No. 14/944,886, filed on Nov. 18, 2015, now issued as U.S. Pat. No. 9,758,783, which is a continuation of U.S. application Ser. No. 14/108,137, filed on Dec. 16, 2013, now issued as U.S. Pat. No. 9,228,187, which is a continuation of U.S. application Ser. No. 13/509,331, filed on Jul. 9, 2012, now issued as U.S. Pat. No. 8,637,483, which is a 35 U.S.C. § 371 U.S. National Phase application of International Patent Application No. PCT/AU2010/001520, filed on Nov. 12, 2010, claiming the benefit of priority to Australian Patent Application No. 2009905549, filed on Nov. 12, 2009. The contents of the aforementional applications are hereby incorporated by reference.

FIELD OF THE INVENTION

The present invention relates to novel antisense compounds and compositions suitable for facilitating exon skipping. It also provides methods for inducing exon skipping using the novel antisense compounds as well as therapeutic compositions adapted for use in the methods of the invention.

STATEMENT REGARDING SEQUENCE LISTING

The instant application contains a Sequence Listing which has been submitted in ASCII format via EFS-Web and is hereby incorporated by reference in its entirety. Said ASCII copy, created on Mar. 19, 2019, is named "4140_0160005_Seqlisting_ST25" and is 105,850 bytes in size. The Sequence Listing is being submitted by EFS Web and is hereby incorporated by reference into the specification.

BACKGROUND ART

The following discussion of the background art is intended to facilitate an understanding of the present invention only. The discussion is not an acknowledgement or admission that any of the material referred to is or was part of the common general knowledge as at the priority date of the application.

Significant effort is currently being expended into researching methods for suppressing or compensating for disease-causing mutations in genes. Antisense technologies are being developed using a range of chemistries to affect gene expression at a variety of different levels (transcription, splicing, stability, translation). Much of that research has focused on the use of antisense compounds to correct or compensate for abnormal or disease-associated genes in a myriad of different conditions.

Antisense molecules are able to inhibit gene expression with exquisite specificity and because of this many research efforts concerning oligonucleotides as modulators of gene expression have focused on inhibiting the expression of targeted genes such as oncogenes or viral genes. The antisense oligonucleotides are directed either against RNA (sense strand) or against DNA where they form triplex structures inhibiting transcription by RNA polymerase II.

To achieve a desired effect in specific gene down-regulation, the oligonucleotides must either promote the decay of the targeted mRNA or block translation of that mRNA, thereby effectively preventing de novo synthesis of the undesirable target protein.

Such techniques are not useful where the object is to up-regulate production of the native protein or compensate for mutations which induce premature termination of translation such as nonsense or frame-shifting mutations.

Furthermore, in cases where a normally functional protein is prematurely terminated because of mutations therein, a means for restoring some functional protein production through antisense technology has been shown to be possible through intervention during the splicing processes (Sierakowska H, et al., (1996) Proc Natl Acad Sci USA 93, 12840-12844; Wilton S D, et al., (1999) Neuromusc Disorders 9, 330-338; van Deutekom J C et al., (2001) Human Mol Genet 10, 1547-1554). In these cases, the defective gene transcript should not be subjected to targeted degradation so the antisense oligonucleotide chemistry should not promote target mRNA decay.

In a variety of genetic diseases, the effects of mutations on the eventual expression of a gene can be modulated through a process of targeted exon skipping during the splicing process. The splicing process is directed by complex multiparticle machinery that brings adjacent exon-intron junctions in pre-mRNA into close proximity and performs cleavage of phosphodiester bonds at the ends of the introns with their subsequent reformation between exons that are to be spliced together. This complex and highly precise process is mediated by sequence motifs in the pre-mRNA that are relatively short semi-conserved RNA segments to which bind the various nuclear splicing factors that are then involved in the splicing reactions. By changing the way the splicing machinery reads or recognises the motifs involved in pre-mRNA processing, it is possible to create differentially spliced mRNA molecules. It has now been recognised that the majority of human genes are alternatively spliced during normal gene expression, although the mechanisms invoked have not been identified. Using antisense oligonucleotides, it has been shown that errors and deficiencies in a coded mRNA could be bypassed or removed from the mature gene transcripts.

In nature, the extent of genetic deletion or exon skipping in the splicing process is not fully understood, although many instances have been documented to occur, generally at very low levels (Sherrat T G, et al., (1993) Am J Hum Genet 53, 1007-1015). However, it is recognised that if exons associated with disease-causing mutations can be specifically deleted from some genes, a shortened protein product can sometimes be produced that has similar biological properties of the native protein or has sufficient biological activity to ameliorate the disease caused by mutations associated with the target exon (Lu Q L, et al., (2003) Nature Medicine 9, 1009-1014; Aartsma-Rus A et al., (2004) Am J Hum Genet 74: 83-92).

This process of targeted exon skipping is likely to be particularly useful in long genes where there are many exons and introns, where there is redundancy in the genetic constitution of the exons or where a protein is able to function without one or more particular exons (e.g. with the dystrophin gene, which consists of 79 exons; or possibly some collagen genes which encode for repeated blocks of sequence or the huge nebulin or titin genes which are comprised of ~80 and over 370 exons, respectively).

Efforts to redirect gene processing for the treatment of genetic diseases associated with truncations caused by mutations in various genes have focused on the use of antisense oligonucleotides that either: (1) fully or partially overlap with the elements involved in the splicing process; or (2) bind to the pre-mRNA at a position sufficiently close to the element to disrupt the binding and function of the splicing factors that would normally mediate a particular splicing reaction which occurs at that element (e.g., binds to the pre-mRNA at a position within 3, 6, or 9 nucleotides of the element to be blocked).

For example, modulation of mutant dystrophin pre-mRNA splicing with antisense oligoribonucleotides has been reported both in vitro and in vivo. In one type of dystrophin mutation reported in Japan, a 52-base pair deletion mutation causes exon 19 to be removed with the flanking introns during the splicing process (Matsuo et al., (1991) J Clin Invest. 87:2127-2131). An in vitro minigene splicing system has been used to show that a 31-mer 2'-O-methyl oligoribonucleotide complementary to the 5' half of the deleted sequence in dystrophin Kobe exon 19 inhibited splicing of wild-type pre-mRNA (Takeshima et al. (1995), J. Clin. Invest. 95:515-520). The same oligonucleotide was used to induce exon skipping from the native dystrophin gene transcript in human cultured lymphoblastoid cells.

Dunckley et al. (1997) Nucleosides & Nucleotides, 16, 1665-1668 described in vitro constructs for analysis of splicing around exon 23 of mutated dystrophin in the mdx mouse mutant, a model for muscular dystrophy. Plans to analyse these constructs in vitro using 2' modified oligonucleotides targeted to splice sites within and adjacent to mouse dystrophin exon 23 were discussed, though no target sites or sequences were given.

2'-O-methyl oligoribonucleotides were subsequently reported to correct dystrophin deficiency in myoblasts from the mdx mouse from this group. An antisense oligonucleotide targeted to the 3' splice site of murine dystrophin intron 22 was reported to cause skipping of the mutant exon as well as several flanking exons and created a novel in-frame dystrophin transcript with a novel internal deletion. This mutated dystrophin was expressed in 1-2% of antisense treated mdx myotubes. Use of other oligonucleotide modifications such as 2'-0-methoxyethyl phosphodiesters are described (Dunckley et al. (1998) Human Mol. Genetics, 5:1083-90).

Thus, antisense molecules may provide a tool in the treatment of genetic disorders such as Duchenne Muscular Dystrophy (DMD). However, attempts to induce exon skipping using antisense molecules have had mixed success.

Studies on dystrophin exon 19, where successful skipping of that exon from the dystrophin pre-mRNA was achieved using a variety of antisense molecules directed at the flanking splice sites or motifs within the exon involved in exon definition as described by Errington et al. (2003) J Gen Med 5: 518-527).

In contrast to the apparent ease of exon 19 skipping, the first report of exon 23 skipping in the mdx mouse by Dunckley et al., (1998) is now considered to be reporting only a naturally occurring revertant transcript or artefact rather than any true antisense activity. In addition to not consistently generating transcripts missing exon 23, Dunckley et al, (1998) did not show any time course of induced exon skipping, or even titration of antisense oligonucleotides, to demonstrate dose dependent effects where the levels of exon skipping corresponded with increasing or decreasing amounts of antisense oligonucleotide. Furthermore, this work could not be replicated by other researchers.

The first example of specific and reproducible exon skipping in the mdx mouse model was reported by Wilton et al., (1999) Neuromuscular Disorders 9, 330-338. By directing an antisense molecule to the donor splice site, consistent and efficient exon 23 skipping was induced in the dystrophin mRNA within 6 hours of treatment of the cultured cells. Wilton et al., (1999), also describe targeting the acceptor region of the mouse dystrophin pre-mRNA with longer antisense oligonucleotides and being unable to repeat the published results of Dunckley et al. (1998). No exon skipping, either 23 alone or multiple removal of several flanking exons, could be reproducibly detected using a selection of antisense oligonucleotides directed at the acceptor splice site of intron 22.

While the first antisense oligonucleotide directed at the intron 23 donor splice site induced consistent exon skipping in primary cultured myoblasts, this compound was found to be much less efficient in immortalized cell cultures expressing higher levels of dystrophin. However, with refined targeting and antisense oligonucleotide design, the efficiency of specific exon removal was increased by almost an order of magnitude (see Mann C J et al., (2002) J Gen Med 4, 644-654).

Thus, there remains a need to provide antisense oligonucleotides capable of binding to and modifying the splicing of a target nucleotide sequence. Simply directing the antisense oligonucleotides to motifs presumed to be crucial for splicing is no guarantee of the efficacy of that compound in a therapeutic setting.

The preceding discussion of the background to the invention is intended only to facilitate an understanding of the present invention. It should be appreciated that the discussion is not an acknowledgment or admission that any of the material referred to was part of the common general knowledge as at the priority date of the application.

SUMMARY OF THE INVENTION

The present invention provides antisense molecule compounds and compositions suitable for binding to RNA motifs involved in the splicing of pre-mRNA that are able to induce specific and efficient exon skipping and a method for their use thereof.

The choice of target selection plays a crucial role in the efficiency of exon skipping and hence its subsequent application of a potential therapy. Simply designing antisense molecules to target regions of pre-mRNA presumed to be involved in splicing is no guarantee of inducing efficient and specific exon skipping. The most obvious or readily defined targets for splicing intervention are the donor and acceptor splice sites although there are less defined or conserved motifs including exonic splicing enhancers, silencing elements and branch points. The acceptor and donor splice sites have consensus sequences of about 16 and 8 bases respectively (see FIG. 1 for schematic representation of motifs and domains involved in exon recognition, intron removal and the splicing process).

According to a first aspect, the invention provides antisense molecules capable of binding to a selected target to induce exon skipping.

For example, to induce exon skipping in exons 5, 12, 17, 21, 22, 24, 43-47, 49, 50, 54-64, 66, 67, 70 and 72 in the Dystrophin gene transcript the antisense molecules are preferably selected from the group listed in Table 1A.

In a further example, it is possible to combine two or more antisense oligonucleotides of the present invention together to induce more efficient exon skipping in exons 3, 4, 8, 10, 26, 36, 48, 60, 66 and 68. A combination or "cocktail" of antisense oligonucleotides are directed at exons to induce efficient exon skipping.

According to a second aspect, the present invention provides antisense molecules selected and or adapted to aid in the prophylactic or therapeutic treatment of a genetic disorder comprising at least an antisense molecule in a form suitable for delivery to a patient.

According to a third aspect, the invention provides a method for treating a patient suffering from a genetic disease wherein there is a mutation in a gene encoding a particular protein and the affect of the mutation can be abrogated by exon skipping, comprising the steps of: (a) selecting an antisense molecule in accordance with the methods described herein; and (b) administering the molecule to a patient in need of such treatment.

The invention also addresses the use of purified and isolated antisense oligonucleotides of the invention, for the manufacture of a medicament for treatment of a genetic disease.

The invention further provides a method of treating a condition characterised by Duchenne muscular dystrophy, which method comprises administering to a patient in need of treatment an effective amount of an appropriately designed antisense oligonucleotide of the invention, relevant to the particular genetic lesion in that patient. Further, the invention provides a method for prophylactically treating a patient to prevent or at least minimise Duchene muscular dystrophy, comprising the step of: administering to the patient an effective amount of an antisense oligonucleotide or a pharmaceutical composition comprising one or more of these biological molecules.

The invention also provides kits for treating a genetic disease, which kits comprise at least a antisense oligonucleotide of the present invention, packaged in a suitable container and instructions for its use.

Other aspects and advantages of the invention will become apparent to those skilled in the art from a review of the ensuing description, which proceeds with reference to the following figures.

BRIEF DESCRIPTION OF THE DRAWINGS

FIG. 1. Schematic representation of motifs and domains involved in exon recognition, intron removal and the splicing process.

FIG. 46A. Sequences of antisense molecules.

FIG. 46B. Sequences of antisense molecules.

DETAILED DESCRIPTION

Brief Description of the Sequence Listings

TABLE 1A

Figure 2:
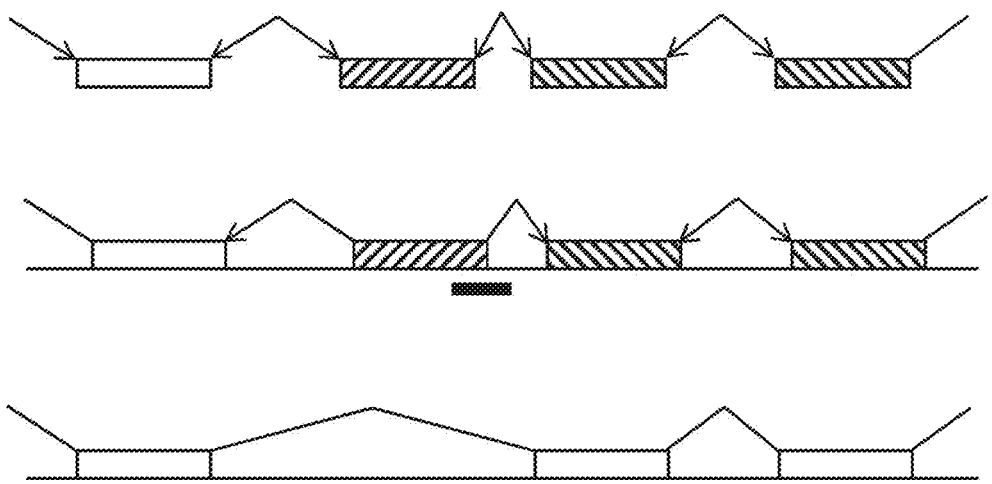
FIG. 2. Diagrammatic representation of the concept of antisense oligonucleotide induced exon skipping to by-pass disease-causing mutations (not drawn to scale). The hatched box represents an exon carrying a mutation that prevents the translation of the rest of the mRNA into a protein. The solid black bar represents an antisense oligonucleotide that prevents inclusion of that exon in the mature mRNA.

| | | Single antisense molecules |
|---|---|---|
| SEQ ID | Exon | Sequence |
| | Exon 5 | |
| 1 | H5A(+35+65) | AAA CCA AGA GUC AGU UUA UGA UUU CCA UCU A |
| | Exon 11 | |
| 52 | H11A(+50+79) | CUG UUC CAA UCA GCU UAC UUC CCA AUU GUA |
| | Exon 12 | |
| 2 | H12A(+52+75) | UCU UCU GUU UUU GUU AGC CAG UCA |
| 53 | H12A(+30+57) | CAG UCA UUC AAC UCU UUC AGU UUC UGA U |
| | Exon 17 | |
| 3 | H17A(−07+23) | GUG GUG GUG ACA GCC UGU GAA AUC UGU GAG |
| 4 | H17A(+61+86) | UGU UCC CUU GUG GUC ACC GUA GUU AC |
| | Exon 21 | |
| 5 | H21A(+86+114) | CAC AAA GUC UGC AUC CAG GAA CAU GGG UC |
| 6 | H21A(+90+119) | AAG GCC ACA AAG UCU GCA UCC AGG AAC AUG |
| | Exon 22 | |
| 7 | H22A(+125+146) | CUG CAA UUC CCC GAG UCU CUG C |
| | Exon 24 | |
| 8 | H24A(+51+73) | CAA GGG CAG GCC AUU CCU CCU UC |

TABLE 1A-continued

Single antisense molecules

| SEQ ID | Exon | Sequence |
|---|---|---|
| | Exon 43 | |
| 9 | H43A(+92+117) | GAG AGC UUC CUG UAG CUU CAC CCU UU |
| | Exon 44 | |
| 10 | H44A(+65+90) | UGU UCA GCU UCU GUU AGC CAC UGA |
| 54 | H44A(+59+85) | CUG UUC AGC UUC UGU UAG CCA CUG AUU |
| | Exon 45 | |
| 11 | H45A (-09+25) | GCU GCC CAA UGC CAU CCU GGA GUU CCU GUA AGA U |
| 55 | H45A(-03+25) | GCU GCC CAA UGC CAU CCU GGA GUU CCU G |
| 61 | H45A(-06+25) | GCU GCC CAA UGC CAU CCU GGA GUU CCU GUA A |
| 62 | H45A(-12+19) | CAA UGC CAU CCU GGA GUU CCU GUA AGA UAC C |
| | Exon 46 | |
| 12 | H46A(+81+109) | UCC AGG UUC AAG UGG GAU ACU AGC AAU GU |
| 56 | H46A(+93+122) | GUU GCU GCU CUU UUC AGU UCA AGU GGG A |
| | Exon 47 | |
| 13 | H47A(+01+29) | UGG CGC AGG GGC AAC UCU UCC ACC AGU AA |
| | Exon 49 | |
| 14 | H49A(+45+70) | ACA AAU GCU GCC CUU UAG ACA AAA UC |
| | Exon 50 | |
| 15 | H50A(+48+74) | GGC UGC UUU GCC CUC AGC UCU UGA AGU |
| | Exon 51 | |
| 57 | H51A(+71+100) | GGU ACC UCC AAC AUC AAG GAA GAU GGC AUU |
| | Exon 52 | |
| 58 | H52A(+09+38) | UCC AAC UGG GGA CGC CUC UGU UCC AAA UCC UGC |
| | Exon 53 | |
| 59 | H53A(+33+65) | UUC AAC UGU UGC CUC CGG UUC UGA AGG UGU UCU |
| | Exon 54 | |
| 16 | H54A(+67+97) | UGG UCU CAU CUG CAG AAU AAU CCC GGA GAA G |
| | Exon 55 | |
| 17 | H55A(-10+20) | CAG CCU CUC GCU CAC UCA CCC UGC AAA GGA |
| | Exon 56 | |
| 18 | H56A(+92+121) | CCA AAC GUC UUU GUA ACA GGA CUG CAU |
| 19 | H56A(+112+141) | CCA CUU GAA GUU CAU GUU AUC CAA ACG UCU |
| | Exon 57 | |
| 20 | H57A(-10+20) | AAC UGG CUU CCA AAU GGG ACC UGA AAA AGA |
| | Exon 58 | |
| 21 | H58A(+34+64) | UUC GUA CAG UCU CAA GAG UAC UCA UGA UUA C |
| 22 | H58D(+17-07) | CAA UUA CCU CUG GGC UCC UGG UAG |

TABLE 1A-continued

Single antisense molecules

| SEQ ID | Exon | Sequence |
|---|---|---|
| | Exon 59 | |
| 23 | H59A(+96+120) | CUA UUU UUC UCU GCC AGU CAG CGG A |
| | Exon 60 | |
| 24 | H60A(+33+62) | CGA GCA AGG UCA UUG ACG UGG CUC ACG UUC |
| | Exon 61 | |
| 25 | H61A(+10+40) | GGG CUU CAU GCA GCU GCC UGA CUC GGU CCU C |
| | Exon 62 | |
| 26 | H62A(23+52) | UAG GGC ACU UUG UUU GGC GAG AUG GCU CUC |
| | Exon 63 | |
| 27 | H63A(+20+49) | GAG CUC UGU CAU UUU GGG AUG UCC CCA GCA |
| | Exon 64 | |
| 28 | H64A(+34+62) | CUG CAG UCU UCG GAG UUU CAU GGC AGU CC |
| | Exon 66 | |
| 29 | H66A(-8+19) | GAU CCU CCC UGU UCG UCC CCU AUU AUG |
| | Exon 67 | |
| 30 | H67A(+17+47) | GCG CUG GUC ACA AAA UCC UGU UGA ACU UGC |
| | Exon 73 | |
| 60 | H73A(+02+26) | CAU UGC UGU UUU CCA UUU CUG GUA G |

TABLE 1B

Cocktails of antisense molecules

| SEQ ID | Exon | Sequence |
|---|---|---|
| | Exon 3 cocktails | |
| 31 | H3A(+30+60) | UAG GAG GCG CCU CCC AUC CUG UAG GUC ACU G |
| 32 | H3A(+61+85) | G CCC UGU CAG GCC UUC GAG GAG GUC |
| | Exon 4 cocktails | |
| 33 | H4A(+11+40) | UGU UCA GGG CAU GAA CUC UUG UGG AUC CUU |
| 34 | H4D(+14-11) | GUA CUA CUU ACA UUA UUG UUC UGC A |
| | Exon 8 cocktails | |
| 35 | H8A(-06+24) | UAU CUG GAU AGG UGG UAU CAA CAU CUG UAA |
| 36 | H8A(+134+158) | AUG UAA CUG AAA AUG UUC UUC UUU A |
| | Exon 10 cocktails | |
| 37 | H10A(-05+16) | CAG GAG CUU CCA AAU GCU GCA |
| 38 | H10A(+98+119) | UCC UCA GCA GAA AGA AGC CAC G |
| | Exon 26 cocktails | |
| 39 | H26A(-07+19) | CCU CCU UUC UGG CAU AGA CCU UCC AC |
| 40 | H26A(+24+50) | CUU ACA GUU UUC UCC AAA CCU CCC UUC |
| 41 | H26A(+68+92) | UGU GUC AUC CAU UCG UGC AUC UCU G |

TABLE 1B-continued

Cocktails of antisense molecules

| SEQ ID | Exon | Sequence |
|---|---|---|
| | Exon 36 cocktails | |
| 42 | H36A(-16+09) | CUG GUA UUC CUU AAU UGU ACA GAG A |
| 43 | H36A(+22+51) | UGU GAU GUG GUC CAC AUU CUG GUC AAA AGU |
| | Exon 48 cocktails | |
| 44 | H48A(+01+28) | CUU GUU UCU CAG GUA AAG CUC UGG AAA C |
| 45 | H48A(+40+67) | CAA GCU GCC CAA GGU CUU UUA UUU GAG C |
| | Exon 60 cocktails | |
| 46 | H60A(+87+116) | UCC AGA GUG CUG AGG UUA UAC GGU GAG AGC |
| 47 | H60A(+37+66) | CUG GCG AGC AAG GUC CUU GAC GUG GCU CAC |
| | Exon 66 cocktails | |
| 48 | H66A(-02+28) | CAG GAC ACG GAU CCU CCC UGU UCG UCC CCU |
| 49 | H66D(+13-17) | UAA UAU ACA CGA CUU ACA UCU GUA CUU GUC |
| | Exon 68 cocktails | |
| 50 | H68A(+48+72) | CAC CAU GGA CUG GGG UUC CAG UCU C |
| 51 | H68D(+23-03) | UAC CUG AAU CCA AUG AUU GGA CAC UC |

General

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

Sequence identity numbers (SEQ ID NO:) containing nucleotide and amino acid sequence information included in this specification are collected at the end of the description and have been prepared using the programme PatentIn Version 3.0. Each nucleotide or amino acid sequence is identified in the sequence listing by the numeric indicator <210> followed by the sequence identifier (e.g. <210>1, <210>2, etc.). The length, type of sequence and source organism for each nucleotide or amino acid sequence are indicated by information provided in the numeric indicator fields <211>, <212> and <213>, respectively. Nucleotide and amino acid sequences referred to in the specification are defined by the information provided in numeric indicator field <400> followed by the sequence identifier (e.g. <400>1, <400>2, etc.).

An antisense molecule nomenclature system was proposed and published to distinguish between the different antisense molecules (see Mann et al., (2002) *J Gen Med* 4, 644-654). This nomenclature became especially relevant when testing several slightly different antisense molecules, all directed at the same target region, as shown below:

H # A/D(x:y).

The first letter designates the species (e.g. H: human, M: murine, C: canine) "#" designates target dystrophin exon number.

"A/D" indicates acceptor or donor splice site at the beginning and end of the exon, respectively.

(x y) represents the annealing coordinates where "−" or "+" indicate intronic or exonic sequences respectively. As an example, A(−6+18) would indicate the last 6 bases of the intron preceding the target exon and the first 18 bases of the target exon. The closest splice site would be the acceptor so these coordinates would be preceded with an "A". Describing annealing coordinates at the donor splice site could be D(+2−18) where the last 2 exonic bases and the first 18 intronic bases correspond to the annealing site of the antisense molecule. Entirely exonic annealing coordinates that would be represented by A(+65+85), that is the site between the 65$^{th}$ and 85$^{th}$ nucleotide from the start of that exon.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

As used herein the term "derived" and "derived from" shall be taken to indicate that a specific integer may be obtained from a particular source albeit not necessarily directly from that source.

Throughout this specification, unless the context requires otherwise, the word "comprise", or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

DESCRIPTION OF THE PREFERRED EMBODIMENT

When antisense molecule(s) are targeted to nucleotide sequences involved in splicing in exons within pre-mRNA sequences, normal splicing of the exon may be inhibited, causing the splicing machinery to by-pass the entire mutated exon from the mature mRNA. The concept of antisense oligonucleotide induced exon skipping is shown in FIG. 2.

In many genes, deletion of an entire exon would lead to the production of a non-functional protein through the loss of important functional domains or the disruption of the reading frame. However, in some proteins it is possible to shorten the protein by deleting one or more exons from within the protein, without disrupting the reading frame and without seriously altering the biological activity of the protein. Typically, such proteins have a structural role and or possess functional domains at their ends. The present invention describes antisense molecules capable of binding to specified dystrophin pre-mRNA targets and re-directing processing of that gene.

A preferred aim of a therapy based on antisense molecules is to get maximum exon skipping by providing the lowest possible concentration of the antisense molecule. Generally, an antisense molecule may cause strong, robust exon skipping; weak, sporadic exon skipping or no exon skipping at all. It is preferable to develop antisense molecules (alone or in combination) which can deliver strong, robust consistent exon skipping at a low therapeutic dose.

Antisense Molecules

According to a first aspect of the invention, there is provided antisense molecules capable of binding to a selected target to induce exon skipping. To induce exon skipping in exons of the Dystrophin gene transcript, the antisense molecules are preferably selected from the group of compounds shown in Table 1A.

There is also provided a combination or "cocktail" of two or more antisense oligonucleotides capable of binding to a selected target to induce exon skipping. To induce exon skipping in exons of the Dystrophin gene transcript, the antisense molecules in a "cocktail" are preferably selected from the group of compounds shown in Table 1B.

Designing antisense molecules to completely mask consensus splice sites may not necessarily generate any skipping of the targeted exon. Furthermore, the inventors have discovered that size or length of the antisense oligonucleotide itself is not always a primary factor when designing antisense molecules. With some targets such as exon 19, antisense oligonucleotides as short as 12 bases were able to induce exon skipping, albeit not as efficiently as longer (20-31 bases) oligonucleotides. In some other targets, such as murine dystrophin exon 23, antisense oligonucleotides only 17 residues long were able to induce more efficient skipping than another overlapping compound of 25 nucleotides. However, in the present invention it has been generally found that longer antisense molecules are often more effective at inducing exon skipping than shorter molecules. Thus preferably, the antisense molecules of the present invention are between 24 and 30 nucleic acids in length, preferably about 28 nucleotides in length. For example, it has previously been found that an antisense oligonucleotide of 20 bases (H16A(-07+13)) was ineffective at inducing exon skipping of exon 16, but an oligonucleotide of 31 bases (H16A(-06+25)), which completely encompassed the shorter oligonucleotide, was effective at inducing skipping (Harding et al (2007) Mol Ther 15:157-166).

The inventors have also discovered that there does not appear to be any standard motif that can be blocked or masked by antisense molecules to redirect splicing. In some exons, such as mouse dystrophin exon 23, the donor splice site was the most amenable to target to re-direct skipping of that exon. It should be noted that designing and testing a series of exon 23 specific antisense molecules to anneal to overlapping regions of the donor splice site showed considerable variation in the efficacy of induced exon skipping. As reported in Mann et al., (2002) there was a significant variation in the efficiency of bypassing the nonsense mutation depending upon antisense oligonucleotide annealing ("Improved antisense oligonucleotide induced exon skipping in the mdx mouse model of muscular dystrophy". *J Gen Med* 4: 644-654). Targeting the acceptor site of exon 23 or several internal domains was not found to induce any consistent exon 23 skipping.

In other exons targeted for removal, masking the donor splice site did not induce any exon skipping. However, by directing antisense molecules to the acceptor splice site (human exon 8 as discussed below), strong and sustained exon skipping was induced. It should be noted that removal of human exon 8 was tightly linked with the co-removal of exon 9. There is no strong sequence homology between the exon 8 antisense oligonucleotides and corresponding regions of exon 9 so it does not appear to be a matter of cross reaction. Rather, the splicing of these two exons is generally linked. This is not an isolated instance, as the same effect is observed in canine cells where targeting exon 8 for removal also resulted in the skipping of exon 9. Targeting exon 23 for removal in the mouse dystrophin pre-mRNA also results in the frequent removal of exon 22 as well. This effect occurs in a dose dependent manner and also indicates close coordinated processing of 2 adjacent exons.

In other targeted exons, antisense molecules directed at the donor or acceptor splice sites did not induce exon skipping or induce poor skipping, while annealing antisense molecules to intra-exonic regions (i.e. exon splicing enhancers within human dystrophin exon 4) was most efficient at inducing exon skipping. Some exons, both mouse and human exon 19 for example, are readily skipped by targeting antisense molecules to a variety of motifs. That is, targeted exon skipping is induced after using antisense oligonucleotides to mask donor and acceptor splice sites or exon splicing enhancers.

It is also not possible to predict which cocktails of antisense molecules will induce exon skipping. For example, the combination of two antisense molecules which, on their own, are very good at inducing skipping of a given exon may not cause skipping of an exon when combined in a cocktail. For example, each of H50A(+02+30) and H50A(+66+95) on their own induce good skipping of exon 50 and 51. However, in combination as a cocktail, they only induced poor skipping of the two exons. Likewise, the combination of H50A(+02+30) and H51A(+66+90) or H50A(+02+30) and H51A(+61+90) did not cause efficient skipping of exons 50 and 51, even though the individual antisense molecules were effective. Yet the introduction of a third antisense molecule ([H51D(+16-07)] which by itself did not cause skipping), created a three element cocktail ([H50A(+02+30)], H51A(+66+90) and [H51D(+16-07)]) that was able to cause skipping of exons 50 and 51 down to 1 nM.

Alternatively, the combination of two or three antisense molecules which are ineffective or only moderately effective on their own may cause excellent skipping when combined. For example, individually H26A(-07+19) [SEQ ID NO: 39], H26A(+24+50) [SEQ ID NO: 40] and H26A(+68+92)

[SEQ ID NO: 41] cause inefficient skipping of exon 26, and also induce multiple exon skipping (26-29 or 27-30). However, when the three exons are combined as a cocktail, highly efficient skipping of exon 26 occurs.

From the above examples and discussion, it is clear that there is no way to accurately predict whether a combination will work or not.

Figure 15:
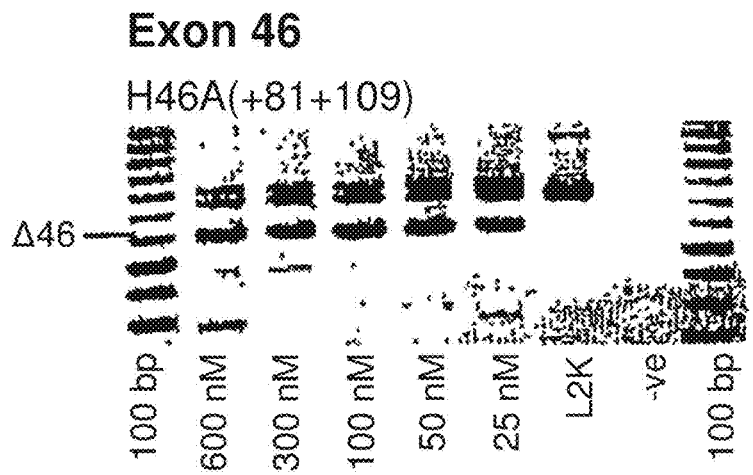
FIG. 15. Gel electrophoresis showing strong and consistent exon 46 skipping using antisense molecule H46A(+81+109).
Figure 24:
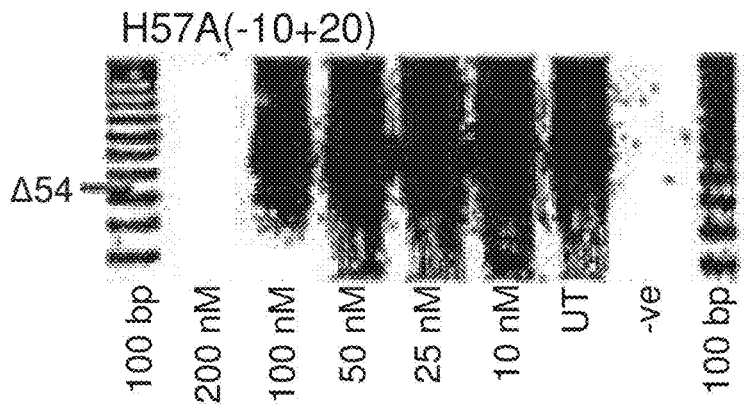
FIG. 24. Gel electrophoresis showing antisense molecule H57A(−10+20) induced dose dependant exon 57 skipping.

Antisense molecules may cause skipping of exons in a 'dose dependant' or 'non-dose dependant' manner. By dose dependant, it is meant that a larger amount of the antisense molecule induces better skipping of the exon, whereas non-dose dependant antisense molecules are able to induce skipping even at very low doses. For example, from FIG. 15 it can be seen that H46A(+81+109) [SEQ ID NO: 12] gives equally good skipping of exon 46 regardless of the amount of antisense molecule present (from 600 nM to 25 nM). In contrast, H57A(-10+20) [SEQ ID NO: 20] (FIG. 24) induces strong skipping of exon 57 at 100 nM, but reduced skipping at 50 nM and an even greater reduction in skipping at 25 nM.

It is preferable to select antisense molecules that induce skipping in a dose independent manner, as these molecules may be administered at very low concentrations and still give a therapeutic effect. However, it is also acceptable to select as preferred molecules those antisense molecules that induce skipping in a dose dependant manner, particularly if those molecules induce good or excellent skipping at low concentrations. Preferably, the antisense molecules of the present invention are able to induce good or excellent exon skipping at concentrations of less than 500 nM, preferably less than 200 nM and more preferably as low as 100 nM, 50 nM or even 25 nM. Most preferably, the oligonucleotide molecules of the present invention are able to induce skipping at levels of greater that 30% at a concentration of 100 nM.

To identify and select antisense oligonucleotides suitable for use in the modulation of exon skipping, a nucleic acid sequence whose function is to be modulated must first be identified. This may be, for example, a gene (or mRNA transcribed form the gene) whose expression is associated with a particular disorder or disease state, or a nucleic acid molecule from an infectious agent. Within the context of the present invention, preferred target site(s) are those involved in mRNA splicing (i.e. splice donor sites, splice acceptor sites, or exonic splicing enhancer elements). Splicing branch points and exon recognition sequences or splice enhancers are also potential target sites for modulation of mRNA splicing.

Preferably, the present invention aims to provide antisense molecules capable of binding to a selected target in the dystrophin pre-mRNA to induce efficient and consistent exon skipping. Duchenne muscular dystrophy arises from mutations that preclude the synthesis of a functional dystrophin gene product. These Duchenne muscular dystrophy gene defects are typically nonsense mutations or genomic rearrangements such as deletions, duplications or microdeletions or insertions that disrupt the reading frame. As the human dystrophin gene is a large and complex gene (with 79 exons being spliced together to generate a mature mRNA with an open reading frame of approximately 11,000 bases), there are many positions where these mutations can occur. Consequently, a comprehensive antisense oligonucleotide based therapy to address many of the different disease-causing mutations in the dystrophin gene will require that many exons can be targeted for removal during the splicing process.

Within the context of the present invention, preferred target site(s) are those involved in mRNA splicing (i.e. splice donor sites, splice acceptor sites or exonic splicing enhancer elements). Splicing branch points and exon recognition sequences or splice enhancers are also potential target sites for modulation of mRNA splicing.

The oligonucleotide and the DNA or RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or precise pairing such that stable and specific binding occurs between the oligonucleotide and the DNA or RNA target. It is understood in the art that the sequence of an antisense molecule need not be 100% complementary to that of its target sequence to be specifically hybridisable. An antisense molecule is specifically hybridisable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

While the above method may be used to select antisense molecules capable of deleting any exon from within a protein that is capable of being shortened without affecting its biological function, the exon deletion should not lead to a reading frame shift in the shortened transcribed mRNA. Thus, if in a linear sequence of three exons the end of the first exon encodes two of three nucleotides in a codon and the next exon is deleted then the third exon in the linear sequence must start with a single nucleotide that is capable of completing the nucleotide triplet for a codon. If the third exon does not commence with a single nucleotide there will be a reading frame shift that would lead to the generation of a truncated or a non-functional protein.

It will be appreciated that the codon arrangements at the end of exons in structural proteins may not always break at the end of a codon. Consequently, there may be a need to delete more than one exon from the pre-mRNA to ensure in-frame reading of the mRNA. In such circumstances, a plurality of antisense oligonucleotides may need to be selected by the method of the invention, wherein each is directed to a different region responsible for inducing splicing in the exons that are to be deleted.

The length of an antisense molecule may vary so long as it is capable of binding selectively to the intended location within the pre-mRNA molecule. The length of such sequences can be determined in accordance with selection procedures described herein. Generally, the antisense molecule will be from about 10 nucleotides in length up to about 50 nucleotides in length. However, it will be appreciated that any length of nucleotides within this range may be used in the method. Preferably, the length of the antisense molecule is between 17 to 30 nucleotides in length. Surprisingly, it has been found that longer antisense molecules are often more effective at inducing exon skipping. Thus, most preferably the antisense molecule is between 24 and 30 nucleotides in length.

In order to determine which exons can be connected in a dystrophin gene, reference should be made to an exon boundary map. Connection of one exon with another is based on the exons possessing the same number at the 3' border as is present at the 5' border of the exon to which it is being connected. Therefore, if exon 7 were deleted, exon 6 must connect to either exons 12 or 18 to maintain the reading frame. Thus, antisense oligonucleotides would need to be selected which redirected splicing for exons 7 to 11 in the first instance or exons 7 to 17 in the second instance. Another and somewhat simpler approach to restore the reading frame around an exon 7 deletion would be to remove the two flanking exons. Induction of exons 6 and 8 skipping should result in an in-frame transcript with the splicing of exons 5 to 9. In practise however, targeting exon 8 for removal from the pre-mRNA results in the co-removal of exon 9 so the resultant transcript would have exon 5 joined to exon 10. The inclusion or exclusion of exon 9 does not alter the reading frame.

Once the antisense molecules to be tested have been identified, they are prepared according to standard techniques known in the art. The most common method for producing antisense molecules is the methylation of the 2' hydroxyribose position and the incorporation of a phosphorothioate backbone.

This produces molecules that superficially resemble RNA but that are much more resistant to nuclease degradation.

To avoid degradation of pre-mRNA during duplex formation with the antisense molecules, the antisense molecules used in the method may be adapted to minimise or prevent cleavage by endogenous RNase H. This property is highly preferred, as the presence of unmethylated RNA oligonucleotides in an intracellularly environment or in contact with crude extracts that contain RNase H will lead to degradation of the pre-mRNA: antisense oligonucleotide duplexes. Any form of modified antisense molecules that are capable of by-passing or not inducing such degradation may be used in the present method. The nuclease resistance may be achieved by modifying the antisense molecules of the invention so that it comprises partially unsaturated aliphatic hydrocarbon chain and one or more polar or charged groups including carboxylic acid groups, ester groups, and alcohol groups.

An example of antisense molecules which, when duplexed with RNA, are not cleaved by cellular RNase H are 2'-O-methyl derivatives. 2'-O-methyl-oligoribonucleotides are very stable in a cellular environment and in animal tissues, and their duplexes with RNA have higher Tm values than their ribo- or deoxyribo-counterparts. Alternatively, the nuclease resistant antisense molecules of the invention may have at least one of the last 3'-terminus nucleotides fluoridated. Still alternatively, the nuclease resistant antisense molecules of the invention have phosphorothioate bonds linking between at least two of the last 3-terminus nucleotide bases, preferably having phosphorothioate bonds linking between the last four 3'-terminal nucleotide bases.

Antisense molecules that do not activate RNase H can be made in accordance with known techniques (see, e.g., U.S. Pat. No. 5,149,797). Such antisense molecules, which may be deoxyribonucleotide or ribonucleotide sequences, simply contain any structural modification which sterically hinders or prevents binding of RNase H to a duplex molecule containing the oligonucleotide as one member thereof, which structural modification does not substantially hinder or disrupt duplex formation. Because the portions of the oligonucleotide involved in duplex formation are substantially different from those portions involved in RNase H binding thereto, numerous antisense molecules that do not activate RNase H are available. For example, such antisense molecules may be oligonucleotides wherein at least one, or all, of the inter-nucleotide bridging phosphate residues are modified phosphates, such as methyl phosphonates, methyl phosphorothioates, phosphoromorpholidates, phosphoropiperazidates and phosphoramidates. For example, every other one of the internucleotide bridging phosphate residues may be modified as described. In another non-limiting example, such antisense molecules are molecules wherein at least one, or all, of the nucleotides contain a 2' lower alkyl moiety (e.g., $C_1$-$C_4$, linear or branched, saturated or unsaturated alkyl, such as methyl, ethyl, ethenyl, propyl, 1-propenyl, 2-propenyl, and isopropyl). For example, every other one of the nucleotides may be modified as described.

While antisense oligonucleotides are a preferred form of the antisense molecules, the present invention comprehends other oligomeric antisense molecules, including but not limited to oligonucleotide mimetics such as are described below.

Specific examples of preferred antisense compounds useful in this invention include oligonucleotides containing modified backbones or non-natural inter-nucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their inter-nucleoside backbone can also be considered to be oligonucleosides.

In other preferred oligonucleotide mimetics, both the sugar and the inter-nucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleo-bases are retained and are bound directly or indirectly to aza nitrogen atoms of the amide portion of the backbone.

Modified oligonucleotides may also contain one or more substituted sugar moieties. Oligonucleotides may also include nucleobase (often referred to in the art simply as "base") modifications or substitutions. Certain nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Another modification of the oligonucleotides of the invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of this invention, are antisense molecules, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the increased resistance to nuclease degradation, increased cellular uptake, and an additional region for increased binding affinity for the target nucleic acid.

Methods of Manufacturing Antisense Molecules

The antisense molecules used in accordance with this invention may be conveniently and routinely made through the well-known technique of solid phase synthesis. Equipment for such synthesis is sold by several vendors including, for example, Applied Biosystems (Foster City, Calif.). One method for synthesising oligonucleotides on a modified solid support is described in U.S. Pat. No. 4,458,066.

Any other means for such synthesis known in the art may additionally or alternatively be employed. It is well known to use similar techniques to prepare oligonucleotides such as the phosphorothioates and alkylated derivatives. In one such automated embodiment, diethyl-phosphoramidites are used as starting materials and may be synthesized as described by Beaucage, et al., (1981) *Tetrahedron Letters,* 22:1859-1862.

The antisense molecules of the invention are synthesised in vitro and do not include antisense compositions of biological origin, or genetic vector constructs designed to direct the in vivo synthesis of antisense molecules. The molecules of the invention may also be mixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption.

Therapeutic Agents

The present invention also can be used as a prophylactic or therapeutic, which may be utilised for the purpose of treatment of a genetic disease.

Accordingly, in one embodiment the present invention provides antisense molecules that bind to a selected target in the dystrophin pre-mRNA to induce efficient and consistent exon skipping described herein in a therapeutically effective amount admixed with a pharmaceutically acceptable carrier, diluent, or excipient.

The phrase "pharmaceutically acceptable" refers to molecular entities and compositions that are physiologically tolerable and do not typically produce an allergic or similarly untoward reaction, such as gastric upset and the like, when administered to a patient. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or saline solutions and aqueous dextrose and glycerol solutions are preferably employed as carriers, particularly for injectable solutions. Suitable pharmaceutical carriers are described in Martin, *Remington's Pharmaceutical Sciences,* 18th Ed., Mack Publishing Co., Easton, Pa., (1990).

In a more specific form of the invention there are provided pharmaceutical compositions comprising therapeutically effective amounts of an antisense molecule together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The material may be incorporated into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., *Martin, Remington's Pharmaceutical Sciences,* 18th Ed. (1990, Mack Publishing Co., Easton, Pa. 18042) pages 1435-1712 that are herein incorporated by reference. The compositions may be prepared in liquid form, or may be in dried powder, such as lyophilised form.

It will be appreciated that pharmaceutical compositions provided according to the present invention may be administered by any means known in the art. Preferably, the pharmaceutical compositions for administration are administered by injection, orally, or by the pulmonary, or nasal route. The antisense molecules are more preferably delivered by intravenous, intra-arterial, intraperitoneal, intramuscular, or subcutaneous routes of administration.

Antisense Molecule Based Therapy

Also addressed by the present invention is the use of antisense molecules of the present invention, for manufacture of a medicament for modulation of a genetic disease.

The delivery of a therapeutically useful amount of antisense molecules may be achieved by methods previously published. For example, intracellular delivery of the antisense molecule may be via a composition comprising an admixture of the antisense molecule and an effective amount of a block copolymer. An example of this method is described in US patent application US 20040248833.

Other methods of delivery of antisense molecules to the nucleus are described in Mann C J et al., (2001) ["*Antisense-induced exon skipping and the synthesis of dystrophin in the mdx mouse*". Proc., Natl. Acad. Science, 98(1) 42-47] and in Gebski et al., (2003). Human Molecular Genetics, 12(15): 1801-1811.

A method for introducing a nucleic acid molecule into a cell by way of an expression vector either as naked DNA or complexed to lipid carriers, is described in U.S. Pat. No. 6,806,084.

It may be desirable to deliver the antisense molecule in a colloidal dispersion system. Colloidal dispersion systems include macromolecule complexes, nanocapsules, microspheres, beads, and lipid-based systems including oil-in-water emulsions, micelles, mixed micelles, and liposomes or liposome formulations.

Liposomes are artificial membrane vesicles which are useful as delivery vehicles in vitro and in vivo. These formulations may have net cationic, anionic or neutral charge characteristics and are useful characteristics with in vitro, in vivo and ex vivo delivery methods. It has been shown that large unilamellar vesicles (LUV), which range in size from 0.2-4.0.PHI.m can encapsulate a substantial percentage of an aqueous buffer containing large macromolecules. RNA and DNA can be encapsulated within the aqueous interior and be delivered to cells in a biologically active form (Fraley, et al., Trends Biochem. Sci., 6:77, 1981).

In order for a liposome to be an efficient gene transfer vehicle, the following characteristics should be present: (1) encapsulation of the antisense molecule of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Alternatively, the antisense construct may be combined with other pharmaceutically acceptable carriers or diluents to produce a pharmaceutical composition. Suitable carriers and diluents include isotonic saline solutions, for example phosphate-buffered saline. The composition may be formulated for parenteral, intramuscular, intravenous, subcutaneous, intraocular, oral or transdermal administration.

The routes of administration described are intended only as a guide since a skilled practitioner will be able to determine readily the optimum route of administration and any dosage for any particular animal and condition.

The antisense molecules of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such pro-drugs, and other bioequivalents.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. The pharmaceutical compositions of the present invention may be administered in a number of ways depending upon whether local or systemic treatment is desired and upon the area to be treated. Administration may be topical (including ophthalmic and to mucous membranes including rectal delivery), pulmonary, e.g., by inhalation or insufflation of powders or aerosols, (including by nebulizer, intratracheal, intranasal, epidermal and transdermal), oral or parenteral. Parenteral administration includes intravenous, intra-arterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

Kits of the Invention

The invention also provides kits for treatment of a patient with a genetic disease which kit comprises at least an antisense molecule, packaged in a suitable container, together with instructions for its use.

In a preferred embodiment, the kits will contain at least one antisense molecule as shown in Table 1A, or a cocktail of antisense molecules as shown in Table 1B. The kits may also contain peripheral reagents such as buffers, stabilizers, etc.

The contents of the kit can be lyophilized and the kit can additionally contain a suitable solvent for reconstitution of the lyophilized components. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale for human administration.

When the components of the kit are provided in one or more liquid solutions, the liquid solution can be an aqueous solution, for example a sterile aqueous solution. For in vivo use, the expression construct may be formulated into a pharmaceutically acceptable syringeable composition. In this case the container means may itself be an inhalant, syringe, pipette, eye dropper, or other such like apparatus, from which the formulation may be applied to an affected area of the animal, such as the lungs, injected into an animal, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container means. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle.

Those of ordinary skill in the field should appreciate that applications of the above method has wide application for identifying antisense molecules suitable for use in the treatment of many other diseases.

Examples

The following Examples serve to more fully describe the manner of using the above-described invention, as well as to set forth the best modes contemplated for carrying out various aspects of the invention. It is understood that these Examples in no way serve to limit the true scope of this invention, but rather are presented for illustrative purposes. The references cited herein are expressly incorporated by reference.

Methods of molecular cloning, immunology and protein chemistry, which are not explicitly described in the following examples, are reported in the literature and are known by those skilled in the art. General texts that described conventional molecular biology, microbiology, and recombinant DNA techniques within the skill of the art, included, for example: Sambrook et al., *Molecular Cloning: A Laboratory Manual*, Second Edition, Cold Spring Harbor Laboratory Press, Cold Spring Harbor, N.Y. (1989); Glover ed., DNA Cloning: A Practical Approach, Volumes I and II, MRL Press, Ltd., Oxford, U.K. (1985); and Ausubel, F., Brent, R., Kingston, R. E., Moore, D. D., Seidman, J. G., Smith, J. A., Struhl, K. *Current Protocols in Molecular Biology*. Greene Publishing Associates/Wiley Intersciences, New York (2002).

Determining Induced Exon Skipping in Human Muscle Cells

Attempts by the inventors to develop a rational approach in antisense molecules design were not completely successful as there did not appear to be a consistent trend that could be applied to all exons. As such, the identification of the most effective and therefore most therapeutic antisense molecules compounds has been the result of empirical studies.

These empirical studies involved the use of computer programs to identify motifs potentially involved in the splicing process. Other computer programs were also used to identify regions of the pre-mRNA which may not have had extensive secondary structure and therefore potential sites for annealing of antisense molecules. Neither of these approaches proved completely reliable in designing antisense oligonucleotides for reliable and efficient induction of exon skipping.

Annealing sites on the human dystrophin pre-mRNA were selected for examination, initially based upon known or predicted motifs or regions involved in splicing. 2OMe antisense oligonucleotides were designed to be complementary to the target sequences under investigation and were synthesised on an Expedite 8909 Nucleic Acid Synthesiser. Upon completion of synthesis, the oligonucleotides were cleaved from the support column and de-protected in ammonium hydroxide before being desalted. The quality of the oligonucleotide synthesis was monitored by the intensity of the trityl signals upon each deprotection step during the synthesis as detected in the synthesis log. The concentration of the antisense oligonucleotide was estimated by measuring the absorbance of a diluted aliquot at 260 nm.

Specified amounts of the antisense molecules were then tested for their ability to induce exon skipping in an in vitro assay, as described below.

Briefly, normal primary myoblast cultures were prepared from human muscle biopsies obtained after informed consent. The cells were propagated and allowed to differentiate into myotubes using standard culturing techniques. The cells were then transfected with the antisense oligonucleotides by delivery of the oligonucleotides to the cells as cationic lipoplexes, mixtures of antisense molecules or cationic liposome preparations.

The cells were then allowed to grow for another 24 hours, after which total RNA was extracted and molecular analysis commenced. Reverse transcriptase amplification (RT-PCR) was undertaken to study the targeted regions of the dystrophin pre-mRNA or induced exonic re-arrangements.

For example, in the testing of an antisense molecule for inducing exon 19 skipping the RT-PCR test scanned several exons to detect involvement of any adjacent exons. For example, when inducing skipping of exon 19, RT-PCR was carried out with primers that amplified across exons 17 and 21. Amplifications of even larger products in this area (i.e. exons 13-26) were also carried out to ensure that there was minimal amplification bias for the shorter induced skipped transcript. Shorter or exon skipped products tend to be amplified more efficiently and may bias the estimated of the normal and induced transcript.

The sizes of the amplification reaction products were estimated on an agarose gel and compared against appropriate size standards. The final confirmation of identity of these products was carried out by direct DNA sequencing to establish that the correct or expected exon junctions have been maintained.

Once efficient exon skipping had been induced with one antisense molecule, subsequent overlapping antisense molecules may be synthesized and then evaluated in the assay as described above. Our definition of an efficient antisense molecule is one that induces strong and sustained exon skipping at transfection concentrations in the order of 300 nM or less. Most preferably, the oligonucleotide molecules of the present invention are able to induce skipping at levels of greater that 30% at a concentration of 100 nM.

Densitometry Methods

Densitometry analysis of the results of the exon skipping procedures was carried out, in order to determine which antisense molecules achieved the desired efficiency. Amplification products were fractionated on 2% agarose gels, stained with ethidium bromide and the images captured by a Chemi-Smart 3000 gel documentation system (Vilber Lourmat, Marne La Vallee). The bands were then analyzed using gel documentation system (Bio-Profil, Bio-1 D version 11.9, Vilber Lourmat, Marne La Vallee), according to the manufacturer's instructions.

Densitometry was carried out on the following antisense molecules:

FIG. 35

Exon 3 H3A(+30+60) & H3A(+61+85)
Exon 4 H4D(+14−11) & H4A(+11+40)
Exon 14 H14A(+32+61)
Exon 17 H17A(+10+35)
Exon 26 H26A(−07+19), H26A(+24+50) & H26A(+68+92)
Exon 36 H36A(−16+09) & H36A(+22+51)

FIG. 36

Exon 46 H46A(+81+109)
Exon 47 H47A(+01+29)
Exon 48 H48A(+01+28) & H48A(+40+67)
Exon 49 H49A(+45+70)

Antisense Oligonucleotides Directed at Exon 17

Antisense oligonucleotides directed at exon 17 were prepared and tested for their ability to induce exon skipping in human muscle cells using similar methods as described above.

From Table 2 below, it can be seen that the effect of antisense molecules directed at the same site (the exon 17 acceptor splice site) can be very different, even though the binding location of the two antisense molecules are overlapping.

H17A(−07+23) [SEQ ID NO:3], which anneals to the last 7 bases of intron 16 and the first 23 bases of exon 17, induces exon 17 skipping when delivered into the cell at a concentration of 25 nM. In contrast, the antisense molecule H17A(−12+18), which anneals to the last 12 bases of intron 16 and the first 18 bases of exon 17, and thus overlaps the location of binding of H17A(−07+23), was not able to induce exon skipping at all. Furthermore, H17A(−07+16), which anneals to the last 7 bases of intron 16 and the first 16 bases of exon 17 caused skipping of both exon 17 and 18 at 200 nM. Antisense molecule H17A(+61+86) [SEQ ID NO:4], which binds in an intra-exonic splicing enhancer motif of exon 17, is also able to induce good skipping. It can be seen that the ability of antisense molecules to induce exon skipping cannot be predicted simply from their binding location and must be determined through rigorous testing.

TABLE 2

Antisense molecule sequences tested to determine if they induce exon 17 skipping

| Antisense SEQOligonucleotide ID name | Sequence | Ability to induce skipping |
|---|---|---|
| 459H17A(-12 +18) | GGU GAC AGC CUG UGA AAU CUG UGA GAA GUA | No Skipping |
| 3H17A(-07+23) | GUG GUG GUG ACA GCC UGU GAA AUC UGU GAG | Skipping at 25 nM |
| 460H17A(-07+16) | UGA CAG CCU GUG AAA UCU GUG AG | Skipping ex 17 + 18 at 200 nM |
| 461H17A(+10 +35) | AGU GAU GGC UGA GUG GUG GUG ACA GC | Skipping at 50 nM |
| 462H17A(+31+50) | ACA GUU GUC UGU GUU AGU GA | inconsistent skipping |
| 4H17A(+61 +86) | UGU UCC CUU GUG GUC ACC GUA GUU AC | Skipping at 50 nM |
| 463H17A(+144+163) | CAG AAU CCA CAG UAA UCU GC | skipping at 300 nM |

This data shows that some particular antisense molecules induce efficient exon skipping while another antisense molecule, which targets a near-by or overlapping region, can be much less efficient. Titration studies show one molecule is able to induce targeted exon skipping at 20-25 nM while a less efficient antisense molecule might only induced exon skipping at concentrations of 300 nM and above. Therefore, we have shown that targeting of the antisense molecules to motifs involved in the splicing process plays a crucial role in the overall efficacy of that compound.

Efficacy refers to the ability to induce consistent skipping of a target exon. However, sometimes skipping of the target exons is consistently associated with a flanking exon. That is, we have found that the splicing of some exons is tightly linked. For example, in targeting exon 23 in the mouse model of muscular dystrophy with antisense molecules directed at the donor site of that exon, dystrophin transcripts missing exons 22 and 23 are frequently detected. As another example, when using an antisense molecule directed to exon 8 of the human dystrophin gene, many induced transcripts are missing both exons 8 and 9.

Antisense Oligonucleotides Directed at Exon 2

Antisense oligonucleotides directed at exon 2 were prepared and tested for their ability to induce exon skipping in human muscle cells using similar methods as described above.

TABLE 3

Antisense molecule sequences tested to determine if they induce exon 2 skipping

| Antisense SEQOligonucleotide ID name | Sequence | Ability to induce skipping |
|---|---|---|
| 75 H2A(-14+10) | UCU CUU UCA UCU AAA AUG CAA AAU | No Skipping |
| 76 H2A(-1+23) | CUU UUG AAC AUC UUC UCU UUC AUC | No Skipping |
| 77 H2A(+7+38) | UUU UGU GAA UGU UUU CUU UUG AAC AUC UUC UC | No Skipping |
| 78 H2A(+16+39) | AUU UUG UGA AUG UUU UCU UUU GAA | No Skipping |
| 79 H2A(+30+60) | UAG AAA AUU GUG CAU UUA CCC AUU UUG UGA A | No Skipping |
| 80 H2D(+19-11) | ACC AUU CUU ACC UUA GAA AAU UGU GCA UUU | No Skipping |
| 81 H2D(+03-21) | AAA GUA ACA AAC CAU UCU UAC CUU | No Skipping |

Antisense Oligonucleotides Directed at Exon 3

Antisense oligonucleotides directed at exon 3 were prepared and tested for their ability to induce exon skipping in human muscle cells using similar methods as described above.

Figure 3:
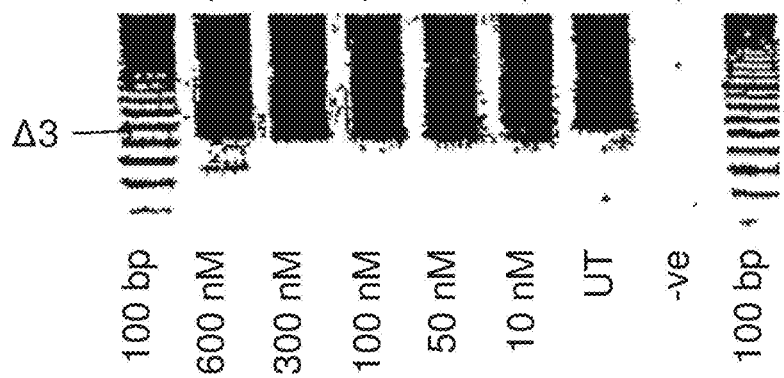
FIG. 3. Gel electrophoresis showing a "cocktail" of antisense molecules directed at exon 3 which induce strong and consistent exon skipping at a transfection concentration of 10 nanomolar in cultured normal human muscle cells.

Each used alone, antisense molecules H3A(+30+60) [SEQ ID NO: 31] and H3A(+61+85) [SEQ ID NO: 32] induce exon 3 skipping. However, in combination, the two molecules are even more effective at inducing skipping (FIG. 3), and are also able to induce skipping of exons 4 and 5 at 300 nM and 600 nM, a result not seen or predicted by the results of the use of each antisense molecule alone. Additional products above the induced transcript missing exon 3 arise from amplification from carry-over outer primers from the RT-PCR as well as heteroduplex formation.

TABLE 4

Antisense molecule sequences tested to determine if they induce exon 3 skipping

| SEQ ID | Antisense Oligonucleotide name | Sequence | Ability to induce skipping |
|---|---|---|---|
| 82 | H3A(+14+38) | AGG UCA CUG AAG AGG UUC UCA AUA U | Moderate skipping to 10 nM |
| 83 | H3A(+20+40) | GUA GGU CAC UGA AGA GGU UCU | Strong skipping to 50 nM |
| 84 | H3A(+25+60) | AGG AGG CGU CUC CCA UCC UGU AGG UCA CUG AAG AG | weak skipping |
| 85 | H3A(+45+65) | AGG UCU AGG AGG CGC CUC CCA | No skipping |
| 86 | H3A(+48+73) | CUU CGA GGA GGU CUA GGA GGC GCC UC | No Skipping |
| 32 | H3A(+61+85) | GCC CUG UCA GGC CUU CGA GGA GGU C | Skipping to 300 nM |
| 87 | H3D(+17-08) | uca cau acA GUU UUU GCC CUG UCA G | No skipping |
| 88 | H3D(+19-02) | UAC AGU UUU UGC CCU GUC AGG | No skipping |
| 89 | H3D(+14-10) | AAG UCA CAU ACA GUU UUU GCC CUG | No skipping |
| 90 | H3D(+12-07) | UCA CAU ACA GUU UUU GCC C | No skipping |
| | Cocktails for exon 3 | | |
| 31 & 32 | H3A(+30+60) H3A(+61+85) | UAG GAG GCG CCU CCC AUC CUG UAG GUC ACU G<br>G CCC UGU CAG GCC UUC GAG GAG GUC | Excellent skipping to 100 nM, skipping to 10 nM. Also taking out 4&5 to 300 nM |
| 32 & 464 | H3A(+61+85) H3A(+30+54) | G CCC UGU CAG GCC UUC GAG GAG GUC<br>GCG CCU CCC AUC CUG UAG GUC ACU G | Very strong skipping to 50 nM |
| 32 & 84 | H3A(+61+85) H3A(+25+60) | G CCC UGU CAG GCC UUC GAG GAG GUC<br>AGG AGG CGU CUC CCA UCC UGU AGG UCA CUG AAG AG | Very strong skipping to 50 nM |

Antisense Oligonucleotides Directed at Exon 4

Figure 4:
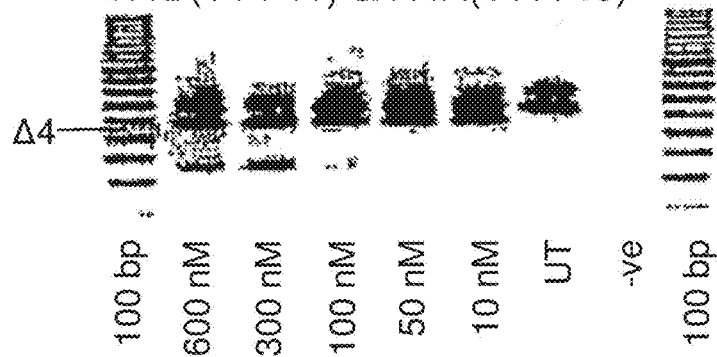
FIG. 4. Gel electrophoresis showing a "cocktail" of antisense molecules directed at exon 4 which induce strong and consistent exon skipping at a transfection concentration of 25 nanomolar in cultured normal human muscle cells.

Antisense oligonucleotides directed at exon 4 were prepared and tested for their ability to induce exon skipping in human muscle cells using similar methods as described above. FIG. 4 shows skipping of exon 4 using a cocktail of H4A(+11+40) [SEQ ID NO: 33] and H4D(+14−11) [SEQ ID NO: 34].

Antisense Oligonucleotides Directed at Exon 5

Figure 5:
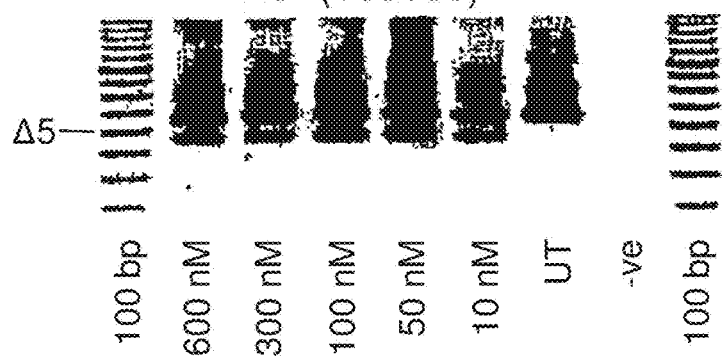
FIG. 5 Gel electrophoresis showing strong and efficient human exon 5 skipping using an antisense molecules [H5A(+35+65)] directed at an exon 5 internal domain, presumably an exon splicing enhancer. This preferred compound induces consistent exon skipping at a transfection concentration of 25 nanomolar in cultured human muscle cells.

Antisense oligonucleotides directed at exon 5 were prepared and tested for their ability to induce exon skipping in human muscle cells using similar methods as described above. H5D(+26−05) would be regarded as a non-preferred antisense molecule as it failed to induce even low level skipping of exon 5. However, H5A(+35+65) [SEQ ID NO: 1], which presumably targets an exonic splicing enhancer was evaluated, found to be highly efficient at inducing skipping of that target exon, as shown in FIG. 5 and is regarded as the preferred compound for induced exon 5 skipping.

TABLE 5

Antisense molecule sequences tested to determine if they induce exon 4 skipping

| SEQ ID | Antisense Oligonucleotide name | Sequence | Ability to induce skipping |
|---|---|---|---|
| 91 | H4A(−08+17) | GAU CCU UUU UCU UUU GGC UGA GAA C | Weak skipping down to 10 nM |
| 92 | H4A(+36+60) | CCG CAG UGC CUU GUU GAC AUU GUU C | Good skipping to 10 nM |
| 93 | H4D(+14−11) | GUA CUA CUU ACA UUA UUG UUC UGC A | Very poor skipping to 10 nM |
| | Exon 4 Cocktails | | |
| 33 & 34 | H4A(+11+40) H4D(+14−11) | UGU UCA GGG CAU GAA CUC UUG UGG AUC CUU<br>GUA CUA CUU ACA UUA UUG UUC UGC A | Excellent skipping(100% to 100 nM) and good skipping down to 5 nM |

TABLE 6

Antisense molecule sequences tested to determine if they induce exon 5 skipping

| SEQ ID | Antisense Oligonucleotide name | Sequence | Ability to induce skipping |
|---|---|---|---|
| 1 | H5A(+35+65) | AAA CCA AGA GUC AGU UUA UGA UUU CCA UCU A | Great skipping to 10 nM |
| 94 | H5D(+26-05) | CUU ACC UGC CAG UGG AGG AUU AUA UUC CAA A | No skipping |

Antisense Oligonucleotides Directed at Exon 6

Antisense oligonucleotides directed at exon 6 were prepared and tested for their ability to induce exon skipping in human muscle cells using similar methods as described above.

TABLE 7

Antisense molecule sequences tested to determine if they induce exon 6 skipping

| SEQ ID | Antisense Oligonucleotide name | Sequence | Ability to induce skipping |
|---|---|---|---|
| 95 | H6A(-09+17) | UUC AUU ACA UUU UUG ACC UAC AUG UG | faint to 600 nM |
| 96 | H6A(+32+57) | CUU UUC ACU GUU GGU UUG UUG CAA UC | skipping at 25 nM |
| 97 | KH9 6A(+66+94) | AAU UAC GAG UUG AUU GUC GGA CCC AGC UC | skipping at 25 nM |
| 98 | H6A(+69+96) | AUA AUU ACG AGU UGA UUG UCG GAC CCA G | skipping to 100 nM |
| 99 | H6A(+98+123) | GGU GAA GUU GAU UAC AUU AAC CUG UG | No skipping |
| 100 | H6D(+18-06) | UCU UAC CUA UGA CUA UGG AUG AGA | No skipping |
| 101 | H6D(+07-15) | CAG UAA UCU UCU UAC CUA UGA C | No skipping |
| 102 | H6D(+07-16) | UCA GUA AUC UUC UUA CCU AUG AC | No skipping |
| 103 | H6D(+04-20) | UGU CUC AGU AAU CUU CUU ACC UAU | No skipping |

Antisense Oligonucleotides Directed at Exon 7

Antisense oligonucleotides directed at exon 7 were prepared and tested for their ability to induce exon skipping in human muscle cells using similar methods as described above.

TABLE 8

Antisense molecule sequences tested to determine if they induce exon 7 skipping

| SEQ ID | Antisense Oligonucleotide name | Sequence | Ability to induce skipping |
|---|---|---|---|
| 104 | H7A(-07+15) | UCA AAU AGG UCU GGC CUA AAA C | no skipping |
| 105 | H7A(-03+18) | CCA GUC AAA UAG GUC UGG CCU A | no skipping |
| 106 | H7A(+41+63) | UGU UCC AGU CGU UGU GUG GCU GA | skipping 50 nM |
| 73 | H7A(+41+67) | UGC AUG UUC CAG UCG UUG UGU GGC UGA | skipping 25 nM |
| 107 | H7A(+47+74) | UGU UGA AUG CAU GUU CCA GUC GUU GUG U | skippking 25 nM but weak |
| 72 | H7A(+49+71) | UGA AUG CAU GUU CCA GUC GUU GU | good skipping to 25 nM |

Antisense Oligonucleotides Directed at Exon 8

Figure 6:
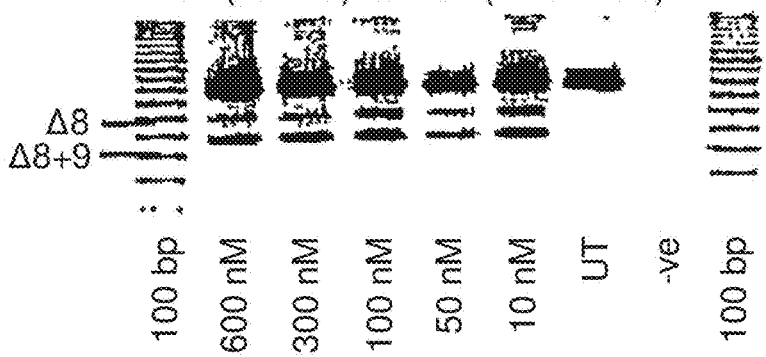
FIG. 6. Gel electrophoresis showing a "cocktail" of antisense molecules directed at exon 8 which induce strong and consistent exon skipping of both exon 8 and exon8/9 at a transfection concentration of 10 nanomolar in cultured normal human muscle cells.

Antisense oligonucleotides directed at exon 8 were prepared and tested for their ability to induce exon skipping in human muscle cells using similar methods as described above. See FIG. 6.

TABLE 9

Antisense molecule sequences tested to determine if they induce exon 8 skipping

| SEQ ID | Antisense Oligonucleotide name | Sequence | Ability to induce skipping |
|---|---|---|---|
| 108 | H8A(-10+20) | UGG AUA GGU GGU AUC AAC AUC UGU AAG CAC | Very weak skipping of 8 + 9 to 10 nM |
| 109 | H8A(-07+15) | GAU AGG UGG UAU CAA CAU CUG U | Very, very weak skipping of 8 + 9 to 10 nM |
| 35 | H8A(-06+24) | UAU CUG GAU AGG UGG UAU CAA CAU CUG UAA | Weak skipping of 8 + 9 to 10 nM |
| 110 | H8A(-04+18) | GAU AGG UGG UAU CAA CAU CUG U | works strongly to 40 nM |
| 71 | H8A(+42+66) | AAA CUU GGA AGA GUG AUG UGA UGU A | good skipping of 8 + 9 to 10 nM |
| 70 | H8A(+57+83) | GCU CAC UUG UUG AGG CAA AAC UUG GAA | good skipping of 8 + 9 at high conc, down to 10 nM |
| 111 | H8A(+96+120) | GCC UUG GCA ACA UUU CCA CUU CCU G | Weak skipping of 8 + 9 to 300 nM |
| 36 | H8A(+134+158) | AUG UAA CUG AAA AUG UUC UUC UUU A | Weak skipping of 8 + 9 to 100 nM |
| 112 | H8D(+13-12) | UAC ACA CUU UAC CUG UUG AGA AUA G | Weak skipping of 8 + 9 to 50 nM |
| Exon 8 Cocktails | | | |
| 35 & 36 | H8A(-06+24) H8A(+134+158) | UAU CUG GAU AGG UGG UAU CAA CAU CUG UAA AUG UAA CUG AAA AUG UUC UUC UUU A | Good skipping to 10 nM (8 + 9) but also 8 on its own |
| 35 & 112 | H8A(-06+24) H8D(+13-12) | UAU CUG GAU AGG UGG UAU CAA CAU CUG UAA UAC ACA CUU UAC CUG UUG AGA AUA G | Good skipping to 10 nM (8 + 9) but also 8 on its own |
| 35 & 70 | H8A(-06+24) H8A(+57+83) | UAU CUG GAU AGG UGG UAU CAA CAU CUG UAA GCU CAC UUG UUG AGG CAA AAC UUG GAA | Good skipping to 10 nM (8 + 9) but also 8 on its own |
| 35 & 111 | H8A(-06+24) H8A(+96+120) | UAU CUG GAU AGG UGG UAU CAA CAU CUG UAA GCC UUG GCA ACA UUU CCA CUU CCU G | Good skipping to 10 nM (8 + 9) but also 8 on its own |

Antisense Oligonucleotides Directed at Exon 9

Antisense oligonucleotides directed at exon 9 were prepared and tested for their ability to induce exon skipping in human muscle cells using similar methods as described above.

TABLE 10

Antisense molecule sequences tested to determine if they induce exon 9 skipping

| SEQ ID | Antisense Oligonucleotide name | Sequence | Ability to induce skipping |
|---|---|---|---|
| 113 | H9A(+154+184) | AGC AGC CUG UGU GUA GGC AUA GCU CUU GAA U | working strongly to 100 nM |
| 114 | H9D(+26-04) | AGA CCU GUG AAG GAA AUG GGC UCC GUG UAG | working strongly to 200 nM |

Antisense Oligonucleotides Directed at Exon 10

Figure 7:
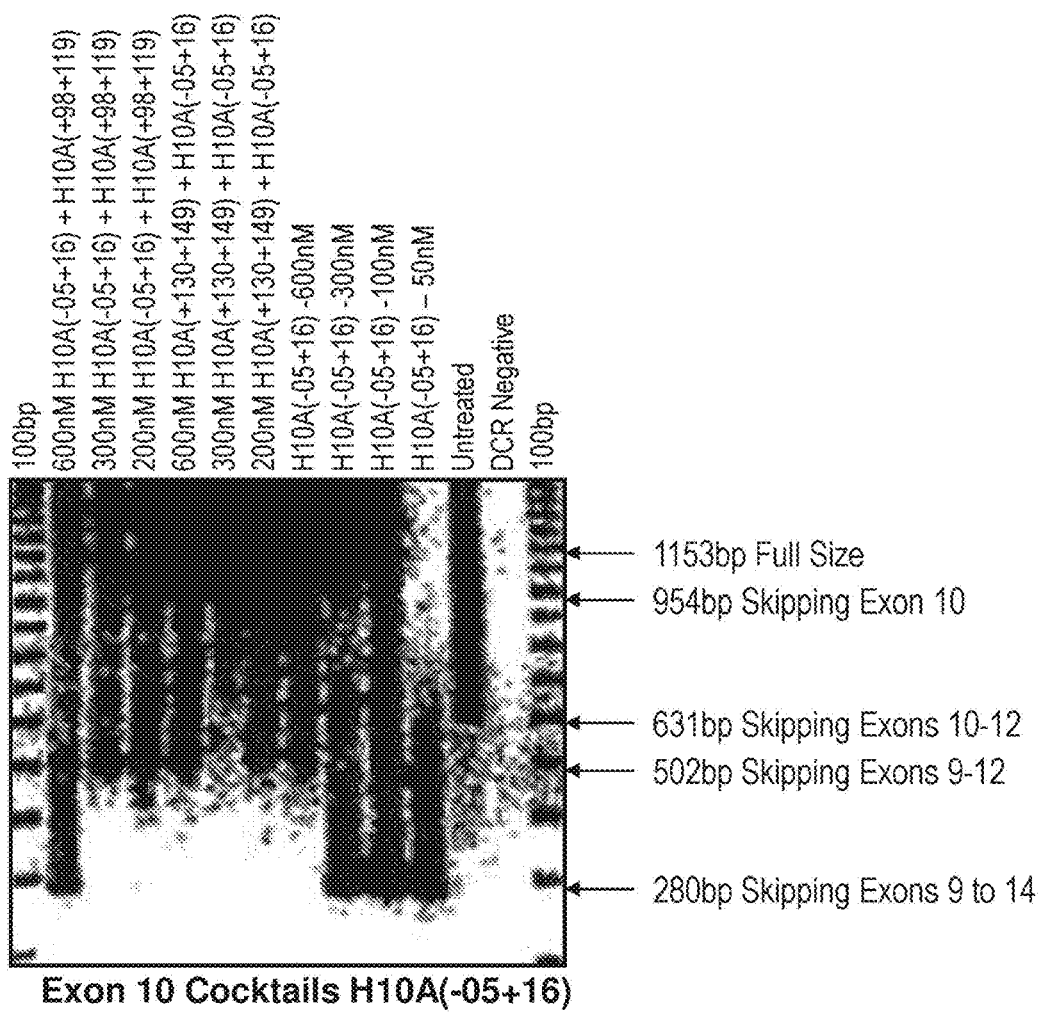
FIG. 7. Gel electrophoresis showing various cocktails and single antisense molecules which induce skipping of exon 10 and surrounding exons. A combination of [H10A(−05+16)] and [H10A(+98+119)] or [H10A(−05+16)] and [H10A(+130+149)] induces skipping of exon 10 and exons 9–12, whilst [H10A(−05+16)] alone induces skipping of exons 9–14.

Antisense oligonucleotides directed at exon 10 were prepared and tested for their ability to induce exon skipping in human muscle cells using similar methods as described above. See FIG. 7 for examples of a single antisense oligonucleotide molecule and cocktails which induce skipping of exon 10 and surrounding exons. Single antisense oligonucleotide molecule H10A(−05+16) [SEQ ID NO: 37] was able to induce skipping of exons 9-14, whilst the combination with H10A(+98+119) [SEQ ID NO: 38] was able to induce skipping of exon 10 alone and exons 9-12 (and some skipping of exons 10-12). The combination of H10A(−05+16) and H10A(+130+149) was able to induce skipping of exon 10 and exons 9-12.

TABLE 11

Antisense molecule sequences tested to determine if they induce exon 10 skipping

| SEQ ID | Antisense Oligonucleotide name | Sequence | Ability to induce skipping |
|---|---|---|---|
| 115 | H10A(-09+16) | CAG GAG CUU CCA AAU GCU GCA CAA U | no skipping |
| 116 | H10A(+08+27) | UGA CUU GUC UUC AGG AGC UU | no skipping |
| 117 | H10A (+21 +42) | CAA UGA ACU GCC AAA UGA CUU G | Skipping at 100 nM |
| 118 | H10A(+27+51) | ACU CUC CAU CAA UGA ACU GCC AAA U | No Skipping |
| 119 | H10A(+55+79) | CUG UUU GAU AAC GGU CCA GGU UUA C | No Skipping |
| 120 | H10A(+80+103) | GCC ACG AUA AUA CUU CUU CUA AAG | No Skipping |
| 121 | H10D(+16-09) | UUA GUU UAC CUC AUG AGU AUG AAA C | No Skipping |
| Cocktails Exon 10 | | | |
| 37 & 38 | H10A(-05+16) H10A(+98+119) | CAG GAG CUU CCA AAU GCU GCA UCC UCA GCA GAA AGA AGC CAC G | Strong skipping at 200 nM |
| 37 & 122 | H10A(-05+16) H10A(+130+149) | CAG GAG CUU CCA AAU GCU GCA UUA GAA AUC UCU CCU UGU GC | Skipping at 200 nM |

Antisense Oligonucleotides Directed at Exon 11

Figure 37:
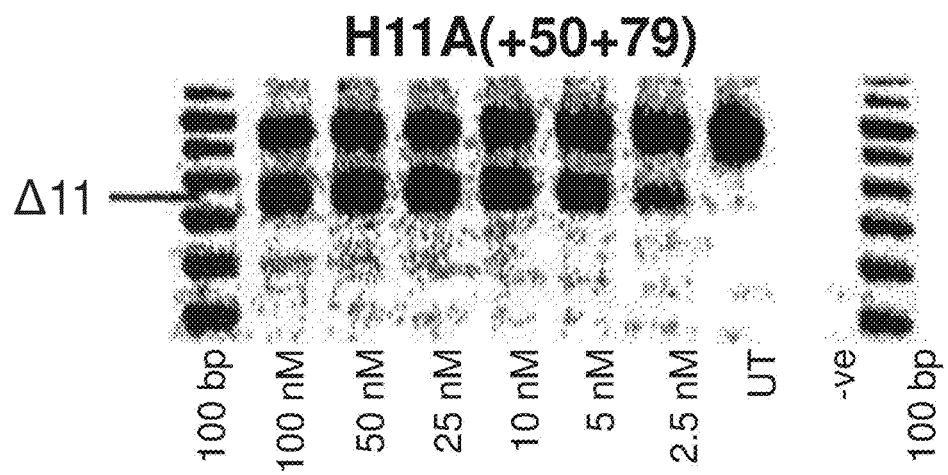
FIG. 37. Gel electrophoresis showing exon 11 skipping using antisense molecule H11A(+50+79).

Antisense oligonucleotides directed at exon 11 were prepared and tested for their ability to induce exon skipping in human muscle cells using similar methods as described above. See FIG. 37.

TABLE 12

Antisense molecule sequences tested to determine if they induce exon 11 skipping

| SEQ ID | Antisense Oligonucleotide name | Sequence | Ability to induce skipping |
|---|---|---|---|
| 123 | H11A(-07+13) | CCA UCA UGU ACC CCU GAC AA | Skipping at 300 nM |
| 124 | H11A+(+134+157) | CCC UGA GGC AUU CCC AUC UUG AAU | Skipping at 100 nM |
| 125 | H11A(+20+45) | AUU ACC AAC CCG GCC CUG AUG GGC UG | skipping to 25 nM |
| 126 | H11A(+46+75) | UCC AAU CAG CUU ACU UCC CAA UUG UAG AAU | Strong skipping to 25 nM hint at 2.5 nM |
| 127 | H11A(+50+75) | UCC AAU CAG CUU ACU UCC CAA UUG UA | Strong skipping to 10 nM faint at 2.5 nM |
| 52 | H11A(+50+79) | CUG UUC CAA UCA GCU UAC UUC CCA AUU GUA | Strong skipping to 5 nM faint at 2.5 nM |
| 128 | H11A(+80+105) | AGU UUC UUC AUC UUC UGA UAA UUU UC | Faint skipping to 25 nM |
| 129 | H11A(+106+135) | AUU UAG GAG AUU CAU CUG CUC UUG UAC UUC | Strong skipping to 25 nM (20%) |
| 130 | H11A(+110+135) | AUU UAG GAG AUU CAU CUG CUC UUG UA | Strong skipping to 25 nM (20%) |
| 131 | H11A(+110+139) | UUG AAU UUA GGA GAU UCA UCU GCU CUU GUA | Strong skipping to 25 nM (20%) |

Antisense Oligonucleotides Directed at Exon 12

Figure 38:
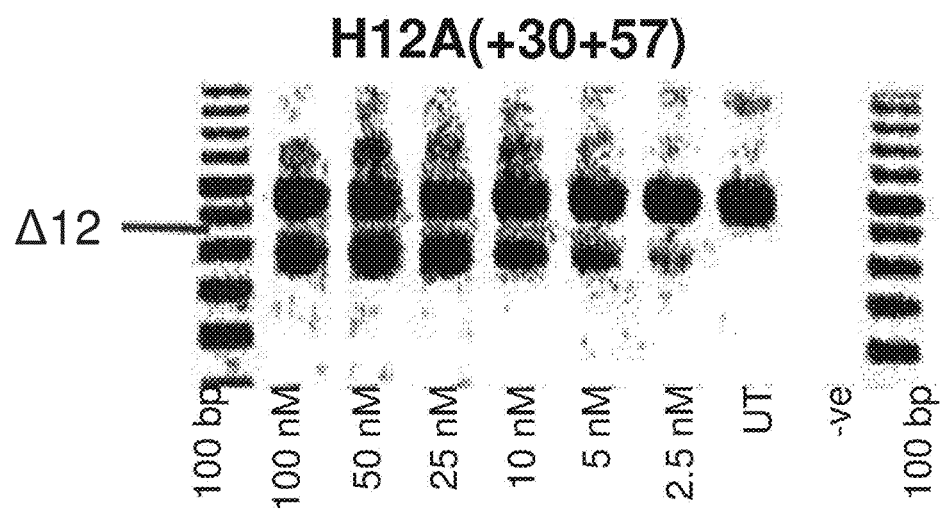
FIG. 38. Gel electrophoresis showing exon 12 skipping using antisense molecule H12A(+30+57).

Antisense oligonucleotides directed at exon 12 were prepared and tested for their ability to induce exon skipping in human muscle cells using similar methods as described above. See FIG. 38.

TABLE 13

Antisense molecule sequences tested to determine if they induce exon 12 skipping

| SEQ ID | Antisense Oligonucleotide name | Sequence | Ability to induce skipping |
|---|---|---|---|
| 132 | H12D(+06-16) | CAU AAG AUA CAC CUA CCU UAU G | No Skipping |
| 2 | H12A(+52+75) | UCU UCU GUU UUU GUU AGC CAG UCA | Strong skipping |
| 53 | H12A(+30+57) | CAG UCA UUC AAC UCU UUC AGU UUC UGA U | Strong skipping to 10 nM faint at 2.5 nM |
| 133 | H12A(+60+87) | UUC CUU GUU CUU UCU UCU GUU UUU GUU A | Strong skipping to 25 nM faint at 5 nM |
| 134 | H12A(+90+117) | AGA UCA GGU CCA AGA GGC UCU UCC UCC A | Strong skipping to 25 nM (30%) |
| 135 | H12A(+120+147) | UGU UGU UGU ACU UGG CGU UUU AGG UCU U | Strong skipping to 25 nM (30%) |

Antisense Oligonucleotides Directed at Exon 13

Antisense oligonucleotides directed at exon 13 were prepared and tested for their ability to induce exon skipping in human muscle cells using similar methods as described above.

TABLE 14

Antisense molecule sequences tested to determine if they induce exon 13 skipping

| SEQ ID | Antisense oligonucleotide name | Sequence | Ability to induce skipping |
|---|---|---|---|
| 136 | H13A(-12+12) | UUC UUG AAG CAC CUG AAA GAU AAA | No Skipping |

Antisense Oligonucleotides Directed at Exon 14

Figure 8:
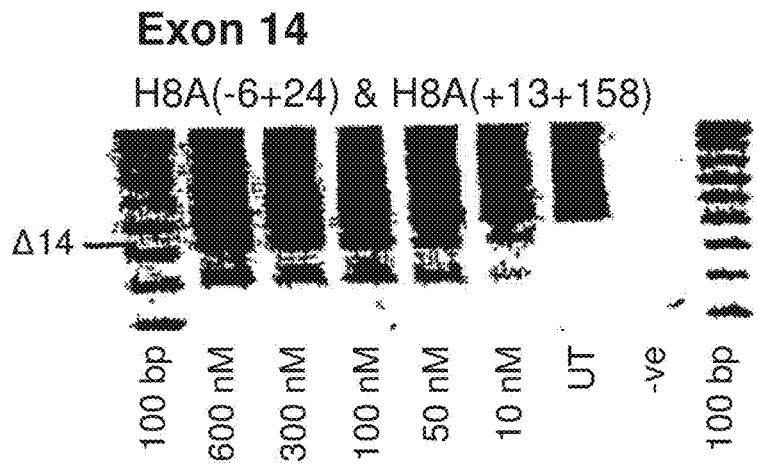
FIG. 8. Gel electrophoresis showing exon 14 skipping using antisense molecule H14A(+31+61) directed at exon 14.

Antisense oligonucleotides directed at exon 14 were prepared and tested for their ability to induce exon skipping in human muscle cells using similar methods as described above. See FIG. 8.

TABLE 15

Antisense molecule sequences tested to determine if they induce exon 14 skipping

| SEQ ID | Antisense oligonucleotide name | Sequence | Ability to induce skipping |
|---|---|---|---|
| 137 | H14A(+45 +73) | GAA GGA UGU CUU GUA AAA GAA CCC AGC GG | Skipping at 25 nM |

Antisense Oligonucleotides Directed at Exon 16

Antisense oligonucleotides directed at exon 16 were prepared and tested for their ability to induce exon skipping in human muscle cells using similar methods as described above.

TABLE 16

Antisense molecule sequences tested to determine if they induce exon 16 skipping

| SEQ ID | Antisense oligonucleotide name | Sequence | Ability to induce skipping |
|---|---|---|---|
| 138 | H16A(-07+19) | CUA GAU CCG CUU UUA AAA CCU GUU AA | No skipping |
| 139 | H16A(+09+31) | GCU UUU UCU UUU CUA GAU CCG CU | No skipping |
| 140 | H16D(+18-07) | CAC UAA CCU GUG CUG UAC UCU UUU C | No skipping |

Antisense Oligonucleotides Directed at Exon 17

Antisense oligonucleotides directed at exon 17 were prepared and tested for their ability to induce exon skipping in human muscle cells using similar methods as described above.

TABLE 64

Antisense molecule sequences tested to determine if they induce exon 17 skipping

| SEQ ID | Antisense Oligonucleotide name | Sequence | Ability to induce skipping |
|---|---|---|---|
| 141 | H17A(+48+78) | UGU GGU CAC CGU AGU UAC UGU UUC CAU UCA A | No skipping |
| 142 | H17A(+55+85) | GUU CCC UUG UGG UCA CCG UAG UUA CUG UUU C | Skipping to 100 nM |

Antisense Oligonucleotides Directed at Exon 18

Figure 9:
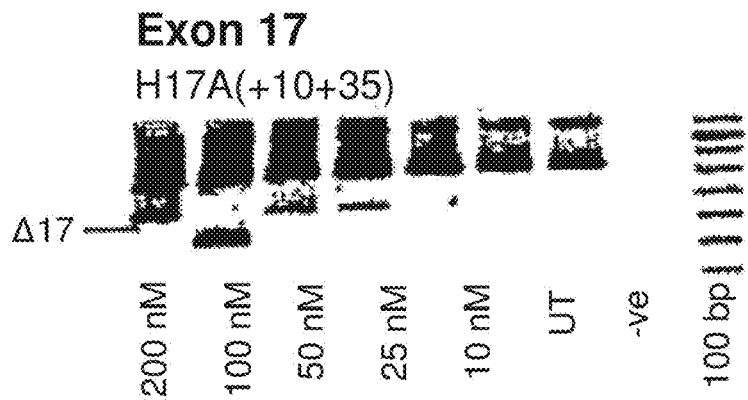
FIG. 9. Gel electrophoresis showing exon 17 skipping using antisense molecule H17A(+10+35) directed at exon 17.

Antisense oligonucleotides directed at exon 18 were prepared and tested for their ability to induce exon skipping in human muscle cells using similar methods as described above. See FIG. 9.

TABLE 17

Antisense molecule sequences tested to determine if they induce exon 18 skipping

| Antisense SEQ Oligonucleotide ID name | Sequence | Ability to induce skipping |
|---|---|---|
| 143 H18A(-09+11) | CAA CAU CCU UCC UAA GAC UG | No skipping |
| 144 H18A(+24+43) | GCG AGU AAU CCA GCU GUG AA | Inconsistent skipping of both exon 17 + 18 |
| 145 H18A(+41 +70) | UUC AGG ACU CUG CAA CAG AGC UUC UGA GCG | Skipping exons 17 + 18 300 nM |
| 146 H18A(+83+108) | UUG UCU GUG AAG UUG CCU UCC UUC CG | Skipping exons 17 + 18 300 nM |
| 147 H18D(+04-16) | UUA AUG CAU AAC CUA CAU UG | No skipping |

Antisense Oligonucleotides Directed at Exon 19

Antisense oligonucleotides directed at exon 19 were prepared and tested for their ability to induce exon skipping in human muscle cells using similar methods as described above.

TABLE 18

Antisense molecule sequences tested to determine if they induce exon 19 skipping

| Antisense SEQ Oligonucleotide ID name | Sequence | Ability to induce skipping |
|---|---|---|
| 148 H19A(+19+48) | GGC AUC UUG CAG UUU UCU GAA CUU CUC AGC | skipping to 25 nM |
| 149 H19A(+27+54) | UCU GCU GGC AUC UUG CAG UUU UCU GAA C | skipping to 25 nM |
| 150 H19D(+3-17) | UCA ACU CGU GUA AUU ACC GU | skipping |

Antisense Oligonucleotides Directed at Exon 20

Antisense oligonucleotides directed at exon 20 were prepared and tested for their ability to induce exon skipping in human muscle cells using similar methods as described above.

TABLE 19

Antisense molecule sequences tested to determine if they induce exon 20 skipping

| Antisense SEQ Oligonucleotide ID name | Sequence | Ability to induce skipping |
|---|---|---|
| 151 H20A(+23+47) | GUU CAG UUG UUC UGA GGC UUG UUU G | faint shadow at 600 nM |
| 152 H20A(+140+164) | AGU AGU UGU CAU CUG CUC CAA UUG U | no skipping |

Antisense Oligonucleotides Directed at Exon 23

Antisense oligonucleotides directed at exon 23 were prepared and tested for their ability to induce exon skipping in human muscle cells using similar methods as described above. Antisense oligonucleotides directed at exon 23 were prepared and tested for their ability to induce exon skipping in human muscle cells using similar methods as described above. H23(+69+98)-SNP contains a single nucleotide polymorphism (SNP) that has been previously documented.

TABLE 65

Antisense molecule sequences tested to determine if they induce exon 23 skipping

| Antisense SEQ ID name | Oligonucleotide Sequence | Ability to induce skipping |
|---|---|---|
| 153 H23(+69+98)-SNP | CGG CUA AUU UCA GAG GGC GCU UUC UUU GAC | skipping to 25 nM |

Antisense Oligonucleotides Directed at Exon 24

Antisense oligonucleotides directed at exon 24 were prepared and tested for their ability to induce exon skipping in human muscle cells using similar methods as described above.

TABLE 20

Antisense molecule sequences tested to determine if they induce exon 24 skipping.

| Antisense SEQ ID name | Oligonucleotide Sequence | Ability to induce skipping |
|---|---|---|
| 8 H24A(+51+73) | CAA GGG CAG GCC AUU CCU CCU UC | Strong skipping to 25 nM |

Antisense Oligonucleotides Directed at Exon 25

Antisense oligonucleotides directed at exon 25 were prepared and tested for their ability to induce exon skipping in human muscle cells using similar methods as described above. Oligonucleotide H25A(+95+119)-DupA is a patient specific antisense molecule.

TABLE 21

Antisense molecule sequences tested to determine if they induce exon 25 skipping.

| SEQ ID | Antisense Oligonucleotide name | Sequence | Ability to induce skipping |
|---|---|---|---|
| 154 | H25A(+10+33) | UGG GCU GAA UUG UCU GAA UAU CAC | strong at 25 nM but did not reduce the full length product |
| 155 | H25D(+06-14) | GAG AUU GUC UAU ACC UGU UG | very strong at 25 nM |
| 156 | H25A(+10+38) | AGA CUG GGC UGA AUU GUC UGA AUA UCA CU | Strong skipping at 5 nM faint 2.5 nM |
| 157 | H25A(+95+119)-DupA* | UUG AGU UCU GUU CUC AAG UCU CGA AG | Strong skipping at 25 nM faint 5 nM (patient specific) |
| 158 | H25D(+13-14) | GAG AUU GUC UAU ACC UGU UGG CAC AUG | Strong skipping at 10 nM |

Antisense Oligonucleotides Directed at Exon 26

Figure 10:
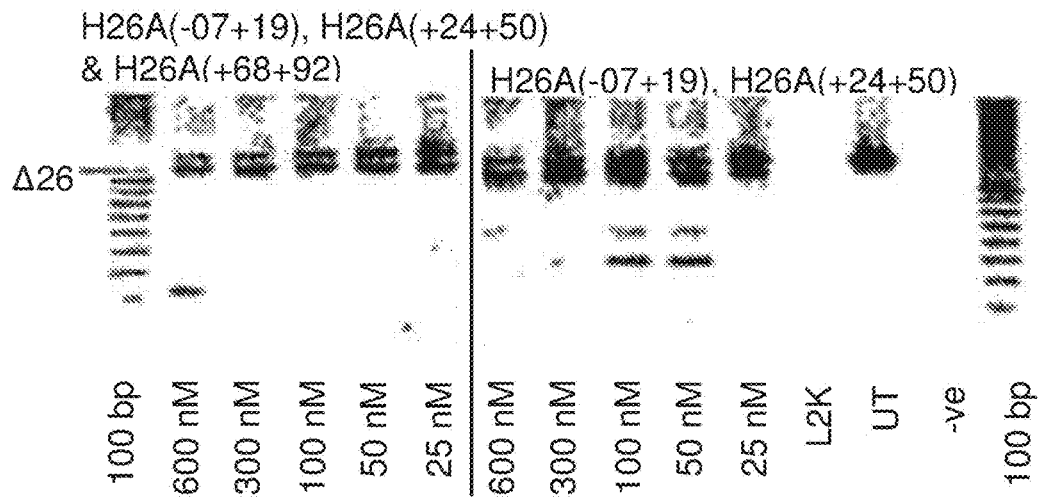
FIG. 10. Gel electrophoresis showing two cocktails of antisense molecules directed at exon 26. The double cocktail of [H26A(−07+19)] and [H26A(+24+50)] induces good skipping of exon 26, and the addition of a further antisense molecule to the cocktail does not affect the efficiency of skipping.

Antisense oligonucleotides directed at exon 26 were prepared and tested for their ability to induce exon skipping in human muscle cells using similar methods as described above. See FIG. 10.

TABLE 22

Antisense molecule sequences tested to determine if they induce exon 26 skipping.

| SEQ | Antisense Oligonucleotide name | Sequence | Ability to induce skipping |
|---|---|---|---|
| 159 | H26A(-16+09) | GGC AUA GAC CUU CCA CAA AAC AAA C | Faint skipping 600 nM & 300 nM |
| 160 | H26A(-7+23) | AAG GCC UCC UUU CUG GCA UAG ACC UUC CAC | Faint at 600, 300 nM, multiple exons 26-29 or 27-30 |
| 161 | H26A(-03+27) | CUU CAA GGC CUC UUU UCU GGC AUA GAC CUU | Faint at 600, 300 nM, multiple exons 26-29 or 27-30 |
| 162 | H26A(+5+35) | AAC CUC CUU UCA AGG CCU CCU UUC UGG CAU | No skipping |
| 40 | H26A(+24+50) | CUU ACA GUU UUC UCC AAA CCU CCC UUC | Faint at 600, 300 nM, multiple exons 26-29 or 27-30 |
| 163 | H26D(+06-19) | UUU CUU UUU UUU UUU UUA CCU UCA U | Faint at 600, multiple exons 26-29 or 27-30 |
| 164 | H26D(+21-04) | UUA CCU UCA UCU CUU CAA CUG CUU U | multiple exons 26-29 or 27-30 |
| 165 | H26D(+10-10) | UUU UUU UUA CCU UCA UCU CU | Not skipping 26 other bands |
| Exon 26 cocktails | | | |
| 39, 40 & 41 | H26A(-07+19) H26A(+24+50) H26A(+68+92) | CCU CCU UUC UGG CAU AGA CCU UCC AC CUU ACA GUU UUC UCC AAA CCU CCC UUC UGU GUC AUC CAU UCG UGC AUC UCU G | strong skipping down to 25 nM |

Antisense Oligonucleotides Directed at Exon 31

Antisense oligonucleotides directed at exon 31 were prepared and tested for their ability to induce exon skipping in human muscle cells using similar methods as described above.

TABLE 23

Antisense molecule sequences tested to determine if they induce exon 31 skipping

| SEQ ID | Antisense Oligonucleotide name | Sequence | Ability to induce skipping |
|---|---|---|---|
| 166 | H31D(+12-18) | UUC UGA AAU UUC AUA UAC CUG UGC AAC AUC | skipping to 100 nM |
| 167 | H31D(+08-22) | UAG UUU CUG AAA UAA CAU AUA CCU GUG CAA | skipping to 100 nM |
| 168 | H31D(+06-24) | CUU AGU UUC UGA AAU AAC AUA UAC CUG UGC | skipping to 100 nM |
| 169 | H31D(+02-22) | UAG UUU CUG AAA UAA CAU AUA CCU | skipping to 100 nM |
| 170 | H31D(+01-25) | CCU AG UUU CUG AAA UAA CAU AUA CC | strong skipping at 300 nM |

Antisense Oligonucleotides Directed at Exon 32

Antisense oligonucleotides directed at exon 32 were prepared and tested for their ability to induce exon skipping in human muscle cells using similar methods as described above.

TABLE 24

Antisense molecule sequences tested to determine if they induce exon 32 skipping

| SEQ ID | Antisense Oligonucleotide name | Sequence | Ability to induce skipping |
|---|---|---|---|
| 171 | H32A(+49+78) | ACU UUC UUG UAG ACG CUG CUC AAA AUU GGC | skipping to 100 nM |

Antisense Oligonucleotides Directed at Exon 34

Antisense oligonucleotides directed at exon 34 were prepared and tested for their ability to induce exon skipping in human muscle cells using similar methods as described above.

TABLE 25

Antisense molecule sequences tested to determine if they induce exon 34 skipping

| SEQ ID | Antisense Oligonucleotide name | Sequence | Ability to induce skipping |
|---|---|---|---|
| 172 | H34A(+36+59) | UUU CGC AUC UUA CGG GAC AAU UUC | skipping to 200 nM |
| 173 | H34A(+41+70) | CAU UCA UUU CCU UUC GCA UCU UAC GGG ACA | skipping to 200 nM |
| 174 | H34A(+43+72) | GAC AUU CAU UUC CUU UCG CAU CUU ACG GGA | skipping to 100 nM |
| 175 | H34A(+51+83) | UCU GUC AAG ACA UUC AUU UCC UUU CGC AUC | skipping to 200 nM |
| 176 | H34A(+91+120) | UGA UCU CUU UGU CAA UUC CAU AUC UGU AGC | skipping to 100 nM |
| 177 | H34A(+92+121) | CUG AUC UCU UUG UCA AUU CCA UAU CUG UGG | skipping to 100 nM |
| 178 | H34A(+95+120) | UGA UCU CUU UGU CAA UUC CAU AUC UG | Faint to 25 nM |
| 179 | H34A(+95+124) | CUG CUG AUC UCU UUG UCA AUU CCA UAU CUG | skipping to 100 nM |

Antisense Oligonucleotides Directed at Exon 35

Antisense oligonucleotides directed at exon 35 were prepared and tested for their ability to induce exon skipping in human muscle cells using similar methods as described above.

TABLE 26

Antisense molecule sequences tested to determine if they induce exon 35 skipping

| SEQ ID | Antisense Oligonucleotide name | Sequence | Ability to induce skipping |
|---|---|---|---|
| 180 | H35A(+14+43) | UCU UCA GGU GCA CCU UCU GUU UCU CAA UCU | skipping to 100 nM |
| 181 | H35A(+24+53) | UCU GUG AUA CUC UUC AGG UGC ACC UUC UGU | skipping to 100 nM |

Antisense Oligonucleotides Directed at Exon 36

Figure 11:
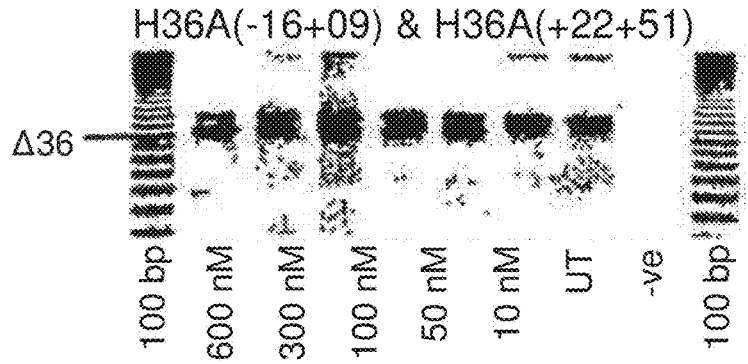
FIG. 11. Gel electrophoresis showing a "cocktail" of antisense molecules directed at exon 36 which induce strong and consistent exon skipping at a transfection concentration of 25 nanomolar in cultured normal human muscle cells.

Antisense oligonucleotides directed at exon 36 were prepared and tested for their ability to induce exon skipping in human muscle cells using similar methods as described above. See FIG. 11.

TABLE 27

Antisense molecule sequences tested to determine if they induce exon 36 skipping

| SEQ ID | Antisense Oligonucleotide name | Sequence | Ability to induce skipping |
|---|---|---|---|
| 42 | H36A(-16+09) | CUG GUA UUC CUU AAU UGU ACA GAG A | no skipping |
| 182 | H36A(-01+19) | CCA UGU GUU UCU GGU AUU CC | very faint skipping 300 nM |
| 183 | H36A(+10+39) | CAC AUU CUG GUC AAA AGU UUC AUG UGU UUU | Skipping to 25 nM |
| 43 | H36A(+22+51) | UGU GAU GUG GUC CAC AUU CUG GUC AAA AGU | Skipping at 100 nM |
| 184 | H36A(+27+51) | UGU GAU GUG GUC CAC AUU CUG GUC A | Skipping at 100 nM |
| 185 | H36A(+27+56) | CAC UUU GUG AUG UGG UCC ACA UUC UGG UCA | Skipping at 300 nM |
| 186 | H36A(+32+61) | UGA UCC ACU UUG UGA UGU GGU CCA CAU UCU | Skipping to 25 nM |
| 187 | H36A(+59+78) | AAG UGU GUC AGC CUG AAU GA | very weak skipping |
| 188 | H36A(+65+94) | UCU CUG AUU CAU CCA AAA GUG UGU CAG CCU | 100% skipping at 600 nM, skipoping to 25 nM |
| 189 | H36A(+80+109) | GCU GGG GUU UCU UUU UCU CUG AUU CAU CCA | 100% skipping at 600 nM, skipoping to 25 nM |
| 190 | H36D(+15-10) | UAU UUG CUA CCU UAA GCA CGU CUU C | very weak skipping |
| Exon 36 cocktails | | | |
| 42 & 43 | H36A(-16+09) H36A(+22+51) | CUG GUA UUC CUU AAU UGU ACA GAG A UGU GAU GUG GUC CAC AUU CUG GUC AAA AGU | good skipping down to 25 nM |

Antisense Oligonucleotides Directed at Exon 38

Antisense oligonucleotides directed at exon 38 were prepared and tested for their ability to induce exon skipping in human muscle cells using similar methods as described above.

TABLE 28

Antisense molecule sequences tested to determine if they induce exon 38 skipping

| SEQ ID | Antisense Oligonucleotide name | Sequence | Ability to induce skipping |
|---|---|---|---|
| 191 | H38A(-21-01) | CUA AAA AAA AAG AUA GUG CUA | skipping to 25 nM |
| 192 | H38A(-12+14) | AAA GGA AUG GAG GCC UAA AAA AAA AG | skipping to 25 nM |
| 193 | H38D(+14-11) | AAC CAA UUU ACC AUA UCU UUA UUG A | skipping to 25 nM |

Antisense Oligonucleotides Directed at Exon 39

Antisense oligonucleotides directed at exon 39 were prepared and tested for their ability to induce exon skipping in human muscle cells using similar methods as described above.

TABLE 29

Antisense molecule sequences tested to determine if they induce exon 39 skipping

| SEQ ID | Antisense Oligonucleotide name | Sequence | Ability to induce skipping |
|---|---|---|---|
| 194 | H39A(-07+23) | ACA GUA CCA UCA UUG UCU UCA UUC UGA UC | skipping to 600 nM |
| 195 | H39A(-07+23) | ACA GUA CCC UCA UUG UCU UCA UUC UGA UC | skipping to 600 nM |
| 196 | H39A(+58+87) | CUC UCG CUU UCU CUC AUC UGU GAU UCU UUG | skipping to 100 nM |
| 197 | H39A(+60+89) | UCC UCU CGC UUU CUC UCA UCU GUG AUU CUU | skipping to 100 nM |
| 198 | H39A(+102+126) | UAU GUU UUG UCU GUA ACA GCU GCU G | skipping to 600 nM |

Antisense Oligonucleotides Directed at Exon 41

Antisense oligonucleotides directed at exon 41 were prepared and tested for their ability to induce exon skipping in human muscle cells using similar methods as described above.

TABLE 30

Antisense molecule sequences tested to determine if they induce exon 41 skipping

| SEQ ID | Antisense Oligonucleotide name | Sequence | Ability to induce skipping |
|---|---|---|---|
| 199 | H41A(-15+5) | AUU UCC UAU UGA GCA AAA CC | Skipping down to 200 nM |
| 200 | H41A(+66+90) | CAU UGC GGC CCC AUC CUC AGA CAA G | Skipping down to 100 nM |
| 201 | H41A(+92+120) | GCU GAG CUG GAU CUG AGU UGG CUC CAC UG | Skipping down to 10 nM |
| 202 | H41A(+143+171) | GUU GAG UCU UCG AAA CUG AGC AAA UUU GC | No visible skipping |
| 203 | H41D(+5-15) | CCA GUA ACA ACU CAC AAU UU | Skipping down to 200 nM |

Antisense Oligonucleotides Directed at Exon 42

Antisense oligonucleotides directed at exon 42 were prepared and tested for their ability to induce exon skipping in human muscle cells using similar methods as described above.

TABLE 31

Antisense molecule sequences tested to determine if they induce exon 20 skipping

| SEQ ID | Antisense Oligonucleotide name Exon 42 | Sequence | Ability to induce skipping |
|---|---|---|---|
| 204 | H42D(+18-02) | ACC UUC AGA GAC UCC UCU UGC | strong skipping |

Antisense Oligonucleotides Directed at Exon 43

Figure 12:
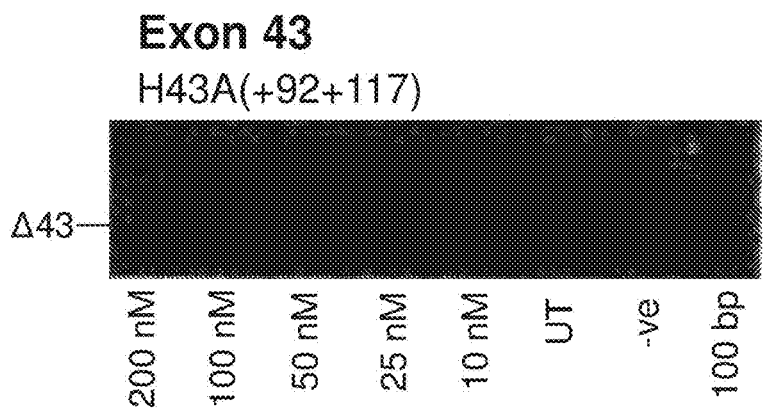
FIG. 12. Gel electrophoresis showing strong and consistent exon 43 skipping to 25 nanomolar in cultured normal human muscle cells using antisense molecule H43A(+92+117).

Antisense oligonucleotides directed at exon 43 were prepared and tested for their ability to induce exon skipping in human muscle cells using similar methods as described above. See FIG. 12.

TABLE 32

Antisense molecule sequences tested to determine if they induce exon 20 skipping

| Antisense SEQ ID Exon 43 | Oligonucleotide name | Sequence | Ability to induce skipping |
|---|---|---|---|
| 205 | H43A(+83+110) | UCC UGU AGC UUC ACC CUU UCC ACA GGC G | No skipping |
| 9 | H43A(+92 +117) | GAG AGC UUC CUG UAG CUU CAC CCU UU | Skipping at 10 nM |
| 206 | H43A(+101 +130) | AAU CA GCU GGG AGA GAG CUU CCU GUA GCU | No skipping |
| 207 | H43D(+08-12) | UGU GUU ACC UAC CCU UGU CG | Skipping down to 200 nM |
| 208 | H43A(-09+18) | UAG ACU AUC UUU UAU AUU CUG UAA UAU | Faint skipping to 25 nM |
| 209 | H43A(+89+117) | GAG AGC UUC CUG UAG CUU CAC CCU UUC CA | Strong skipping at 25 nM faint 2.5 nM |
| 210 | H43A(+81+111) | UUC CUG UAG CUU CAC CCU UUC CAC AGG CGU U | Strong skipping at 50 nM faint 2.5 nM |
| 211 | H43A(+92+114) | AGC UUC CUG UAG CUU CAC CCU UU | Faint skipping to 2.5 nM |
| 74 | H43A(+92+120) | GGA GAG AGC UUC CUG UAG CUU CAC CCU UU | Strong skipping at 10 nM faint 5 nM |
| 212 | H43A(+95+117) | GAG AGC UUC CUG UAG CUU CAC CC | Strong skipping at 25 nM faint 10 nM |

Antisense Oligonucleotides Directed at Exon 44

Figure 13:
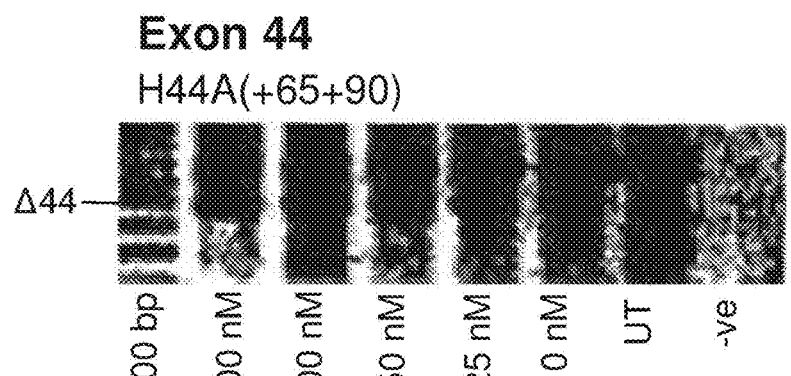
FIG. 13. Gel electrophoresis showing dose dependant exon 55 skipping using antisense molecule H44A(+65+90).
Figure 39:
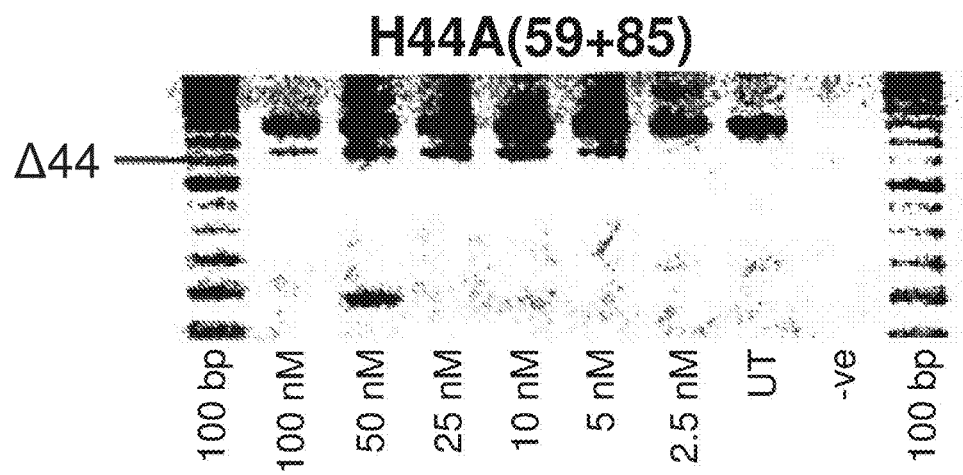
FIG. 39. Gel electrophoresis showing exon 44 skipping using antisense molecule H44A(+59+85).

Antisense oligonucleotides directed at exon 44 were prepared and tested for their ability to induce exon skipping in human muscle cells using similar methods as described above. See FIG. 13 and FIG. 39.

TABLE 33

Antisense molecule sequences tested to determine if they induce exon 44 skipping

| Antisense SEQ Exon 44 | Oligonucleotide name | Sequence | Ability to induce skipping |
|---|---|---|---|
| 213 | H44A(-13+13) | UCU GUC AAA UCG CCU GCA GGU AAA AG | |
| 214 | H44A(-06+24) | UUC UCA ACA GAU CUG UCA AAU CGC CUG CAG | No skipping |
| 215 | H44A(+44+68) | GCC ACU GAU UAA AUA UCU UUA UAU C | Skipping at 100 nM |
| 216 | H44A(+46+75) | UCU GUU AGC CAC UGA UUA AAU AUC UUU AUA | Skipping at 50 nM |
| 217 | H44A(+61+84) | UGU UCA GCU UCU GUU AGC CAC UGA | Skipping at 100 nM |
| 218 | H44A(+61+91) | GAG AAA CUG UUC AGC UUC UGU UAG CCA CUG A | Skipping at 25 nM |
| 10 | H44A(+65+90) | UGU UCA GCU UCU GUU AGC CAC UGA | Skipping at 10 nM |
| 219 | H44A(+68+98) | UCU UUC UGA GAA ACU GUU CAG CUU CUG UUA G | weak at 50 nM |
| 220 | H44A(-09+17) | CAG AUC UGU CAA AUC GCC UGC AGG UA | Faint skipping to 10 nM |
| 68 | H44A(-06+20) | CAA CAG AUC UGU CAA AUC GCC UGC AG | Faint skipping to 2.5 nM |
| 221 | H44A(+56+88) | AAA CUG UUC AGC UUC UGU UAG CCA CUG AUU AAA | Strong skipping at 5 nM faint 2.5 nM |
| 54 | H44A(+59+85) | CUG UUC AGC UUC UGU UAG CCA CUG AUU | Strong skipping at 5 nM |
| 222 | H44A(+59+89) | GAA ACU GUU CAG CUU CUG UUA GCC ACU GAU U | Faint skipping to 10 nM |
| 223 | H44A(+61+88) | AAA CUG UUC AGC UUC UGU UAG CCA CUG A | Faint skipping to 25 nM |
| 224 | H44A(+65+92) | UGA GAA ACU GUU CAG CUU CUG UUA GCC A | Faint skipping to 25 nM |

TABLE 33-continued

Antisense molecule sequences tested to determine if they induce exon 44 skipping

| SEQ ID | Antisense Oligonucleotide name Exon 44 | Sequence | Ability to induce skipping |
|---|---|---|---|
| 225 | H44A(+64+95) | UUC UGA GAA ACU GUU CAG CUU CUG UUA GCCA C | Faint skipping to 25 nM |
| 226 | H44A(+70+95) | UUC UGA GAA ACU GUU CAG CUU CUG UU | Faint skipping to 50 nM |

Antisense Oligonucleotides Directed at Exon 45

Figure 14:
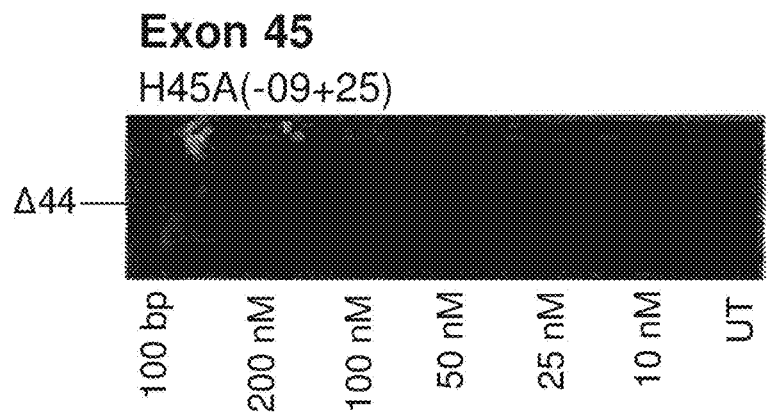
FIG. 14. Gel electrophoresis showing strong and consistent exon 45 skipping using antisense molecule H45A(−09+25).
Figure 40:
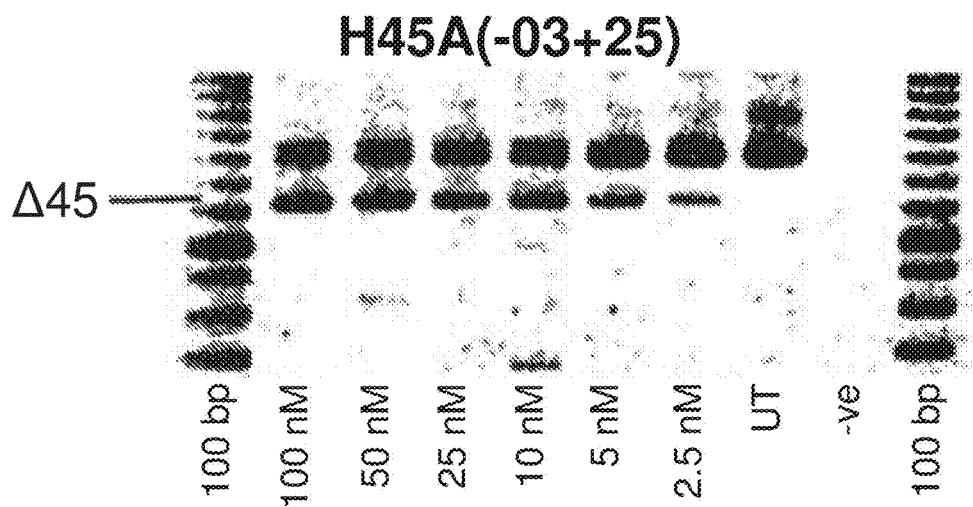
FIG. 40. Gel electrophoresis showing exon 45 skipping using antisense molecule H45A(−03+25).

Antisense oligonucleotides directed at exon 45 were prepared and tested for their ability to induce exon skipping in human muscle cells using similar methods as described above. See FIG. 14 and FIG. 40.

TABLE 34

Antisense molecule sequences tested to determine if they induce exon 45 skipping

| SEQ ID | Antisense Oligonucleotide name Exon 45 | Sequence | Ability to induce skipping |
|---|---|---|---|
| 227 | H45A(-14+25) | GCU GCC CAA UGC CAU CCU GGA GUU CCU GUA AG | Generates multiple bands |
| 228 | H45A(-10 +20) | CCA AUG CCA UCC UGG AGU UCC UGU AAG AUA | Skipping at 10 nM |
| 229 | H45A(-09+30) | UUG CCG CUG CCC AAU GCC AUC CUG GAG UUC CUG UAA GAU | No Skipping |
| 11 | H45A (-09+25) | GCU GCC CAA UGC CAU CCU GGA GUU CCU GUA AGA U | Skipping at 10 nM (100% skipping at 25 nM) |
| 230 | H45A(-08 +19) | CAA UGC CAU CCU GGA GUU CCU GUA AGA | Skipping at 50 nM |
| 231 | HM45A(-07+25) | GCU GCC CAA UGC CAU CCU GGA GUU CCU GUA AG | Skipping at 25 nM |
| 232 | H45A(+09 +34) | CAG UUU GCC GCU GCC CAA UGC CAU CC | No Skipping |
| 233 | H45A(+41 +64) | CUU CCC CAG UUG CAU UCA AUG UUC | No Skipping |
| 234 | H45A(+76 +98) | CUG GCA UCU GUU UUU GAG GAU UG | No Skipping |
| 235 | H45D(+02-18) | UUA GAU CUG UCG CCC UAC CU | No Skipping |
| 236 | H45A(-14+25) | GCU GCC CAA UGC CAU CCU GGA GUU CCU GUA AGA UAC CAA | |
| 237 | H45A(-12+22) | GCC CAA UGC CAU CCU GGA GUU CCU GUA AGA UAC C | Strong skipping at 5 nM faint 2.5 nM |
| 238 | H45A(-12+13) | CAU CCU GGA GUU CCU GUA AGA UAC C | No skipping |
| 66 | H45A(-12+16) | UGC CAU CCU GGA GUU CCU GUA AGA UAC C | Strong skipping at 25 nM faint 5 nM |
| 65 | H45A(-09+16) | UGC CAU CCU GGA GUU CCU GUA AGA U | skipping to 10 nM |
| 64 | H45A(-09+19) | CAA UGC CAU CCU GGA GUU CCU GUA AGA U | Strong skipping at 25 nM faint 2.5 nM |
| 239 | H45A(-09+22) | GCC CAA UGC CAU CCU GGA GUU CCU GUA AGA U | Strong skipping at 10 nM faint 5 nM |
| 240 | H45A(-09+30) | UUG CCG CUG CCC AAU GCC AUC CUG GAG UUC CUG UAA GAU | Strong skipping at 5 nM faint 2.5 nM |
| 241 | HM45A(-07+25) | GCU GCC CAA UGC CAU CCU GGA GUU CCU GUA AG | Strong skipping at 2.5 nM |
| 242 | H45A(-06+22) | GCC CAA UGC CAU CCU GGA GUU CCU GUA A | Strong skipping at 5 nM faint 2.5 nM |

TABLE 34-continued

Antisense molecule sequences tested to determine if they induce exon 45 skipping

| SEQ ID | Antisense Oligonucleotide name Exon 45 | Sequence | Ability to induce skipping |
|---|---|---|---|
| 243 | H45A(-06+28) | GCC GCU GCC CAA UGC CAU CCU GGA GUU CCU GUA A | Strong skipping at 2.5 nM |
| 63 | H45A(-03+19) | CAA UGC CAU CCU GGA GUU CCU G | Strong skipping at 5 nM faint 2.5 nM |
| 244 | H45A(-03+22) | GCC CAA UGC CAU CCU GGA GUU CCU G | Strong skipping at 10 nM faint 2.5 nM |
| 55 | H45A(-03+25) | GCU GCC CAA UGC CAU CCU GGA GUU CCU G | Strong skipping at 2.5 nM |
| 245 | H45A(-03+28) | GCC GCU GCC CAA UGC CAU CCU GGA GUU CCU G | Strong skipping at 10 nM faint 2.5 nM |
| 246 | H45D(+10-19) | AUU AGA UCU GUC GCC CUA CCU CUU UUU UC | No skipping |
| 247 | H45D(+16-11) | UGU CGC CCU ACC UCU UUU UUC UGU CUG | No skipping |
| 61 | H45A(-06+25) | GCU GCC CAA UGC CAU CCU GGA GUU CCU GUA A | strong skipping at 2.5 nM |
| 62 | H45A(-12+19) | CAA UGC CAU CCU GGA GUU CCU GUA AGA UAC C | strong skipping at 25 nM |

Antisense Oligonucleotides Directed at Exon 46

Figure 44:
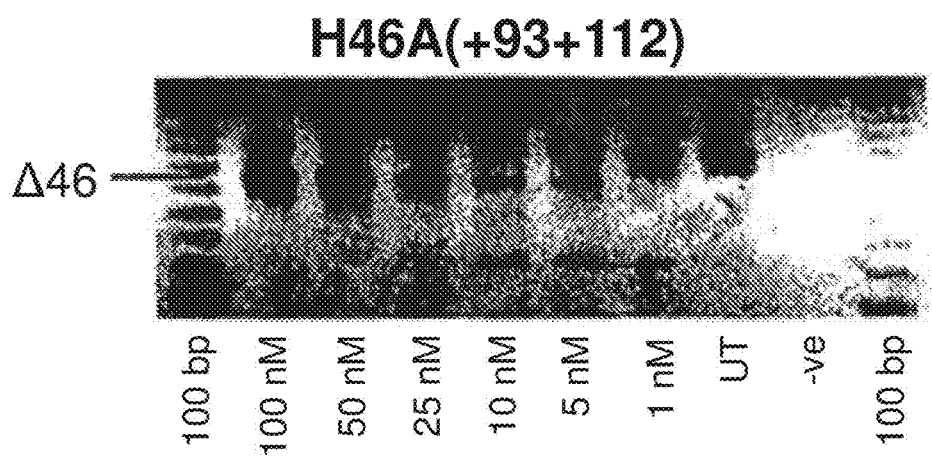
FIG. 44. Gel electrophoresis showing exon 46 skipping using antisense molecule H46A(+93+122).
Figure 45:
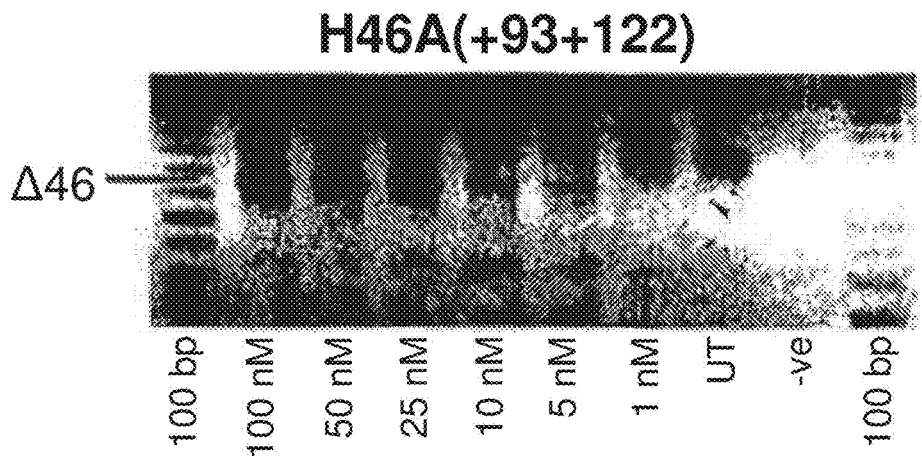
FIG. 45. Gel electrophoresis showing exon 46 skipping using antisense molecule (H46A(+93+2).

Antisense oligonucleotides directed at exon 46 were prepared and tested for their ability to induce exon skipping in human muscle cells using similar methods as described above. See FIG. 15 and FIG. 44.

TABLE 35

Antisense molecule sequences tested to determine if they induce exon 46 skipping

| SEQ | Antisense Oligonucleotide name Exon 46 | Sequence | Ability to induce skipping |
|---|---|---|---|
| 248 | H46A(-05+19) | AUU CUU UUG UUC UUC UAG CCU GGA | No skipping |
| 249 | H46A(+16+42) | UCU CUU UGA AAU UCU GAC AAG AUA UUC | skipping to 25 nM, other bands |
| 250 | H46A(+27+44) | UUA AAU CUC UUU GAA AUU CU | No skipping |
| 251 | H46A(+35+60) | AAA ACA AAU UCA UUU AAA UCU CUU UG | very faint skipping to 50 nM |
| 252 | H46A(+56+77) | CUG CUU CCU CCA ACC AUA AAA C | No skipping |
| 253 | H46A(+63+87) | GCA AUG UUA UCU GCU UCC UCC AAC C | No skipping |
| 12 | H46A(+81+109) | UCC AGG UUC AAG UGG GAU ACU AGC AAU GU | strong skipping at 25 nM |
| 254 | H46A(+83+103) | UUC AAG UGG GAU ACU AGC AAU | skipping at 25 nM |
| 255 | H46A(+90+109) | UCC AGG UUC AAG UGG GAU AC | no skipping |
| 256 | H46A(+91+118) | CUG CUC UUU UCC AGG UUC AAG UGG GAU A | strong skipping at 25 nM |
| 257 | H46A(+95+122) | GUU GCU GCU CUU UUC CAG GUU CAA GUG G | strong skipping at 25 nM |
| 258 | H46A(+101+128) | CUU UUA GUU GCU GCU CUU UUC CAG GUU C | strong skipping at 25 nM |
| 259 | H46A(+113+136) | AAG CUU UUC UUU UAG UUG CUG CUC | skipping at 100 nM |
| 260 | H46A(+115+134) | GCU UUU CUU UUA GUU GCU GC | skipping at 100 nM |
| 261 | H46A(+116+145) | GAC UUG CUC AAG CUU UUC UUU UAG UUG CUG | strong skipping at 25 nM |
| 262 | H46D(+02-18) | UUC AGA AAA UAA AAU UAC CU | no skipping |

TABLE 35-continued

Antisense molecule sequences tested to determine if they induce exon 46 skipping

| SEQ | Antisense Oligonucleotide name Exon 46 | Sequence | Ability to induce skipping |
|---|---|---|---|
| 56 | H46A(+93+122) | GUU GCU GCU CUU UUC CAG GUU CAA GUG GGA | 100% skipping at 25 nM strong at 5 nM |
| 263 | H46A(+95+124) | UAG UUG CUG CUC UUU UCC AGG UUC AAG UGG | 100% skipping at 25 nM |

Antisense Oligonucleotide Cocktails Directed at Exons 44 to 46

Antisense oligonucleotide cocktails directed at exons 44 to 46 were prepared and tested for their ability to induce exon skipping in human muscle cells using similar methods as described above.

TABLE 36

Antisense molecule sequence cocktails that induce exon 44 to 45 skipping

| SEQ ID | Antisense Oligonucleotide name | Sequence | Ability to induce skipping |
|---|---|---|---|
| | Cocktails for skipping 44 + 45 | | |
| 10 & 228 | H44A(+65 +90) H45A(-10 +20) | AGA AAC UGU UCA GCU UCU GUU AGC CA CCA AUG CCA UCC UGG AGU UCC UGU AAG AUA | Skipping at 25 nM |
| | Cocktails for skipping exons 45 and 46 | | |
| 228 & 256 | H45A(-10 +20) H46A(+91 +118) | CCA AUG CCA UCC UGG AGU UCC UGU AAG AUA CUG CUC UUU UCC AGG UUC AGG UGG GAU A | Skipping at 25 nM |
| 228 & 264 | H45A(-10 +20) H46A(+107 +137) | CCA AUG CCA UCC UGG AGU UCC UGU AAG AUA CAA GCU UUU CUU UUA GUU GCU GCU CUU UUC C | Skipping at 25 nM |
| | Cocktail for skipping exon 44/45/46 | | |
| 228, 10 & 256 | H45A(-10 +20) H44A(+65 +90) H46A(+91 +118) | CCA AUG CCA UCC UGG AGU UCC UGU AAG AUA AGA AAC UGU UCA GCU UCU GUU AGC CA CUG CUC UUU UCC AGG UUC AGG UGG GAU A | Skipping at 25 nM |

Antisense Oligonucleotides Directed at Exon 47

Figure 16:
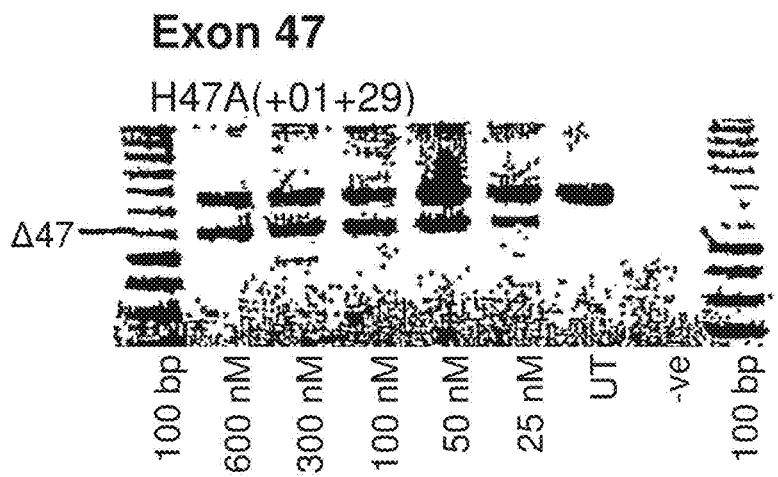
FIG. 16. Gel electrophoresis showing strong and consistent exon 47 skipping using antisense molecule H47A(+01+29).

Antisense oligonucleotides directed at exon 47 were prepared and tested for their ability to induce exon skipping in human muscle cells using similar methods as described above. See FIG. 16.

TABLE 37

Antisense molecule sequences tested to determine if they induce exon 47 skipping

| SEQ ID | Antisense Oligonucleotide name Exon 47 | Sequence | Ability to induce skipping |
|---|---|---|---|
| 265 | H47A(-07+19) | GCA ACU CUU CCA CCA GUA ACU GAA AC | Skipping at 100 nM |
| 13 | H47A(+01+29) | UGG CGC AGG GGC AAC UCU UCC ACC AGU AA | strong skipping at 25 nM |
| 266 | H47A(+44+70) | GCA CGG GUC CUC CAG UUU CAU UUA AUU | Skipping at 600 nM |
| 267 | H47A(+68+92) | GGG CUU AUG GGA GCA CUU ACA AGC A | No skipping |
| 268 | H47A(+73+103) | CUU GCU CUU CUG GGC UUA UGG GAG CAC UUA C | No skipping |

TABLE 37-continued

Antisense molecule sequences tested to determine if they induce exon 47 skipping

| SEQ ID | Antisense Oligonucleotide name Exon 47 | Sequence | Ability to induce skipping |
|---|---|---|---|
| 269 | H47A(+76+103) | CUU GCU CUU CUG GGC UUA UGG GAG CAC U | Faint skipping at 200 nM, full length product not reduced |
| 270 | H47D(+17-10) | AAU GUC UAA CCU UUA UCC ACU GGA GAU | No skipping |

Antisense Oligonucleotides Directed at Exon 48

Figure 17:
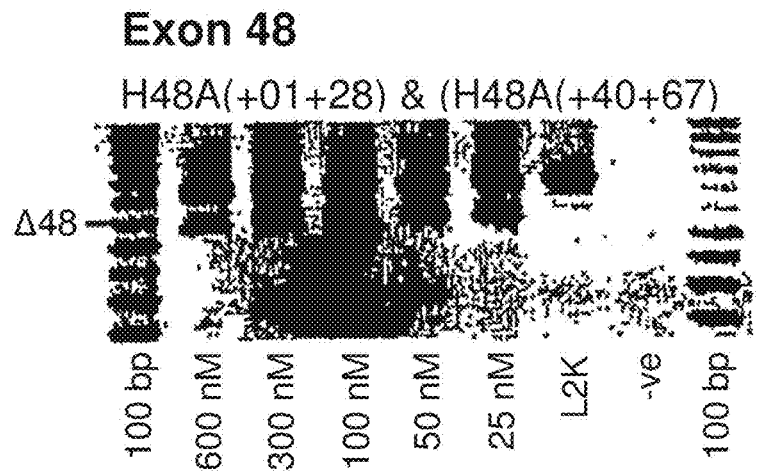
FIG. 17. Gel electrophoresis showing a "cocktail" of antisense molecules directed at exon 48 which induce strong and consistent exon skipping.

Antisense oligonucleotides directed at exon 48 were prepared and tested for their ability to induce exon skipping in human muscle cells using similar methods as described above. See FIG. 17.

TABLE 38

Antisense molecule sequences tested to determine if they induce exon 48 skipping

| SEQ ID | Antisense Oligonucleotide name | Sequence | Ability to induce skipping |
|---|---|---|---|
| | Exon 48 | | |
| 271 | H48A(-09+21) | CUC AGG UAA AGC UCU GGA AAC CUG AAA GGA | No skipping |
| 272 | H48A(-08+19) | CAG GUA AAG CUC UGG AAA CCU GAA AGG | No skipping |
| 273 | H48A(-07+23) | UUC UCA GGU AAA GCU CUG GAA ACC UGA AAG | Skipping at 600, 300 nM |
| 274 | H48A(-05+25) | GUU UCU CAG GUA AAG CUC UGG AAA CCU GAA | No skipping |
| 44 | H48A(+01+28) | CUU GUU UCU CAG GUA AAG CUC UGG AAA C | faint to 50 nM |
| 275 | H48A(+07+33) | UUC UCC UUG UUU CUC AGG UAA AGC UCU | faint to 50 nM |
| 45 | H48A(+40+67) | CAA GCU GCC AAG GUC UUU UUA UUU GAG C | No skipping (sporadic) |
| 276 | H48A(+75+100) | UUA ACU GCU CUU CAA GGU CUU CAA GC | faint to 1000 nM |
| 277 | H48A(+96+122) | GAU AAC CAC AGC AGC AGA UGA UUU AAC | No skipping |
| 278 | H48D(+17-10) | AGU UCC CUA CCU GAA CGU CAA AUG GUC | No skipping |
| 279 | H48D(+16-09) | GUU CCC UAC CUG AAC GUC AAA UGG U | No skipping |
| | Cocktail 48 | | |
| 44 & 45 | H48A(+01+28) H48A(+40+67) | CUU GUU UCU CAG GUA AAG CUC UGG AAA C CAA GCU GCC AAG GUC UUU UUA UUU GAG C | Strong skipping at 25 nM |

Antisense Oligonucleotides Directed at Exon 49

Figure 18:
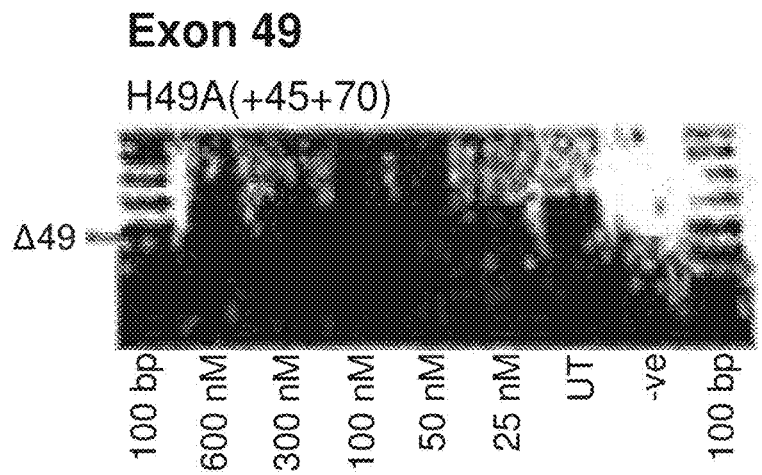
FIG. 18. Gel electrophoresis showing strong and consistent exon 49 skipping using antisense molecule H49A(+45+70).

Antisense oligonucleotides directed at exon 49 were prepared and tested for their ability to induce exon skipping in human muscle cells using similar methods as described above. See FIG. 18.

TABLE 39

Antisense molecule sequences tested to determine if they induce exon 49 skipping

| SEQ ID | Antisense Oligonucleotide name Exon 49 | Sequence | Ability to induce skipping |
|---|---|---|---|
| 280 | H49A(-07+19) | GAA CUG CUA UUU CAG UUU CCU GGG GA | Skipping to 100 nM |
| 281 | H49A(+22+47) | AUC UCU UCC ACA UCC GGU UGU UUA GC | Skipping to 25 nM |

TABLE 39-continued

Antisense molecule sequences tested to determine if they induce exon 49 skipping

| SEQ ID | Antisense Oligonucleotide name Exon 49 | Sequence | Ability to induce skipping |
|---|---|---|---|
| 14 | H49A(+45+70) | ACA AAU GCU GCC CUU UAG ACA AAA UC | Skipping to 25 nM |
| 282 | H49D(+18-08) | UUC AUU ACC UUC ACU GGC UGA GUG GC | Skipping to 100 nM |

Antisense Oligonucleotides Directed at Exon 50

Figure 19:
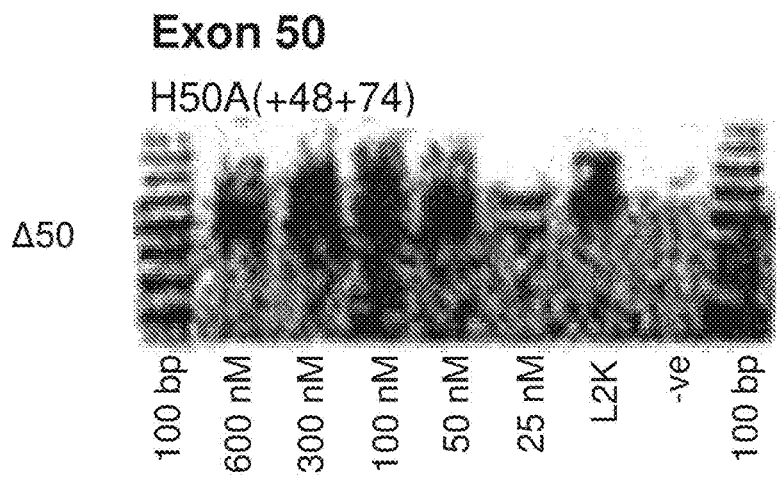
FIG. 19. Gel electrophoresis showing strong and consistent exon 50 skipping using antisense molecule H50A(+48+74).
Figure 33:
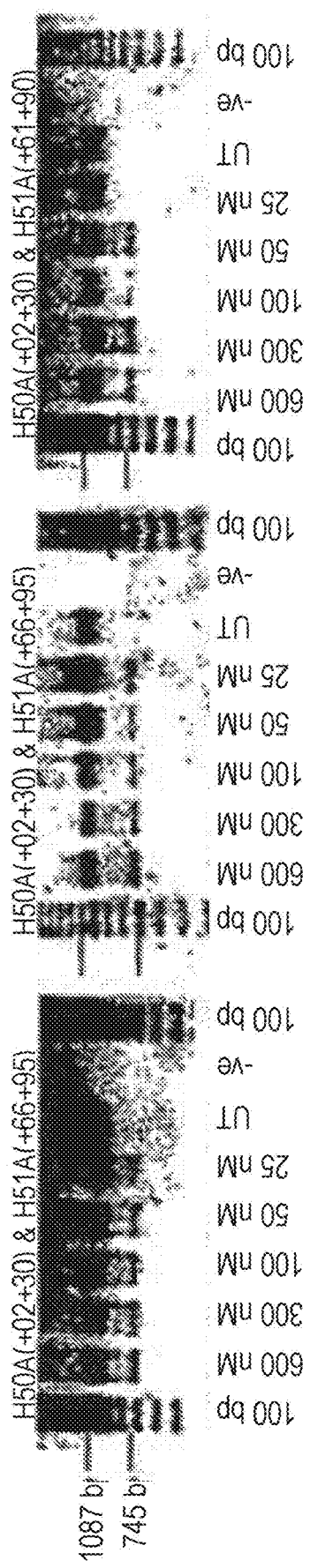
FIG. 33. Gel electrophoresis showing various "cocktails" of antisense molecules which induce various levels of skipping in exon 50.
Figure 34:
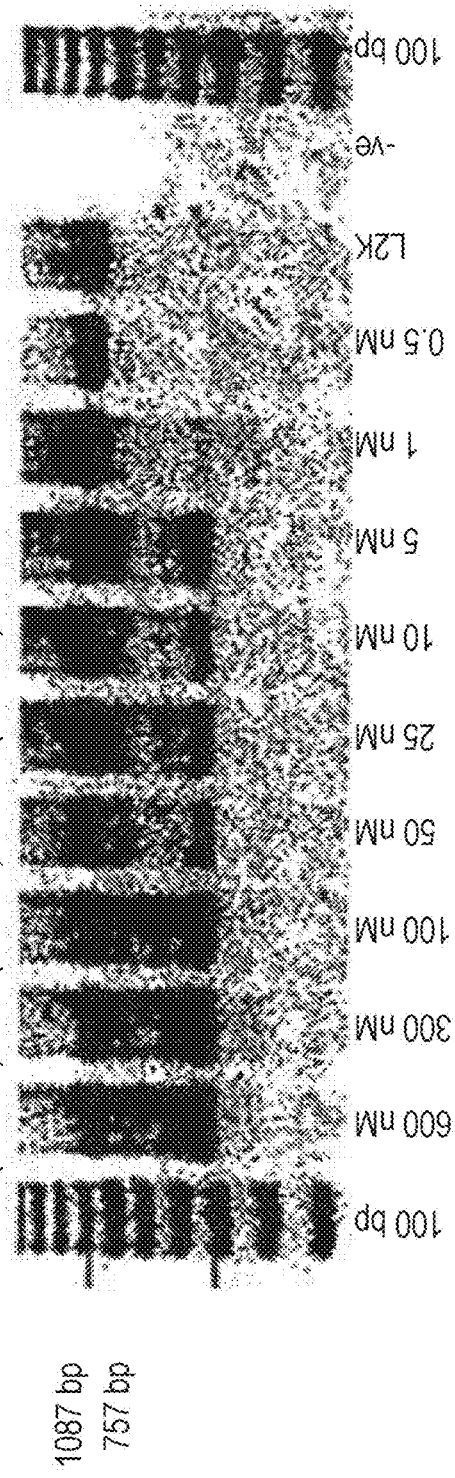
FIG. 34. Gel electrophoresis showing a cocktail of three antisense molecules which induce efficient skipping of exons 50/51.
Figure 35:
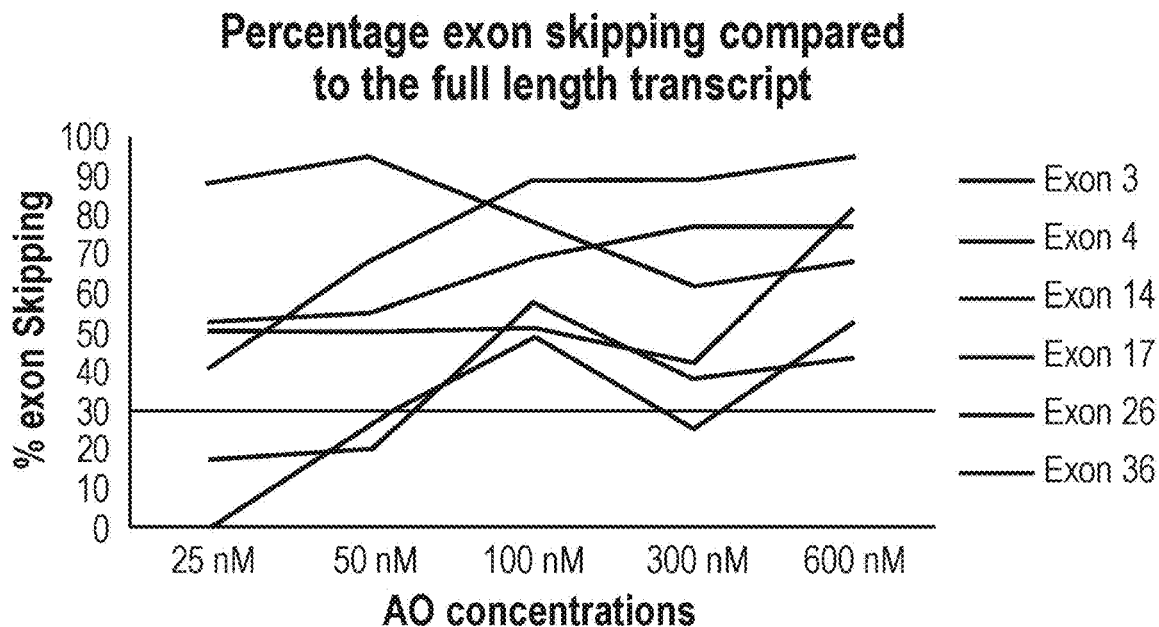
FIG. 35. Graph of densitometry results showing various efficiencies of exon skipping. The antisense molecules tested were Exon 3 [H3A(+30+60) & H3A(+61+85)]; Exon 4 [H4D(+14−11) & H4A(+11+40)]; Exon 14 [H14A(+32+61)]; Exon 17 [H17A(+10+35)]; Exon 26 [H26A(−07+19), H26A(+24+50) & H26A(+68+92)]; Exon 36 [H36A(−16+09) & H36A(+22+51)].
Figure 36:
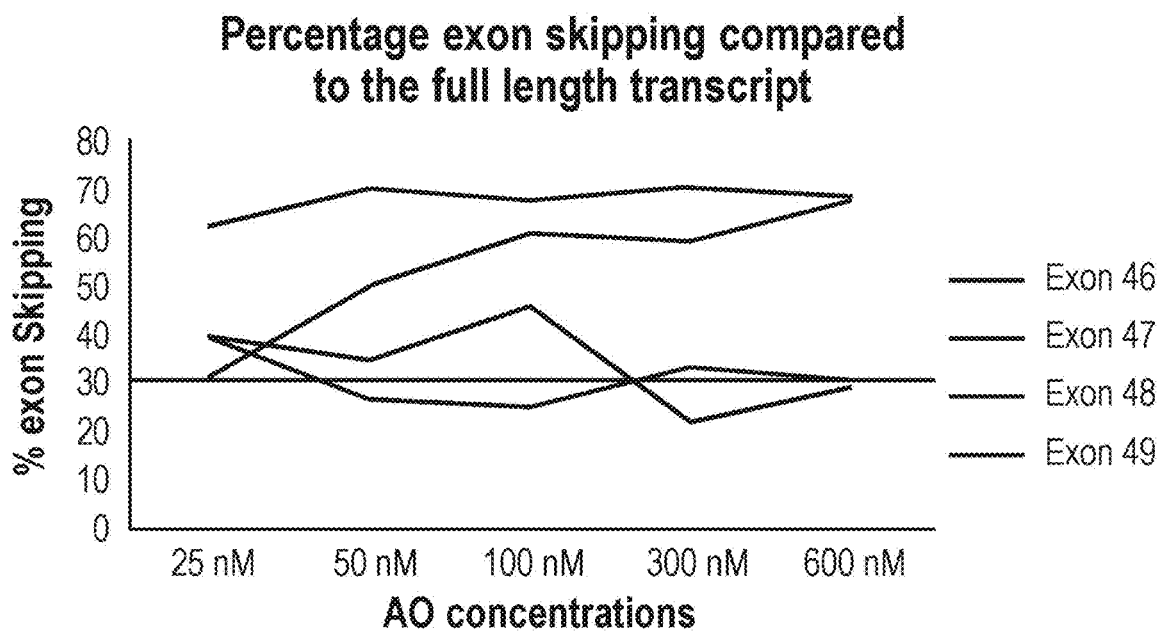
FIG. 36. Graph of densitometry results showing various efficiencies of exon skipping. The antisense molecules tested were Exon 46 [H46A(+81+109)]; Exon 47 [H47A(+01+29)]; Exon 48 [H48A(+01+28) & H48A(+40+67)]; Exon 49 [H49A(+45+70)].

Antisense oligonucleotides directed at exon 50 were prepared and tested for their ability to induce exon skipping in human muscle cells using similar methods as described above. See FIGS. 19 and 33.

TABLE 40

Antisense molecule sequences tested to determine if they induce exon 50 skipping

| SEQ ID | Antisense Oligonucleotide name Exon 50 | Sequence | Ability to induce skipping |
|---|---|---|---|
| 283 | H50A(-07+20) | CUC AGA UCU UCU AAC UUC CUC UUU AAC | Faint skipping 25 nM |
| 284 | H50A(-02+27) | CUC AGA GCU CAG AUC UUC UAA CUU CCU CU | faint skipping 100 nM |
| 285 | H50A(+10+36) | CGC CUU CCA CUC AGA GCU CAG AUC UUC | skipping faintly to 25 |
| 286 | H50A(+35+61) | UCA GCU CUU GAA GUA AAC GGU UUA CCG | strong skipping to 25 nM |
| 287 | H50A(+42+68) | UUU GCC CUC AGC UCU UGA AGU AAA CGG | reasonable skipping to 25 nM |
| 15 | H50A(+48+74) | GGC UGC UUU GCC CUC AGC UCU UGA AGU | strong skipping at 25 nM |
| 288 | H50A(+63+88) | CAG GAG CUA GGU CAG GCU GCU UUG CC | strong skipping to 25 nM |
| 289 | H50A(+81+105) | UCC AAU AGU GGU CAG UCC AGG AGC U | |
| 290 | H50D(-01-27) | AAA GAG AAU GGG AUC CAG UAU ACU UAC | faint skipping 100 nM |
| 291 | H50D(-15-41) | AAA UAG CUA GAG CCA AAG AGA AUG GGA | No skipping |
| 292 | H50A(+42+74) | GGC UGC UUU GCC CUC AGC UCU UGA AGU AAA CGG | Strong skipping to 10 nM faint at 5 nM |
| 293 | H50A(+46+75) | AGG CUG CUU UGC CCU CAG CUC UUG AAG UAA | Strong skipping to 25 nM faint at 10 nM |
| 294 | H50A(+48+78) | GUC AGG CUG CUU UGC CCU CAG CUC UUG AAG U | Strong skipping to 10 nM faint at 2.5 nM |
| 295 | H50A(+51+80) | AGG UCA GGC UGC UUU GCC CUC AGC UCU UGA | Strong skipping to 25 nM faint at 2.5 nM |
| 296 | Hint49(-72-46) | AAG AUA AUU CAU GAA CAU CUU AAU CCA | No skipping |

Antisense Oligonucleotides Directed at Exon 51

Figure 20:
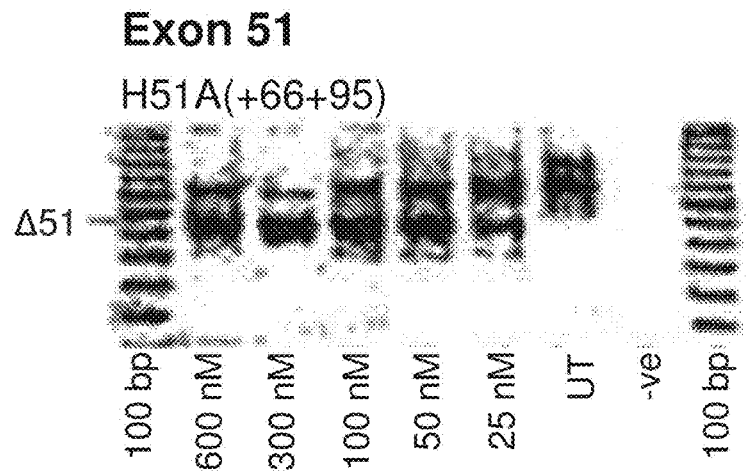
FIG. 20. Gel electrophoresis showing strong and consistent exon 51 skipping using antisense molecule H51A(+66+95).
Figure 41:
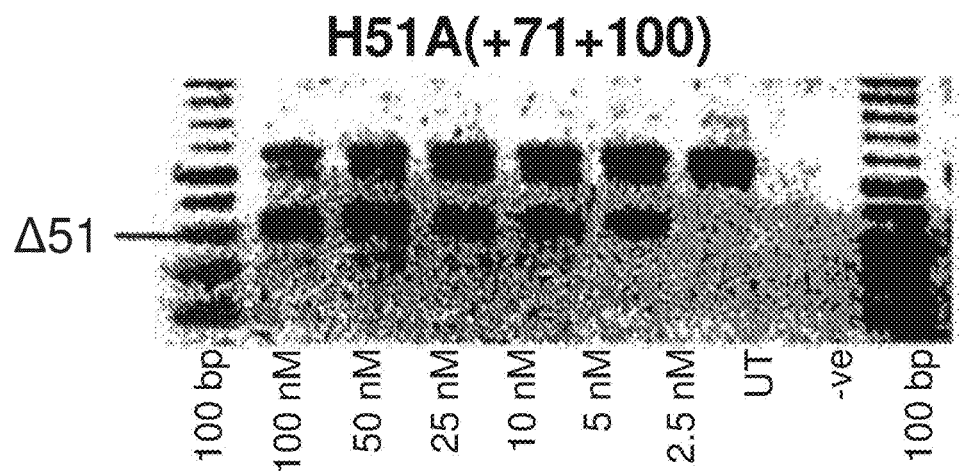
FIG. 41. Gel electrophoresis showing exon 51 skipping using antisense molecule H51A(+71+100).

Antisense oligonucleotides directed at exon 51 were prepared and tested for their ability to induce exon skipping in human muscle cells using similar methods as described above. See FIG. 20 and FIG. 41.

TABLE 41

Antisense molecule sequences tested to determine if they induce exon 51 skipping

| SEQ ID | Antisense Oligonucleotide name Exon 51 | Sequence | Ability to induce skipping |
|---|---|---|---|
| 297 | H51A(−29−10) | UUU GGG UUU UUG CAA AAA GG | No skipping |
| 298 | H51A(−22−01) | CUA AAA UAU UUU GGG UUU UUG C | No skipping |
| 299 | H51A(−14+10) | UGA GUA GGA GCU AAA AUA UUU UGG | No skipping |
| 300 | H51(+26+52) | GUU UCC UUA GUA ACC ACA GGU UGU GUC | very faint skipping to 25 nM |
| 301 | H51A(+40+67) | AGU UUG GAG AUG GCA GUU UCC UUA GUA A | skipping to 25 nM also skips 50 or 52 a well |
| 302 | H51A(+66+77) | UGG CAU UUC UAG | No skipping |
| 303 | H51A(+66+80) | AGA UGG CAU UUC UAG | No skipping |
| 304 | H51A(+66+83) | GGA AGA UGG CAU UUC UAG | No skipping |
| 305 | H51A(+78+95) | CUC CAA CAU CAA GGA AGA | No skipping |
| 306 | H51A(+81+95) | CUC CAA CAU CAA GGA | No skipping |
| 307 | H51A(+84+95) | CUC CAA CAU CAA | No skipping |
| 308 | H51A(+90+116) | GAA AUC UGC CAG AGC AGG UAC CUC CAA | No skipping |
| 309 | H51A(+53+79) | GAU GGC AUU UCU AGU UUG GAG AUG GCA | Strong skipping to 25 nM |
| 310 | H51A(+57+85) | AAG GAA GAU GGC AUU UCU AGU UUG GAG AU | Strong skipping to 25 nM faint at 2.5 nM |
| 69 | H51A(+71+100) | GGU ACC UCC AAC AUC AAG GAA GAU GGC AUU | Strong skipping to 5 nM |
| 311 | H51A(+76+104) | AGC AGG UAC CUC CAA CAU CAA GGA AGA UG | Strong skipping to 25 nM |

Antisense Oligonucleotides Directed at Exon 52

Figure 42:
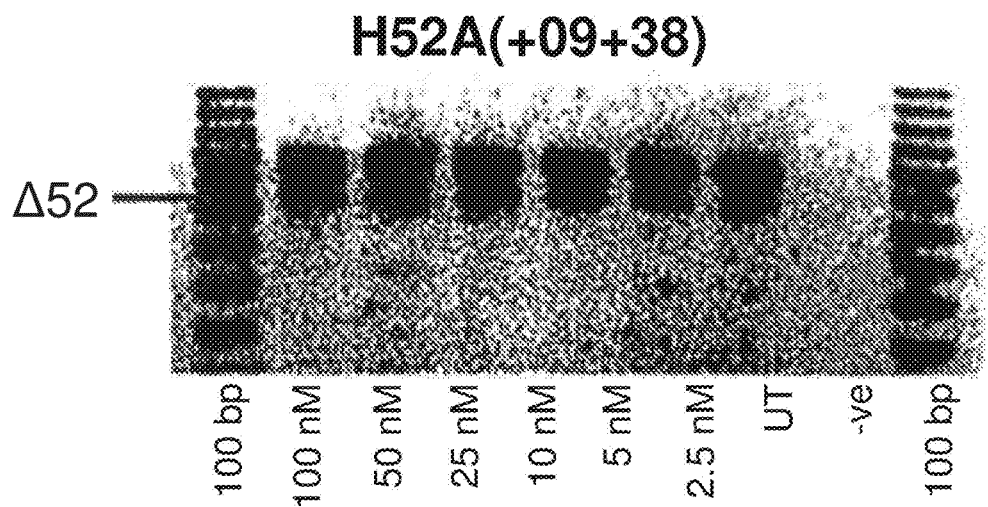
FIG. 42. Gel electrophoresis showing exon 52 skipping using antisense molecule H52A(+09+38).

Antisense oligonucleotides directed at exon 52 were prepared and tested for their ability to induce exon skipping in human muscle cells using similar methods as described above. See FIG. 42.

TABLE 42

Antisense molecule sequences tested to determine if they induce exon 52 skipping

| SEQ ID | Antisense Oligonucleotide name Exon 52 | Sequence | Ability to induce skipping |
|---|---|---|---|
| 312 | H52A(−12+13) | CCU GCA UUG UUG CCU GUA AGA ACA A | No skipping |
| 313 | H52A(−10+10) | GCA UUG UUG CCU GUA AGA AC | No skipping |
| 314 | H52A(+07+33) | GGG ACG CCU CUG UUC AAU CUG CAU | skippping 50 nM |
| 315 | H52A(+17+46) | GUU CUU CCA ACU GGG GAC GCC UCU GUU CCA | skippping 25 nM |
| 316 | H52A(+17+37) | ACU GGG GAC GCC UCU GUU CCA | skippping 25 nM |
| 317 | H52A(+67+94) | CCU CUU GAU UGC UGG UCU UGU UUU UCA A | vey very faint skipping to 25 nM |
| 318 | Hint51(−40−14) | UAC CCC UUA GUA UCA GGG UUC UUC AGC | No skipping (SNP C or T) |
| 58 | H52A(+09+38) | AAC UGG GGA CGC CUC UGU UCC AAA UCC UGC | Strong skipping to 2.5 nM |
| 319 | H52A(+09+41) | UCC AAC UGG GGA CGC CUC UGU UCC AAA UCC UGC | Strong skipping to 5 nM faint at 5 nM |

TABLE 42-continued

Antisense molecule sequences tested to determine if they induce exon 52 skipping

| SEQ ID | Antisense Oligonucleotide name Exon 52 | Sequence | Ability to induce skipping |
|---|---|---|---|
| 320 | H52A(+15+44) | UCU UCC AAC UGG GGA CGC CUC UGU UCC AAA | Strong skipping to 10 nM faint at 5 nM |

Antisense Oligonucleotides Directed at Exon 53

Figure 43:
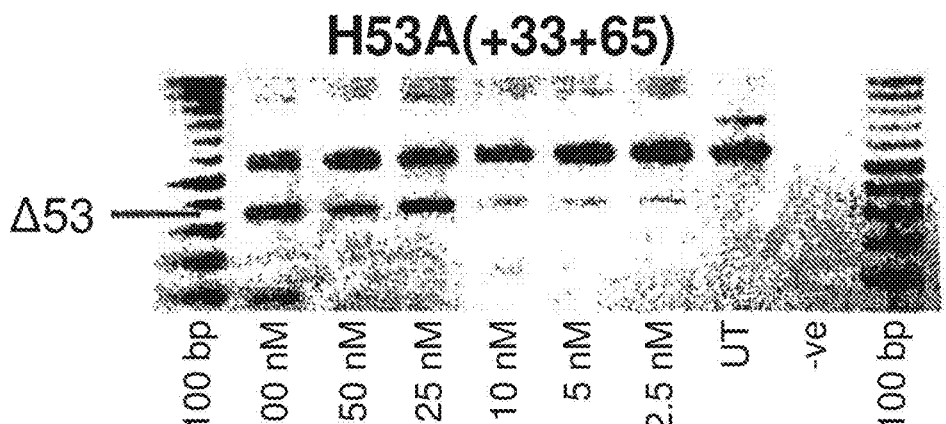
FIG. 43. Gel electrophoresis showing exon 53 skipping using antisense molecule H53A(+33+65).

Antisense oligonucleotides directed at exon 53 were prepared and tested for their ability to induce exon skipping in human muscle cells using similar methods as described above. See FIG. 43.

TABLE 43

Antisense molecule sequences tested to determine if they induce exon 53 skipping

| SEQ ID | Antisense Oligonucleotide name Exon 53 | Sequence | Ability to induce skipping |
|---|---|---|---|
| 321 | H53A(-49-26) | AUA GUA GUA AAU GCU AGU CUG GAG | No skipping |
| 322 | H53A(-38-13) | GAA AAA UAA AUA UAU AGU AGU AAA UG | No skipping |
| 323 | H53A(-32-06) | AUA AAA GGA AAA AUA AAU AUA UAG UAG | No skipping |
| 324 | H53A(-15+15) | UCU GAA UUC UUU CAA CUA GAA UAA AAG GAA | No skipping |
| 325 | H53A(+39+65) | CAA CUG UUG CCU CCG GUU CUG AAG GUG | skippping 50 nM |
| 326 | H53A(+39+67) | UUC AAC UGU UGC CUC CGG UUC UGA AGG UG | skippping 100 nM |
| 327 | H39A(+39+69)SNP | CGU UCA ACU GUU GCC UCC GGU UCU GAA GGU G | skipping to 25 nM |
| 328 | H53A(+40+70) | UCA UUC AAC UGU UGC CUC CGG UUC UGA AGG U | skippping 50 nM |
| 329 | H53A(+41+69) | CAU UCA ACU GUU GCC UCC GGU UCU GAA GG | skippping 50 nM |
| 330 | H53A(+43+69) | CAU UCA ACU GUU GCC UCC GGU UCU GAA | skippping 50 nM |
| 331 | H53A(+69+98) | CAG CCA UUG UGU UGA AUC CUU UAA CAU UUC | Skipping at 50 nM |
| 332 | Hint52(-47-23) | UAU AUA GUA GUA AAU GCU AGU CUG G | No skipping |
| 67 | H53A(+27+56) | CCU CCG GUU CUG AAG GUG UUC UUG UAC UUC | strong skipping to 25 nM faint at 5 nM |
| 333 | H53A(+27+59) | UUG CCU CCG GUU CUG AAG GUG UUC UUG UAC UUC | strong skipping to 10 nM faint at 5 nM |
| 334 | H53A(+30+59) | UUG CCU CCG GUU CUG AAG GUG UUC UUG UAC | |
| 335 | H53A(+30+64) | AAC UGU UGC CUC CGG UUC UGA AGG UGU UCU UGU AC | strong skipping to 25 nM faint at 10 nM |
| 336 | H53A(+30+69) | CAU UCA ACU GUU GCC UCC GGU UCU GAA GGU GUU CUU GUA C | strong skipping to 25 nM faint at 5 nM |
| 337 | H53A(+33+63) | ACU GUU GCC UCC GGU UCU GAA GGU GUU CUU G | strong skipping to 25 nM faint at 5 nM |
| 338 | H53A(+33+67) | UUC AAC UGU UGC CUC CGG UUC UGA AGG UGU UCU UG | strong skipping to 50 nM faint at 5 nM |
| 59 | H53A(+33+65) | CAA CUG UUG CCU CCG GUU CUG AAG GUG UUC UUG | strong skipping to 25 nM faint at 2.5 nM |
| 339 | H53A(+35+67) | UUC AAC UGU UGC CUC CGG UUC UGA AGG UGU UCU | strong skipping to 25 nM |
| 340 | H53A(+37+67) | UUC AAC UGU UGC CUC CGG UUC UGA AGG UGU U | strong skipping to 25 nM |

TABLE 43-continued

Antisense molecule sequences tested to determine if they induce exon 53 skipping

| SEQ ID | Antisense Oligonucleotide name Exon 53 | Sequence | Ability to induce skipping |
|---|---|---|---|
| 341 | H53A(+36+70) | UCA UUC AAC UGU UGC CUC CGG UUC UGA AGG UGU UC | reasonable sipping to 5 nM |
| 342 | H53A(+39+71) | UUC AUU CAA CUG UUG CCU CCG GUU CUG AAG GUG | strong skipping to 25 nM |
| 343 | H53A(+42+71) | UUC AUU CAA CUG UUG CCU CCG GUU CUG AAG | strong skipping to 100 nM faint at 5 nM |

Antisense Oligonucleotides Directed at Exon 54

Figure 21:
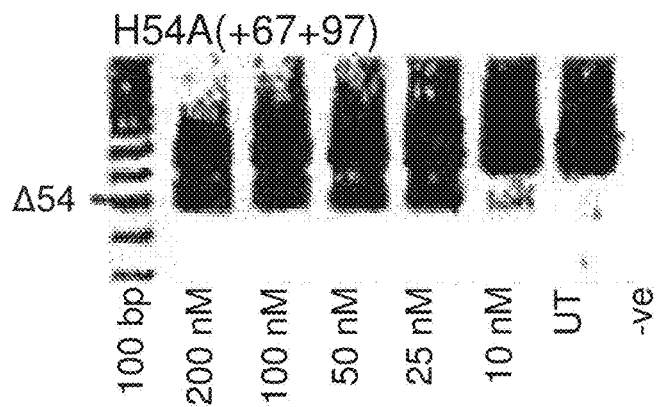
FIG. 21. Gel electrophoresis showing strong and consistent exon 54 skipping using antisense molecule H54A(+67+97).

Antisense oligonucleotides directed at exon 54 were prepared and tested for their ability to induce exon skipping in human muscle cells using similar methods as described above. See FIG. 21.

TABLE 44

Antisense molecule sequences tested to determine if they induce exon 54 skipping

| SEQ ID | Antisense Oligonucleotide name | Sequence | Ability to induce skipping |
|---|---|---|---|
| | Exon 54 | | |
| 344 | H54A(+13+34) | UUG UCU GCC ACU GGC GGA GGU C | Skipping at 300 nM brings out 55 + 54 |
| 345 | H54A(+60+90) | AUC UGC AGA AUA AUC CGG GAG AAG UUU CAG | Skipping at 25 nM |
| 346 | H54A (+67+89) | UCU GCA GAA UAA UCC CGG AGA AG | Weak skipping to 40 nM- both 54 + 55 |
| 16 | H54A(+67+97) | UGG UCU CAU CUG CAG AAU AAU CCC GGA GAA G | Skipping at 10 nM |
| 347 | H54A(+77+106) | GGA CUU UUC UGG UAU CAU CUG CAG AAU AAU | Skipping 50 nM |
| | Cocktail for Exons 54 + 55 | | |
| 16 & 348 | H54A(+67+97) H55A(-10+14) | UGG UCU CAU CUG CAG AAU AAU CCC GGA GAA G CUC GCU CAC UCA CCC UGC AAA GGA | Specific for 54&55 Skipping at 10 nM No additional bands |

Antisense Oligonucleotides Directed at Exon 55

Figure 22:
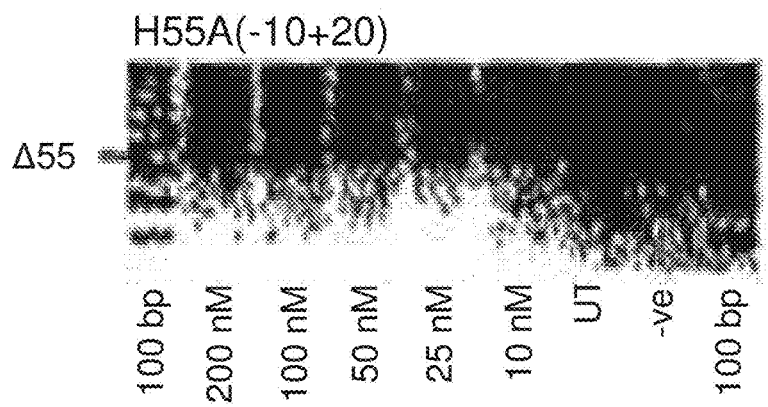
FIG. 22. Gel electrophoresis showing antisense molecule H55A(−10+20) induced dose dependant exon 55 skipping.

Antisense oligonucleotides directed at exon 55 were prepared and tested for their ability to induce exon skipping in human muscle cells using similar methods as described above. See FIG. 22.

TABLE 45

Antisense molecule sequences tested to determine if they induce exon 55 skipping

| SEQ ID | Antisense Oligonucleotide name Exon 55 | Sequence | Ability to induce skipping |
|---|---|---|---|
| 348 | H55A(-10+14) | CUC GCU CAC UCA CCC UGC AAA GGA | No Skipping |
| 17 | H55A(-10 +20) | CAG CCU CUC GCU CAC UCA CCC UGC AAA GGA | Skipping at 10 nM |
| 349 | H55A(+39 +61) | CAG GGG GAA CUG UUG CAG UAA UC | No Skipping |
| 350 | H55A(+41+71) | UCU UUU ACU CCC UUG GAG UCU UCU AGG AGC C | No Skipping |

TABLE 45-continued

Antisense molecule sequences tested to determine if they induce exon 55 skipping

| SEQ ID | Antisense Oligonucleotide name Exon 55 | Sequence | Ability to induce skipping |
|---|---|---|---|
| 351 | H55A(+73+93) | UCU GUA AGC CAG GCA AGA AAC | No Skipping |
| 352 | H55A(+107+137) | CCU UAC GGG UAG CAU CCU GAU GGA CAU UGG C | No Skipping |
| 353 | H55A(+112 +136) | CUU ACG GGU AGC AUC CUG UAG GAC A | very weak skipping at 100 nM |
| 354 | H55A(+132 +161) | CCU UGG AGU CUU CUA GGA GCC UUU CCU UAC | Skipping at 200 nM |
| 355 | H55A(+141 +160) | CUU GGA GUC UUC UAG GAG CC | Skipping at 100 nM |
| 356 | H55A(+143 +171) | CUC UUU UAC UCC UUG GAG UC UUC UAG GAG | No skipping |
| 357 | H55D(+11 -09) | CCU GAC UUA CUU GCC AUU GU | No skipping |

Antisense Oligonucleotides Directed at Exon 56

Figure 23:
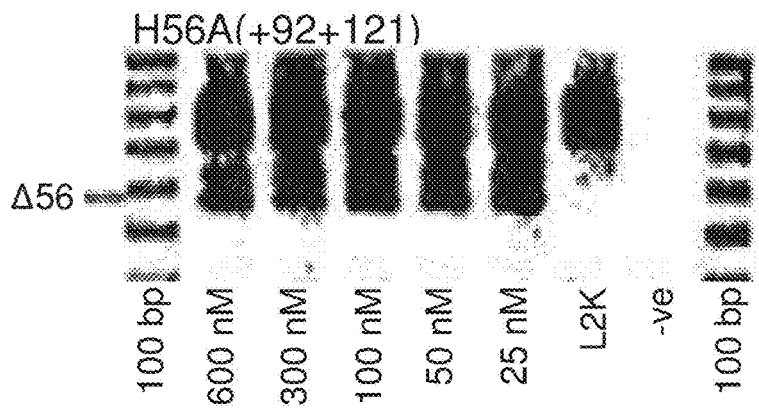
FIG. 23. Gel electrophoresis showing strong and consistent exon 56 skipping using antisense molecule H56A(+92+121).

Antisense oligonucleotides directed at exon 56 were prepared and tested for their ability to induce exon skipping in human muscle cells using similar methods as described above. See FIG. 23.

TABLE 46

Antisense molecule sequences tested to determine if they induce exon 56 skipping

| SEQ ID | Antisense Oligonucleotide name Exon 56 | Sequence | Ability to induce skipping |
|---|---|---|---|
| 358 | H56A(-06+23) | GCU UCA AUU UCA CCU UGG AGG UCC UAC AG | Skipping at 25 nM |
| 359 | H56A(-06+15) | UUC ACC UUG GAG GUC CUA CAG | No Skipping |
| 360 | H56A(+23 +44) | GUU GUG AUA AAC AUC UGU GUG A | No skipping |
| 361 | H56A(+56 +81) | CCA GGG AUC UCA GGA UUU UUU GGC UG | No skipping |
| 362 | H56A(+67+91) | CGG AAC CUU CCA GGG AUC UCA GGA U | Skipping at 200 nM |
| 18 | H56A(+92+121) | CCA AAC GUC UUU GUA ACA GGA CUG CAU | skipping at 25 nM |
| 363 | H56A(+102+126) | GUU AUC CAA ACG UCU UUG UAA CAG G | skipping at 100 nM |
| 364 | H56A(+102+131) | UUC AUG UUA UCC AAA CGU CUU UGU AAC AGG | skipping at 25 nM |
| 19 | H56A(+112+141) | CCA CUU GAA GUU CAU GUU AUC CAA ACG UCU | skipping at 25 nM |
| 365 | H56A(+117+146) | UCA CUC CAC UUG AAG UUC AUG UUA UCC AAA | skipping weakly at 25 nM |
| 366 | H56A(+121+143) | CUC CAC UUG AAG UUC AUG UUA UC | No Skipping |
| 367 | H56D(+11-10) | CUU UUC CUA CCA AAU GUU GAG | Skipping at 600 nM |

Antisense Oligonucleotides Directed at Exon 57

Antisense oligonucleotides directed at exon 57 were prepared and tested for their ability to induce exon skipping in human muscle cells using similar methods as described above. See FIG. 24.

TABLE 47

Antisense molecule sequences tested to determine if they induce exon 57 skipping

| SEQ ID | Antisense Oligonucleotide name Exon 57 | Sequence | Ability to induce skipping |
|---|---|---|---|
| 368 | H57A(-15+18) | CUG GCU UCC AAA UGG GAC CUG AAA AAG AAC AGC | No Skipping |
| 369 | H57A (-12 +18) | CUG GCU UCC AAA UGG GAC CUG AAA AAG AAC | Skipping at 50 nM |
| 20 | H57A(-10+20) | AAC UGG CUU CCA AAU GGG ACC UGA AAA AGA | Skipping at 300 nM |
| 370 | H57A(-06 +24) | UCA GAA CUG GCU UCC AAA UGG GAC CUG AAA | Skipping at 300 nM |
| 371 | H57A(+21+44) | GGU GCA GAC GCU UCC ACU GGU CAG | No Skipping |
| 372 | H57A(+47 +77) | GCU GUA GCC ACA CCA GAA GUU CCU GCA GAG A | No Skipping |
| 373 | H57A(+79+103) | CUG CCG GCU UAA UUC AUC AUC UUU C | No Skipping |
| 374 | H57A(+105+131) | CUG CUG GAA AGU CGC CUC CAA UAG GUG | No Skipping |

Antisense Oligonucleotides Directed at Exon 59

Figure 25:
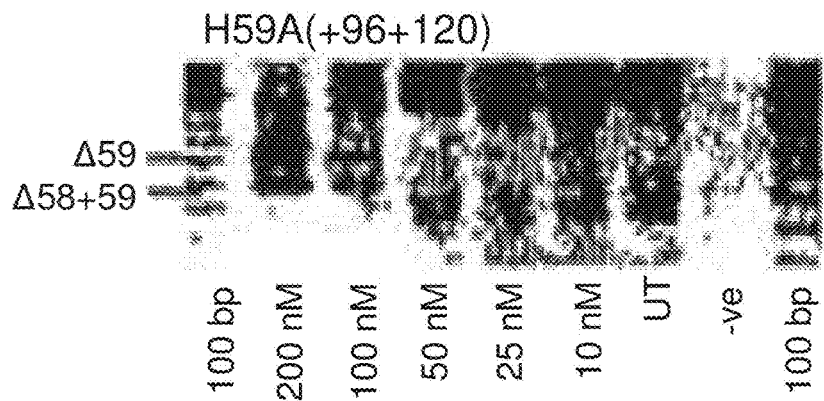
FIG. 25. Gel electrophoresis showing exon 59 and exon 58/59 skipping using antisense molecule H59A(+96+120) directed at exon 59.

Antisense oligonucleotides directed at exon 59 were prepared and tested for their ability to induce exon skipping in human muscle cells using similar methods as described above. See FIG. 25.

TABLE 48

Antisense molecule sequences tested to determine if they induce exon 59 skipping

| SEQ ID | Antisense Oligonucleotide name Exon 59 | Sequence | Ability to induce skipping |
|---|---|---|---|
| 375 | H59A (-06 +16) | UCC UCA GGA GGC AGC UCU AAA U | No skipping |
| 376 | H59A(+31 +61) | UCC UC GCC UGC UUU CGU AGA AGC CGA GUG A | No skipping |
| 377 | H59A(+66+91) | AGG UUC AAU UUU UCC CAC UCA GUA UU | No Skipping |
| 23 | H59A(+96 +120) | CUA UUU UUC UCU GCC AGU CAG CGG A | Skipping at 100 nM |
| 378 | H59A(+96+125) | CUC AUC UAU UUU UCU CUG CCA GUC AGC GGA | No skipping |
| 379 | H59A(+101 +132) | CA GGG UCU CAU CUA UUU UUC UCU GCC AGU CA | No skipping |
| 380 | H59A(+141 +165) | CAU CCG UGG CCU CUU GAA GUU CCU G | Skipping exon 58 & 59 at 200 nM |
| 381 | H59A(+151 +175) | AGG UCC AGC UCA UCC GUG GCC UCU U | Skipping at 300 nM |
| 382 | H59A(+161 +185) | GCG CAG CUU GAG GUC CAG CUC AUC C | weak skipping at 200 nM |
| 383 | H59A(+161+190) | GCU UGG CGC AGC UUG AGG UCC AGC UCA UCC | Skipping at 100 nM |
| 384 | H59A(+171+197) | CAC CUC AGC UUG GCG CAG CUU GAG GUC | No skipping |
| 385 | H59A(+181+205) | CCC UUG AUC ACC UCA GCU UGG CGC A | No Skipping |
| 386 | H59A(+200+220) | ACG GGC UGC CAG GAU CCC UUG | No Skipping |
| 387 | H59A(+221+245) | GAG AGA GUC AAU GAG GAG AUC GCC C | No Skipping |
| 388 | H59A(+92+125) | CUC AUC UAU UUU UCU CUG CCA GUC AGC GGA GUG C | |

Antisense Oligonucleotides Directed at Exon 60

Figure 26:
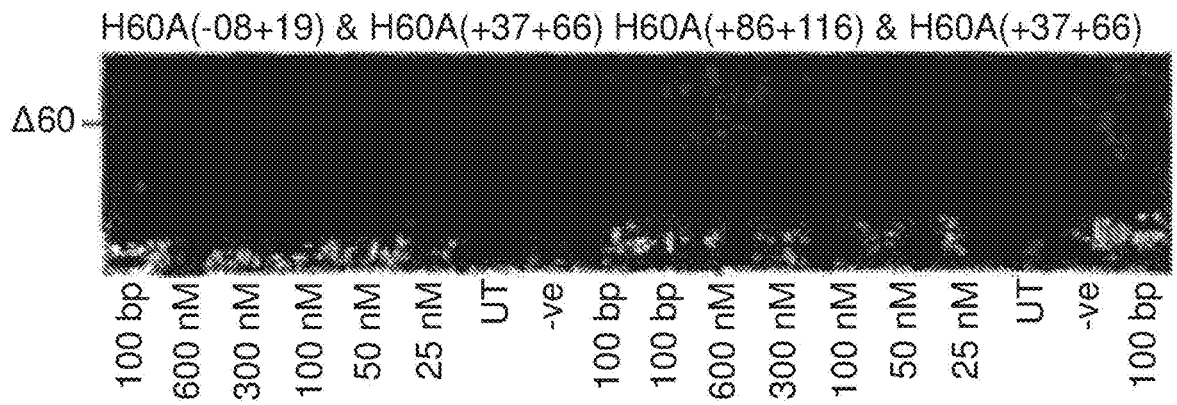
FIG. 26. Gel electrophoresis showing two different cocktails which induce exon skipping of exon 60.

Antisense oligonucleotides directed at exon 60 were prepared and tested for their ability to induce exon skipping in human muscle cells using similar methods as described above. See FIG. 26.

TABLE 49

Antisense molecule sequences tested to determine if they induce exon 60 skipping

| SEQ ID | Antisense Oligonucleotide name | Sequence | Ability to induce skipping |
|---|---|---|---|
| | Exon 60 | | |
| 389 | H60A(-10+20) | GCA AUU UCU CCU CGA AGU GCC UGU GUG CAA | no skipping |
| 390 | H60A(-8+19) | CAA UUU CUC CUC GAA GUG CCU GUG UGC | no skipping |
| 391 | H60A(+29+58) | CAA GGU CAU UGA CGU GGC UCA CGU UCU CUU | skipping to 50 nM |
| 24 | H60A(+33+62) | CGA GCA AGG UCA UUG ACG UGG CUC ACG UUC | strong skipping to 50 nM |
| 47 | H60A(+37+66) | CUG GCG AGC AAG GUC CUU GAC GUG GCU CAC | good skipping at 100 nM |
| 392 | H60A(+37+66) | CUG GCG AGC AAG GUC AUU GAC GUG GCU CAC | SNP |
| 393 | H60A(+39+66) | CUG GCG AGC AAG GUC CUU GAC GUG GCU C | good skipping at 100 nM |
| 394 | H60A(+43+73) | UGG UAA GCU GGC GAG CAA GGU CCU UGA CGU G | weak skipping at 100 nM |
| 395 | H60A(+51+75) | AGU GGU AAG CUG GCG UGC AAG GUC A | weak skipping at 100 nM |
| 396 | H60A(+72+102) | UUA UAC GGU GAG AGC UGA AUG CCC AAA GUG | no skipping |
| 397 | H60A(+75+105) | GAG GUU AUA CGG UGA GAG CUG AAU GCC AAA | no skipping |
| 398 | H60A(+80+109) | UGC UGA GGU UAU ACG GUG AGA GCU GAA | good skipping at 100 nM |
| 46 | H60A(+87+116) | UCC AGA GUG CUG AGG UUA UAC GGU GAG AGC | weak skipping at 100 nM |
| 399 | H60D(+25-5) | CUU UCC UGC AGA AGC UUC CAU CUG GUG UUC | weak skipping at 600 nM |
| | Exon 60 cocktails | | |
| 390 | H60A(-8+19) | CAA UUU CUC CUC GAA GUG CCU GUG UGC | weak skipping at 10 nM |
| 392 | H60A(+37+66) | CUG GCG AGC AAG GUC CUU GAC GUG GCU CAC | |
| 46 & | H60A(+87+116) | UCC AGA GUG CUG AGG UUA UAC GGU GAG AGC | skipping at 10 nM |
| 47 | H60A(+37+66) | CUG GCG AGC AAG GUC CUU GAC GUG GCU CAC | |
| 389 | H60A(-10+20) | GCA AUU UCU CCU CGA AGU GCC UGU GUG CAA | skipping at 10 nM |
| 394 | H60A(+43+73) | UGG UAA GCU GGC GAG CAA GGU CCU UGA CGU G | |
| 393 | H60A(+39+66) | CUG GCG AGC AAG GUC CUU GAC GUG GCU C | skipping at 10 nM |
| 389 | H60A(-10+20) | GCA AUU UCU CCU CGA AGU GCC UGU GUG CAA | |

Antisense Oligonucleotides Directed at Exon 61

Antisense oligonucleotides directed at exon 61 were prepared and tested for their ability to induce exon skipping in human muscle cells using similar methods as described above.

TABLE 50

Antisense molecule sequences tested to determine if they induce exon 61 skipping

| SEQ ID | Antisense Oligonucleotide name Exon 61 | Sequence | Ability to induce skipping |
|---|---|---|---|
| 400 | H61A(-7+19) | CUC GGU CCU CGA CGG CCA CCU GGG AG | no skipping |
| 401 | H61A(+05+34) | CAU GCA GCU GCC UGA CUC GGU CCU CGC CGG | skipping to 50 nM |
| 25 | H61A(+10+40) | GGG CUU CAU GCA GCU GCC UGA CUC GGU CCU C | Skipping at 100 nM |
| 402 | H61A(+16+40) | GGG CUU CAU GCA GCU GCC UGA CUC G | no skipping |
| 403 | H61A(+16+45) | CCU GUG GGC UUC AUG CAG CUG CCU GAC UCG | skipping to 50 nM |

TABLE 50-continued

Antisense molecule sequences tested to determine if they induce exon 61 skipping

| SEQ ID | Antisense Oligonucleotide name Exon 61 | Sequence | Ability to induce skipping |
|---|---|---|---|
| 404 | H61A(+42+67) | GCU GAG AUG CUG GAC CAA AGU CCC UG | no skipping |
| 405 | H61D(+10-16) | GCU GAA AAU GAC UUA CUG GAA AGA AA | no skipping |

Antisense Oligonucleotides Directed at Exon 62

Antisense oligonucleotides directed at exon 62 were prepared and tested for their ability to induce exon skipping in human muscle cells using similar methods as described above.

TABLE 51

Antisense molecule sequences tested to determine if they induce exon 62 skipping

| SEQ ID | Antisense Oligonucleotide name Exon 62 | Sequence | Ability to induce skipping |
|---|---|---|---|
| 406 | H62A(-15+15) | GAC CCU GGA CAG ACG CUG AAA AGA AGG GAG | No skipping |
| 407 | H62A(-10+20) | CCA GGG ACC CUG GAC AGA CGC UGA AAA GAA | No skipping |
| 408 | H62A(-05+15) | GAC CCU GGA CAG ACG CUG AA | Faint to 25 nM |
| 409 | H62A(-3+25) | CUC UCC CAG GGA CCC UGG ACA GAC GCU G | No skipping |
| 410 | H62A(+01+30) | UGG CUC UCU CCC AGG GAC CCU GGA CAG ACG | almost 100% skipping to 300 nM |
| 411 | H62A(+8+34) | GAG AUG GCU CUC UCC CAG GGA CCC UGG | Skipping at 300 nM |
| 412 | H62A(+13+43) | UUG UUU GGU GAG AUG GCU CUC UCC CAG GGA C | Faint to 25 nM |
| 26 | H62A(23+52) | UAG GGC ACU UUG UUU GGC GAG AUG GCU CUC | Skipping at 100 nM |
| 413 | H62D(+17-03) | UAC UUG AUA UAG UAG GGC AC | Faint to 100 nM |
| 414 | H62D(+25-5) | CUU ACU UGA UAU AGU AGG GCA CUU UGU UUG | No skipping |

Antisense Oligonucleotides Directed at Exon 63

Figure 27:
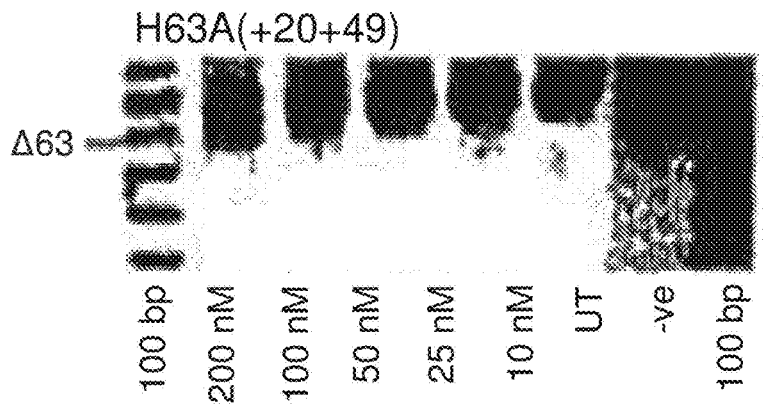
FIG. 27. Gel electrophoresis showing exon 63 skipping using antisense molecule H63A(+20+49).

Antisense oligonucleotides directed at exon 63 were prepared and tested for their ability to induce exon skipping in human muscle cells using similar methods as described above. See FIG. 27.

TABLE 52

Antisense molecule sequences tested to determine if they induce exon 63 skipping

| SEQ ID | Antisense Oligonucleotide name Exon 63 | Sequence | Ability to induce skipping |
|---|---|---|---|
| 415 | H63A(-14+11) | GAG UCU CGU GGC UAA AAC ACA AAA C | No visible skipping |
| 416 | H63A(+11+35) | UGG GAU GGU CCC AGC AAG UUG UUU G | Possible skipping at 600 nM |
| 27 | H63A(+20+49) | GAG CUC UGU CAU UUU GGG AUG GUC CCA GCA | Skipping to 100 nM |
| 417 | H63A(+33+57) | GAC UGG UAG AGC UCU GUC AUU UUG G | No visible skipping |
| 418 | H63A(+40+62) | CUA AAG ACU GGU AGA GCU CUG UC | No Skipping |
| 419 | H63D(+8-17) | CAU GGC CAU GUC CUU ACC UAA AGA C | No visible skipping |

Antisense Oligonucleotides Directed at Exon 64

Figure 28:
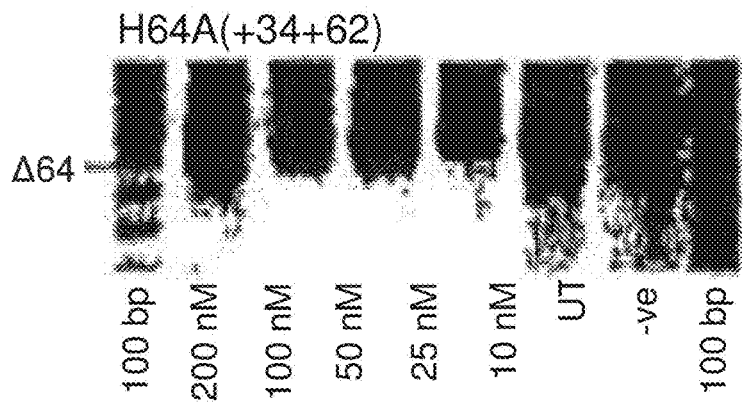
FIG. 28. Gel electrophoresis showing exon 64 skipping using antisense molecule H64A(+34+62).

Antisense oligonucleotides directed at exon 64 were prepared and tested for their ability to induce exon skipping in human muscle cells using similar methods as described above. See FIG. 28.

TABLE 53

Antisense molecule sequences tested to determine if they induce exon 64 skipping

| SEQ ID | Antisense Oligonucleotide name Exon 64 | Sequence | Ability to induce skipping |
|---|---|---|---|
| 420 | H64A(-3+27) | CUG AGA AUC UGA CAU UAU UCA GGU CAG CUG | No skipping |
| 28 | H64A(+34+62) | CUG CAG UCU UCG GAG UUU CAU GGC AGU CC | Skipping at 50 nM |
| 421 | H64A(+43+72) | AAA GGG CCU UCU GCA GUC UUC GGA GUU UCA | Skipping at 50 nM |
| 422 | H64A(+47+74) | GCA AAG GGC CUU CUG CAG UCU UCG GAG | Skipping at 200 nM |
| 423 | H64D(+15-10) | CAA UAC UUA CAG CAA AGG GCC UUC U | No skipping |

Antisense Oligonucleotides Directed at Exon 65

Antisense oligonucleotides directed at exon 65 were prepared and tested for their ability to induce exon skipping in human muscle cells using similar methods as described above.

TABLE 54

Antisense molecule sequences tested to determine if they induce exon 65 skipping

| SEQ ID | Antisense Oligonucleotide name Exon 65 | Sequence | Ability to induce skipping |
|---|---|---|---|
| 424 | H65A(+123+148) | UUG ACC AAA UUG UUG UGC UCU UGC UC | No skipping |

Antisense Oligonucleotides Directed at Exon 66

Figure 29:
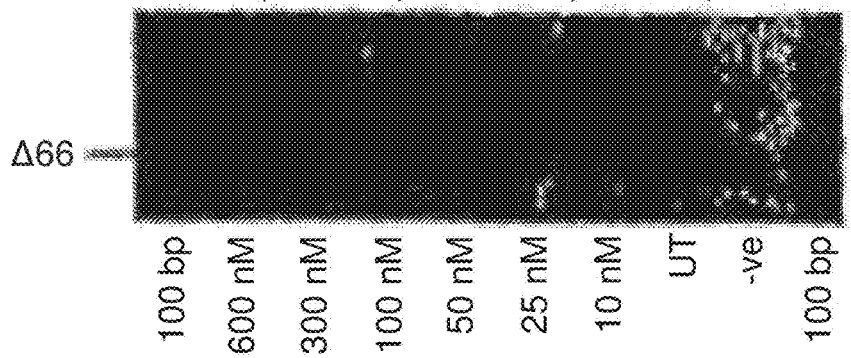
FIG. 29. Gel electrophoresis showing a "cocktail" of antisense molecules directed at exon 66 which induce dose dependant exon skipping.

Antisense oligonucleotides directed at exon 66 were prepared and tested for their ability to induce exon skipping in human muscle cells using similar methods as described above. See FIG. 29.

TABLE 55

Antisense molecule sequences tested to determine if they induce exon 66 skipping

| SEQ ID | Antisense Oligonucleotide name | Sequence | Ability to induce skipping |
|---|---|---|---|
| | Exon 66 | | |
| 29 | H66A(-8+19) | GAU CCU CCC UGU UCG UCC CCU AUU AUG | Skipping at 100 nM |
| 48 | H66A(-02+28) | CAG GAC ACG GAU CCU CCC UGU UCG UCC CCU | No skipping |
| 49 | H66D(+13-17) | UAA UAU ACA CGA CUU ACA UCU GUA CUU GUC | No skipping |
| | Exon 66 cocktails | | |
| 48 & 49 | H66A(-02+28) H66D(+13-17) | CAG GAC ACG GAU CCU CCC UGU UCG UCC CCU UAA UAU ACA CGA CUU ACA UCU GUA CUU GUC | skipping at 25 nM |

Antisense Oligonucleotides Directed at Exon 67

Figure 30:
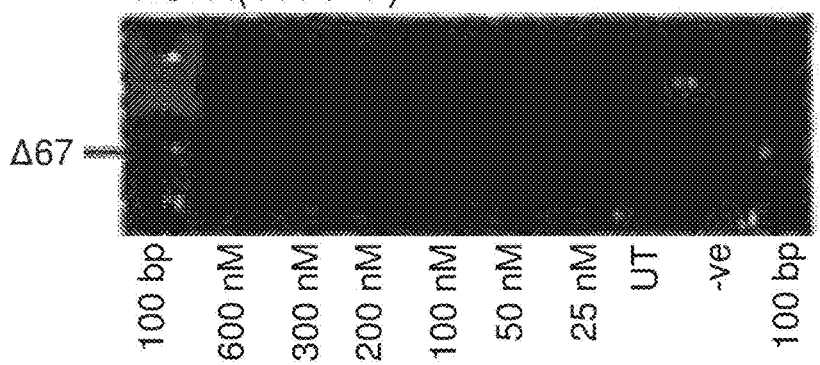
FIG. 30. Gel electrophoresis showing exon 67 skipping using antisense molecule H67A(+17+47).

Antisense oligonucleotides directed at exon 67 were prepared and tested for their ability to induce exon skipping in human muscle cells using similar methods as described above. See FIG. 30.

TABLE 56

Antisense molecule sequences tested to determine if they induce exon 67 skipping

| SEQ ID | Antisense Oligonucleotide name Exon 67 | Sequence | Ability to induce skipping |
|---|---|---|---|
| 30 | H67A(+17+47) | GCG CUG GUC ACA AAA UCC UGU UGA ACU UGC | strong skipping at 25 nM |
| 425 | H67A(+120+147) | AGC UCC GGA CAC UUG GCU CAA UGU UAC U | No skipping |
| 426 | H67A(+125+149) | GCA GCU CCG GAC ACU UGG CUC AAU G | Skipping at 600 nM |
| 427 | H67D(+22-08) | UAA CUU ACA AAU GGA AGC AGC UC CGG ACA | No skipping |

Antisense Oligonucleotides Directed at Exon 68

Figure 31:
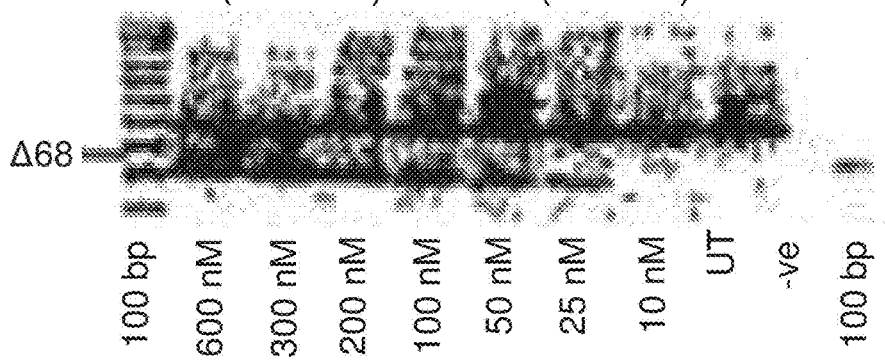
FIG. 31. Gel electrophoresis showing a "cocktail" of antisense molecules directed at exon 68 which induce dose dependant exon skipping.

Antisense oligonucleotides directed at exon 68 were prepared and tested for their ability to induce exon skipping in human muscle cells using similar methods as described above. See FIG. 31.

TABLE 57

Antisense molecule sequences tested to determine if they induce exon 68 skipping

| SEQ ID | Antisense Oligonucleotide name | Sequence | Ability to induce skipping |
|---|---|---|---|
| | Exon 68 | | |
| 428 | H68A(-4+21) | GAU CUC UGG CUU AUU AUU AGC CUG C | Skipping at 100 nM |
| 429 | H68A(+22+48) | CAU CCA GUC UAG GAA GAG GGC CGC UUC | Skipping at 200 nM |
| 50 | H68A(+48+72) | CAC CAU GGA CUG GGG UUC CAG UCU C | Skipping at 200 nM |
| 430 | H68A(+74+103) | CAG CAG CCA CUC UGU GCA GGA CGG GCA GCC | No skipping |
| 51 | H68D(+23-03) | UAC CUG AAU CCA AUG AUU GGA CAC UC | No skipping |
| | Exon 68 cocktails | | |
| 50 & 51 | H68A(+48+72) H68D(+23-03) | CAC CAU GGA CUG GGG UUC CAG UCU C UAC CUG AAU CCA AUG AUU GGA CAC UC | skipping at 10 nM |

Antisense Oligonucleotides Directed at Exon 69

Figure 32:
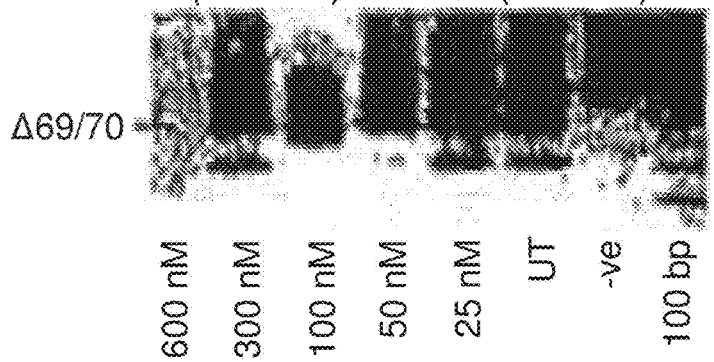
FIG. 32. Gel electrophoresis showing a "cocktail" of antisense molecules which induce strong and consistent exon skipping of exons 69/70 at a transfection concentration of 25 nanomolar.

Antisense oligonucleotides directed at exon 69 were prepared and tested for their ability to induce exon skipping in human muscle cells using similar methods as described above. See FIG. 32 which shows a cocktail of H69A(+32+60) and H70A(-06+18) to remove both exons 69 and 70.

TABLE 58

Antisense molecule sequences tested to determine if they induce exon 69 skipping

| SEQ ID | Antisense Oligonucleotide name Exon 69 | Sequence | Ability to induce skipping |
|---|---|---|---|
| 431 | H69A(-12+19) | GUG CUU UAG ACU CCU GUA CCU GAU AAA GAG C | No skipping |
| 432 | H69A(+09 +39) | UGG CAG AUG UCA UAA UUA AAG UGC UUU AGAC | Skipping 68-71 at 200 nM |
| 433 | H69A(+29 +57) | CCA GAA AAA AAG CAG CUU UGG CAG AUG UC | Skipping 68-71 at 200 nM |

TABLE 58-continued

Antisense molecule sequences tested to determine if they induce exon 69 skipping

| SEQ ID | Antisense Oligonucleotide name Exon 69 | Sequence | Ability to induce skipping |
|---|---|---|---|
| | | | also 68 + 69 & 69 + 70 |
| 434 | H69A(+51+74) | GGC CUU UUG CAA CUC GAC CAG AAA | Skipping 68-71 |
| 435 | H69A(+51 +80) | UUU UAU GGC CUU UUG CAA CUC GAC CAG AAA | ~90% Skipping of 68-71 at 200 nM |
| 436 | H69D(+08-16) | CUG GCG UCA AAC UUA CCG GAG UGC | no skipping |

Antisense Oligonucleotides Directed at Exon 70

Antisense oligonucleotides directed at exon 70 were prepared and tested for their ability to induce exon skipping in human muscle cells using similar methods as described above.

TABLE 59

Antisense molecule sequences tested to determine if they induce exon 70 skipping

| SEQ ID | Antisense Oligonucleotide name Exon 70 | Sequence | Ability to induce skipping |
|---|---|---|---|
| 437 | H70A(-09+15) | UUC UCC UGA UGU AGU CUA AAA GGG | no skipping |
| 438 | H70A(-07 +23) | CGA ACA UCU UCU CCU GAU GUA GUC UAA AAG | No skipping |
| 439 | H70A(+16 +40) | GUA CCU UGG CAA AGU CUC GAA CAU C | No skipping |
| 440 | H70A(+25 +48) | GUU UUU UAG UAC CUU GGC AAA GUC | No Skipping |
| 441 | H70A(+32+60) | GGU UCG AAA UUU GUU UUU UAG UAC CUU GG | No skipping |
| 442 | H70A(+64 +93) | GCC CAU UCG GGG AUG CUU CGC AAA AUA CCU | No skipping |

Antisense Oligonucleotides Directed at Exon 71

Antisense oligonucleotides directed at exon 71 were prepared and tested for their ability to induce exon skipping in human muscle cells using similar methods as described above.

TABLE 60

Antisense molecule sequences tested to determine if they induce exon 71 skipping

| SEQ ID | Antisense Oligonucleotide name Exon 71 | Sequence | Ability to induce skipping |
|---|---|---|---|
| 443 | H71A(-08+16) | GAU CAG AGU AAC GGG ACU GCA AAA | |
| 444 | H71A(+07+30) | ACU GGC CAG AAG UUG AUC AGA GUA | weak skipping at 100 nM |
| 445 | H71A(+16+39) | GCA GAA UCU ACU GGC CAG AAG UUG | skipping at 100 nM |
| 446 | H71D(+19-05) | CUC ACG CAG AAU CUA CUG GCC AGA | |

Antisense Oligonucleotides Directed at Exon 72

Antisense oligonucleotides directed at exon 72 were prepared and tested for their ability to induce exon skipping in human muscle cells using similar methods as described above.

TABLE 61

Antisense molecule sequences tested to determine if they induce exon 72 skipping

| SEQ ID | Antisense Oligonucleotide name Exon 72 | Sequence | Ability to induce skipping |
|---|---|---|---|
| 447 | H72A(-8+22) | AAG CUG AGG GGA CGA GGC AGG CCU AUA AGG | faint skipping at 600 nM |
| 448 | H72A(+02+28) | GUG UGA AAG CUG AGG GGA CGA GGC AGG | no skipping |
| 449 | H72D(+14-10) | AGU CUC AUA CCU GCU AGC AUA AUG | no skipping |

Antisense Oligonucleotides Directed at Exon 73

Antisense oligonucleotides directed at exon 73 were prepared and tested for their ability to induce exon skipping in human muscle cells using similar methods as described above.

TABLE 62

Antisense molecule sequences tested to determine if they induce exon 73 skipping

| SEQ ID | Antisense Oligonucleotide name Exon 73 | Sequence | Ability to induce skipping |
|---|---|---|---|
| 450 | H73A(+24+49) | AUG CUA UCA UUU AGA UAA GAU CCA U | weak skipping |
| 451 | H73A(-16+10) | UUC UGC UAG CCU GAU AAA AAA CGU AA | Faint to 25 nM |
| 60 | H73A(+02+26) | CAU UGC UGU UUU CCA UUU CUG GUA G | Strong to 25 nM |
| 452 | H73D(+23-02) | ACA UGC UCU CAU UAG GAG AGA UGC U | Skipping to 25 nM |
| 453 | HM73A(+19+44) | UAU CAU UUA GAU AAG AUC CAU UGC UG | Faint skipping to 25 nM |

Antisense Oligonucleotides Directed at Exon 74

Antisense oligonucleotides directed at exon 74 were prepared and tested for their ability to induce exon skipping in human muscle cells using similar methods as described above.

TABLE 66

Antisense molecule sequences tested to determine if they induce exon 74 skipping

| SEQ ID | Antisense Oligonucleotide name | Sequence | Ability to induce skipping |
|---|---|---|---|
| 454 | HM74A(+20+46) | GUU CAA ACU UUG GCA GUA AUG CUG GAU | skipping 25 nM |
| 455 | HM74A(+50+77) | GAC UAC GAG GCU GGC UCA GGG GGG AGU C | 100% skipping at 25 nM |
| 456 | HM74A(+96+122) | GCU CCC CUC UUU CCU CAC UCU CUA AGG | skipping 25 nM |

Antisense Oligonucleotides Directed at Exon 76

Antisense oligonucleotides directed at exon 76 were prepared and tested for their ability to induce exon skipping in human muscle cells using similar methods as described above.

TABLE 63

Antisense molecule sequences tested to determine if they induce exon 76 skipping

| Antisense Oligonucleotide SEQname ID Exon 76 | Sequence | Ability to induce skipping |
|---|---|---|
| 457H76A(−02+25) | CAU UCA CUU UGG CCU CUG CCU GGG GCU | no detectable skipping |
| 458H76A(+80+106) | GAC UGC CAA CCA CUC GGA GCA GCA UAG | no detectable skipping |

Modifications of the above-described modes of carrying out the various embodiments of this invention will be apparent to those skilled in the art based on the above teachings related to the disclosed invention. The above embodiments of the invention are merely exemplary and should not be construed to be in any way limiting.

---

The claim defining the invention is as follows:

1. A method for restoring an mRNA reading frame to induce dystrophin protein production in a patient with Duchenne muscular dystrophy (DMD) in need thereof who has a mutation of the DMD gene that is amenable to exon 45 skipping, comprising administering to the patient an antisense oligonucleotide of 22 bases in length, wherein the antisense oligonucleotide is 100% complementary to a target region of exon 45 of the human dystrophin pre-mRNA, wherein the target region is annealing site H45A(−03+19), wherein the antisense oligonucleotide is a morpholino antisense oligonucleotide, and wherein the antisense oligonucleotide specifically hybridizes to the annealing site inducing exon 45 skipping, or a pharmaceutically acceptable salt thereof, thereby restoring the mRNA reading frame to induce dystrophin protein production in the patient.

2. The method of claim 1, wherein the antisense oligonucleotide or pharmaceutically acceptable salt thereof is chemically linked to one or more moieties or conjugates that enhance the activity, cellular distribution or cellular uptake of the oligonucleotide.

3. The method of claim 1, wherein the antisense oligonucleotide or pharmaceutically acceptable salt thereof is chemically linked to a polyethylene glycol chain.

4. A method for restoring an mRNA reading frame to induce dystrophin protein production in a patient with Duchenne muscular dystrophy (DMD) in need thereof who has a mutation of the DMD gene that is amenable to exon 45 skipping, comprising administering to the patient an antisense oligonucleotide of 22 bases in length, wherein the antisense oligonucleotide is 100% complementary to a target region of exon 45 of the human dystrophin pre-mRNA, wherein the target region is annealing site H45A(−03+19), wherein the antisense oligonucleotide is a morpholino antisense oligonucleotide, and wherein the antisense oligonucleotide specifically hybridizes to the annealing site inducing exon 45 skipping, thereby restoring the mRNA reading frame to induce dystrophin protein production in the patient.

5. The method of claim 4, wherein the antisense oligonucleotide is chemically linked to one or more moieties or conjugates that enhance the activity, cellular distribution or cellular uptake of the oligonucleotide.

6. The method of claim 4, wherein the antisense oligonucleotide is chemically linked to a polyethylene glycol chain.

7. A method for restoring an mRNA reading frame to induce dystrophin protein production in a patient with Duchenne muscular dystrophy (DMD) in need thereof who has a mutation of the DMD gene that is amenable to exon 45 skipping, comprising administering to the patient a pharmaceutical composition comprising (i) an antisense oligonucleotide of 22 bases in length, wherein the antisense oligonucleotide is 100% complementary to a target region of exon 45 of the human dystrophin pre-mRNA, wherein the target region is annealing site H45A(−03+19), wherein the antisense oligonucleotide is a morpholino antisense oligonucleotide, and wherein the antisense oligonucleotide specifically hybridizes to the annealing site inducing exon 45 skipping, or a pharmaceutically acceptable salt thereof, and (ii) a pharmaceutically acceptable carrier, thereby restoring the mRNA reading frame to induce dystrophin protein production in the patient.

8. The method of claim 7, wherein the antisense oligonucleotide or pharmaceutically acceptable salt thereof is chemically linked to one or more moieties or conjugates that enhance the activity, cellular distribution or cellular uptake of the oligonucleotide.

9. The method of claim 7, wherein the antisense oligonucleotide or pharmaceutically acceptable salt thereof is chemically linked to a polyethylene glycol chain.

10. A method for restoring an mRNA reading frame to induce dystrophin protein production in a patient with Duchenne muscular dystrophy (DMD) in need thereof who has a mutation of the DMD gene that is amenable to exon 45 skipping, comprising administering to the patient a pharmaceutical composition comprising (i) an antisense oligonucleotide of 22 bases in length, wherein the antisense oligonucleotide is 100% complementary to a target region of exon 45 of the human dystrophin pre-mRNA, wherein the target region is annealing site H45A(−03+19), wherein the antisense oligonucleotide is a morpholino antisense oligonucleotide, and wherein the antisense oligonucleotide specifically hybridizes to the annealing site inducing exon 45 skipping, and (ii) a pharmaceutically acceptable carrier, thereby restoring the mRNA reading frame to induce dystrophin protein production in the patient.

11. The method of claim 10, wherein the antisense oligonucleotide is chemically linked to one or more moieties or conjugates that enhance the activity, cellular distribution or cellular uptake of the oligonucleotide.

12. The method of claim 10, wherein the antisense oligonucleotide is chemically linked to a polyethylene glycol chain.

* * * * *

UNITED STATES PATENT AND TRADEMARK OFFICE
CERTIFICATE OF CORRECTION

PATENT NO. : 10,781,450 B2  
APPLICATION NO. : 16/357918  
DATED : September 22, 2020  
INVENTOR(S) : Wilton et al.

Page 1 of 1

It is certified that error appears in the above-identified patent and that said Letters Patent is hereby corrected as shown below:

On the Title Page

Item (73), "Sarepta Therapeutics, Inc., Cambridge, MA (US)" should read --The University of Western Australia, Crawley, (AU)--.

Signed and Sealed this  
Thirty-first Day of August, 2021

Drew Hirshfeld  
*Performing the Functions and Duties of the*  
*Under Secretary of Commerce for Intellectual Property and*  
*Director of the United States Patent and Trademark Office*